United States Patent
Beghyn et al.

(10) Patent No.: US 10,329,565 B2
(45) Date of Patent: Jun. 25, 2019

(54) DOWN-REGULATING GENE EXPRESSION IN INSECT PESTS

(71) Applicant: DEVGEN NV, Zwijnaarde (BE)

(72) Inventors: Myriam Beghyn, Ghent (BE); Thierry Andre Olivier Eddy Bogaert, Kortrijk (BE); Pascale Feldmann, Ghent (BE); Romaan Raemaekers, Brussels (BE)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/838,522

(22) Filed: Dec. 12, 2017

(65) Prior Publication Data

US 2018/0094265 A1  Apr. 5, 2018

Related U.S. Application Data

(60) Division of application No. 14/930,753, filed on Nov. 3, 2015, now Pat. No. 9,914,925, which is a division of application No. 13/462,636, filed on May 2, 2012, now Pat. No. 9,206,438, which is a continuation-in-part of application No. PCT/EP2012/057332, filed on Apr. 20, 2012.

(60) Provisional application No. 61/477,371, filed on Apr. 20, 2011, provisional application No. 61/508,826, filed on Jul. 18, 2011.

(51) Int. Cl.
| | |
|---|---|
| *C12N 15/82* | (2006.01) |
| *A01N 57/16* | (2006.01) |
| *A01N 63/00* | (2006.01) |
| *C07K 14/435* | (2006.01) |
| *C12N 15/113* | (2010.01) |

(52) U.S. Cl.
CPC ............ *C12N 15/113* (2013.01); *A01N 57/16* (2013.01); *A01N 63/00* (2013.01); *C07K 14/43563* (2013.01); *C12N 15/8218* (2013.01); *C12N 15/8286* (2013.01); *C12N 2310/14* (2013.01); *Y02A 40/162* (2018.01)

(58) Field of Classification Search
None
See application file for complete search history.

(56) References Cited

U.S. PATENT DOCUMENTS

| | | |
|---|---|---|
| 7,560,542 B2 | 7/2009 | Anderson et al. |
| 2012/0297501 A1 | 11/2012 | Beghyn et al. |

FOREIGN PATENT DOCUMENTS

| | | |
|---|---|---|
| WO | 2007074405 | 7/2007 |
| WO | 2009091864 | 7/2009 |

OTHER PUBLICATIONS

Keeling et al, 2012, Insect Biochemistry and Molecular Biology, 42:525-536.*
Thomas et al, 2001, Plant J., 25:417-425.*
Landais et al, 2003, Bioinformatics, 19:2343-2350.*
Landais et al., 2003, Bioinformatics, vol. 19, 2343-2350.
Thomas et al., 2001, Plant J., vol. 25, 417-425.
Genbank Submission NCBI, Accession No. CB408878, Eigenheer et al. Oct. 25, 2003.
Genbank Submission NCBI, Accession No. DV392288, Loftus et al., Oct. 21, 2005.
Crowhurst et al., 2008, BMC Genomics, vol. 9, 1-26.

* cited by examiner

*Primary Examiner* — Jason Deveau Rosen
(74) *Attorney, Agent, or Firm* — Karen A. Magri

(57) ABSTRACT

The present invention relates to genetic control of infestation by insect pest species, particularly prevention and/or control of pest infestation of plants, using interfering ribonucleic acid (RNA) molecules. Compositions and combinations containing the interfering RNA molecules of the invention for use in topical applications, for example in the form of insecticides.

Figure 1:
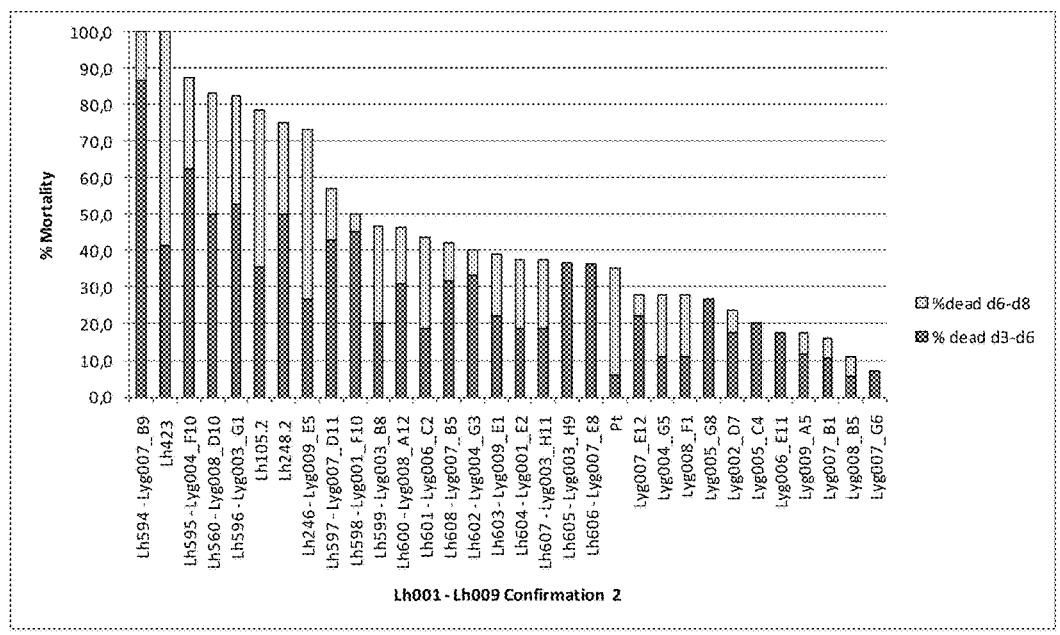

38 Claims, 24 Drawing Sheets
Specification includes a Sequence Listing.

A.

B.

SEQUENCE LISTING

```
<160> NUMBER OF SEQ ID NOS: 405

<210> SEQ ID NO 1
<211> LENGTH: 1096
<212> TYPE: DNA
<213> ORGANISM: Lygus hesperus

<400> SEQUENCE: 1
gcgatctaag gcaggtggca gacagctcga tgacggcagt gggccaagca ataatggata      60
gtcattcata gcaccccagc tttactaagc tctgccgtag tgttggattg ggagcggata     120
caattcacca cagaacagct atgacatgat acgcagtccg aataccctca taaaggacta     180
gtctgcaggt ttaacgatcg cgtagcagtg tatcacgcag agtacatggg gagtgactgt     240
gtgaacctgc tgggtacatc atcacccctc tccttcttca gttatataag acacagtccc     300
taaaggacac cagcaaaaat ggcggatgat gaggcgaaga aggccaaaca ggccgaaatc     360
gagaggaagc gcgctgaagt gcgcaagagg atggaggaag cctctaaggc gaagaaagcc     420
aagaagggtt tcatgacccc ggaaaggaag aagaaactcc gactcctgct gaggaaaaaa     480
gccgctgagg aactgaagaa ggagcaggaa cgcaaagcag ctgagaggag gcgaacgatt     540
gaggagcgct gcgggcaaat tgccgacgtc gacaacgcca atgaagcaac cttgaagaaa     600
ctctgcacag actaccataa gcgaattgac gctctggaga ggagtaaaat tgacatcgaa     660
ttcgaagtgg agagacgtga ccttgagatc gccgacctca acagccaggt caacgacctc     720
cgtggtaaat tcgtcaaacc taccttgaaa aaggtttcca agtacgaaaa caaattcgcc     780
aagctccaga agaaggctgc cgagttcaac ttcagaaacc aactcaaggt cgtcaaaaag     840
aaagaattca ccctggaaga agaagacaaa gagccgaaga aatcggaaaa ggcggagtgg     900
cagaagaaat gaagggaaaa caagcacacc atctcacaaa ataaaataaa cgaaaatctt     960
tcacacgttt accaattttta taacgggtc ctcacaaatt atgttcctta aataatttgt    1020
ataatccatc ctcgcactac aatcaatatt aatatttaaa tacaaaacca aaaaaaaaa    1080 aaaaaaaaaa aaaaaa                                                    1096

<210> SEQ ID NO 2
<211> LENGTH: 491
<212> TYPE: DNA
```

<213> ORGANISM: Lygus hesperus

<400> SEQUENCE: 2

```
caaacaggcc gaaatcgaga ggaagcgcgc tgaagtgcgc aagaggatgg aggaagcctc      60
taaggcgaag aaagccaaga agggtttcat gaccccggaa aggaagaaga aactccgact     120
cctgctgagg aaaaaagccg ctgaggaact gaagaaggag caggaacgca aagcagctga     180
gaggaggcga acgattgagg agcgctgcgg gcaaattgcc gacgtcgaca acgccaatga     240
agcaaccttg aagaaactct gcacagacta ccataagcga attgacgctc tggagaggag     300
taaaattgac atcgaattcg aagtggagag acgtgacctt gagatcgccg acctcaacag     360
ccaggtcaac gacctccgtg gtaaattcgt caaacctacc ttgaaaaagg tttccaagta     420
cgaaaacaaa ttcgccaagc tccagaagaa ggctgccgag ttcaacttca gaaaccaact     480
caaggtcgtc a                                                          491
```

<210> SEQ ID NO 3
<211> LENGTH: 431
<212> TYPE: DNA
<213> ORGANISM: Lygus hesperus

<400> SEQUENCE: 3

```
atgggcatca tgtcgaaagc tgaactcgct tgtgtttact ccgctctcat cctcatcgac      60
gacgatgtcg ccgtgacggg tgagaagatt caaaccatcc tgaaggctgc cagtgtcgac     120
atcgagccgt actggcccgg tctgttcgcc aaggccctcg agggtatcaa ccccaaagac     180
ctcatctcct ccattggaag cggagttggt gctggagcgc cggctgtcgg tgagctgcac     240
cctgccgccg ctgctgcccc tgccgctgag gctaagaagg aagagaagaa gaaggtcgaa     300
agcgatccag aatccgatga tgacatgggc ttcggtcttt tcgactaaga gcattccaca     360
gcgggttctc atttgttttt aagattttct tttaaaaaat aaaacttcca aaaaaaaaaa     420
aaaaaaaaaa g                                                          431
```

<210> SEQ ID NO 4
<211> LENGTH: 332
<212> TYPE: DNA
<213> ORGANISM: Lygus hesperus

<400> SEQUENCE: 4

```
gggcatcatg tcgaaagctg aactcgcttg tgtttactcc gctctcatcc tcatcgacga      60
cgatgtcgcc gtgacgggtg agaagattca aaccatcctg aaggctgcca gtgtcgacat     120
cgagccgtac tggcccggtc tgttcgccaa ggccctcgag ggtatcaacc ccaaagacct     180
catctcctcc attggaagcg gagttggtgc tggagcgccg gctgtcggtg agctgcacc      240
tgccgccgct gctgcccctg ccgctgaggc taagaaggaa gagaagaaga aggtcgaaag     300
cgatccagaa tccgatgatg acatgggctt cg                                    332
```

<210> SEQ ID NO 5
<211> LENGTH: 468
<212> TYPE: DNA
<213> ORGANISM: Lygus hesperus

<400> SEQUENCE: 5

```
atgggggcag gtcttctcca taaccataga ttatcttcgt gtatcgtgtc gggctttcgg      60
ctgaggtcct aattagtaaa taatgattcc gcctacgtcg cggcctcagg tcactgtcta     120
cagtgacaaa aatgaggcca ccgggactct cctcaacctc ccggctgtct tcaacgcccc     180
```

```
cattcgcccc gatgttgtga acttcgttca ccaaaatgtc gctaaaaacc acaggcagcc      240
ctactgtgtc tccgctcaag ctggtcatca gacttcagct gagtcctggg gtaccggtcg      300
tgctgtggct cgtatccccc gtgttcgcgg aggtggtact caccgctcag gtcagggtgc      360
ttttggcaac atgtgtcgcg gcggtaggat gttcgctccc actcgcccat ggcgtcgttg      420
gcaccgcaaa atcaacgtta accaaaaaaa aaaaaaaaa aaaaaaaa                    468

<210> SEQ ID NO 6
<211> LENGTH: 429
<212> TYPE: DNA
<213> ORGANISM: Lygus hesperus

<400> SEQUENCE: 6
gggcaggtct tctccataac catagattat cttcgtgtat cgtgtcgggc tttcggctga       60
ggtcctaatt agtaaataat gattccgcct acgtcgcggc ctcaggtcac tgtctacagt      120
gacaaaaatg aggccaccgg gactctcctc aacctcccgg ctgtcttcaa cgccccatt      180 cgccccgatg ttgtgaactt cgttcaccaa aatgtcgcta aaaccacag gcagccctac      240 tgtgtctccg ctcaagctgg tcatcagact tcagctgagt cctggggtac cggtcgtgct      300
gtggctcgta tcccccgtgt tcgcggaggt ggtactcacc gctcaggtca gggtgctttt      360
ggcaacatgt gtcgcggcgg taggatgttc gctcccactc gcccatggcg tcgttggcac      420
cgcaaaatc                                                              429

<210> SEQ ID NO 7
<211> LENGTH: 523
<212> TYPE: DNA
<213> ORGANISM: Lygus hesperus

<400> SEQUENCE: 7
atgggatctc tatgctgaaa aggtcgccac cagaggtttg tgtgctattg cacaagctga       60
atccctccgt tacaaactca ttggcggtct tgctgtccga ggggcttgct atggtgtcct      120
tcgcttcatc atggaaaatg gtgccaaggg ttgcgaagtc gtagtatctg aaaactgcg      180 tggtcagaga gccaagtcaa tgaagttcgt ggatggtttg atgatccaca gtggggatcc      240
ctgtaacgaa tatgttgata ctgctacccg acatgtgctc cttagacaag gtgtcctggg      300
aataaaggtg aagattatgt tgccgtggga cgttaccggc aaaatgggc cgaagaaccc      360 tcttcccgac cacgtcagcg ttctcttacc taaggaggag ctaccaaatt tggccgttag      420
tgtgcctgga tccgacatca aaccaaagcc tgaagtacca gcacccgctt tgtgaatata      480
aacttctttt ttgtaaaaaa aaaaaaaaa aaaaaaaaa aaa                          523

<210> SEQ ID NO 8
<211> LENGTH: 431
<212> TYPE: DNA
<213> ORGANISM: Lygus hesperus

<400> SEQUENCE: 8
attgcacaag ctgaatccct ccgttacaaa ctcattggcg gtcttgctgt ccgaggggct       60
tgctatggtg tccttcgctt catcatggaa aatggtgcca agggttgcga agtcgtagta      120
tctggaaaac tgcgtggtca gagagccaag tcaatgaagt tcgtggatgg tttgatgatc      180
cacagtgggg atccctgtaa cgaatatgtt gatactgcta cccgacatgt gctccttaga      240
caaggtgtcc tgggaataaa ggtgaagatt atgttgccgt gggacgttac cggcaaaaat      300
```

```
gggccgaaga acccctcttcc cgaccacgtc agcgttctct tacctaagga ggagctacca      360
aatttggccg ttagtgtgcc tggatccgac atcaaaccaa agcctgaagt accagcaccc      420
gctttgtgaa t                                                           431
```

<210> SEQ ID NO 9
<211> LENGTH: 823
<212> TYPE: DNA
<213> ORGANISM: Lygus hesperus

<400> SEQUENCE: 9

```
catggggaca ctctcttttt cttcatcgcg tggctcgctg ccgtgtggtt agggagtttc       60
ctactttaat tttttagtgt aattcatctt caaaatgacg tcgaaggttt ctcgtgagac      120
cctctacgag tgcatcaatg gagtcatcca gtcctcccag gagaagaaga ggaacttcgt      180
ggagactgtg gagatccaga tcggtctgaa gaactacgat ccccagaagg acaagcgttt      240
ctcgggaact gtcaagctga agcacattcc aaggcctaaa atgcaggttt gcatcctcgg      300
agatcaacag cattgcgacg aggccaaagc caacaacgtg ccctacatgg acgtcgaggc      360
tctgaagaag ctcaacaaaa acaagaagct cgtcaagaaa ttggccaaga aatacgacgc      420
tttcctcgcc tcagaagccc tcatcaagca gatccccagg ctcctcggac ccggtctcaa      480
caaggcgggc aagttccctg gtctcctctc tcaccaggag tccatgatga tgaagatcga      540
cgaagtcaag gccaccatca agttccaaat gaagaaggtt ttgtgcctct cagtggctgt      600
cggtcacgtc ggcatgactg ctgatgagct cgtccagaac gtgcacttgt cggtcaactt      660
cctcgtttcg ctcctcaaga agcactggca gaacgtcagg tctctccacg tcaaatccac      720
gatgggacct ccccagaggc tttactaaac atcttgtttt ttacttttga cgaataaaat      780
tcgttttatt ctcgaaaaaa aaaaaaaaaa aaaaaaaaa aaa                         823
```

<210> SEQ ID NO 10
<211> LENGTH: 607
<212> TYPE: DNA
<213> ORGANISM: Lygus hesperus

<400> SEQUENCE: 10

```
ccctctacga gtgcatcaat ggagtcatcc agtcctccca ggagaagaag aggaacttcg       60
tggagactgt ggagatccag atcggtctga agaactacga tccccagaag gacaagcgtt      120
tctcgggaac tgtcaagctg aagcacattc aaggcctaa atgcaggtt tgcatcctcg       180 gagatcaaca gcattgcgac gaggccaaag ccaacaacgt gccctacatg gacgtcgagg      240
ctctgaagaa gctcaacaaa aacaagaagc tcgtcaagaa attggccaag aaatacgacg      300 cttttcctcgc tcagaagcc ctcatcaagc agatccccag gctcctcgga cccggtctca      360
acaaggcggg caagttccct ggtctcctct ctcaccagga gtccatgatg atgaagatcg      420
acgaagtcaa ggccaccatc aagttccaaa tgaagaaggt gttgtgcctc tcagtggctg      480
tcggtcacgt cggcatgact gctgatgagc tcgtccagaa cgtgcacttg tcggtcaact      540
tcctcgtttc gctcctcaag aagcactggc agaacgtcag gtctctccac gtcaaatcca      600
cgatggg                                                               607
```

<210> SEQ ID NO 11
<211> LENGTH: 435
<212> TYPE: DNA
<213> ORGANISM: Lygus hesperus

<400> SEQUENCE: 11

```
atgggaccaa taaagatcaa ctttcccaga gaaagacttg ctatgcccag cataatcagg    60
tccgagaaat ccgcaaaaag atggttaaaa acatcagtga cagcatttcc agctgtgatt   120
tgaggagtgt tgtgaacaag ctgatcccag actccatcgc taaagatata gaaaagaatt   180
gccaaggaat ctacccactc cacgatgtgt acattcggaa ggtgaaggtg ttgaagaagc   240
cgaggttcga gctcagcaag ctccttgagc ttcacgtcga tggcaaaggg atcgacgaac   300
ccggcgcgaa agtgacgagg actgacgctt acgagcctcc agttcaagag tctgtctaag   360
taaacatttt atataaagtt aacaaaaaat aaaggtgtct cgcctgacta aaaaaaaaa    420 aaaaaaaaaa aaaaa                                                    435
```

<210> SEQ ID NO 12
<211> LENGTH: 353
<212> TYPE: DNA
<213> ORGANISM: Lygus hesperus

<400> SEQUENCE: 12

```
ccaataaaga tcaactttcc cagagaaaga cttgctatgc ccagcataat caggtccgag    60
aaatccgcaa aaagatggtt aaaaacatca gtgacagcat ttccagctgt gatttgagga   120
gtgttgtgaa caagctgatc ccagactcca tcgctaaaga tatagaaaag aattgccaag   180
gaatctaccc actccacgat gtgtacattc ggaaggtgaa ggtgttgaag aagccgaggt   240
tcgagctcag caagctcctt gagcttcacg tcgatggcaa agggatcgac gaacccggcg   300
cgaaagtgac gaggactgac gcttacgagc ctccagttca agagtctgtc taa          353
```

<210> SEQ ID NO 13
<211> LENGTH: 474
<212> TYPE: DNA
<213> ORGANISM: Lygus hesperus

<400> SEQUENCE: 13

```
catgggtacg aatatcgacg gtaaaagaaa ggtgatgttc gccatgaccg ccatcaaagg    60
tgtcggcaga cggtacgcca acattgtcct caagaaggcc gatgtcaact tggacaagag   120
ggccggcgaa tgctccgaag aagaagttga aaagatcgtt accatcatgc aaaaccctag   180
gcaatacaaa attcccaact ggttcctcaa cagacaaaaa gacaccgtcg agggcaaata   240
ctctcagttg acttcctccc tgctggattc caagctccgt gacgaccttg agcgactcaa   300
gaagatcagg gcccacagag gcatgaggca ctactgggt tgagggtgc gtggtcaaca    360 cacgaagacc accggaagga gaggacgaac tgttggtgtg tccaagaaga agtaatttta   420
atttcctaat aaattggttt tttcaaaaaa aaaaaaaaa aaaaaaaaa aaaa            474
```

<210> SEQ ID NO 14
<211> LENGTH: 332
<212> TYPE: DNA
<213> ORGANISM: Lygus hesperus

<400> SEQUENCE: 14

```
gaaaggtgat gttcgccatg accgccatca aggtgtcggc agacggtac gccaacattg    60 tcctcaagaa ggccgatgtc aacttggaca agagggccgg cgaatgctcc gaagaagaag   120
ttgaaaagat cgttaccatc atgcaaaacc ctaggcaata caaaattccc aactggttcc   180
tcaacagaca aaaagacacc gtcgagggca atactctca gttgacttcc tccctgctgg   240
attccaagct ccgtgacgac cttgagcgac tcaagaagat cagggcccac agaggcatga   300
```

```
ggcactactg gggtttgagg gtgcgtggtc aa                              332
```

<210> SEQ ID NO 15
<211> LENGTH: 440
<212> TYPE: DNA
<213> ORGANISM: Lygus hesperus

<400> SEQUENCE: 15

```
gtgagttctt ctgttgatta gttttccctt ccctgaaatt atttcgttga agttaatttg    60
gattaccctg aaagaatccg ctgcttttc tctcgctaaa atctttac acccgtcacc     120
acggcccct gtgggcaggc acaagctgaa gcacctgccc gtgcaccta actcgcactt    180
catggacgtc aactgccctg ggtgttataa atcccaacg gtgttctccc ccgcccagaa   240
cgacttcggc tgctggacct gttccaccat cctctgcctg cccacagggg gccgtgccga   300
cctcaccaaa agatgctcgt ttaggagaaa tcaacattat tattcttggt gggaacactt    360
attttttttg taattaaatt tcaaactaca aaataacttt tccgaaaaac actacaaaaa   420
aaattaaaaa caaaaaaaaa                                             440
```

<210> SEQ ID NO 16
<211> LENGTH: 324
<212> TYPE: DNA
<213> ORGANISM: Lygus hesperus

<400> SEQUENCE: 16

```
cttccctgaa attatttcgt tgaagttaat ttggattacc ctgaaagaat ccgctgcttt    60
ttctctcgct aaaatctttt acacccgtc accacggccc cctgtgggca ggcacaagct   120
gaagcacctg cccgtgcacc ctaactcgca cttcatggac gtcaactgcc ctgggtgtta   180
taaaatccca acggtgttct ccccgccca gaacgacttc ggctgctgga cctgttccac   240
catcctctgc ctgcccacag ggggccgtgc cgacctcacc aaaagatgct cgtttaggag   300
aaatcaacat tattattctt ggtg                                        324
```

<210> SEQ ID NO 17
<211> LENGTH: 357
<212> TYPE: DNA
<213> ORGANISM: Lygus hesperus

<400> SEQUENCE: 17

```
atgggttcaa gagagttaaa gccaagaggg ccaagaagga cgacggtgag atatttgccg    60
ctaaaaagga agtctacaag cccctctgagc agaggaaagc agaccagaaa acattgaca   120
aacagaccct gaaagccatc aagcgactca agggagacgc ttgcctcatg aggaaatacc   180
tttgcaccat gttcggattc aggagcagtc aatatcccca ccgtatgaag ttttaatatg   240
ttttcagcca ataaataagt gaaagtttct cttttttatt actacagact caaattttta   300
ttttctgaaa attattaaaa attcttaatg gcaaaaaaaa aaaaaaaaa aaaaaa       357
```

<210> SEQ ID NO 18
<211> LENGTH: 223
<212> TYPE: DNA
<213> ORGANISM: Lygus hesperus

<400> SEQUENCE: 18

```
gttcaagaga gttaaagcca agagggccaa gaaggacgac ggtgagatat tgccgctaa    60
aaaggaagtc tacaagccct ctgagcagag gaaagcagac cagaaaaaca ttgacaaaca   120
gaccctgaaa gccatcaagc gactcaaggg agacgcttgc ctcatgagga aataccttg   180
```

```
caccatgttc ggattcagga gcagtcaata tccccaccgt atg              223
```

<210> SEQ ID NO 19
<211> LENGTH: 632
<212> TYPE: DNA
<213> ORGANISM: Lygus hesperus

<400> SEQUENCE: 19

```
atgggacctt ttttccgtgt gtctggctta ggcctcgcgt gttcttgtat ttttacggga    60
aatttagtga aaaagtgtaa atttaacgcg taaaaatggg tcgtatgcac gcacctggta   120
agggtatttc ccagtcagct ctccctatc gtcgtagcgc cccaacatgg ctgaagctca    180
ctcctgacga cgtcaaggat cagattttca aactcaccaa gaaaggactg actccatctc   240
agatcggtgt catcctcagg gattctcacg gtgtggctca agtcagattc gtcaccgggt   300
cgaagatcct caggatcatg aaagccatcg cctcgctcc tgacctccca gaggacctct    360
acttcctcat caaaaaagcc gttgctatca ggaaacatct tgaaagaaat aggaaagaca   420
aagactctaa attcggactt atccccgtcg agtccaggat ccacaggttg caagatact    480
acaaaaccaa gggcaccctt ccacccacct ggaaatacga gtccagcacc gcctctgctc   540
tggtggcttg aatattcaac ttttatttg tctactgttt aattaatata atgtgattta    600
gcaaaaaaaa aaaaaaaaaa aaaaaaaaaa aa                                 632
```

<210> SEQ ID NO 20
<211> LENGTH: 457
<212> TYPE: DNA
<213> ORGANISM: Lygus hesperus

<400> SEQUENCE: 20

```
gggtcgtatg cacgcacctg gtaagggtat ttcccagtca gctctcccct atcgtcgtag    60
cgtcccaaca tggctgaagc tcactcctga cgacgtcaag gatcagattt tcaaactcac   120
caagaaagga ctgactccat ctcagatcgg tgtcatcctc aggattctc acggtgtggc    180
tcaagtcaga ttcgtcaccg gtcgaagat cctcaggatc atgaaagcca tcggcctcgc    240
tcctgacctc ccagaggacc tctacttcct catcaaaaaa gccgttgcta tcaggaaaca   300
tcttgaaaga aataggaaag acaaagactc taaattcgga cttatccccg tcgagtccag    360
gatccacagg ttggcaagat actacaaaac caagggcacc cttccaccca cctggaaata   420
cgagtccagc accgcctctg ctctggtggc ttgaata                            457
```

<210> SEQ ID NO 21
<211> LENGTH: 407
<212> TYPE: DNA
<213> ORGANISM: Lygus hesperus

<400> SEQUENCE: 21

```
atgggaccgt tgcctcaca atccagaaca gacaggctgc catatccgtc gtccctctg     60
cagcctccct cgtaatcaag gccctcaaag agccccgag ggacaggaag aagaacaaga   120
acatcaaaca cgacggtaac ctgagtatgg atgacattct cggaattgcc aaaaccatga   180
ggccgaggtc gatgtccagg aaactggaag gaaccgtcaa ggaaatcctt gggacagctc   240
agtctgtcgg atgcacgatc gaaggccgag ctccccacga cgtcatcgac tccatcaaca   300
acggcgaaat ggaaatccct gacgaataaa ctgttcatga gtttatggat tttatataaa   360
aaataaaaag ttgaaaaatc caaaaaaaaa aaaaaaaaag aaaaaa                  407
```

<210> SEQ ID NO 22
<211> LENGTH: 302
<212> TYPE: DNA
<213> ORGANISM: Lygus hesperus

<400> SEQUENCE: 22

| | | | | | |
|---|---|---|---|---|---|
| accgtttgcc | tcacaatcca | gaacagacag | gctgccatat | ccgtcgtccc | ctctgcagcc | 60 |
| tccctcgtaa | tcaaggccct | caaagagccc | ccgagggaca | ggaagaagaa | caagaacatc | 120 |
| aaacacgacg | gtaacctgag | tatggatgac | attctcggaa | ttgccaaaac | catgaggccg | 180 |
| aggtcgatgt | ccaggaaact | ggaaggaacc | gtcaaggaaa | tccttgggac | agctcagtct | 240 |
| gtcggatgca | cgatcgaagg | ccgagctccc | cacgacgtca | tcgactccat | caacaacggc | 300 |
| ga | | | | | | 302 |

<210> SEQ ID NO 23
<211> LENGTH: 794
<212> TYPE: DNA
<213> ORGANISM: Lygus hesperus

<400> SEQUENCE: 23

| | | | | | |
|---|---|---|---|---|---|
| catggggagt | caatttggat | ctatcgccag | atgaagatgt | ctcctgccgt | gttcgctgtt | 60 |
| ctgctggtac | tttcagcttc | ccaggtcttg | ggagatgatg | catccaagtt | ccaacacgag | 120 |
| gaaatcatgg | aagtcctcag | ctcggtcaac | aaaaccgtca | acaaattgta | cgacttgatg | 180 |
| tccacgcaga | aggaaagaga | tattgacttt | atcgagaaga | aatggatga | gacgtaccag | 240 |
| caactcagga | caagaggga | ggcgccggct | gagaaccctg | aagccattga | caagatccaa | 300 |
| aacgcgttca | aaagctttca | agacggcgtc | aaggacttcg | tcaagtccgc | ttcttcctcg | 360 |
| gacctctaca | gaaggttca | ggaaatcggc | gaggacctgt | agaacaaagg | caaagagctc | 420 |
| ggagagaagc | tgcaagaaac | catcaataac | gccagaacga | aaaactcaga | cgagaagaag | 480 |
| gactaaactg | aggattttga | ctctgcacaa | acgcccgttg | gtgtttaaac | gtatttctta | 540 |
| cgtttattat | catcggggtt | catgaaatca | aaaatacacc | atcgcatacc | acctcgaaaa | 600 |
| gaacataata | tatgtgaaaa | gacaagaaaa | ggtgttcaat | tgtgtctttta | actggtggtt | 660 |
| atcacgattc | acatgaaata | ctactaagaa | aacccaaaaa | ccgtcatgaa | acccgaagta | 720 |
| tgcttctgta | ttacctaatt | gtgctgataa | ttcttaataa | aatattatac | tgagaaaaaa | 780 |
| aaaaaaaaa | aaaa | | | | | 794 |

<210> SEQ ID NO 24
<211> LENGTH: 278
<212> TYPE: DNA
<213> ORGANISM: Lygus hesperus

<400> SEQUENCE: 24

| | | | | | |
|---|---|---|---|---|---|
| ttctgctggt | actttcagct | tcccaggtct | tgggagatga | tgcatccaag | ttccaacacg | 60 |
| aggaaatcat | ggaagtcctc | agctcggtca | acaaaaccgt | caacaaattg | tacgacttga | 120 |
| tgtccacgca | gaaggaaaga | gatattgact | ttatcgagaa | gaaatggat | gagacgtacc | 180 |
| agcaactcag | gacaagagg | gaggcgccgg | ctgagaaccc | tgaagccatt | gacaagatcc | 240 |
| aaaacgcgtt | caaaagcttt | caagacggcg | tcaaggac | | | 278 |

<210> SEQ ID NO 25
<211> LENGTH: 437
<212> TYPE: DNA
<213> ORGANISM: Lygus hesperus -continued

<400> SEQUENCE: 25

```
atgggatcca ataataacca ttaaggcaat tggacatcaa tgatactgaa catatgaata    60
ttcagatatc aaaaatatcg aaatagaatc atatataaaa ccaactaacg cattagaaaa   120
taacgaattc cgattacttg aagtagacaa tcgaatcgta ttacctataa aatcaactat   180
ccgaattcta gttacatcat ctgatgtaat tcattcatga accatcccaa gtttgggaat   240
caaaattgat ggcacaccag gacgattaaa tcaagggaga ataaacataa accgaccagg   300
actaatatat gggcaatgtt ctgaaatttg tggagcaaac cacagattta taccaatcgt   360
aattgaaaga gtttcaatta atcaatttat aaactgatta aattcaaaat aaaaaaaaaa   420
aaaaaaaaaa aaaaaa                                                   437
```

<210> SEQ ID NO 26
<211> LENGTH: 327
<212> TYPE: DNA
<213> ORGANISM: Lygus hesperus

<400> SEQUENCE: 26

```
aacgcagagt acatgggatc caataataac cattaaggca attggacatc aatgatactg    60
aacatatgaa tattcagata tcaaaaatat cgaaatagaa tcatatataa aaccaactaa   120
cgcattagaa aataacgaat tccgattact tgaagtagac aatcgaatcg tattacctat   180
aaaatcaact atccgaattc tagttacatc atctgatgta attcattcat gaaccatccc   240
aagtttggga tcaaaattg atggcacacc aggacgatta aatcaaggga gaataaacat   300
aaaccgacca ggactaatat atgggca                                       327
```

<210> SEQ ID NO 27
<211> LENGTH: 42
<212> TYPE: DNA
<213> ORGANISM: Artificial
<220> FEATURE:
<223> OTHER INFORMATION: Primer

<400> SEQUENCE: 27

```
gcgtaatacg actcactata ggcaaacagg ccgaaatcga ga                       42
```

<210> SEQ ID NO 28
<211> LENGTH: 23
<212> TYPE: DNA
<213> ORGANISM: Artificial
<220> FEATURE:
<223> OTHER INFORMATION: Primer

<400> SEQUENCE: 28

```
tgacgacctt gagttggttt ctg                                            23
```

<210> SEQ ID NO 29
<211> LENGTH: 20
<212> TYPE: DNA
<213> ORGANISM: Artificial
<220> FEATURE:
<223> OTHER INFORMATION: Primer

<400> SEQUENCE: 29

```
caaacaggcc gaaatcgaga                                                20
```

<210> SEQ ID NO 30
<211> LENGTH: 45
<212> TYPE: DNA

```
<213> ORGANISM: Artificial
<220> FEATURE:
<223> OTHER INFORMATION: Primer

<400> SEQUENCE: 30
gcgtaatacg actcactata ggtgacgacc ttgagttggt ttctg            45

<210> SEQ ID NO 31
<211> LENGTH: 42
<212> TYPE: DNA
<213> ORGANISM: Artificial
<220> FEATURE:
<223> OTHER INFORMATION: Primer

<400> SEQUENCE: 31
gcgtaatacg actcactata gggggcatca tgtcgaaagc tg               42

<210> SEQ ID NO 32
<211> LENGTH: 20
<212> TYPE: DNA
<213> ORGANISM: Artificial
<220> FEATURE:
<223> OTHER INFORMATION: Primer

<400> SEQUENCE: 32
cgaagcccat gtcatcatcg                                        20

<210> SEQ ID NO 33
<211> LENGTH: 20
<212> TYPE: DNA
<213> ORGANISM: Artificial
<220> FEATURE:
<223> OTHER INFORMATION: Primer

<400> SEQUENCE: 33
gggcatcatg tcgaaagctg                                        20

<210> SEQ ID NO 34
<211> LENGTH: 42
<212> TYPE: DNA
<213> ORGANISM: Artificial
<220> FEATURE:
<223> OTHER INFORMATION: Primer

<400> SEQUENCE: 34
gcgtaatacg actcactata ggcgaagccc atgtcatcat cg               42

<210> SEQ ID NO 35
<211> LENGTH: 44
<212> TYPE: DNA
<213> ORGANISM: Artificial
<220> FEATURE:
<223> OTHER INFORMATION: Primer

<400> SEQUENCE: 35
gcgtaatacg actcactata gggggcaggt cttctccata acca             44

<210> SEQ ID NO 36
<211> LENGTH: 20
<212> TYPE: DNA
<213> ORGANISM: Artificial
<220> FEATURE:
<223> OTHER INFORMATION: Primer

<400> SEQUENCE: 36
gattttgcgg tgccaacgac                                        20
```

<210> SEQ ID NO 37
<211> LENGTH: 22
<212> TYPE: DNA
<213> ORGANISM: Artificial
<220> FEATURE:
<223> OTHER INFORMATION: Primer

<400> SEQUENCE: 37
gggcaggtct tctccataac ca                                          22

<210> SEQ ID NO 38
<211> LENGTH: 42
<212> TYPE: DNA
<213> ORGANISM: Artificial
<220> FEATURE:
<223> OTHER INFORMATION: Primer

<400> SEQUENCE: 38
gcgtaatacg actcactata gggattttgc ggtgccaacg ac                    42

<210> SEQ ID NO 39
<211> LENGTH: 44
<212> TYPE: DNA
<213> ORGANISM: Artificial
<220> FEATURE:
<223> OTHER INFORMATION: Primer

<400> SEQUENCE: 39
gcgtaatacg actcactata ggattgcaca agctgaatcc ctcc                  44

<210> SEQ ID NO 40
<211> LENGTH: 20
<212> TYPE: DNA
<213> ORGANISM: Artificial
<220> FEATURE:
<223> OTHER INFORMATION: Primer

<400> SEQUENCE: 40
attcacaaag cgggtgctgg                                             20

<210> SEQ ID NO 41
<211> LENGTH: 22
<212> TYPE: DNA
<213> ORGANISM: Artificial
<220> FEATURE:
<223> OTHER INFORMATION: Primer

<400> SEQUENCE: 41
attgcacaag ctgaatccct cc                                          22

<210> SEQ ID NO 42
<211> LENGTH: 42
<212> TYPE: DNA
<213> ORGANISM: Artificial
<220> FEATURE:
<223> OTHER INFORMATION: Primer

<400> SEQUENCE: 42
gcgtaatacg actcactata ggattcacaa agcgggtgct gg                    42

<210> SEQ ID NO 43
<211> LENGTH: 44
<212> TYPE: DNA
<213> ORGANISM: Artificial
<220> FEATURE:

<223> OTHER INFORMATION: Primer

<400> SEQUENCE: 43
gcgtaatacg actcactata ggccctctac gagtgcatca atgg        44

<210> SEQ ID NO 44
<211> LENGTH: 20
<212> TYPE: DNA
<213> ORGANISM: Artificial
<220> FEATURE:
<223> OTHER INFORMATION: Primer

<400> SEQUENCE: 44
cccatcgtgg atttgacgtg        20

<210> SEQ ID NO 45
<211> LENGTH: 22
<212> TYPE: DNA
<213> ORGANISM: Artificial
<220> FEATURE:
<223> OTHER INFORMATION: Primer

<400> SEQUENCE: 45
ccctctacga gtgcatcaat gg        22

<210> SEQ ID NO 46
<211> LENGTH: 42
<212> TYPE: DNA
<213> ORGANISM: Artificial
<220> FEATURE:
<223> OTHER INFORMATION: Primer

<400> SEQUENCE: 46
gcgtaatacg actcactata ggcccatcgt ggatttgacg tg        42

<210> SEQ ID NO 47
<211> LENGTH: 47
<212> TYPE: DNA
<213> ORGANISM: Artificial
<220> FEATURE:
<223> OTHER INFORMATION: Primer

<400> SEQUENCE: 47
gcgtaatacg actcactata ggccaataaa gatcaacttt cccagag        47

<210> SEQ ID NO 48
<211> LENGTH: 25
<212> TYPE: DNA
<213> ORGANISM: Artificial
<220> FEATURE:
<223> OTHER INFORMATION: Primer

<400> SEQUENCE: 48
ttagacagac tcttgaactg gaggc        25

<210> SEQ ID NO 49
<211> LENGTH: 25
<212> TYPE: DNA
<213> ORGANISM: Artificial
<220> FEATURE:
<223> OTHER INFORMATION: Primer

<400> SEQUENCE: 49
ccaataaaga tcaactttcc cagag        25

```
<210> SEQ ID NO 50
<211> LENGTH: 47
<212> TYPE: DNA
<213> ORGANISM: Artificial
<220> FEATURE:
<223> OTHER INFORMATION: Primer

<400> SEQUENCE: 50
gcgtaatacg actcactata ggttagacag actcttgaac tggaggc         47

<210> SEQ ID NO 51
<211> LENGTH: 44
<212> TYPE: DNA
<213> ORGANISM: Artificial
<220> FEATURE:
<223> OTHER INFORMATION: Primer

<400> SEQUENCE: 51
gcgtaatacg actcactata gggaaaggtg atgttcgcca tgac            44

<210> SEQ ID NO 52
<211> LENGTH: 20
<212> TYPE: DNA
<213> ORGANISM: Artificial
<220> FEATURE:
<223> OTHER INFORMATION: Primer

<400> SEQUENCE: 52
ttgaccacgc accctcaaac                                       20

<210> SEQ ID NO 53
<211> LENGTH: 22
<212> TYPE: DNA
<213> ORGANISM: Artificial
<220> FEATURE:
<223> OTHER INFORMATION: Primer

<400> SEQUENCE: 53
gaaaggtgat gttcgccatg ac                                    22

<210> SEQ ID NO 54
<211> LENGTH: 42
<212> TYPE: DNA
<213> ORGANISM: Artificial
<220> FEATURE:
<223> OTHER INFORMATION: Primer

<400> SEQUENCE: 54
gcgtaatacg actcactata ggttgaccac gcaccctcaa ac              42

<210> SEQ ID NO 55
<211> LENGTH: 47
<212> TYPE: DNA
<213> ORGANISM: Artificial
<220> FEATURE:
<223> OTHER INFORMATION: Primer

<400> SEQUENCE: 55
gcgtaatacg actcactata ggcttccctg aaattatttc gttgaag         47

<210> SEQ ID NO 56
<211> LENGTH: 28
<212> TYPE: DNA
<213> ORGANISM: Artificial
<220> FEATURE:
<223> OTHER INFORMATION: Primer
```

<400> SEQUENCE: 56
caccaagaat aataatgttg atttctcc                               28

<210> SEQ ID NO 57
<211> LENGTH: 25
<212> TYPE: DNA
<213> ORGANISM: Artificial
<220> FEATURE:
<223> OTHER INFORMATION: Primer

<400> SEQUENCE: 57
cttccctgaa attatttcgt tgaag                                  25

<210> SEQ ID NO 58
<211> LENGTH: 50
<212> TYPE: DNA
<213> ORGANISM: Artificial
<220> FEATURE:
<223> OTHER INFORMATION: Primer

<400> SEQUENCE: 58
gcgtaatacg actcactata ggcaccaaga ataatgt tgatttctcc          50

<210> SEQ ID NO 59
<211> LENGTH: 47
<212> TYPE: DNA
<213> ORGANISM: Artificial
<220> FEATURE:
<223> OTHER INFORMATION: Primer

<400> SEQUENCE: 59
gcgtaatacg actcactata gggttcaaga gagttaaagc caagagg          47

<210> SEQ ID NO 60
<211> LENGTH: 22
<212> TYPE: DNA
<213> ORGANISM: Artificial
<220> FEATURE:
<223> OTHER INFORMATION: Primer

<400> SEQUENCE: 60
catacggtgg ggatattgac tg                                     22

<210> SEQ ID NO 61
<211> LENGTH: 25
<212> TYPE: DNA
<213> ORGANISM: Artificial
<220> FEATURE:
<223> OTHER INFORMATION: Primer

<400> SEQUENCE: 61
gttcaagaga gttaaagcca agagg                                  25

<210> SEQ ID NO 62
<211> LENGTH: 44
<212> TYPE: DNA
<213> ORGANISM: Artificial
<220> FEATURE:
<223> OTHER INFORMATION: Primer

<400> SEQUENCE: 62
gcgtaatacg actcactata ggcatacggt ggggatattg actg             44

<210> SEQ ID NO 63
<211> LENGTH: 42

<212> TYPE: DNA
<213> ORGANISM: Artificial
<220> FEATURE:
<223> OTHER INFORMATION: Primer

<400> SEQUENCE: 63
gcgtaatacg actcactata gggggtcgta tgcacgcacc tg        42

<210> SEQ ID NO 64
<211> LENGTH: 23
<212> TYPE: DNA
<213> ORGANISM: Artificial
<220> FEATURE:
<223> OTHER INFORMATION: Primer

<400> SEQUENCE: 64
tattcaagcc accagagcag agg        23

<210> SEQ ID NO 65
<211> LENGTH: 20
<212> TYPE: DNA
<213> ORGANISM: Artificial
<220> FEATURE:
<223> OTHER INFORMATION: Primer

<400> SEQUENCE: 65
gggtcgtatg cacgcacctg        20

<210> SEQ ID NO 66
<211> LENGTH: 45
<212> TYPE: DNA
<213> ORGANISM: Artificial
<220> FEATURE:
<223> OTHER INFORMATION: Primer

<400> SEQUENCE: 66
gcgtaatacg actcactata ggtattcaag ccaccagagc agagg        45

<210> SEQ ID NO 67
<211> LENGTH: 42
<212> TYPE: DNA
<213> ORGANISM: Artificial
<220> FEATURE:
<223> OTHER INFORMATION: Primer

<400> SEQUENCE: 67
gcgtaatacg actcactata ggaccgtttg cctcacaatc ca        42

<210> SEQ ID NO 68
<211> LENGTH: 20
<212> TYPE: DNA
<213> ORGANISM: Artificial
<220> FEATURE:
<223> OTHER INFORMATION: Primer

<400> SEQUENCE: 68
tcgccgttgt tgatggagtc        20

<210> SEQ ID NO 69
<211> LENGTH: 20
<212> TYPE: DNA
<213> ORGANISM: Artificial
<220> FEATURE:
<223> OTHER INFORMATION: Primer

<400> SEQUENCE: 69
accgtttgcc tcacaatcca                                              20

<210> SEQ ID NO 70
<211> LENGTH: 42
<212> TYPE: DNA
<213> ORGANISM: Artificial
<220> FEATURE:
<223> OTHER INFORMATION: Primer

<400> SEQUENCE: 70
gcgtaatacg actcactata ggtcgccgtt gttgatggag tc                    42

<210> SEQ ID NO 71
<211> LENGTH: 45
<212> TYPE: DNA
<213> ORGANISM: Artificial
<220> FEATURE:
<223> OTHER INFORMATION: Primer

<400> SEQUENCE: 71
gcgtaatacg actcactata ggggtatcaa cgcagagtac atggg                 45

<210> SEQ ID NO 72
<211> LENGTH: 20
<212> TYPE: DNA
<213> ORGANISM: Artificial
<220> FEATURE:
<223> OTHER INFORMATION: Primer

<400> SEQUENCE: 72
gtccttgacg ccgtcttgaa                                              20

<210> SEQ ID NO 73
<211> LENGTH: 23
<212> TYPE: DNA
<213> ORGANISM: Artificial
<220> FEATURE:
<223> OTHER INFORMATION: Primer

<400> SEQUENCE: 73
ggtatcaacg cagagtacat ggg                                          23

<210> SEQ ID NO 74
<211> LENGTH: 42
<212> TYPE: DNA
<213> ORGANISM: Artificial
<220> FEATURE:
<223> OTHER INFORMATION: Primer

<400> SEQUENCE: 74
gcgtaatacg actcactata gggtccttga cgccgtcttg aa                    42

<210> SEQ ID NO 75
<211> LENGTH: 44
<212> TYPE: DNA
<213> ORGANISM: Artificial
<220> FEATURE:
<223> OTHER INFORMATION: Primer

<400> SEQUENCE: 75
gcgtaatacg actcactata ggtgcccata tattagtcct ggtc                  44

<210> SEQ ID NO 76
<211> LENGTH: 20
<212> TYPE: DNA
<213> ORGANISM: Artificial

```
<220> FEATURE:
<223> OTHER INFORMATION: Primer

<400> SEQUENCE: 76
aacgcagagt acatgggatc                                                    20

<210> SEQ ID NO 77
<211> LENGTH: 22
<212> TYPE: DNA
<213> ORGANISM: Artificial
<220> FEATURE:
<223> OTHER INFORMATION: Primer

<400> SEQUENCE: 77
tgcccatata ttagtcctgg tc                                                 22

<210> SEQ ID NO 78
<211> LENGTH: 42
<212> TYPE: DNA
<213> ORGANISM: Artificial
<220> FEATURE:
<223> OTHER INFORMATION: Primer

<400> SEQUENCE: 78
gcgtaatacg actcactata ggaacgcaga gtacatggga tc                           42

<210> SEQ ID NO 79
<211> LENGTH: 197
<212> TYPE: PRT
<213> ORGANISM: Lygus hesperus

<400> SEQUENCE: 79
```

Met Ala Asp Asp Glu Ala Lys Lys Ala Lys Gln Ala Glu Ile Glu Arg
1               5                   10                  15

Lys Arg Ala Glu Val Arg Lys Arg Met Glu Glu Ala Ser Lys Ala Lys
            20                  25                  30

Lys Ala Lys Lys Gly Phe Met Thr Pro Glu Arg Lys Lys Lys Leu Arg
        35                  40                  45

Leu Leu Leu Arg Lys Lys Ala Ala Glu Glu Leu Lys Lys Glu Gln Glu
50                  55                  60

Arg Lys Ala Ala Glu Arg Arg Thr Ile Glu Glu Arg Cys Gly Gln
65                  70                  75                  80

Ile Ala Asp Val Asp Asn Ala Asn Glu Ala Thr Leu Lys Lys Leu Cys
                85                  90                  95

Thr Asp Tyr His Lys Arg Ile Asp Ala Leu Glu Arg Ser Lys Ile Asp
            100                 105                 110

Ile Glu Phe Glu Val Glu Arg Arg Asp Leu Glu Ile Ala Asp Leu Asn
        115                 120                 125

Ser Gln Val Asn Asp Leu Arg Gly Lys Phe Val Lys Pro Thr Leu Lys
130                 135                 140

Lys Val Ser Lys Tyr Glu Asn Lys Phe Ala Lys Leu Gln Lys Lys Ala
145                 150                 155                 160

Ala Glu Phe Asn Phe Arg Asn Gln Leu Lys Val Val Lys Lys Glu
                165                 170                 175

Phe Thr Leu Glu Glu Asp Lys Glu Pro Lys Lys Ser Glu Lys Ala
            180                 185                 190

Glu Trp Gln Lys Lys
        195

<210> SEQ ID NO 80
<211> LENGTH: 115
<212> TYPE: PRT
<213> ORGANISM: Lygus hesperus

<400> SEQUENCE: 80

```
Met Gly Ile Met Ser Lys Ala Glu Leu Ala Cys Val Tyr Ser Ala Leu
1               5                   10                  15

Ile Leu Ile Asp Asp Val Ala Val Thr Gly Glu Lys Ile Gln Thr
            20                  25                  30

Ile Leu Lys Ala Ala Ser Val Asp Ile Glu Pro Tyr Trp Pro Gly Leu
            35                  40                  45

Phe Ala Lys Ala Leu Glu Gly Ile Asn Pro Lys Asp Leu Ile Ser Ser
        50                  55                  60

Ile Gly Ser Gly Val Gly Ala Gly Ala Pro Val Gly Gly Ala Ala
65                  70                  75                  80

Pro Ala Ala Ala Ala Pro Ala Ala Glu Ala Lys Lys Glu Lys
                85                  90                  95

Lys Lys Val Glu Ser Asp Pro Glu Ser Asp Asp Met Gly Phe Gly
                100                 105                 110

Leu Phe Asp
        115
```

<210> SEQ ID NO 81
<211> LENGTH: 121
<212> TYPE: PRT
<213> ORGANISM: Lygus hesperus

<400> SEQUENCE: 81

```
Met Ile Pro Pro Thr Ser Arg Pro Gln Val Thr Val Tyr Ser Asp Lys
1               5                   10                  15

Asn Glu Ala Thr Gly Thr Leu Leu Asn Leu Pro Ala Val Phe Asn Ala
            20                  25                  30

Pro Ile Arg Pro Asp Val Val Asn Phe Val His Gln Asn Val Ala Lys
            35                  40                  45

Asn His Arg Gln Pro Tyr Cys Val Ser Ala Gln Ala Gly His Gln Thr
        50                  55                  60

Ser Ala Glu Ser Trp Gly Thr Gly Arg Ala Val Ala Arg Ile Pro Arg
65                  70                  75                  80

Val Arg Gly Gly Gly Thr His Arg Ser Gly Gln Gly Ala Phe Gly Asn
                85                  90                  95

Met Cys Arg Gly Gly Arg Met Phe Ala Pro Thr Arg Pro Trp Arg Arg
                100                 105                 110

Trp His Arg Lys Ile Asn Val Asn Gln
        115                 120
```

<210> SEQ ID NO 82
<211> LENGTH: 133
<212> TYPE: PRT
<213> ORGANISM: Lygus hesperus

<400> SEQUENCE: 82

```
Trp Asp Leu Tyr Ala Glu Lys Val Ala Thr Arg Gly Leu Cys Ala Ile
1               5                   10                  15

Ala Gln Ala Glu Ser Leu Arg Tyr Lys Leu Ile Gly Gly Leu Ala Val
            20                  25                  30

Arg Gly Ala Cys Tyr Gly Val Leu Arg Phe Ile Met Glu Asn Gly Ala
            35                  40                  45
```

```
Lys Gly Cys Glu Val Val Ser Gly Lys Leu Arg Gly Gln Arg Ala
    50                  55                  60

Lys Ser Met Lys Phe Val Asp Gly Leu Met Ile His Ser Gly Asp Pro
65                  70                  75                  80

Cys Asn Glu Tyr Val Asp Thr Ala Thr Arg His Val Leu Leu Arg Gln
                85                  90                  95

Gly Val Leu Gly Ile Lys Val Lys Ile Met Leu Pro Trp Asp Val Thr
            100                 105                 110

Gly Lys Asn Gly Pro Lys Asn Pro Leu Pro Asp His Val Ser Val Leu
        115                 120                 125

Leu Pro Lys Glu Glu
    130
```

<210> SEQ ID NO 83
<211> LENGTH: 217
<212> TYPE: PRT
<213> ORGANISM: Lygus hesperus

<400> SEQUENCE: 83

```
Met Thr Ser Lys Val Ser Arg Glu Thr Leu Tyr Glu Cys Ile Asn Gly
1               5                   10                  15

Val Ile Gln Ser Ser Gln Glu Lys Lys Arg Asn Phe Val Glu Thr Val
            20                  25                  30

Glu Ile Gln Ile Gly Leu Lys Asn Tyr Asp Pro Gln Lys Asp Lys Arg
        35                  40                  45

Phe Ser Gly Thr Val Lys Leu Lys His Ile Pro Arg Pro Lys Met Gln
    50                  55                  60

Val Cys Ile Leu Gly Asp Gln Gln His Cys Asp Glu Ala Lys Ala Asn
65                  70                  75                  80

Asn Val Pro Tyr Met Asp Val Glu Ala Leu Lys Lys Leu Asn Lys Asn
                85                  90                  95

Lys Lys Leu Val Lys Lys Leu Ala Lys Lys Tyr Asp Ala Phe Leu Ala
            100                 105                 110

Ser Glu Ala Leu Ile Lys Gln Ile Pro Arg Leu Leu Gly Pro Gly Leu
        115                 120                 125

Asn Lys Ala Gly Lys Phe Pro Gly Leu Leu Ser His Gln Glu Ser Met
    130                 135                 140

Met Met Lys Ile Asp Glu Val Lys Ala Thr Ile Lys Phe Gln Met Lys
145                 150                 155                 160

Lys Val Leu Cys Leu Ser Val Ala Val Gly His Val Gly Met Thr Ala
                165                 170                 175

Asp Glu Leu Val Gln Asn Val His Leu Ser Val Asn Phe Leu Val Ser
            180                 185                 190

Leu Leu Lys Lys His Trp Gln Asn Val Arg Ser Leu His Val Lys Ser
        195                 200                 205

Thr Met Gly Pro Pro Gln Arg Leu Tyr
    210                 215
```

<210> SEQ ID NO 84
<211> LENGTH: 118
<212> TYPE: PRT
<213> ORGANISM: Lygus hesperus

<400> SEQUENCE: 84

```
Gly Thr Asn Lys Asp Gln Leu Ser Gln Arg Lys Thr Cys Tyr Ala Gln
1               5                   10                  15
```

-continued

His Asn Gln Val Arg Glu Ile Arg Lys Lys Met Val Lys Asn Ile Ser
            20                  25                  30

Asp Ser Ile Ser Ser Cys Asp Leu Arg Ser Val Val Asn Lys Leu Ile
            35                  40                  45

Pro Asp Ser Ile Ala Lys Asp Ile Glu Lys Asn Cys Gln Gly Ile Tyr
50                  55                  60

Pro Leu His Asp Val Tyr Ile Arg Lys Val Lys Val Leu Lys Lys Pro
65                  70                  75                  80

Arg Phe Glu Leu Ser Lys Leu Leu Glu Leu His Val Asp Gly Lys Gly
            85                  90                  95

Ile Asp Glu Pro Gly Ala Lys Val Thr Arg Thr Asp Ala Tyr Glu Pro
            100                 105                 110

Pro Val Gln Glu Ser Val
            115

<210> SEQ ID NO 85
<211> LENGTH: 128
<212> TYPE: PRT
<213> ORGANISM: Lygus hesperus

<400> SEQUENCE: 85

Lys Val Met Phe Ala Met Thr Ala Ile Lys Gly Val Gly Arg Arg Tyr
1               5                   10                  15

Ala Asn Ile Val Leu Lys Lys Ala Asp Val Asn Leu Asp Lys Arg Ala
            20                  25                  30

Gly Glu Cys Ser Glu Glu Glu Val Glu Lys Ile Val Thr Ile Met Gln
            35                  40                  45

Asn Pro Arg Gln Tyr Lys Ile Pro Asn Trp Phe Leu Asn Arg Gln Lys
50                  55                  60

Asp Thr Val Glu Gly Lys Tyr Ser Gln Leu Thr Ser Ser Leu Leu Asp
65                  70                  75                  80

Ser Lys Leu Arg Asp Asp Leu Glu Arg Leu Lys Lys Ile Arg Ala His
            85                  90                  95

Arg Gly Met Arg His Tyr Trp Gly Leu Arg Val Arg Gly Gln His Thr
            100                 105                 110

Lys Thr Thr Gly Arg Arg Gly Arg Thr Val Gly Val Ser Lys Lys Lys
            115                 120                 125

<210> SEQ ID NO 86
<211> LENGTH: 122
<212> TYPE: PRT
<213> ORGANISM: Lygus hesperus

<400> SEQUENCE: 86

Val Leu Leu Leu Ile Ser Phe Ser Phe Pro Glu Ile Ile Ser Leu Lys
1               5                   10                  15

Leu Ile Trp Ile Thr Leu Lys Glu Ser Ala Ala Phe Ser Leu Ala Lys
            20                  25                  30

Asn Leu Leu His Pro Ser Pro Arg Pro Val Gly Arg His Lys Leu
            35                  40                  45

Lys His Leu Pro Val His Pro Asn Ser His Phe Met Asp Val Asn Cys
            50                  55                  60

Pro Gly Cys Tyr Lys Ile Pro Thr Val Phe Ser Pro Ala Gln Asn Asp
65                  70                  75                  80

Phe Gly Cys Trp Thr Cys Ser Thr Ile Leu Cys Leu Pro Thr Gly Gly
            85                  90                  95

-continued

Arg Ala Asp Leu Thr Lys Arg Cys Ser Phe Arg Arg Asn Gln His Tyr
             100                 105                 110

Tyr Ser Trp Trp Glu His Leu Phe Phe Leu
            115                 120

<210> SEQ ID NO 87
<211> LENGTH: 77
<212> TYPE: PRT
<213> ORGANISM: Lygus hesperus

<400> SEQUENCE: 87

Gly Phe Lys Arg Val Lys Ala Lys Arg Ala Lys Lys Asp Asp Gly Glu
1               5                   10                  15

Ile Phe Ala Ala Lys Lys Glu Val Tyr Lys Pro Ser Glu Gln Arg Lys
            20                  25                  30

Ala Asp Gln Lys Asn Ile Asp Lys Gln Thr Leu Lys Ala Ile Lys Arg
        35                  40                  45

Leu Lys Gly Asp Ala Cys Leu Met Arg Lys Tyr Leu Cys Thr Met Phe
    50                  55                  60

Gly Phe Arg Ser Ser Gln Tyr Pro His Arg Met Lys Phe
65                  70                  75

<210> SEQ ID NO 88
<211> LENGTH: 151
<212> TYPE: PRT
<213> ORGANISM: Lygus hesperus

<400> SEQUENCE: 88

Met Gly Arg Met His Ala Pro Gly Lys Gly Ile Ser Gln Ser Ala Leu
1               5                   10                  15

Pro Tyr Arg Arg Ser Val Pro Thr Trp Leu Lys Leu Thr Pro Asp Asp
            20                  25                  30

Val Lys Asp Gln Ile Phe Lys Leu Thr Lys Lys Gly Leu Thr Pro Ser
        35                  40                  45

Gln Ile Gly Val Ile Leu Arg Asp Ser His Gly Val Ala Gln Val Arg
    50                  55                  60

Phe Val Thr Gly Ser Lys Ile Leu Arg Ile Met Lys Ala Ile Gly Leu
65              70                  75                  80

Ala Pro Asp Leu Pro Glu Asp Leu Tyr Phe Leu Ile Lys Lys Ala Val
            85                  90                  95

Ala Ile Arg Lys His Leu Glu Arg Asn Arg Lys Asp Lys Asp Ser Lys
        100                 105                 110

Phe Gly Leu Ile Pro Val Glu Ser Arg Ile His Arg Leu Ala Arg Tyr
    115                 120                 125

Tyr Lys Thr Lys Gly Thr Leu Pro Pro Thr Trp Lys Tyr Glu Ser Ser
    130                 135                 140

Thr Ala Ser Ala Leu Val Ala
145                 150

<210> SEQ ID NO 89
<211> LENGTH: 108
<212> TYPE: PRT
<213> ORGANISM: Lygus hesperus

<400> SEQUENCE: 89

Gly Thr Val Cys Leu Thr Ile Gln Asn Arg Gln Ala Ala Ile Ser Val
1               5                   10                  15

```
Val Pro Ser Ala Ala Ser Leu Val Ile Lys Ala Leu Lys Glu Pro Pro
            20                  25                  30

Arg Asp Arg Lys Lys Asn Lys Asn Ile Lys His Asp Gly Asn Leu Ser
        35                  40                  45

Met Asp Asp Ile Leu Gly Ile Ala Lys Thr Met Arg Pro Arg Ser Met
 50                  55                  60

Ser Arg Lys Leu Glu Gly Thr Val Lys Glu Ile Leu Gly Thr Ala Gln
 65                  70                  75                  80

Ser Val Gly Cys Thr Ile Glu Gly Arg Ala Pro His Asp Val Ile Asp
                 85                  90                  95

Ser Ile Asn Asn Gly Glu Met Glu Ile Pro Asp Glu
            100                 105
```

<210> SEQ ID NO 90
<211> LENGTH: 133
<212> TYPE: PRT
<213> ORGANISM: Lygus hesperus

<400> SEQUENCE: 90

```
His Gly Glu Ser Ile Trp Ile Tyr Arg Gln Met Lys Met Ser Pro Ala
 1               5                  10                  15

Val Phe Ala Val Leu Leu Val Leu Ser Ala Ser Gln Val Leu Gly Asp
            20                  25                  30

Asp Ala Ser Lys Phe Gln His Glu Glu Ile Met Glu Val Leu Ser Ser
        35                  40                  45

Val Asn Lys Thr Val Asn Lys Leu Tyr Asp Leu Met Ser Thr Gln Lys
 50                  55                  60

Glu Arg Asp Ile Asp Phe Ile Glu Lys Lys Met Asp Glu Thr Tyr Gln
 65                  70                  75                  80

Gln Leu Arg Asn Lys Arg Glu Ala Pro Ala Gly Asn Pro Glu Ala Ile
                 85                  90                  95

Asp Lys Ile Gln Asn Ala Phe Lys Ser Phe Gln Asp Gly Val Lys Asp
            100                 105                 110

Phe Val Lys Ser Ala Ser Ser Ser Asp Leu Tyr Lys Lys Val Gln Glu
        115                 120                 125

Ile Gly Glu Asp Leu
            130
```

<210> SEQ ID NO 91
<211> LENGTH: 118
<212> TYPE: PRT
<213> ORGANISM: Lygus hesperus

<400> SEQUENCE: 91

```
Thr Tyr Glu Tyr Ser Asp Ile Lys Asn Ile Glu Ile Glu Ser Tyr Ile
 1               5                  10                  15

Lys Pro Thr Asn Ala Leu Glu Asn Asn Glu Phe Arg Leu Leu Glu Val
            20                  25                  30

Asp Asn Arg Ile Val Leu Pro Ile Lys Ser Thr Ile Arg Ile Leu Val
        35                  40                  45

Thr Ser Ser Asp Val Ile His Ser Thr Ile Pro Ser Leu Gly Ile Lys
 50                  55                  60

Ile Asp Gly Thr Pro Gly Arg Leu Asn Gln Gly Arg Ile Asn Ile Asn
 65                  70                  75                  80

Arg Pro Gly Leu Ile Tyr Gly Gln Cys Ser Glu Ile Cys Gly Ala Asn
                 85                  90                  95
```

His Arg Phe Ile Pro Ile Val Ile Glu Arg Val Ser Ile Asn Gln Phe
            100                 105                 110

Ile Asn Leu Asn Ser Lys
        115

<210> SEQ ID NO 92
<211> LENGTH: 20
<212> TYPE: DNA
<213> ORGANISM: Artificial
<220> FEATURE:
<223> OTHER INFORMATION: Adaptor

<400> SEQUENCE: 92
aagcagtggt atcaacgcag                                              20

<210> SEQ ID NO 93
<211> LENGTH: 20
<212> TYPE: DNA
<213> ORGANISM: Artificial
<220> FEATURE:
<223> OTHER INFORMATION: Primer

<400> SEQUENCE: 93
aagcagtggt atcaacgcag                                              20

<210> SEQ ID NO 94
<211> LENGTH: 42
<212> TYPE: DNA
<213> ORGANISM: Artificial
<220> FEATURE:
<223> OTHER INFORMATION: Primer

<400> SEQUENCE: 94
gcgtaatacg actcactata ggaagcagtg gtatcaacgc ag                     42

<210> SEQ ID NO 95
<211> LENGTH: 717
<212> TYPE: DNA
<213> ORGANISM: Lygus hesperus

<400> SEQUENCE: 95
aaagtgtggt tctcttcgtc cgaccatgag ttcgctcaaa ctgcagaaga ggctcgccgc    60
ctcggtgatg agatgcggca agaagaaagt gtggttggac cctaatgaaa tcaacgaaat   120
cgccaacacc aactctaggc aaaacatccg taagctgatc aaggatggtt tgatcatcaa   180
aaagcctgtg gctgtccact ccagagcccg cgtccgtaaa acacagaagc cagacggaa    240 gggtcgtcat tgtggcttcg gtaagaggaa gggtaccgcc aacgccagaa tgcctgtgaa    300
ggtcctgtgg gtcaacagaa tgagagtcct gcgacggctc cttaaaaaat acagagaagc    360
caagaagatc gataggcaaa tgtaccacga cctttacatg aaagccaaag gtaacgtctt    420
caaaaacaag agggtactga tggacttcat tcacaagaag aaggctgaaa aggcgagatc    480
aaagatgttg aaggaccagg cagaggcgag acgtttcaag gtcaaggagg cgaagaagag    540
gcgcgaggag aggatcgcca ccaagaagca agagatcatg caggcgtacg cccgagaaga    600
cgaggctgcc gtcaaaaagt gatctcgccc cctccgtttt taaattttaa acaaaaaacg    660
tattttgtac aaaaatttac aaaaaaaaaa aaaaaaaaaa aaaaaaaaaa aaaaaaa       717

<210> SEQ ID NO 96
<211> LENGTH: 2304
<212> TYPE: DNA
<213> ORGANISM: Lygus hesperus

<400> SEQUENCE: 96

```
atgacgacct acgaggagtt cattcaacag agcgaggagc gcgacggtat caggttcact      60
tggaacgtct ggccatcaag tcgcatcgaa gccaccaggt tggtcgtacc cgtaggatgt     120
ctctatcaac cactaaaaga acgcacggat cttccagcta ttcaatacga tcccgttcta     180
tgcactagga atacctgtag agccatactc aacccgatgt gccaagtaaa ctatagggca     240
aagttgtggg tgtgtaactt ctgtttccag aggaatccgt tcccaccaca atacgccgca     300
atttccgagc agcatcagcc tgctgagttg attccatcat tctcaactat agagtatact     360
atatctagag ctcaattttt gcctcctata ttcctattgg tggtggatac gtgtttggat     420
gatgacgagc taggagctct gaaagattcg ttacaaacgt ctctatcttt gctaccaacc     480
aactccctag ttggtctgat cacgtttggt aaaatggtcc aagttcacga acttgggtgt     540
gaaggttgtt cccggagcta cgtgttcaga ggcaccaagg atttgacgtc caagcaagta     600
caggacatgc ttgggatcgg aaaggtttcc gcttctcctc agcaacagca gcaaagggca     660
atgggcggtc agcagccatt ccccaccaat cggttcattc agccgattca aagttgtgac     720
atgagcctca ccgacttgtt gggcgaaatg cagcgtgatc catggccagt gggtcagggt     780
aagcgacctc ttagatcaac gggtgctgct ctagctattg ccattgggtt gttggagtgc     840
tcctacccca acacgggagc aaaagtcatg ttgttccttg gtggcccttg tcccaaggg      900
cctggtcaag ttgtcaatga tgacctgagg gaacctatcc gctctcatca tgacatccag     960
aaagataatg cccgctacat gaaaaaagcc attaaacatt acgattcttt ggcattgaga    1020
gcagccacta atgggcattc agtagacatt tattcctgtg ctttagatca gacaggtttg    1080
gcggaaatga agcaatgttg caattctact ggggtcata tggtgatggg tgacaccttc    1140
aactccactt tgttcaaaca gacgttccag agggtgctct cccgtgatca aaaaggcgaa    1200
ttcaaaatgg cttcaatgg cgtagttgaa gtcaaaacct cccgagagct aaaagttatg    1260
ggagccattg ggccttgcgt ttcattgaat acgaaaggtc cgtgtgttag tgaaactgac    1320
ataggcttg gaggaacttg ccagtggaag ttctgcacat ttaaccaaaa taccactgct    1380
gccatgttct ttgaggtagt aaaccaacac gctgctccta tccctcaagg tggaagagga    1440
tgtatacagt tcataactca ataccagcat gcgtcgggcc aaaggcgcat ccgagtaacc    1500
actgtagcca ggaattgggc tgatgcgact accaacatgc accatgttag tgcaggattt    1560
gatcaggaag ctggagcggt actcatggcc aggatggtcg ttcacagagc tgaaactgat    1620
gatgacctg atgtcatgag atgggctgat cgcatgttga ttcgtctttg ccagaaattc    1680
ggcgagtaca caaggatga tccaaatagt ttccgcctcc cagaaaactt ctcgctttac    1740
ccacagttca tgtatcactt gagaaggtcc caattcttgc aggtattcaa caacagccca    1800
gacgaaacgt cgtactatcg tcacatcttg atgcgggaag atttgtcgca gagcttgatc    1860
atgattcagc cgatcctgta cagttacagt ttcaacggtc cagaaccagt cctttttggac   1920
acttccagca ttcaacctga tcggatcctg ctgatggaca ccttcttcca aatcctcatc    1980
ttccacggcg agaccatcgc ccagtggcgt gcccaaaggt accaggacct acctgaatat    2040
gagaacttca gcagctcct acaggctcct gtagacgatg ctaaggaaat cctgcacact    2100
cggttcccca tgccgaggta cattgacacc gaacagggcg gatcacaagc tagattcctt    2160
ctctccaaag tcaacccatc ccaaactcac aacaacatgt acggctatgg aggggaattt    2220
ggagcccctg tgctcactga tgatgtttcc ctccaagtct tcatggaaca ccttaaaaag    2280
```

```
ctagccgttt catttactgc ctag                                              2304
```

<210> SEQ ID NO 97
<211> LENGTH: 311
<212> TYPE: DNA
<213> ORGANISM: Artificial
<220> FEATURE:
<223> OTHER INFORMATION: GUS

<400> SEQUENCE: 97

```
ccagcgtatc gtgctgcgtt tcgatgcggt cactcattac ggcaaagtgt gatggagcat         60
cagggcggct atacgccatt tgaagccgat gtcacgccgt atgttattgc cgggaaaagt        120
gtacgtatct gaaatcaaaa aactcgacgg cctgtgggca ttcagtctgg atcgcgaaaa        180
ctgtggaatt gatccagcgc cgtcgtcggt gaacaggtat ggaatttcgc cgattttgcg        240
acctcgcaag gcatattcgg gtgaaggtta tctctatgaa ctgtgcgtca cagccaaaag        300
ccagacagag t                                                             311
```

<210> SEQ ID NO 98
<211> LENGTH: 170
<212> TYPE: DNA
<213> ORGANISM: Artificial
<220> FEATURE:
<223> OTHER INFORMATION: Intron

<400> SEQUENCE: 98

```
ctcgagcctg agagaaaagc atgaagtata cccataacta acccattagt tatgcattta         60
tgttatatct attcatgctt ctactttaga taatcaatca ccaaacaatg agaatctcaa        120
cggtcgcaat aatgttcatg aaaatgtagt gtgtacactt accttctaga                   170
```

<210> SEQ ID NO 99
<211> LENGTH: 198
<212> TYPE: PRT
<213> ORGANISM: Lygus hesperus

<400> SEQUENCE: 99

Met Ser Ser Leu Lys Leu Gln Lys Arg Leu Ala Ala Ser Val Met Arg
1               5                   10                  15

Cys Gly Lys Lys Lys Val Trp Leu Asp Pro Asn Glu Ile Asn Glu Ile
                20                  25                  30

Ala Asn Thr Asn Ser Arg Gln Asn Ile Arg Lys Leu Ile Lys Asp Gly
            35                  40                  45

Leu Ile Ile Lys Lys Pro Val Ala Val His Ser Arg Ala Arg Val Arg
        50                  55                  60

Lys Asn Thr Glu Ala Arg Arg Lys Gly Arg His Cys Gly Phe Gly Lys
65                  70                  75                  80

Arg Lys Gly Thr Ala Asn Ala Arg Met Pro Val Lys Val Leu Trp Val
                85                  90                  95

Asn Arg Met Arg Val Leu Arg Arg Leu Leu Lys Lys Tyr Arg Glu Ala
                100                 105                 110

Lys Lys Ile Asp Arg Gln Met Tyr His Asp Leu Tyr Met Lys Ala Lys
            115                 120                 125

Gly Asn Val Phe Lys Asn Lys Arg Val Leu Met Asp Phe Ile His Lys
        130                 135                 140

Lys Lys Ala Glu Lys Ala Arg Ser Lys Met Leu Lys Asp Gln Ala Glu
145                 150                 155                 160

Ala Arg Arg Phe Lys Val Lys Glu Ala Lys Lys Arg Arg Glu Glu Arg 165                 170                 175
Ile Ala Thr Lys Lys Gln Glu Ile Met Gln Ala Tyr Ala Arg Glu Asp
            180                 185                 190

Glu Ala Ala Val Lys Lys
        195

<210> SEQ ID NO 100
<211> LENGTH: 767
<212> TYPE: PRT
<213> ORGANISM: Lygus hesperus

<400> SEQUENCE: 100

Met Thr Thr Tyr Glu Glu Phe Ile Gln Gln Ser Glu Glu Arg Asp Gly
1               5                   10                  15

Ile Arg Phe Thr Trp Asn Val Trp Pro Ser Ser Arg Ile Glu Ala Thr
            20                  25                  30

Arg Leu Val Val Pro Val Gly Cys Leu Tyr Gln Pro Leu Lys Glu Arg
        35                  40                  45

Thr Asp Leu Pro Ala Ile Gln Tyr Asp Pro Val Leu Cys Thr Arg Asn
    50                  55                  60

Thr Cys Arg Ala Ile Leu Asn Pro Met Cys Gln Val Asn Tyr Arg Ala
65                  70                  75                  80

Lys Leu Trp Val Cys Asn Phe Cys Phe Gln Arg Asn Pro Phe Pro Pro
                85                  90                  95

Gln Tyr Ala Ala Ile Ser Glu Gln His Gln Pro Ala Glu Leu Ile Pro
            100                 105                 110

Ser Phe Ser Thr Ile Glu Tyr Thr Ile Ser Arg Ala Gln Phe Leu Pro
        115                 120                 125

Pro Ile Phe Leu Leu Val Val Asp Thr Cys Leu Asp Asp Asp Glu Leu
    130                 135                 140

Gly Ala Leu Lys Asp Ser Leu Gln Thr Ser Leu Ser Leu Leu Pro Thr
145                 150                 155                 160

Asn Ser Leu Val Gly Leu Ile Thr Phe Gly Lys Met Val Gln Val His
                165                 170                 175

Glu Leu Gly Cys Glu Gly Cys Ser Arg Ser Tyr Val Phe Arg Gly Thr
            180                 185                 190

Lys Asp Leu Thr Ser Lys Gln Val Gln Asp Met Leu Gly Ile Gly Lys
        195                 200                 205

Val Ser Ala Ser Pro Gln Gln Gln Gln Arg Ala Met Gly Gly Gln
    210                 215                 220

Gln Pro Phe Pro Thr Asn Arg Phe Ile Gln Pro Ile Gln Ser Cys Asp
225                 230                 235                 240

Met Ser Leu Thr Asp Leu Leu Gly Glu Met Gln Arg Asp Pro Trp Pro
                245                 250                 255

Val Gly Gln Gly Lys Arg Pro Leu Arg Ser Thr Gly Ala Ala Leu Ala
            260                 265                 270

Ile Ala Ile Gly Leu Leu Glu Cys Ser Tyr Pro Asn Thr Gly Ala Lys
        275                 280                 285

Val Met Leu Phe Leu Gly Gly Pro Cys Ser Gln Gly Pro Gly Gln Val
    290                 295                 300

Val Asn Asp Asp Leu Arg Glu Pro Ile Arg Ser His His Asp Ile Gln
305                 310                 315                 320

Lys Asp Asn Ala Arg Tyr Met Lys Ala Ile Lys His Tyr Asp Ser
                325                 330                 335

-continued

Leu Ala Leu Arg Ala Ala Thr Asn Gly His Ser Val Asp Ile Tyr Ser
                340                 345                 350

Cys Ala Leu Asp Gln Thr Gly Leu Ala Glu Met Lys Gln Cys Cys Asn
            355                 360                 365

Ser Thr Gly Gly His Met Val Met Gly Asp Thr Phe Asn Ser Thr Leu
        370                 375                 380

Phe Lys Gln Thr Phe Gln Arg Val Leu Ser Arg Asp Gln Lys Gly Glu
385                 390                 395                 400

Phe Lys Met Ala Phe Asn Gly Val Val Glu Val Lys Thr Ser Arg Glu
                405                 410                 415

Leu Lys Val Met Gly Ala Ile Gly Pro Cys Val Ser Leu Asn Thr Lys
            420                 425                 430

Gly Pro Cys Val Ser Glu Thr Asp Ile Gly Leu Gly Thr Cys Gln
        435                 440                 445

Trp Lys Phe Cys Thr Phe Asn Gln Asn Thr Thr Ala Ala Met Phe Phe
    450                 455                 460

Glu Val Val Asn Gln His Ala Ala Pro Ile Pro Gln Gly Gly Arg Gly
465                 470                 475                 480

Cys Ile Gln Phe Ile Thr Gln Tyr Gln His Ala Ser Gly Gln Arg Arg
                485                 490                 495

Ile Arg Val Thr Thr Val Ala Arg Asn Trp Ala Asp Ala Thr Thr Asn
            500                 505                 510

Met His His Val Ser Ala Gly Phe Asp Gln Glu Ala Gly Ala Val Leu
        515                 520                 525

Met Ala Arg Met Val Val His Arg Ala Glu Thr Asp Asp Gly Pro Asp
    530                 535                 540

Val Met Arg Trp Ala Asp Arg Met Leu Ile Arg Leu Cys Gln Lys Phe
545                 550                 555                 560

Gly Glu Tyr Asn Lys Asp Pro Asn Ser Phe Arg Leu Pro Glu Asn
                565                 570                 575

Phe Ser Leu Tyr Pro Gln Phe Met Tyr His Leu Arg Arg Ser Gln Phe
            580                 585                 590

Leu Gln Val Phe Asn Asn Ser Pro Asp Glu Thr Ser Tyr Tyr Arg His
        595                 600                 605

Ile Leu Met Arg Glu Asp Leu Ser Gln Ser Leu Ile Met Ile Gln Pro
    610                 615                 620

Ile Leu Tyr Ser Tyr Ser Phe Asn Gly Pro Glu Pro Val Leu Leu Asp
625                 630                 635                 640

Thr Ser Ser Ile Gln Pro Asp Arg Ile Leu Leu Met Asp Thr Phe Phe
                645                 650                 655

Gln Ile Leu Ile Phe His Gly Glu Thr Ile Ala Gln Trp Arg Ala Gln
            660                 665                 670

Arg Tyr Gln Asp Leu Pro Glu Tyr Glu Asn Phe Lys Gln Leu Leu Gln
        675                 680                 685

Ala Pro Val Asp Asp Ala Lys Glu Ile Leu His Thr Arg Phe Pro Met
    690                 695                 700

Pro Arg Tyr Ile Asp Thr Glu Gln Gly Gly Ser Gln Ala Arg Phe Leu
705                 710                 715                 720

Leu Ser Lys Val Asn Pro Ser Gln Thr His Asn Asn Met Tyr Gly Tyr
                725                 730                 735

Gly Gly Glu Phe Gly Ala Pro Val Leu Thr Asp Asp Val Ser Leu Gln
            740                 745                 750

Val Phe Met Glu His Leu Lys Lys Leu Ala Val Ser Phe Thr Ala

<210> SEQ ID NO 101
<211> LENGTH: 511
<212> TYPE: DNA
<213> ORGANISM: Lygus hesperus

<400> SEQUENCE: 101

```
ggtgatgaga tgcggcaaga agaaagtgtg gttggaccct aatgaaatca acgaaatcgc      60
caacaccaac tctaggcaaa acatccgtaa gctgatcaag gatggtttga tcatcaaaaa     120
gcctgtggct gtccactcca gagcccgcgt ccgtaaaaac acagaagcca gacgaagggg     180
tcgtcactgt ggcttcggta gaggaaggga taccgccaac gccagaatgc ctgtgaaggt     240
cctgtgggtc aacagaatga gagtcctgcg acggctcctt aaaaaataca gagaagccaa     300
gaagatcgat aggcaaatgt accacgacct ttacatgaaa gccaaggta acgtcttcaa      360
aaacaagagg gtactgatgg acttcattca caagaagaag gctgaaaagg cgagatcaaa     420
gatgttgaag gaccaggcag aggcgagacg tctcaaggtc aaggaggcga agaagaggcg     480
cgaggagagg atcgccacca gaagcaaga g                                     511
```

<210> SEQ ID NO 102
<211> LENGTH: 1145
<212> TYPE: DNA
<213> ORGANISM: Lygus hesperus

<400> SEQUENCE: 102

```
tgggttgttg gagtgctcct accccaacac gggagcaaaa gtcatgttgt tccttggtgg      60
cccttgttcc caagggcctg gtcaagttgt caatgatgac ctgagggaac ctatccgctc     120
tcatcatgac atccagaaag ataatgcccg ctacatgaaa aaagccatta acattacga      180
ttctttggca ttgagagcag ccactaatgg gcattcagta gacatttatt cctgtgcttt     240
agatcagaca ggtttggcgg aaatgaagca atgttgcaat tctactgggg gtcatatggt     300
gatgggtgac accttcaact ccactttgtt caaacagacg ttccagaggg tgctctcccg     360
tgatcaaaaa ggcgaattca aaatggcttt caatggcgta gttgaagtca aaacctcccg     420
agagctaaaa gttatgggag ccattgggcc ttgcgtttca ttgaatacga aggtccgtg      480
tgttagtgaa actgacatag ggcttggagg aacttgccag tggaagttct gcacatttaa     540
ccaaaatacc actgctgcca tgttctttga ggtagtaaac caacacgctg ctcctatccc     600
tcaaggtgga agaggatgta tacagttcat aactcaatac cagcatgcgt cgggccaaag     660
gcgcatccga gtaaccactg tagccaggaa ttgggctgat gcgactacca acatgcacca     720
tgttagtgca ggattttgatc aggaagctgg agcggtactc atggccagga tggtcgttca     780
cagagctgaa actgatgatg gacctgatgt catgagatgg gctgatcgca tgttgattcg     840
tctttgccag aaattcggcg agtacaacaa ggatgatcca aatagtttcc gcctcccaga     900
aaacttctcg ctttacccac agttcatgta tcacttgaga aggtcccaat tcttgcaggt     960
attcaacaac agcccagacg aaacgtcgta ctatcgtcac atcttgatgc gggaagattt    1020
gtcgcagagc ttgatcatga ttcagccgat cctgtacagt tacagtttca acggtccaga    1080
accagtcctt ttggacactt ccagcattca acctgatcgg atcctgctga tggacaccct    1140
cttcc                                                                 1145
```

<210> SEQ ID NO 103
<211> LENGTH: 258

```
<212> TYPE: DNA
<213> ORGANISM: Artificial
<220> FEATURE:
<223> OTHER INFORMATION: GFP

<400> SEQUENCE: 103
agatacccag atcatatgaa acggcatgac tttttcaaga gtgccatgcc cgaaggttat    60
gtacaggaaa gaactatatt tttcaaagat gacgggaact acaagacacg taagtttaaa   120
cagttcggta ctaactaacc atacatattt aaattttcag gtgctgaagt caagtttgaa   180
ggtgataccc ttgttaatag aatcgagtta aaaggtattg attttaaaga agatggaaac   240
attcttggac acaaattg                                                 258

<210> SEQ ID NO 104
<211> LENGTH: 745
<212> TYPE: DNA
<213> ORGANISM: Artificial
<220> FEATURE:
<223> OTHER INFORMATION: Pt coral fluorescent protein

<400> SEQUENCE: 104
agtgtaataa cttactttga gtctaccgtc atgagtgcaa ttaaaccagt catgaagatt    60
gaattggtca tggaaggaga ggtgaacggg cacaagttca cgatcacggg agagggacaa   120
ggcaagcctt acgagggaac acagactcta aaccttacag tcactaaagg cgtgcccctt   180
cctttcgctt tcgatatctt gtcaacagca ttccagtatg gcaacagggt atttaccaaa   240
tacccagatg atataccgga ctatttcaag cagacctttc cggaaggata ttcgtgggaa   300
agaactttca aatatgaaga gggcgtttgc accacaaaga gtgacataag cctcaagaaa   360
ggccaaccag actgctttca atataaaatt aactttaaag gggagaagct tgaccccaac   420
ggcccaatta tgcagaagaa gaccctgaaa tgggagccat ccactgagag gatgtacatg   480
gacgtggata agacggtgc aaaggtgctg aagggcgatg ttaatgcggc cctgttgctt   540
gaaggaggtg gccattatcg ttgtgacttt aacagtactt acaaggcgaa gaaaactgtg   600
tccttcccag catatcactt tgtggaccac cgcattgaga ttttgagcca caatacggat   660
tacagcaagg ttacactgta tgaagttgcc gtggctcgca attctcctct tcagattatg   720
gcgccccagt aaaggcttaa cgaaa                                         745

<210> SEQ ID NO 105
<211> LENGTH: 42
<212> TYPE: DNA
<213> ORGANISM: Artificial
<220> FEATURE:
<223> OTHER INFORMATION: Primer

<400> SEQUENCE: 105
gcgtaatacg actcactata ggtgatgaga tgcggcaaga ag                       42

<210> SEQ ID NO 106
<211> LENGTH: 22
<212> TYPE: DNA
<213> ORGANISM: Artificial
<220> FEATURE:
<223> OTHER INFORMATION: Primer

<400> SEQUENCE: 106
ctcttgcttc ttggtggcga tc                                             22

<210> SEQ ID NO 107
```

```
<211> LENGTH: 22
<212> TYPE: DNA
<213> ORGANISM: Artificial
<220> FEATURE:
<223> OTHER INFORMATION: Primer

<400> SEQUENCE: 107
ggtgatgaga tgcggcaaga ag                                              22

<210> SEQ ID NO 108
<211> LENGTH: 44
<212> TYPE: DNA
<213> ORGANISM: Artificial
<220> FEATURE:
<223> OTHER INFORMATION: Primer

<400> SEQUENCE: 108
gcgtaatacg actcactata ggctcttgct tcttggtggc gatc                      44

<210> SEQ ID NO 109
<211> LENGTH: 44
<212> TYPE: DNA
<213> ORGANISM: Artificial
<220> FEATURE:
<223> OTHER INFORMATION: Primer

<400> SEQUENCE: 109
gcgtaatacg actcactata ggtgggttgt tggagtgctc ctac                      44

<210> SEQ ID NO 110
<211> LENGTH: 22
<212> TYPE: DNA
<213> ORGANISM: Artificial
<220> FEATURE:
<223> OTHER INFORMATION: Primer

<400> SEQUENCE: 110
ggaagaaggt gtccatcagc ag                                              22

<210> SEQ ID NO 111
<211> LENGTH: 22
<212> TYPE: DNA
<213> ORGANISM: Artificial
<220> FEATURE:
<223> OTHER INFORMATION: Primer

<400> SEQUENCE: 111
tgggttgttg gagtgctcct ac                                              22

<210> SEQ ID NO 112
<211> LENGTH: 44
<212> TYPE: DNA
<213> ORGANISM: Artificial
<220> FEATURE:
<223> OTHER INFORMATION: Primer

<400> SEQUENCE: 112
gcgtaatacg actcactata ggggaagaag gtgtccatca gcag                      44

<210> SEQ ID NO 113
<211> LENGTH: 46
<212> TYPE: DNA
<213> ORGANISM: Artificial
<220> FEATURE:
<223> OTHER INFORMATION: Primer

<400> SEQUENCE: 113
```

```
gcgtaatacg actcactata ggagataccc agatcatatg aaacgg          46
```

<210> SEQ ID NO 114
<211> LENGTH: 24
<212> TYPE: DNA
<213> ORGANISM: Artificial
<220> FEATURE:
<223> OTHER INFORMATION: Primer

<400> SEQUENCE: 114

```
caatttgtgt ccaagaatgt ttcc                                  24
```

<210> SEQ ID NO 115
<211> LENGTH: 24
<212> TYPE: DNA
<213> ORGANISM: Artificial
<220> FEATURE:
<223> OTHER INFORMATION: Primer

<400> SEQUENCE: 115

```
agatacccag atcatatgaa acgg                                  24
```

<210> SEQ ID NO 116
<211> LENGTH: 46
<212> TYPE: DNA
<213> ORGANISM: Artificial
<220> FEATURE:
<223> OTHER INFORMATION: Primer

<400> SEQUENCE: 116

```
gcgtaatacg actcactata ggcaatttgt gtccaagaat gtttcc          46
```

<210> SEQ ID NO 117
<211> LENGTH: 43
<212> TYPE: DNA
<213> ORGANISM: Artificial
<220> FEATURE:
<223> OTHER INFORMATION: Primer

<400> SEQUENCE: 117

```
gcgtaatacg actcactata ggagtgtaat aacttacttt gag             43
```

<210> SEQ ID NO 118
<211> LENGTH: 20
<212> TYPE: DNA
<213> ORGANISM: Artificial
<220> FEATURE:
<223> OTHER INFORMATION: Primer

<400> SEQUENCE: 118

```
tttcgttaag cctttactgg                                       20
```

<210> SEQ ID NO 119
<211> LENGTH: 21
<212> TYPE: DNA
<213> ORGANISM: Artificial
<220> FEATURE:
<223> OTHER INFORMATION: Primer

<400> SEQUENCE: 119

```
agtgtaataa cttactttga g                                     21
```

<210> SEQ ID NO 120
<211> LENGTH: 42
<212> TYPE: DNA

<213> ORGANISM: Artificial
<220> FEATURE:
<223> OTHER INFORMATION: Primer

<400> SEQUENCE: 120

```
gcgtaatacg actcactata ggtttcgtta agcctttact gg                          42
```

<210> SEQ ID NO 121
<211> LENGTH: 473
<212> TYPE: DNA
<213> ORGANISM: Lygus hesperus

<400> SEQUENCE: 121

```
tgccgggccg ctcgccgaac catctgggaa gcttggaatg ggctcgactg ccgaactgat       60
caactttttc ggtccacacc ttttctatca actccttata ccgctccagg atgccgcctt      120
caaacagttt tttcttgtcg tcataagatc tggtgtcaac tcttcgttca tatttggagg      180
cgacttggat tttgggtggg tacttgccgg tgagggcctc agggtccaag cctttttca       240
aggctttgtg ccgaagttgt tgcttctgtc tttccttcag ttctttaaga tcgtagtctt      300
gcctcttttg cctttcctca agatcgtatt tctcggtctc aagtttgaca atggcttccc      360
agagttcctg agctttgatg cgtagcctgt ctatgctcat attttctatc gccaggggct      420
tgagcctaat gctgagggag atacgtttct cttcctccag ctgctccttg gtc             473
```

<210> SEQ ID NO 122
<211> LENGTH: 773
<212> TYPE: DNA
<213> ORGANISM: Lygus hesperus

<400> SEQUENCE: 122

```
gctgctcgcc gtccagttcg ttttcgagtt ccctgacacg ttgttccagc ttggcgatgg       60
ccttcttgcc tcccttgagg gcgttgtttt cggcttcgtc caacctgact ggagttcct       120
tgatttgcgt ttccagagcc ttgcggagct tctcctgggt ctgagcgtgg tcctgttctg      180
ccctgagttc atcagctaac ctagcggcat caaccattgc cttcttggcc ttctcttcgg      240
agttcttggc ttcgttgaga agttcgtcga ggtcagcatg aagtgtctgc aactctccct      300
caagcttgcg tttggcggct gaggcgctgg tagcttgggc agccaactcg ttgatctgtt      360
cgtgggcatc tccaagttct tgttcggctt ggcgcctgcc cctgtcggcc tgttcgagga      420
gagtgcgcga ctcctcgagc tcgtttccga gagcgttggc cctcctttcg gcgattccga      480
gttgttcacg agcatcgtcg cgtgcccttt gttcttcctc aagagcggtc tgtacgtcct      540
tgagttgttg ttggtatttc ttgatggtct tctgggcttc ggcgttagcc ttgttggcgt      600
ggtcgagagc gatttcgagt tcgttgatgt cggcttcaag cttcttcttc atgcgaagag      660
cctcagcctt acccttggct tcagcctcca agctggcttg catggagtcg agtgcccgtt      720
ggtggttctt cctggtgttc tcgaactcct cctccttttc ctggatccgc cgg             773
```

<210> SEQ ID NO 123
<211> LENGTH: 771
<212> TYPE: DNA
<213> ORGANISM: Lygus hesperus

<400> SEQUENCE: 123

```
tggacgccat caagaagaaa atgcaggcga tgaagatgga gaaggacacg gccatggaca       60
aggccgacac ctgcgagggg caggccaagg acgctaacac ccgcgccgac aaaatccttg      120
aagatgtgag ggacctccaa aagaaactca accaggtaga aagtgatctc gaaaggacca      180
```

```
agagggaact cgagacgaaa accaccgaac tcgaagagaa ggagaaggcc aacaccaacg    240
ctgagagcga ggtcgcctcc ctcaacagga agtccagat ggttgaagag gacttggaaa    300
gatctgaaga aggtccggc accgcacaac aaaaactgtc cgaagcctcc cacgccgctg    360
atgaagcctc tcgtatgtgc aaagtattgg agaacaggtc acaacaggat gaggagagga    420
tggaccagct caccaaccag ctgaaagaag cccgactcct cgctgaagac gccgacggca    480
aatcggatga ggtatcaagg aagctggcct tcgttgaaga cgaactggaa gtagctgaag    540
atcgtgtcaa atctggagac tcgaagatca tggagcttga ggaggagttg aaagttgtcg    600
gtaacagctt gaaatctctc gaagtttcag aggagaaggc caaccagcga gtcgaagagt    660
acaaacgtca aatcaagcaa ctgactgtca agttgaagga ggctgaagct cgcgctgagt    720
tcgccgaaaa gacagtcaag aagttgcaga agaggtgga ccggctggag g               771

<210> SEQ ID NO 124
<211> LENGTH: 257
<212> TYPE: DNA
<213> ORGANISM: Lygus hesperus

<400> SEQUENCE: 124
tgcgggccct ggggcagaat cccacagaat ctgacgtgaa gaagttcacc caccagcaca     60
aaccagatga agaatcagc ttcgaggtgt ttctcccgat ataccaagcc atatcgaagg    120
gtaggacgtc agacacagct gaagacttca tcgagggtct cagacacttt gacaaagatg    180
gaaatggctt catttcaaca gctgagcttc gccacttgct cacaactttg ggcgaaaaac    240
tgaccgacga cgaggtg                                                    257

<210> SEQ ID NO 125
<211> LENGTH: 410
<212> TYPE: DNA
<213> ORGANISM: Lygus hesperus

<400> SEQUENCE: 125
gccacctcca acgtgtttgc catgttcgat caggctcaga ttcaagaatt caaggaggca     60
ttcaacatga tcgaccagaa cagggacggc ttcgtggata aggaagacct ccatgacatg    120
ctcgcttccc taggtaagaa ccccctcagac gagtatctcg aggggatgat gaacgaggcg    180
cctggtccca tcaacttcac aatgttcctc accctcttcg gtgagcggct tcagggaact    240
gatccggagg aggttatcaa gaacgcattt gggtgttttg acgaagacaa caacggattc    300
atcaacgagg aaagactgcg cgagctgctc acctccatgg gggacaggtt cactgatgaa    360
gacgtggacg aaatgtaccg agaggccccc atcaagaacg gcatgttcga                410

<210> SEQ ID NO 126
<211> LENGTH: 1021
<212> TYPE: DNA
<213> ORGANISM: Lygus hesperus

<400> SEQUENCE: 126
tgttcatcct ggagcaggag gagtatcaga gagaaggtat tgaatggaag ttcatcgact     60
tcggacttga tcttcagccg accattgatc tcattgataa gccaatggga gtcatggctc    120
tcctggatga agaatgttgg ttccccaaag ccactgacaa gaccttcgtt gagaagctgg    180
tcggtgctca cagcgttcac cccaaattca tcaaaactga tttccgtgga gtcgccgact    240
ttgctgtcgt ccattatgcc ggaaaagtcg attattcggc ggcgcagtgg ctgatgaaga    300
```

| | |
|---|---:|
| acatggaccc tctgaacgaa aacgtcgtgc agctcctcca gaactcgcaa gatccgttcg | 360 |
| tcatccacat ctggaaggac gcagagatcg tcggcatggc tcaccaagct ctcagcgaca | 420 |
| ctcagtttgg agctcgtacc aggaagggta tgttccgaac cgtgtctcaa ctctacaaag | 480 |
| accagctgtc caaactcatg atcacacttc gcaacacgaa ccccaacttc gtccgttgca | 540 |
| tcctccccaa ccacgagaag agagctggca agatcgatgc tcctttggtg ctggatcagc | 600 |
| tcagatgcaa cggtgtgttg gaaggcatca gaatttgcag acaaggtttc ccgaatagaa | 660 |
| tcccattcca ggaattccgg caaagatacg agctcttaac tcccaatgtc atccccaaag | 720 |
| ggttcatgga cggtaaaaag gcttgcgaga agatgatcaa cgctctcgaa ctggacccta | 780 |
| atctctacag agttggtcag tccaagatat tcttcagagc tggagtctta gctcatctag | 840 |
| aagaagagcg cgactataag attactgatc tgatagccaa tttccgggct ttctgtaggg | 900 |
| gatatcttgc ccgaaggaac taccaaaagc gtcttcagca gctcaacgcc attcgtatta | 960 |
| tccagcgaaa ttgctcagct tacttgaagt tgaggaactg gcaatggtgg cggctgtaca | 1020 |
| c | 1021 |

<210> SEQ ID NO 127
<211> LENGTH: 325
<212> TYPE: DNA
<213> ORGANISM: Lygus hesperus

<400> SEQUENCE: 127

| | |
|---|---:|
| cggtcatcat ctccatgaac tcgtcgaagt caacagttcc ggaaccgtca gaatcaattt | 60 |
| cagcaatcat catgtcaagt tcttgggagg tgattttgtc gtcgagttcc ttcaggattt | 120 |
| ccctcaagac gtcagtggta atgtaaccgt tcccttcctt gtcgtagagc ctgaaggcct | 180 |
| ccctcagttc ttgctgcatg gcctcagcat cttgtgtctc atcttctgtc aggaaaccgg | 240 |
| cagccaaggc tacgaactcc tcaaattcaa gttgtccaga gccatcagcg tcgacctccg | 300 |
| caatgatctc ctccaggatc ttctt | 325 |

<210> SEQ ID NO 128
<211> LENGTH: 463
<212> TYPE: DNA
<213> ORGANISM: Lygus hesperus

<400> SEQUENCE: 128

| | |
|---|---:|
| cggtcatcat ctccatgaac tcgtcgaagt cgacagttcc ggatccgtca gagtcgatct | 60 |
| cctcgatgat catgtccagc tcctcgttgg tcagctgctc gtccaattca tgaaggattt | 120 |
| ctttgaggca ggaggtcggg atgtagccat taccttcttt gtcgtagaga cggaaggctt | 180 |
| ctcgcagctc tttctgcatg gcttcatcgt cttcctcaac aatgaacttg gctgccaacg | 240 |
| tgatgaactc ttcaaactcc agccttccg atttgtcagc gtcaacttct tcgatgagtt | 300 |
| catcgagaat cttcttgttg aagggttgac ccatgagtct gaggatgtcg gccaccatgt | 360 |
| ccgtcgggat ggaacccgag tgatcccggt cgaaagcgtt caacgcgatg gtcatgatgg | 420 |
| ggataattcg gttaattctg ttagaccagt ccgattagtg acg | 463 |

<210> SEQ ID NO 129
<211> LENGTH: 413
<212> TYPE: DNA
<213> ORGANISM: Lygus hesperus

<400> SEQUENCE: 129

| | |
|---|---:|
| atgggtgaag gagggtgcct gctcagagca gtcctccagg atgacggcta tggacaacgc | 60 |

```
ctcgaagaac gccgctgaga tgatcgacaa gctgaccttg acgttcaaca ggactcggca    120
agccgtcatc accagggagc tcatcgaaat catctccggt gcctctgctt tggagtaacg    180
tctcagctca cccagccacc tcccgtagat ccactagtgc tgcgagagac cgagtacctc    240
gttctattca ccctgtacat ttcttaatca atattattgg aattcgattc gatagtcgta    300
tgctgggaaa tatcttgttc atattcatga tacttgttca acattgttct ggtaaataat    360
ttatgtaata caggttgagt taccaaaaaa aaaaaaaaa aaaaaaaaaa aaa            413
```

<210> SEQ ID NO 130
<211> LENGTH: 449
<212> TYPE: DNA
<213> ORGANISM: Lygus hesperus

<400> SEQUENCE: 130

```
gcagctggag gaagagaaac gtatctccct cagcattagg ctcaagcccc tggcgataga     60
aaatatgagc atagacaggc tacgcatcaa agctcaggaa ctctgggaag ccattgtcaa    120
acttgagacc gagaaatacg atcttgagga aaggcaaaag aggcaagact acgatcttaa    180
agaactgaag gaaagacaga agcaacaact tcggcacaaa gccttgaaaa aaggcttgga    240
ccctgaggcc ctcaccggca gtacccacc caaaatccaa gtcgcctcca aatatgaacg    300
aagagttgac accagatctt atgacgacaa gaaaaaactg tttgaaggcg gcatcctgga    360
gcggtataag gagttgatag aaaaggtgtg gaccgaaaaa gttgatcagt tcggcagtcg    420
agcccattcc aagcttccca gatggttcg                                     449
```

<210> SEQ ID NO 131
<211> LENGTH: 719
<212> TYPE: DNA
<213> ORGANISM: Lygus hesperus

<400> SEQUENCE: 131

```
aggagttcga gaacaccagg aagaaccacc aacgggcact cgactccatg caagccagct     60
tggaggctga agccaagggt aaggctgagg ctcttcgcat gaagaagaag cttgaagccg    120
acatcaacga actcgaaatc gctctcgacc acgccaacag ggctaacgcc gaagcccaga    180
agaccatcaa gaaataccaa caacaactca aggacgtaca gaccgctctt gaggaagaac    240
aaagggcacg cgacgatgct cgtgaacaac tcggaatcgc cgaaaggagg gccaacgctc    300
tcggaaacga gctcgaggag tcgcgcactc tcctcgaaca ggccgacagg ggcaggcgcc    360
aagccgaaca gaacttggga gatgcccacg aacagatcaa cgagttggct gcccaagcta    420
ccagcgcctc agccgccaaa cgcaagcttg agggagagtt gcagacactt catgctgacc    480
tcgacgaact tctcaacgaa gccaagaact ccgaagagaa ggccaagaag gcaatggttg    540
atgccgctag gttagctgat gaactcaggg cagaacagga ccacgctcag acccaggaga    600
agctccgcaa ggctctggaa acgcaaatca aggaactcca agtcaggttg gacgaagccg    660
aaaacaacgc cctcaaggga ggcaagaagg ccatcgccaa gctggaacaa cgtgtcagg    719
```

<210> SEQ ID NO 132
<211> LENGTH: 737
<212> TYPE: DNA
<213> ORGANISM: Lygus hesperus

<400> SEQUENCE: 132

```
gcaggcgatg aagatggaga aggacacggc catggacaag gccgacacct gcgaggggca     60
```

-continued

```
ggccaaggac gctaacaccc gcgccgacaa aatccttgaa gatgtgaggg acctccaaaa    120
gaaactcaac caggtagaaa gtgatctcga aaggaccaag agggaactcg agacgaaaac    180
caccgaactc gaagagaagg agaaggccaa caccaacgct gagagcgagg tcgcctccct    240
caacaggaaa gtccagatgg ttgaagagga cttggaaaga tctgaagaaa ggtccggcac    300
cgcacaacaa aaactgtccg aagcctccca cgccgctgat gaagcctctc gtatgtgcaa    360
agtattggag aacaggtcac aacaggatga ggagaggatg gaccagctca ccaaccagct    420
gaaagaagcc cgactcctcg ctgaagacgc cgacggcaaa tcggatgagg tatcaaggaa    480
gctggccttc gttgaagacg aactggaagt agctgaagat cgtgtcaaat ctggagactc    540
gaagatcatg gagcttgagg aggagttgaa agttgtcggt aacagcttga aatctctcga    600
agtttcagag gagaaggcca accagcgagt cgaagagtac aaacgtcaaa tcaagcaact    660
gactgtcaag ttgaaggagg ctgaagctcg cgctgagttc gccgaaaaga cagtcaagaa    720
gttgcagaaa gaggtgg                                                   737
```

<210> SEQ ID NO 133
<211> LENGTH: 205
<212> TYPE: DNA
<213> ORGANISM: Lygus hesperus

<400> SEQUENCE: 133

```
cagaatccca cagaatctga cgtgaagaag ttcacccacc agcacaaacc agatgaaaga     60
atcagcttcg aggtgtttct cccgatatac caagccatat cgaagggtag gacgtcagac    120
acagctgaag acttcatcga gggtctcaga cactttgaca agatggaaa tggcttcatt    180 tcaacagctg agcttcgcca cttgc                                          205
```

<210> SEQ ID NO 134
<211> LENGTH: 326
<212> TYPE: DNA
<213> ORGANISM: Lygus hesperus

<400> SEQUENCE: 134

```
ggaggcattc aacatgatcg accagaacag ggacggcttc gtggataagg aagacctcca     60
tgacatgctc gcttccctag gtaagaaccc ctcagacgag tatctcgagg ggatgatgaa    120
cgaggcgcct ggtcccatca acttcacaat gttcctcacc ctcttcggtg agcggcttca    180
gggaactgat ccggaggagg ttatcaagaa cgcatttggg tgttttgacg aagacaacaa    240
cggattcatc aacgaggaaa gactgcgcga gctgctcacc tccatggggg acaggttcac    300
tgatgaagac gtggacgaaa tgtacc                                         326
```

<210> SEQ ID NO 135
<211> LENGTH: 944
<212> TYPE: DNA
<213> ORGANISM: Lygus hesperus

<400> SEQUENCE: 135

```
gacttgatct tcagccgacc attgatctca ttgataagcc aatgggagtc atggctctcc     60
tggatgaaga atgttggttc cccaaagcca ctgacaagac cttcgttgag aagctggtcg    120
gtgctcacag cgttcacccc aaattcatca aaactgattt ccgtggagtc gccgactttg    180
ctgtcgtcca ttatgccgga aaagtcgatt attcggcggc gcagtggctg atgaagaaca    240
tggaccctct gaacgaaaac gtcgtgcagc tcctccagaa ctcgcaagat ccgttcgtca    300
tccacatctg gaaggacgca gagatcgtcg gcatggctca ccaagctctc agcgacactc    360
```

```
agtttggagc tcgtaccagg aagggtatgt tccgaaccgt gtctcaactc tacaaagacc    420
agctgtccaa actcatgatc acacttcgca acacgaaccc caacttcgtc cgttgcatcc    480
tccccaacca cgagaagaga gctggcaaga tcgatgctcc tttggtgctg gatcagctca    540
gatgcaacgg tgtgttggaa ggcatcagaa tttgcagaca aggtttcccg aatagaatcc    600
cattccagga attccggcaa agatacgagc tcttaactcc caatgtcatc cccaaagggt    660
tcatggacgg taaaaaggct tgcgagaaga tgatcaacgc tctcgaactg gaccctaatc    720
tctacagagt tggtcagtcc aagatattct tcagagctgg agtcttagct catctagaag    780
aagagcgcga ctataagatt actgatctga tagccaattt ccgggctttc tgtaggggat    840
atcttgcccg aaggaactac caaaagcgtc ttcagcagct caacgccatt cgtattatcc    900
agcgaaattg ctcagcttac ttgaagttga ggaactggca atgg                     944

<210> SEQ ID NO 136
<211> LENGTH: 318
<212> TYPE: DNA
<213> ORGANISM: Lygus hesperus

<400> SEQUENCE: 136
atcctggagg agatcattgc ggaggtcgac gctgatggct ctggacaact tgaatttgag     60
gagttcgtag ccttggctgc cggtttcctg acagaagatg agacacaaga tgctgaggcc    120
atgcagcaag aactgaggga ggccttcagg ctctacgaca aggaagggaa cggttacatt    180
accactgacg tcttgaggga aatcctgaag gaactgacg acaaaatcac ctcccaagaa    240
```
```
accactgacg tcttgaggga aatcctgaag gaactgacg acaaaatcac ctcccaagaa    240
cttgacatga tgattgctga aattgattct gacggttccg gaactgttga cttcgacgag    300
ttcatggaga tgatgacc                                                  318

<210> SEQ ID NO 137
<211> LENGTH: 423
<212> TYPE: DNA
<213> ORGANISM: Lygus hesperus

<400> SEQUENCE: 137
atccccatca tgaccatcgc gttgaacgct ttcgaccggg atcactcggg ttccatcccg     60
acggacatgg tggccgacat cctcagactc atgggtcaac ccttcaacaa gaagattctc    120
gatgaactca tcgaagaagt tgacgctgac aaatcgggaa ggctggagtt tgaagagttc    180
atcacgttgg cagccaagtt cattgttgag gaagacgatg aagccatgca gaaagagctg    240
cgagaagcct tccgtctcta cgacaaagaa ggtaatggct catcccgac ctcctgcctc    300 aaagaaatcc ttcatgaatt ggacgagcag ctgaccaacg aggagctgga catgatcatc    360
gaggagatcg actctgacgg atccggaact gtcgacttcg acgagttcat ggagatgatg    420
acc                                                                  423

<210> SEQ ID NO 138
<211> LENGTH: 252
<212> TYPE: DNA
<213> ORGANISM: Lygus hesperus

<400> SEQUENCE: 138
ggtgaaggag ggtgcctgct cagagcagtc ctccaggatg acggctatgg acaacgcctc     60
gaagaacgcc gctgagatga tcgacaagct gaccttgacg ttcaacagga ctcggcaagc    120
cgtcatcacc agggagctca tcgaaatcat ctccggtgcc tctgctttgg agtaacgtct    180
```

| | |
|---|---|
| cagctcaccc agccacctcc cgtagatcca ctagtgctgc gagagaccga gtacctcgtt | 240 |
| ctattcaccc tg | 252 |

<210> SEQ ID NO 139
<211> LENGTH: 1110
<212> TYPE: DNA
<213> ORGANISM: Lygus hesperus

<400> SEQUENCE: 139

| | |
|---|---|
| gtctccgctc aagctggtca tcagacttca gctgagtcct ggggtaccgg tcgtgctgtg | 60 |
| gctcgtatcc cccgtgttcg cggaggtggt actcaccgct caggtcaggg tgcttttggc | 120 |
| aacatgtgtc gcggcggtag gatgttcgct cccactcgcc catggcgtcg ttggcaccgc | 180 |
| aagatcaacg ttaaccaaaa acgttatgcc gtcgtgtccg ccatcgctgc atccggcgtc | 240 |
| ccagccctcg tcatgtccaa aggacacatg gtgcaaagcg tccctgaatt ccccttgtt | 300 |
| gtgtctgaca agttcagga atacactaaa accaaacagg ctgtcatctt ccttcaccgc | 360 |
| atcaaagcct ggcaagacat ccagaaagtg tacaagtcga gaggttccg tgctggtaag | 420 |
| ggtaaaatga ggaaccgcag gaggatccag aggcgtggac ccctcatcat ctacgaccag | 480 |
| gatcagggtc tgaacagggc tttccgtaac attcccggcg tcgatttgat cgaagtgagc | 540 |
| cgcctcaact tgctgaagct cgctccagga ggtcacatcg gccggttcgt catctggact | 600 |
| cagtcggcct tcgagaagtt ggacgccctc tacggcacct ggaagaagaa gtccaccctc | 660 |
| aaggctggat acaatctccc catgcccaag atggccaaca ccgacctttc ccgcctcttc | 720 |
| aaggccccgg agatcaaggc tgtcctcagg aatcccaaga gaccatcgt acgacgagtg | 780 |
| cgcaaactga accctctccg caacaccagg gctatgctgc gtctcaaccc atacgctgct | 840 |
| gtcctcaaga ggaaggccat ccttgatcaa ggaagttga actccagaa gctcgtagaa | 900 |
| gctgccaaga agggagatac caagctgtcg ccccgcgtcg agcgtcacct gaagatgatc | 960 |
| gagagaagga aagcccctgat caagaaagcc aaggctgcca gcccaagaa gcccaaaacg | 1020 |
| gccaagaaac ccaagaccgc cgagaaggca ccagcacccg ccaagaaggc ggcagcgccc | 1080 |
| aaaaaggcca ccacccctgc caagaaatga | 1110 |

<210> SEQ ID NO 140
<211> LENGTH: 729
<212> TYPE: DNA
<213> ORGANISM: Lygus hesperus

<400> SEQUENCE: 140

| | |
|---|---|
| atggccaatg ctaagcctat ttctaagaag aagaagtttg tgtctgacgg tgtcttcaaa | 60 |
| gccgaattga cgaatttct taccagagaa ctcgctgaag aggggtactc aggtgttgag | 120 |
| gtccgagtga cccccaacaa gacagaaatt atcatcatgg cgacaaggac acaaagcgtt | 180 |
| cttggtgata agggccgccg aatcaggag ctcacgtctg tagttcagaa aagattcaat | 240 |
| ttcaagcctc agactttgga tctctatgct gaaaaggtcg ccaccagagg tttgtgtgct | 300 |
| attgcacaag ctgaatccct ccgttacaaa ctcattggcg gtcttgctgt ccgaggggct | 360 |
| tgctatggtg tccttcgctt catcatggaa aatggtgcca aggggtgcga agtcgtagta | 420 |
| tctggaaaac tgcgtggtca gagagccaag tcaatgaagt tcgtggatgg tttgatgatc | 480 |
| cacagtgggg atccctgtaa cgaatatgtt gatactgcta cccgacatgt gctccttaga | 540 |
| caaggtgtcc tgggaataaa ggtgaagatt atgttgccgt gggacgttac cggcaaaaat | 600 |
| gggccgaaga accctcttcc cgaccacgtc agcgttctct tacctaagga ggagctacca | 660 |

| | |
|---|---|
| aatttggccg ttagtgtgcc tggatccgac atcaaaccaa agcctgaagt accagcaccc | 720 |
| gctttgtga | 729 |

<210> SEQ ID NO 141
<211> LENGTH: 789
<212> TYPE: DNA
<213> ORGANISM: Lygus hesperus

<400> SEQUENCE: 141

| | |
|---|---|
| atggctgttg gtaaaaataa gggtctatcg aaaggaggaa agaagggagt taaaaaaaag | 60 |
| gtagtggacc ctttcaccag gaaggattgg tacgatgtta aggctccttc catgttcaaa | 120 |
| aagcgtcaag ttggcaaaac tttggtcaac cgaactcagg gaaccaagat tgcttctgaa | 180 |
| gggttgaaag gacgagtttt cgaagtttcg ctcgctgata tccaggagga cactgatgcc | 240 |
| gagcgctcct tcaggaaatt caggctcatc gctgaagatg tccaagccag aaacgtcctt | 300 |
| accaatttcc acggtatgga tttgaccact gacaaactcc ggagcatggt caagaagtgg | 360 |
| cagactctca tcgaagccaa cgttgacgtc aagaccaccg acggctacct cctgcgcgtc | 420 |
| ttctgcatag gattcaccaa taagatcaa ctttcccaga gaaagacttg ctatgcccag | 480 |
| cataatcagg tccgagaaat ccgcaaaaag atggttaaaa acatcagtga cagcatttcc | 540 |
| agctgtgatt tgaggagtgt tgtgaacaag ctgatcccag actccatcgc taaagatata | 600 |
| gaaaagaatt gccaaggaat ctacccactc cacgatgtgt acattcggaa ggtgaaggtg | 660 |
| ttgaagaagc cgaggttcga gctcagcaag ctccttgagc ttcacgtcga tggcaaaggg | 720 |
| atcgacgaac ccggcgcgaa agtgacgagg actgacgctt acgagcctcc agttcaagag | 780 |
| tctgtctaa | 789 |

<210> SEQ ID NO 142
<211> LENGTH: 473
<212> TYPE: DNA
<213> ORGANISM: Lygus hesperus

<400> SEQUENCE: 142

| | |
|---|---|
| gaccaaggag cagctggagg aagagaaacg tatctccctc agcattaggc tcaagcccct | 60 |
| ggcgatagaa aatatgagca tagacaggct acgcatcaaa gctcaggaac tctgggaagc | 120 |
| cattgtcaaa cttgagaccg agaaatacga tcttgaggaa aggcaaaaga ggcaagacta | 180 |
| cgatcttaaa gaactgaagg aaagacagaa gcaacaactt cggcacaaag ccttgaaaaa | 240 |
| aggcttggac cctgaggccc tcaccggcaa gtacccaccc aaaatccaag tcgcctccaa | 300 |
| atatgaacga agagttgaca ccagatctta tgacgacaag aaaaaactgt ttgaaggcgg | 360 |
| catcctggag cggtataagg agttgataga aaaggtgtgg accgaaaaag ttgatcagtt | 420 |
| cggcagtcga gcccattcca agcttcccag atggttcggc gagcggcccg gca | 473 |

<210> SEQ ID NO 143
<211> LENGTH: 1463
<212> TYPE: DNA
<213> ORGANISM: Lygus hesperus

<400> SEQUENCE: 143

| | |
|---|---|
| gggtctcagc tgaggcacat tccatctcgt cgcaaatctt tcctgcatct ctcctgggtg | 60 |
| acctttaggt gaccaatcac atccatcatg tcggacgagg agtattcgga gtcggaggaa | 120 |
| gagacccagc cggaaccaca gaaaaaacca gaggctgaag gaggcggcga cccagaattc | 180 |

```
gtcaagcgta aggaagccca gacctcagcc ttagacgagc agcttaaaga ctatatcgca    240
gaatggagga aacaaagagc tcgcgaagaa gaagacctca agaagctgaa ggagaagcaa    300
gccaagcgca aggtcgctcg ggcagaagaa gaaagagat tggcggaaaa gaagaagcag     360
gaagaagaac gacgtgtgag ggaagcgaaa gagaagaaac agagggaaat cgaagagaag    420
aggcgaaggc ttgaagaggc cgagaagaag agacaagcca tgatggctgc tctcaaggac    480
cagagcaaaa cgaagggacc caattttgtc gttaataaga aagccgaaac ccttggcatg    540
tcctccgctc aaattgagcg caacaagact aaggaacagc ttgaggaaga aaaacgtatc    600
tccctcagca ttaggctcaa gcccctggcg atagaaaata tgagcataga caggctacgc    660
ataaaagctc aggaactctg ggaagccatt gtcaaacttg agaccgagaa atacgatctt    720
gaggaaaggc aaaagaggca agactacgat cttaaagaac tgaaggaaag acagaagcaa    780
caacttcggc acaaagcctt gaaaaaaggc ttggaccctg aggccctcac cggcaagtac    840
ccacccaaaa tccaagtcgc ctccaaatat gaacgaagag ttgacaccag atcttatgac    900
gacaagaaaa aactgtttga aggcggcatc ctggagcggt ataaggagtt gatagaaaag    960
gtgtggaccg aaaagttga tcagttcggc agtcgagccc attccaagct tcccagatgg    1020
ttcggcgagc ggcccggcaa gaagaaggat gcccctgaaa gccggaagaa agaggaagtg    1080
aaggtagaag atgaacctga agctgaacca agcttcatgc tcgacgaaga agaagaagaa    1140
gcggaagaag aggaggcgga gaggaagag gaagccgagg aagaggagga agaagaagag     1200
gaagaggaag aggaggagga ggaagaagaa taggtctttt tcaacatttc actgcaccca    1260
cagttccacg gtctttccgc ccacaaactc aatctgtgct cacgagatct tagcaggaaa    1320
agtattgcga cccgataaga acaaattaaa ttatttttgg aatatctcgt tcagttattt    1380
cgtgagaaac aattttattc atgtaaacga ttaaagatc ccatacatt ccaaaaaaaa      1440
aaaaaaaaaa aaaaaaaaa aaa                                             1463

<210> SEQ ID NO 144
<211> LENGTH: 773
<212> TYPE: DNA
<213> ORGANISM: Lygus hesperus

<400> SEQUENCE: 144
ccggcggatc caggaaaagg aggaggagtt cgagaacacc aggaagaacc accaacgggc     60
actcgactcc atgcaagcca gcttggaggc tgaagccaag ggtaaggctg aggctcttcg    120
catgaagaag aagcttgaag ccgacatcaa cgaactcgaa atcgctctcg accacgccaa    180
caaggctaac gccgaagccc agaagaccat caagaaatac caacaacaac tcaaggacgt    240
acagaccgct cttgaggaag aacaaagggc acgcgacgat gctcgtgaac aactcggaat    300
cgccgaaagg agggccaacg ctctcggaaa cgagctcgag gagtcgcgca ctctcctcga    360
acaggccgac aggggcaggc gccaagccga caagaacttt ggagatgccc acgaacagat    420
caacgagttg gctgcccaag ctaccagcgc ctcagccgcc aaacgcaagc ttgagggaga    480
gttgcagaca cttcatgctg acctcgacga acttctcaac gaagccaaga actccgaaga    540
gaaggccaag aaggcaatgg ttgatgccgc taggttagct gatgaactca gggcagaaca    600
ggaccacgct cagacccagg agaagctccg caaggctctg gaaacgcaaa tcaaggaact    660
ccaagtcagg ttggacgaag ccgaaaacaa cgccctcaag ggaggcaaga aggccatcgc    720
caagctggaa caacgtgtca gggaactcga aaacgaactg gacggcgagc agc           773
```

```
<210> SEQ ID NO 145
<211> LENGTH: 5446
<212> TYPE: DNA
<213> ORGANISM: Lygus hesperus

<400> SEQUENCE: 145
tcaggaaaac tggctggtgc tgatattgag acctatctgc tggagaaggc tcgtgtcatc      60
tcccaacaaa cactcgagag atcctaccac attttctacc agatgatgtc tggagctgtc     120
aagggcgtca aggaaatgtg cttgctggtc gacgatatct atacgtacaa cttcatatcc     180
cagggtaaag tcagcattgc aggcgttgat gacggagagg aaatggttct gaccgatcaa     240
gccttcgaca tcttgggttt caccaagcaa gagaaggaag acatctacaa gatcaccgcc     300
gctgtcattc acatgggtac catgaagttc aagcaaaggg gtcgtgaaga gcaggctgaa     360
gccgatggaa ctgaggaagg cggtaaggtc ggtgtgctcc tcggtatcga cggtgacgac     420
ttgtacaaga atatgtgcaa gcccagaatc aaggtcggaa ctgagttcgt gacccaggga     480
aagaacgtca accaggtctc atactctctc ggtgccatgt ccaagggtat gttcgatcgt     540
ctcttcaaat tcttggtcaa gaaatgtaac gaaactctgg acaccaaaca gaagagacag     600
cacttcattg gtgtactgga tattgccggg ttcgaaattt tcgacttcaa cggttttgag     660
caactgtgta tcaacttcac caacgagaaa ttgcaacaat tcttcaacca ccacatgttc     720
gtactcgagc aagaagagta caagagggaa ggcattaact gggctttcat tgatttcgga     780
atggacttgc tcgcttgtat tgaactgatt gagaagccca tgggtatctt gtccatcctt     840
gaagaagagt ctatgttccc caaggctact gacaagacct tgaggacaa actcatcacc       900 aaccacttgg gcaaatctcc caacttcagg aagcccgccg ttccaaagcc tggccaacaa     960
gctggtcact cgccatcgc tcactacgct ggttgcgtgt catacaacat caccggctgg    1020
cttgagaaga acaaggatcc gttgaacgac actgttgtcg atcagtacaa gaagggaacc    1080
aacaaactgt tgtgcgagat cttcgctgat catcctggcc aatctggtgc ccctggtggt    1140
gatgctggtg gcaagggtgg tcgtggcaag aaaggtggtg gcttcgccac tgtgtcatct    1200
tcctacaagg aacaattgaa caacttgatg accactttga agagcacaca gcctcacttc    1260
gtccgttgta tcatccccaa cgaattgaaa cagcccggtg ttattgattc tcacttggtc    1320
atgcaccagc tgacttgtaa cggtgtactt gaaggcatcc gtatttgccg taaaggcttc    1380
cccaacagga tgaactaccc tgacttcaag ctccgataca agatccttaa ccccgctgcc    1440
gtggacagag agagtgatat cctcaaggct gctggtctcg tccttgagtc aactgggctc    1500
gaccctgata tgtaccgtct cggccacacc aaggtgttct tcagggccgg agttttgggt    1560
caacttgaag aattgcgtga cgacaggctt agcaagatca tcggatggat gcaggccttc    1620
atgcgcggtt acctcgtcag gaaggagtac aagaagctcc aggaacagag gttagccctc    1680
caagttgtcc agcgcaactt gagaaggtac ctccaactga ggacctggcc ctggtggaag    1740
atgtggtcca gggtcaagcc cctcctcaac gtcgccaacg tcgaagagga gatgcggaaa    1800
ctcgaagagt tggtcgccga acccaggcc gctttggaga aggaggagaa gctgaggaag     1860
gaggccgaag cccttaacgc caagcttctc aagagaagaa ccgaccttct caggaacttg    1920
gaaggagaga agggatccat cagcggtatc caggaacgat gtgccaagct gcaagcccaa    1980
aaggccgatc ttgagtctca actcatggac acccaagaaa ggctgcagaa cgaagaagat    2040
gccaggaacc agctcttcca acagaagaag aaattggaac aagaagccgc tgccctcaag    2100
aaggacatcg aagatctcga actctccaac caaaagaccg accaagataa ggccagcaag    2160
```

-continued

```
gaacaccaaa tcagaaacct caatgacgag atcgctcacc aagatgactt gatcaacaag    2220
ctcaacaagg agaagaaaat ccagagcgaa ctcaaccaaa agactgctga agaacttcag    2280
gccgctgaag acaaaatcaa ccacctcacc aaggttaagg tcaagcttga acagaccttg    2340
gatgaactcg aagacaccct cgaacgtgaa aagaaactcc gaggagatgt cgaaaaggcc    2400
aagaggaaga ctgaaggcga cctcaagctc actcaggaag ccgttgccga tcttgaaagg    2460
aacaagaaag aactcgaaca gaccatccag aggaaagaca aggaaattgc ttccctcacc    2520
gccaagctcg aagacgaaca atccatcgtc aacaagactg gcaaacagat caaggaactc    2580
cagagccgca ttgaagagct cgaggaggaa gtcgaggctg agaggcaagc ccgcggaaag    2640
gctgagaagc aacgtgctga cctcgcccgc gaacttgagg aactcggcga gaggttagag    2700
gaagctggtg gtgccacctc tgcccagatc gagctcaaca agaagcgtga agctgagatg    2760
agcaaactca ggagggacct ggaagaagcc aacatccagc acgaaggcac gctcgccaac    2820
ctccgcaaga agcacaacga tgctgtcagt gagatgggag accaaatcga ccagctcaac    2880
aaacttaaga ccaaggttga aaaggagaag tctcaatacc tcggtgaact caacgacgtc    2940
cgcgcctcca ttgaccactt gaccaacgag aaggctgcca ctgaaaaggt tgccaagcaa    3000
ctgcaacacc aaatcaatga agttcaaggc aaacttgatg aagctaacag gacgctcaac    3060
gacttcgatg ctgccaagaa gaagttgtct attgagaact ctgacctcct cagacagttg    3120
gaggaagctg agagccaagt ttctcaactt agcaagatca gatctccct caccactcaa    3180 ctcgaggaca ctaagcgtct cgccgatgag gaagctaggg aacgcgcaac ccttcttggc    3240
aagttccgca acttggaaca cgaccttgac aacctgaggg aacaggtgga ggaagaagcc    3300
gaagctaagg ctgatatcca acgtcaactc agcaaggcca acgctgaagc tcagttgtgg    3360
cgcagcaagt acgaaagcga gggtgttgcc cgcgctgagg agcttgagga ggccaagagg    3420
aaactccagg cccgtttggc tgaggctgag gagaccattg agtccctcaa ccagaaggtt    3480
atcgcccttg agaagacgaa gcagcgcctt gccactgaag tcgaggatct gcagctcgag    3540
gtcgaccgtg ccaacgccat tgccaatgcc gctgaaaaga aggctaaggc tattgacaag    3600
atcattggtg aatggaaact caaggttgat gaccttgctg ctgagcttga tgctagtcaa    3660
aaggaatgca gaaactactc cactgagctc ttcaggctca agggagctta tgaagaagga    3720
caggaacaac ttgaagctgt ccgcagggag aacaagaacc ttgctgatga agtcaaggac    3780
ttgctcgacc agatcggtga gggtggccgc aacatccacg aaattgagaa gcagcgcaag    3840
aggctcgaag ttgagaagga cgaacttcag gccgctcttg aggaggctga agccgctctt    3900
gaacaggagg agaacaaagt actcagggct caacttgagc tcagccaggt gcgtcaagaa    3960
attgaccgcc gcatccagga gaaggaagag gagttcgaga acaccaggaa gaaccaccaa    4020
cgggcactcg actccatgca agccagcttg gaggctgaag ccaagggtaa ggctgaggct    4080
cttcgcatga agaagaagct tgaagccgac atcaacgaac tcgaaatcgc tctcgaccac    4140
gccaacaagg ctaacgccga agcccagaag accatcaaga aataccaaca acaactcaag    4200
gacgtacaga ccgctcttga ggaagaacaa agggcacgcg acgatgctcg tgaacaactc    4260
ggaatcgccg aaaggagggc caacgctctc ggaaacgagc tcgaggagtc gcgcactctc    4320
ctcgaacagg ccgacagggg caggcgccaa gccgaacaag aacttggaga tgcccacgaa    4380
cagatcaacg agttggctgc ccaagctacc agcgcctcag ccgccaaacg caagcttgag    4440
ggagagttgc agacacttca tgctgacctc gacgaacttc tcaacgaagc caagaactcc    4500
gaagagaagg ccaagaaggc aatggttgat gccgctaggt tagctgatga actcagggca    4560
```

```
gaacaggacc acgctcagac ccaggagaag ctccgcaagg ctctggaaac gcaaatcaag    4620
gaactccaag tcaggttgga cgaagccgaa acaacgccc tcaagggagg caagaaggcc     4680
atcgccaagc tggaacaacg tgtcaggaa ctcgaaaacg aactggacgg cgagcagagg     4740
agacacgccg acgcacaaaa gaacctccgt aaatccgagc gtagaattaa ggagctcagt    4800
ttccagtccg acgaggaccg taagaaccac gaacgcatgc aagacctcgt agacaaactg    4860
caacagaaga tcaagactta caagaggcag attgaagaag ccgaagaaat cgcggcccct    4920
aacctcgcca aattccgcaa agcacaacaa gaactcgaag aagctgaaga acgcgctgat    4980
ctcgctgaac aggctgtttc caaattcaga acaaagggtg gacgcgcagg atctgctgcc    5040
agagcgatga gccctgtcgg ccagaagtga aggaacgaat aagcggacgt ataagctatc    5100
aatacctcgc acacaaacct gccaggcctc aatttgacgg caatgccttc ccaccacgat    5160
tcgatctaca tcccgacgac ttttaagatc tttgatagca acgcaaaaca tcaaatgaaa    5220
atcttttaaa ttttatgtat ttattttgac ctattttatt aagttattgt taatacaaac    5280
ataattccat gagctagata tctagccaac gaaccatcac aatcacgatt attcgaactg    5340
tacgatagaa gcattatttg tacagctgga ccatttacaa aatattttg cttcgaataa     5400 taaagagttt atatcgcgaa aaaaaaaaaa aaaaaaaaaa aaaaaa                   5446

<210> SEQ ID NO 146
<211> LENGTH: 964
<212> TYPE: DNA
<213> ORGANISM: Lygus hesperus

<400> SEQUENCE: 146
tcctcctctg gtgcccgact cttcaaatac ccaaatccag tcatgtcttc ccgtaaaacc      60
gctggccgca gggcgaccac caagaagcgc gctcagcgtg cgacgtcaaa cgtattcgcc     120
atgttcgatc aggctcagat tcaagaattc aaggaggcat tcaacatgat cgaccagaac     180
agggacggct tcgtggataa ggaagacctc catgacatgc tcgcttccct aggtaagaac     240
ccctcagacg agtatctcga ggggatgatg aacgaggcgc tggtcccat caacttcaca      300 atgttcctca ccctcttcgg tgagcggctt cagggaactg atccggagga ggttatcaag     360
aacgcatttg ggtgttttga cgaagacaac aacggattca tcaacgagga aagactgcgc     420
gagctgctca cctccatggg ggacaggttc actgatgaag acgtggacga atgtaccga      480 gaggcccca tcaagaacgg catgttcgac tacatcgaat tcactcggat cctcaagcac     540
ggagccaaag acaaagacga gcagtgacct atcaaatcct cgtcaacctc ccttcagtaa     600
tttgaaacca atccatcaaa ttttgtttaa aactcttact taaaatccga tcatctacgt     660
cactttgcca ccaatcggta ttattttttg agccgttcct acataaatcg aattaatttt     720
atacctacga atcatattgt tggaaatttc tctcttgtac ttatactttc tgttatttcc    780
taatttttct aactaaccaa gttagtcgtt agttttatt cattccttta taaattatta     840
gttatccatt tttaatcatc ttgaagttat ttgttttcg agtggtagaa tatttataca    900
ttttccaata tataatggtt tattcattct taaaaaacga aaaaagaa aaaaaaaaa       960 aaaa                                                                 964

<210> SEQ ID NO 147
<211> LENGTH: 5872
<212> TYPE: DNA
<213> ORGANISM: Lygus hesperus
```

```
<400> SEQUENCE: 147
gatcttacct gcctgaacga ggcgtccgtt cttcacaaca tcaaggacag atattactcc      60
ggattgattt atacgtattc gggactcttc tgcgtggtgg tcaacccta caagaaactg     120 ccaatctaca cagagagaat catggagaaa tacaaaggcg tcaaaagaca cgacctccct     180
ccacacgtat tcgccatcac agacacagct taccgttcta tgctgcaaga tagggaagat     240
caatcgatac tctgcaccgg cgaatcgggt gcggggaaaa ccgaaaacac gaaaaaagta     300
atccagtact tggcctacgt tgcagcctcg aaacccaaat cttccgcatc cccacatacg     360
gcccagagtc aagctctgat cattggagaa ctcgaacaac agctgcttca agctaaccca     420
attttggaag cattcggaaa cgccaagact gttaaaaacg ataattcttc tcgattcggt     480
aaattcattc gtatcaattt cgacgcatca ggctacatcg caggagccaa catagaaacg     540
tatcttctag agaaatctag gccatcaga caagcgaaag atgagcgaac gttccacatc     600
ttttaccaac ttctggccgg agcatctgca gaacaaagaa aggagttcat cctcgaagat     660
ccgaaaaact acccttttcct cagcagcggg atggtgtctg tgcctggagt tgacgatggt     720
gttgatttcc aagcaactat cgcctccatg tccatcatgg gcatgaccaa cgacgatctt     780
tccgctctct tccgcatcgt cagtgccgtc atgctgttcg gcagcatgca gttcaagcag     840
gagcgaaaca gcgaccaggc gacgctccca gacaacactg tagcgcaaaa aatcgcccac     900
ctccttggtc tctcaatcac agagatgacc aaagcgttcc tcaggcctag aatcaaagta     960
ggacgggatt tcgtcaccaa ggctcaaact aaggaacaag ttgagttcgc agtggaagcc    1020
atttcgaaag cctgctacga acgtatgttc cgatggctcg tcaacagaat caaccgctcc    1080
ctggatcgta ccaaaaggca gggagcatct ttcattggta ttcttgatat ggctggtttc    1140
gaaatctttg agatcaactc cttcgagcag ctttgtatca attacaccaa tgagaaactt    1200
caacaactct tcaaccacac catgttcatt ttggagcaag aggagtacca gagagaaggt    1260
attgaatgga agttcatcga cttcggactt gatcttcagc cgaccattga tctcattgat    1320
aagccaatgg gagtcatggc tctcctggat gaagaatgtt ggttccccaa agccactgac    1380
aagaccttcg ttgagaagct ggtcggtgct cacagcgttc accccaaatt catcaaaact    1440
gatttccgtg gagtcgccga ctttgctgtc gtccattatg ccggaaaagt cgattattcg    1500
gcggcgcagt ggctgatgaa gaacatggac cctctgaacg aaaacgtcgt gcagctcctc    1560
cagaactcgc aagatccgtt cgtcatccac atctggaagg acgcagagat cgtcggcatg    1620
gctcaccaag ctctcagcga cactcagttt ggagctcgta ccaggaaggg tatgttccga    1680
accgtgtctc aactctacaa agaccagctg tccaaactca tgatcacact tcgcaacacg    1740
aaccccaact tcgtccgttg catcctcccc aaccacgaga agagagctgg caagatcgat    1800
gctcctttgg tgctggatca gctcagatgc aacggtgtgt tggaaggcat cagaatttgc    1860
agacaaggtt tccgaatag aatcccattc caggaattcc ggcaaagata cgagctctta    1920
actcccaatg tcatccccaa agggttcatg acggtaaaa aggcttgcga agatgatc     1980 aacgctctcg aactggaccc taatctctac agagttggtc agtccaagat attcttcaga    2040
gctggagtct tagctcatct agaagaagag cgcgactata agattactga tctgatagcc    2100
aatttccggg ctttctgtag gggatatctt gcccgaagga actaccaaaa gcgtcttcag    2160
cagctcaacg ccattcgtat tatccagcga aattgctcag cttacttgaa gttgaggaac    2220
tggcaatggt ggcggctgta caccaaggtc aaacctctgc ttgaagtgac gaaacaagaa    2280
gagaagctga cgcaaaagga agacgaactg aagcaggtcc gcgagaaact ggacaaccag    2340
```

```
gtgaggtcca aggaagagta tgaaaagagg cttcaggacg ctttggagga gaaagctgct    2400
ctggcagagc aacttcaggc agaagtagag ctgtgtgcgg aagccgaaga aatgagagcc    2460
aggctcgctg tgaggaagca agaactagag gaaattctcc acgatctaga agccagaata    2520
gaggaagaag agcaacgaaa cacggtcctc atcaacgaaa agaagaagtt gaccctcaac    2580
atcgccgacc tcgaagaaca actggaagag gaagaaggag ctcgacagaa actccaactc    2640
gaaaaagtcc agatcgaagc tcggctgaag aaaatggaag aggacctcgc tctgccgaa     2700 gacaccaaca ccaaagtcgt aaaggagaag aaagtgttgg aagagagggc tagtgacttg    2760
gcccagaccc tcgctgagga agaagaaaaa gctaaacacc tcgcgaagct caagaccaag    2820
cacgagacga cgatagcgga attggaagag aggttgctca agacaatca gcagaggcag     2880 gaaatggata ggaacaagag gaagatcgaa tcagaggtga atgatttgaa agaacaaatt    2940
aacgagaaga aggtccaagt agaggagctt cagttgcaac tcgggaagag ggaagaggaa    3000
atcgctcaag ctctgatgag aattgacgag gaaggagcag gcaaagctca gactcaaaag    3060
gctctcaggg aattggagtc tcagctggct gagctacaag aggatctaga ggctgaaaag    3120
gccgctcgcg ccaaggccga aaagcagaag cgcgacctca cgaagaact cgagtccctc     3180 aagaatgaac ttcttgactc actggacacg acagcagctc aacaggaatt gaggaccaag    3240
agagaacacg aactggcaac gctcaagaaa acattagaag aggaaacgca cattcacgaa    3300
gtatctctca ccgaaatgag gcacaaacac actcaagaag tcgctgcact caacgaacag    3360
ttggagcaac tcaaaaaggc caaatctgca ctcgaaaaat cgaaagcaca acttgaaggg    3420
gaagctgctg agctcgccaa cgaactggaa acagcaggaa cgagcaaggg cgagagtgaa    3480
aggaaacgga agcaggccga atcgtctctg caggagctct cgtcgcgact cttggaaatg    3540
gagagaacca agccgagct ccaagagagg gtccagaaac tgtctgcaga agccgactct    3600
gtcaatcagc agttggaagc agcggaactg aaagcatcag cagccctcaa ggcatctggt    3660
accttggaga ctcagctcca ggaggcgcaa gtgctcctgg aagaggaaac tcggcagaag    3720
ctgtcgttga ccaccaaaact gaaaggcctc gaaagcgaaa gagatgctct caaagagcaa    3780
ctctacgaag aggacgaggg taggaagaac ctagaaaaac agatggcgat actcaatcaa    3840
caagtagctg aaagcaagaa gaagtctgaa gaagaaacgg aaaaaataac tgaactcgaa    3900
gaaagtcgca aaaaattgct caaagacata gaaattcttc aaaggcaagt cgaagaactt    3960
caagttacca cgacaaatt agagaaaggc aagaagaagc tgcagtcaga actggaagac    4020
ctcaccatcg acctggagtc tcagagaaca aaggtggtcg agctcgagaa gaaacaaga     4080 aatttcgaca aagttttggc cgaagaaaaa gcgttgtcgc aacaaatcac gcacgagagg    4140
gatgcggctg aaagagaagc ccgtgaaaag gaaactagga tactgtcgct gacgcgagaa    4200
ctcgatgaat tcatggagaa aatcgaggaa ctggagagaa gcaaacggca actccaggct    4260
gaactagacg agctggtcaa caaccaaggc accaccgaca aaagcgtgca cgaattggaa    4320
agggcgaaac gagttctgga gtcacaactt gcagagcaga agcacaaaaa tgaagagctt    4380
gaagatgaac tccaaatgac ggaagacgcc aaattgaggc tcgaagtcaa catgcaagct    4440
ctgagagctc aattcgaaag agatctacag ggcaaagaag agtcgggaga gaaaagagg    4500 agaggattgc tgaaacagct gagggacatt gaggctgaac ttgaagacga gagaaaacaa    4560
aggaccgctg ctgttgcctc tagaaagaag attgaagcgg atttcaaaga tgtagaacag    4620
caactggaaa tgcacactaa ggtaaaggaa gatcttcaga agcaactgaa gaaatgccag    4680
```

```
gtccaactga aggacgcaat cagagacgcg gaagaggctc ggctcggtcg ggaagagctg   4740
caggctgccg ctaaagaggc cgaaaggaag tggaagggtt tggaaacgga gctcattcaa   4800
gtgcaagagg atttgatggc gagcgaaagg cagcggcggg cagcggaagc cgaaagggat   4860
gaagtcgttg aagaagccaa caagaatgtc aagagcttat cgaatcttct cgacgaaaag   4920
aagaggctcg aagcccaatg ctcaggcctg gaagaggaac tcgaagaaga acttagcaac   4980
aatgaggccc tccaagacaa agcgagaaaa gcacaactca gcgttgagca acttaatgca   5040
gaacttgctg ccgaacggag taatgtgcag aaacttgagg gaacgagatt gtcgatggaa   5100
aggcaaaaca aggaactgaa ggccaaactg aacgaactgg aaacgttaca acgcaacaag   5160
ttcaaggcca atgcgtctct ggaggctaag attaccaatc ttgaagagca actggaaaat   5220
gaagccaagg aaaagctact ctccagaaaa ggcaacagga agctcgacaa gaaaatcaaa   5280
gacctcctcg ttcaattgga ggatgaaagg aggcatgccg accagtataa agaacaagtc   5340
gagaagatca acgtcagggt gaagacgcta aagcgaactt tggacgacgc cgaagaagaa   5400
atgagtaggg agaagaccca gaagaggaaa gcacttcgcg aattggaaga cctcagggag   5460
aactacgatt ccctactccg agagaacgat aacctcaaaa acaaactcag gcggggcggc   5520
ggtatttccg ggatctcgag caggctcgga ggctccaagc gaggttccat ccccggagag   5580
gattcccagg gtctcaacaa caccacagac gaatcagtcg atggtgacga tatctcgaat   5640
ccttaaacgc tacttggatt taccagccag catccaactt tccactgaag acgtctccca   5700
taaacgttga agagacccg tcgaggaaga aaaaaaggct ctttaagaaa aactattctg   5760 ccttttttcaa aactttgtac ttaaaagtac tttcgcttaa caatgaaaga gaataaaaaa   5820
tgtaaagttt tcatttatac aaaaaaaaaa aaaaaaaaa aaaaaaaaa aa            5872

<210> SEQ ID NO 148
<211> LENGTH: 325
<212> TYPE: DNA
<213> ORGANISM: Lygus hesperus

<400> SEQUENCE: 148
aagaagatcc tggaggagat cattgcggag gtcgacgctg atggctctgg acaacttgaa     60
tttgaggagt tcgtagcctt ggctgccggt ttcctgacag aagatgagac acaagatgct    120
gaggccatgc agcaagaact gagggaggcc ttcaggctct acgacaagga agggaacggt    180
tacattacca ctgacgtctt gagggaaatc ctgaaggaac tcgacgacaa aatcacctcc    240
caagaacttg acatgatgat tgctgaaatt gattctgacg gttccggaac tgttgacttc    300
gacgagttca tggagatgat gaccg                                          325

<210> SEQ ID NO 149
<211> LENGTH: 428
<212> TYPE: DNA
<213> ORGANISM: Lygus hesperus

<400> SEQUENCE: 149
aattatcccc atcatgacca tcgcgttgaa cgctttcgac cgggatcact cgggttccat     60
cccgacggac atggtggccg acatcctcag actcatgggt caacccttca acaagaagat    120
tctcgatgaa ctcatcgaag aagttgacgc tgacaaatcg ggaaggctgg agtttgaaga    180
gttcatcacg ttggcagcca agttcattgt tgaggaagac gatgaagcca tgcagaaaga    240
gctgcgagaa gccttccgtc tctacgacaa agaaggtaat ggctacatcc cgacctcctg    300
cctcaaagaa atccttcatg aattggacga gcagctgacc aacgaggagc tggacatgat    360
```

```
catcgaggag atcgactctg acggatccgg aactgtcgac ttcgacgagt tcatggagat    420
gatgaccg                                                             428

<210> SEQ ID NO 150
<211> LENGTH: 538
<212> TYPE: DNA
<213> ORGANISM: Lygus hesperus

<400> SEQUENCE: 150
gcttctttta caaatcgcac cacgccgact taattcattc ccggagggtt taaattttat     60
cgaagcagca tggtgcggat gaatgtgctg agcgatgctc tgaaaagcat caacaatgct    120
gagaagaggg gcaaaaggca ggtgctcctg aggccttgtt ccaaagtcat cattaaattc    180
cttacagtga tgatgaagaa aggttatatc ggcgaattcg aaatagtaga tgatcacaga    240
tctggtaaaa tcgtcgtcaa cctcaacggc agattgaaca aatgtggagt tatatcgccc    300
agattcgacg tacccatcac acaaatcgaa aaatggacga caacctcct gccttcccga     360 cagttcggtt atgtcgtact caccactagt ggagggatca tggatcacga agaagccagg    420
cgaaaacatc ttgggggtaa aatattaggg ttttctttt aataaaaaaa gacgagatgt     480
aaattaataa aactctttta cgtttcgcta aaaaaaaaaa aaaaaaaaa aaaaaaa        538

<210> SEQ ID NO 151
<211> LENGTH: 405
<212> TYPE: DNA
<213> ORGANISM: Lygus hesperus

<400> SEQUENCE: 151
ccacgccgac ttaattcatt cccggagggt ttaaattta tcgaagcagc atggtgcgga     60
tgaatgtgct gagcgatgct ctgaaaagca tcaacaatgc tgagaagagg ggcaaaaggc   120
aggtgctcct gaggccttgt tccaaagtca tcattaaatt ccttacagtg atgatgaaga   180
aaggttatat cggcgaattc gaaatagtag atgatcacag atctggtaaa atcgtcgtca   240
acctcaacgg cagattgaac aaatgtggag ttatatcgcc cagattcgac gtacccatca   300
cacaaatcga aaaatggacg aacaacctcc tgccttcccg acagttcggt tatgtcgtac   360
tcaccactag tggagggatc atggatcacg aagaagccag gcgaa                  405

<210> SEQ ID NO 152
<211> LENGTH: 470
<212> TYPE: DNA
<213> ORGANISM: Lygus hesperus

<400> SEQUENCE: 152
tgtcgatggc ggtcttaaca tcccccattc caccaagagg ttccctgggt acgacagtga     60
gtctaaggaa ttcaacgctg aggtccacag gaagcacatt ttcggcattc acgtcgctga   120
ctacatgcgt cagctggctg aagaggatga cgatgcttac aagaagcagt tctcgcagta   180
tgtcaagaac ggagtcactg ctgacagcat tgaaagtatc tacaagaagg ctcacgaagc   240
aatccgagct gatccaactc gcaaaccact tgagaagaag gaagtcaaga agaagaggtg   300
gaaccgcgcc aagctttcct tgtctgaaag gaagaacacc atcaaccaaa agaaggcaac   360
ttatctcaag aaagtggaag ctggagaaat cgaataagtt tttatattcc tgacattacc   420
cattaaaggt ttcgttttaa cctaaaaaaa aaaaaaaaa aaaaaaaaa                470

<210> SEQ ID NO 153
```

```
<211> LENGTH: 387
<212> TYPE: DNA
<213> ORGANISM: Lygus hesperus

<400> SEQUENCE: 153
tgtcgatggc ggtcttaaca tcccccattc caccaagagg ttccctgggt acgacagtga      60
gtctaaggaa ttcaacgctg aggtccacag gaagcacatt ttcggcattc acgtcgctga     120
ctacatgcgt cagctggctg aagaggatga cgatgcttac aagaagcagt tctcgcagta     180
tgtcaagaac ggagtcactg ctgacagcat tgaaagtatc tacaagaagg ctcacgaagc     240
aatccgagct gatccaactc gcaaaccact tgagaagaag gaagtcaaga agaagaggtg     300
gaaccgcgcc aagctttcct tgtctgaaag gaagaacacc atcaaccaaa agaaggcaac     360
ttatctcaag aaagtggaag ctggaga                                         387

<210> SEQ ID NO 154
<211> LENGTH: 745
<212> TYPE: DNA
<213> ORGANISM: Lygus hesperus

<400> SEQUENCE: 154
gtcctacgtg tttccggaaa aacgtgcatt tcgcgtaccc ctcgtggtga tccgttttca      60
tagaaataat ccaaaatggc tcccaagggg aataatatga ttcccaatgg ccatttccac     120
aaggattggc agaggttcat caaaacctgg ttcaaccagc tgcccgcaa gttgaggagg      180
agaaacaaga ggttggagaa ggcccaacgg ctcgcgcccc gccccgcggg acctcttcgc     240
cccgctgtca gatgtcccac cgtcaggtac cacaccaagc tacgacctgg acgtggcttc     300
accttggaag aaatcaagag agccggtctg tgcaaaggat tcgcgatgtc catcggaatc     360
gctgtcgacc ccagaagaag gaataaatcc atcgagtccc tccaactcaa tgtacagaga     420
ctcaaggagt acagggctaa gcttatcctc ttcccacaca gaatgccaa gaaactgaag      480
aagggagaag ctactgagga agagaggaag gtggccaccc aacagcccct gccagttatg     540
cccatcaagc aaccagtcat caaattcaag gctcgcgtca ttacagacga tgagaagaaa     600
tactctgcct tcaccgccct ccgcaaggga cgagcagacc aaaggttggt cggtatccgt     660
gctaagcgcg caaaggaagc cgcagaaaac gccgaagacc cctctaaagc tcctaaaaaa     720
aaaaaaaaaa aaaaaaaaaa aaaaa                                           745

<210> SEQ ID NO 155
<211> LENGTH: 527
<212> TYPE: DNA
<213> ORGANISM: Lygus hesperus

<400> SEQUENCE: 155
aacgtgcatt tcgcgtaccc ctcgtggtga tccgttttca tagaaataat ccaaaatggc      60
tcccaagggg aataatatga ttcccaatgg ccatttccac aaggattggc agaggttcat     120
caaaacctgg ttcaaccagc tgcccgcaa gttgaggagg agaaacaaga ggttggagaa      180
ggcccaacgg ctcgcgcccc gccccgcggg acctcttcgc cccgctgtca gatgtcccac     240
cgtcaggtac cacaccaagc tacgacctgg acgtggcttc accttggaag aaatcaagag     300
agccggtctg tgcaaaggat tcgcgatgtc catcggaatc gctgtcgacc ccagaagaag     360
gaataaatcc atcgagtccc tccaactcaa tgtacagaga ctcaaggagt acagggctaa     420
gcttatcctc ttcccacaca gaatgccaa gaaactgaag aagggagaag ctactgagga      480
agagaggaag gtggccaccc aacagcccct gccagttatg cccatca                   527
```

<210> SEQ ID NO 156
<211> LENGTH: 576
<212> TYPE: DNA
<213> ORGANISM: Lygus hesperus

<400> SEQUENCE: 156

| | | | | | |
|---|---|---|---|---|---|
| gccttattga | acgtggtcga | cagaaaactc | ggtttctgag | ctcatctcaa | catggatatc | 60 |
| gaagaaccgg | ccgcggcccc | tacggagccc | tcggacgtca | acaccgccct | tcaagaggtc | 120 |
| ctcaaggccg | cccttcaaca | cggagtcgtc | gtccacggta | ccacgagtc | cgccaaggcc | 180 |
| ctcgacaaga | ggcaagcttt | gttgtgcgtc | ctcgctgaga | actgcgacga | gccgatgtac | 240 |
| aagaagctgg | tacaagccct | ctgctcagag | caccacatcc | cctcgtcaa | agtagattcc | 300 |
| aataagaaac | tcggcgaatg | gacgggcctt | gcaagatcg | acaagaccgg | caaatctagg | 360 |
| aaaatcgtcg | gctgctcttg | tgtcgtcatc | aaggactggg | gtgaggacac | gccccacttg | 420 |
| gacctcctca | aggactacat | cagggacgtc | ttctaagaag | tttctcctca | atttcctttt | 480 |
| tataatgatt | taacaactga | gaattaataa | taaaaatgtt | aaattaaaca | aaaaaatctc | 540 |
| aaaactgtaa | aaaaaagaa | gaaaaaaaaa | aaaaaa | | | 576 |

<210> SEQ ID NO 157
<211> LENGTH: 442
<212> TYPE: DNA
<213> ORGANISM: Lygus hesperus

<400> SEQUENCE: 157

| | | | | | |
|---|---|---|---|---|---|
| ccttattgaa | cgtggtcgac | agaaaactcg | gtttctgagc | tcatctcaac | atggatatcg | 60 |
| aagaaccggc | cgcggcccct | acggagccct | cggacgtcaa | caccgcccct | caagaggtcc | 120 |
| tcaaggccgc | ccttcaacac | ggagtcgtcg | tccacggtat | ccacgagtcc | gccaaggccc | 180 |
| tcgacaagag | gcaagctttg | ttgtgcgtcc | tcgctgagaa | ctgcgacgag | ccgatgtaca | 240 |
| agaagctggt | acaagccctc | tgctcagagc | accacatccc | cctcgtcaaa | gtagattcca | 300 |
| ataagaaact | cggcgaatgg | acgggccttt | gcaagatcga | caagaccggc | aaatctagga | 360 |
| aaatcgtcgg | ctgctcttgt | gtcgtcatca | aggactgggg | tgaggacacg | ccccacttgg | 420 |
| acctcctcaa | ggactacatc | ag | | | | 442 |

<210> SEQ ID NO 158
<211> LENGTH: 601
<212> TYPE: DNA
<213> ORGANISM: Lygus hesperus

<400> SEQUENCE: 158

| | | | | | |
|---|---|---|---|---|---|
| ctttcatttg | tatagtacgg | acgggtagtt | tagttgtgtc | ggttcatcgt | aattcatcgg | 60 |
| ctgaatcatg | aagatgaata | aattggtcac | ttcctcgagg | aggaagaaca | ggaagaggca | 120 |
| cttcaccgcc | ccatcccaca | tccgtagaaa | gttgatgtcg | gcaccactgt | ccaaagaact | 180 |
| taggcagaag | tacaacgtcc | gaactatgcc | tgtgaggaag | gacgatgaag | tccaggttgt | 240 |
| acgaggacac | tacaaaggcc | aacaggttgg | caaagtcctc | caggtgtaca | ggaagaagtt | 300 |
| cattatttac | attgagcgga | tccaaagaga | aaaagccaat | ggtgccagcg | tttacgttgg | 360 |
| cattcacccc | tcaaagtgtg | tgatcgtcaa | attgaaggtc | gacaaggata | ggaaagaaat | 420 |
| ccttgacaga | agatccaaag | gacgtgactt | ggcacttggc | aaggacaagg | gcaaatacac | 480 |
| cgaagacagt | acgactgcta | tggacacgtc | ttaaattaat | ttggtttatt | tggttcctta | 540 |

```
actccgttct tctttaataa tgactttttt aaagcaaaaa aaaaaaaaaa aaaaaaaaa     600
a                                                                   601
```

<210> SEQ ID NO 159
<211> LENGTH: 448
<212> TYPE: DNA
<213> ORGANISM: Lygus hesperus

<400> SEQUENCE: 159

```
gtacggacgg gtagtttagt tgtgtcggtt catcgtaatt catcggctga atcatgaaga    60
tgaataaatt ggtcacttcc tcgaggagga agaacaggaa gaggcacttc accgccccat   120
cccacatccg tagaaagttg atgtcggcac cactgtccaa agaacttagg cagaagtaca   180
acgtccgaac tatgcctgtg aggaaggacg atgaagtcca ggttgtacga ggacactaca   240
aaggccaaca ggttggcaaa gtcctccagg tgtacggaa gaagttcatt atttacattg    300
agcggatcca agagaaaaa gccaatggtg ccagcgttta cgttggcatt caccctcaa    360
agtgtgtgat cgtcaaattg aaggtcgaca aggataggaa agaaatcctt gacagaagat   420
ccaaaggacg tgacttggca cttggcaa                                      448
```

<210> SEQ ID NO 160
<211> LENGTH: 456
<212> TYPE: DNA
<213> ORGANISM: Lygus hesperus

<400> SEQUENCE: 160

```
ggctgttgtc ggctggtcat atcccgtttt ccacgtggtg tgtcgagtta ttttcttgt     60
aaattcgcat ttaaaatcgg atttataacc gaaattcatt atggaaaagc cagtagtttt   120
ggcccgtgtc atcaaaatcc tcggacgtac cggctcacag gccaatgta cgcaagtgaa    180
ggtggagttc attggtgagc agaaccgaca gatcatcagg aacgtgaaag gaccagttag   240
agaaggcgac atcctcacac tcctagagtc tgaaagagaa gcgagaagac tgaggtagtg   300
ggaggtggcg atgcgttacg ttattttact tcattcaaca tttgaaaaaa accatcttcg   360
tgacaaaaaa catcttcacg caactatttg tattacctat gtttcgtaaa taaagtaacc   420
tcgttactta aaaaaaaaaa aaaaaaaaa aaaaaa                              456
```

<210> SEQ ID NO 161
<211> LENGTH: 321
<212> TYPE: DNA
<213> ORGANISM: Lygus hesperus

<400> SEQUENCE: 161

```
ctgttgtcgg ctggtcatat cccgttttcc acgtggtgtg tcgagttatt tttcttgtaa    60
attcgcattt aaaatcggat ttataaccga aattcattat ggaaaagcca gtagttttgg   120
cccgtgtcat caaaatcctc ggacgtaccg gctcacaggg ccaatgtacg caagtgaagg   180
tggagttcat tggtgagcag aaccgacaga tcatcaggaa cgtgaaagga ccagttagag   240
aaggcgacat cctcacactc ctagagtctg aaagagaagc gagaagactg aggtagtggg   300
aggtggcgat gcgttacgtt a                                             321
```

<210> SEQ ID NO 162
<211> LENGTH: 865
<212> TYPE: DNA
<213> ORGANISM: Lygus hesperus

<400> SEQUENCE: 162

```
aatcccggat tcatcgtttt attgaattgt ttttcgaagt ttctggtatt atcgttaaat      60
tagtctgtta agccctcatc cgtgatttgg caagttgttg attgttctat tttccttttt     120
ccagaaaatg gggagacgtc cagcgaggtg ttatcggtac tgtaaaaaca agccataccc     180
ccaaatcccg gttctgtcgt ggtgtccccg accccaagat caggatcttc gatctgggaa     240
agaagaaggc ccgcgtggaa gacttccccc tctgcgttca cctcgtctcc gatgagtacg     300
agcagctgtc ctccgaagcc ctcgaggcag gacgtatctg ctgcaacaag tacctcgtca     360
agaactgcgg caaggaccag ttccacatca ggatgaggct ccaccccttc cacgtcatta     420
ggatcaacaa aatgttatcg tgcgctggag ctgataggct ccagacaggg atgagaggag     480
cgttcggaaa gccgcaagga accgtcgctc gcgtccgcat cggtcagccc atcatgagcg     540
tccgctcgtc cgacaggtac aaggccgccg tcatcaaggc tctgaggaga gccaaattca     600
agttccctgg tcgccagaag atctacgttt ccaagaaatg gggcttcacc aagttcgacc     660
gcgaagagta cgagggcctt aggaacgaca acaaactagc gaatgacggc tgcaacgtca     720
aattgaggcc ggatcacgga cctttgcagg cgtggaggaa ggctcagctt gacatcgctg     780
ctggcctcta aattactttc aatggtttt  ataaatcaac aaataaaact cgttttatgt     840
aaaaaaaaaa aaaaaaaaa aaaaa                                            865
```

<210> SEQ ID NO 163
<211> LENGTH: 792
<212> TYPE: DNA
<213> ORGANISM: Lygus hesperus

<400> SEQUENCE: 163

```
ggttcctttc tcagattttg actttgccgt gttgtctctc ccaatttttcc aaaatgggga    60 gacgtccagc gaggtgttat cggtactgta aaaacaagcc ataccccaaa tcccggttct   120
gtcgtggtgt ccccgacccc aagatcagga tcttcgatct gggaagaag aaggcccgcg    180 tggaagactt cccctctgc gttcacctcg tctccgatga gtacgagcag ctgtcctccg    240
aagccctcga ggcaggacgt atctgctgca acaagtacct cgtcaagaac tgcggcaagg    300
accagttcca catcaggatg aggctccacc ccttccacgt cattaggatc aacaaaatgt    360
tatcgtgcgc tggagctgat aggctccaga cagggatgag aggagcattc ggaaagccgc    420
aaggaaccgt cgctcgcgtc cgcatcggtc agcccatcat gagcgtccgc tcgtccgaca    480
ggtacaaggc cgccgtcatc gaggctctga ggagagccaa attcaagttc cctggtcgcc    540
agaagatcta cgtttccaag aaatggggct tcaccaagtt cgaccgcgaa gagtacgagg    600
gccttaggaa cgacaacaaa ctagcgaatg cggctgcaa cgtcaaattg aggccggatc    660
acggaccttt gcaggcgtgg aggaaggctc agcttgacat cgctgctggc ctctaaatta    720
ctttccaatg gttttataaa tcaacaaata aaactcgttt tatctaaaaa aaaaaaaaa    780 aaaaaaaaaa aa                                                       792
```

<210> SEQ ID NO 164
<211> LENGTH: 645
<212> TYPE: DNA
<213> ORGANISM: Lygus hesperus

<400> SEQUENCE: 164

```
agccctcatc cgtgatttgg caagttgttg attgttctat tttccttttt ccagaaaatg     60
gggagacgtc cagcgaggtg ttatcggtac tgtaaaaaca agccataccc ccaaatcccg    120
```

```
gttctgtcgt ggtgtccccg accccaagat caggatcttc gatctgggaa agaagaaggc    180
ccgcgtggaa gacttccccc tctgcgttca cctcgtctcc gatgagtacg agcagctgtc    240
ctccgaagcc ctcgaggcag gacgtatctg ctgcaacaag tacctcgtca agaactgcgg    300
caaggaccag ttccacatca ggatgaggct ccaccccttc cacgtcatta ggatcaacaa    360
aatgttatcg tgcgctggag ctgataggct ccagacaggg atgagaggag cgttcggaaa    420
gccgcaagga accgtcgctc gcgtccgcat cggtcagccc atcatgagcg tccgctcgtc    480
cgacaggtac aaggccgccg tcatcaaggc tctgaggaga gccaaattca agttccctgg    540
tcgccagaag atctacgttt ccaagaaatg gggcttcacc aagttcgacc gcgaagagta    600
cgagggcctt aggaacgaca acaaactagc gaatgacggc tgcaa               645
```

<210> SEQ ID NO 165
<211> LENGTH: 619
<212> TYPE: DNA
<213> ORGANISM: Lygus hesperus

<400> SEQUENCE: 165

```
gctttaccga ttccgttctt gtttagtcca cgtttctctg ctcattcgtg cagattttaa     60
aacatgacca actccaaagg ttatcgtcgc ggaacgaggg atctcttctc gaggcccttc    120
cgtcaccatg gtgtcatccc actctcaacg tacatgaaag tataccgagt aggagacatc    180
gtatctatca aaggtaatgg agcagtgcaa aaaggtatgc cccacaaagt ttaccacggc    240
aagaccggac gagtctacaa tgttacacct cgcgcccttg gtgttattgt caacaagagg    300
gttcgtggaa aaatccttcc caagaggatc aacatcagga ttgaacacgt caaccacagt    360
aaatgcagag aagatttctt gaagcgagtg cgagaaaatg aaaggctccg caaattcgcc    420
aaagaaactg gcaccagggt tgaactcaaa agacagcctg ctcagccacg ccctgcacac    480
tttgtacaag ctaaagaagt cccagagctg ctggccccca taccttacga gttcatcgct    540
taaaaaattt tcaattccat cttaactttta tatatttgaa taaaattgtg ttctcaaaaa    600
aaaaaaaaaa aaaaaaaa                                               619
```

<210> SEQ ID NO 166
<211> LENGTH: 461
<212> TYPE: DNA
<213> ORGANISM: Lygus hesperus

<400> SEQUENCE: 166

```
acgtttctct gctcattcgt gcagatttta aacatgacc aactccaaag gttatcgtcg     60
cggaacgagg gatctcttct cgaggccctt ccgtcaccat ggtgtcatcc cactctcaac    120
gtacatgaaa gtataccgag taggagacat cgtatctatc aaaggtaatg gagcagtgca    180
aaaaggtatg ccccacaaag tttaccacgg caagaccgga cgagtctaca atgttacacc    240
tcgcgccctt ggtgttattg tcaacaagag ggttcgtgga aaaatccttc ccaagaggat    300
caacatcagg attgaacacg tcaaccacag taaatgcaga gaagatttct tgaagcgagt    360
gcgagaaaat gaaaggctcc gcaaattcgc caaagaaact ggcaccaggg ttgaactcaa    420
aagacagcct gctcagccac gccctgcaca ctttgtacaa g                        461
```

<210> SEQ ID NO 167
<211> LENGTH: 481
<212> TYPE: DNA
<213> ORGANISM: Lygus hesperus

<400> SEQUENCE: 167

```
caacgtacat gaaagtatac cgagtaggag acatcgtatc tatcaaaggt aatggagcag    60
tgcaaaaagg tatgccccac aaagtttacc acggcaagac cggacgagtc tataatgtta   120
cacctcgcgc ccttggtgtt attgtcaaca agagggttcg tggaaaaatc cttcccaaga   180
ggatcaacat caggattgaa cacgtcaacc acagtaaatg cagagaagat ttcttgaagc   240
gagtgcgaga aaatgagagg ctccgcaaat tcgccaaaga aactggcacc agggttgaac   300
tcaaaagaca gcctgctcag ccacgccctg cacactttgt acaagctaaa gaagtcccag   360
agctgctggc ccccatacct tacgagttca tcgcttaaac aatttttcaat tccatcttaa   420 ctttatatat ttgaataaaa ttgtgttccc taaaaaaaaa aaaaaaaaaa aaaaaaaaaa   480
a                                                                 481

<210> SEQ ID NO 168
<211> LENGTH: 747
<212> TYPE: DNA
<213> ORGANISM: Lygus hesperus

<400> SEQUENCE: 168
gcataaatat ataggggcgat tgatttagcg gccgcgaatt cgcccttaag cagtggtatc    60
aacgcagagg gggggtcttc tctcccggtt ttcttcttgc ccgaatcgtc catcctgatg   120
ttggggtcac tgtcaccacg accataccc aatttgggt atggcttggt tgtcccctac   180
ccataaatcc tgattggaca tctccccatt atgaaagact gcgagaaaca cccctgcccc   240
cggctttaaa cccacggcta agggggggatt cgcgggcggc aaatttcatt cggcccatag   300
tgagtcgtat tacaattcac tgggcgtcct ttttacacct tcggaccggg aaaaacctgg   360
cggttaccca aaatccgtta tttgccacat ccccctttac tccactgggt tatataacaa   420
agaggcccct tccaatgtcc tttcccaaaa gtgcgcagcc ctatactaat ggcctttaaa   480
ggaaccccta ttaaaaaaaa aacccttaac cacaggttgg tgatgtaacc aaggaaaata   540
atgaacacac cgggccaaag aaggtgatac ccctggtctt ggcgaccgcc tgtcaaatct   600
tcctcccgga acgaaacccg tagtggcatc gaggaataac cttgcgcatc atagactcca   660
aatggccact gtggccgctc tcgattcatg aagaaatga gatgacccct accccgcgca   720
aaaggattca gaaccaatac cagaatc                                    747

<210> SEQ ID NO 169
<211> LENGTH: 1052
<212> TYPE: DNA
<213> ORGANISM: Lygus hesperus
<220> FEATURE:
<221> NAME/KEY: misc_feature
<222> LOCATION: (662)..(665)
<223> OTHER INFORMATION: n is a, c, g, or t

<400> SEQUENCE: 169
ggttttcttc ttgcccgaat cgtccatcct gatgttgggg tcactgtcac cacgaccata    60
ccccaatttg gggtatggct tggttgtccc ctacccataa atcctgattg gacatctccc   120
cattatgaaa gactgcgaga aacacccctg ccccggctt taaacccacg gctaaggggg   180
gattcgcggg cggcaaattt cattcggccc atagtgagtc gtattacaat tcactgggcg   240
tcctttttac accttcggac cgggaaaaac ctggcggtta cccaaaatcc gttatttgcc   300
acatccccct ttactccact gggttatata caaagaggc ccttccaat gtcctttccc   360 aaaagtgcgc agccctatac taatggcctt taaaggaacc cctattaaaa aaaaaaccct   420
```

```
taaccacagg ttggtgatgt aaccaaggaa aataatgaac acaccgggcc aaagaaggtg      480
atacccctgg tcttggcgac cgcctgtcaa atcttcctcc cggaacgaaa cccgtagtgg      540
catcgaggaa taaccttgcg catcatagac tccaaatggc cactgtggcc gctctcgatt      600 catgaagaa atgagatgac ccctaccccg cgcaaaagga ttcagaacca ataccagaat       660
cnnnntagca aaacggctat ttcccggttc tttgtcggat tcttttgcca gggccatgcc      720
ttttcccgga atggaaggcg ggctgtttga gaaacgcatt aaatgggatt agtccattca      780
taggccaccc aaggaaacca ctttaatttc gggttggtag gttgagagaa atggtgaggg      840
gtaacaattt tacaccggga accgtttatg cccagaatta ccccagcttc gaattaaccc      900
cccctaaagg ggatagttcc gccgggttaa aagaaattcg ccttaaacca gtgttttaaa      960
gcaggagaca gaagtgtttc tcgcaagctt tcaaatgggg agatgtccaa atcaggattt     1020
atgggtaggg tacaaccaag ccgaacccca aa                                   1052

<210> SEQ ID NO 170
<211> LENGTH: 555
<212> TYPE: DNA
<213> ORGANISM: Lygus hesperus

<400> SEQUENCE: 170
tagcaaaacg gctatttccc ggttctttgt cggattcttt tgccagggcc atgccttttc       60
ccggaatgga aggcgggctg tttgagaaac gcattaaatg ggattagtcc attcataggc      120
cacccaagga aaccacttta atttcgggtt ggtaggttga gagaaatggt gaggggtaac      180
aattttacac cggaaccgt ttatgcccag aattacccca gcttcgaatt aaccccccct       240 aaagggggata gttccgccgg gttaaaagaa attcgcctta aaccagtgtt ttaaagcagg     300
agacagaagt gtttctcgca agctttcaaa atggggagat gtccaatcag gatttatggg     360
tagggtacaa ccaagccgaa ccccaaatcc ctgttctgtc gtggtgacag tgaccccaag      420
atctggatgt tcgttttggg aaagaagaaa accgggaggg accacttcct cctctgcgtt      480
gataccactg cttaagggcg aattcgttta aacctgcagg actagtccct tagtgagggt      540
aatctagcag cccac                                                      555

<210> SEQ ID NO 171
<211> LENGTH: 1052
<212> TYPE: DNA
<213> ORGANISM: Lygus hesperus
<220> FEATURE:
<221> NAME/KEY: misc_feature
<222> LOCATION: (662)..(665)
<223> OTHER INFORMATION: n is a, c, g, or t

<400> SEQUENCE: 171
ggttttcttc ttgcccgaat cgtccatcct gatgttgggg tcactgtcac cacgaccata       60
ccccaatttg gggtatggct tggttgtccc ctacccataa atcctgattg gacatctccc      120
cattatgaaa gactgcgaga acacccctg ccccccggctt taaacccacg gctaaggggg     180
gattcgcggg cggcaaattt cattcggccc atagtgagtc gtattacaat tcactgggcg      240 tccttttac accttcggac cgggaaaaac ctggcggtta cccaaaatcc gttatttgcc      300 acatcccct ttactccact gggttatata acaagaggc ccttccaat gtcctttccc        360 aaaagtgcgc agccctatac taatggcctt taaaggaacc cctattaaaa aaaaaccct      420 taaccacagg ttggtgatgt aaccaaggaa aataatgaac acaccgggcc aaagaaggtg      480
atacccctgg tcttggcgac cgcctgtcaa atcttcctcc cggaacgaaa cccgtagtgg      540
```

```
catcgaggaa taaccttgcg catcatagac tccaaatggc cactgtggcc gctctcgatt      600 catgaagaa atgagatgac ccctaccccg cgcaaaagga ttcagaacca ataccagaat       660
cnnnntagca aaacggctat ttcccggttc tttgtcggat tcttttgcca gggccatgcc     720
ttttcccgga atggaaggcg ggctgtttga gaaacgcatt aaatgggatt agtccattca     780
taggccaccc aaggaaacca ctttaatttc ggggttggtag gttgagagaa atggtgaggg    840
gtaacaattt tacaccggga accgtttatg cccagaatta ccccagcttc gaattaaccc    900
cccctaaagg ggatagttcc gccgggttaa aagaaattcg ccttaaacca gtgttttaaa    960
gcaggagaca gaagtgtttc tcgcaagctt tcaaaatggg gagatgtcca atcaggattt   1020
atgggtaggg tacaaccaag ccgaacccca aa                                 1052

<210> SEQ ID NO 172
<211> LENGTH: 1175
<212> TYPE: DNA
<213> ORGANISM: Lygus hesperus

<400> SEQUENCE: 172
ctcagcgaga tccctaagac aacgcctgcc acgtgggaga atatcggaca cgcctcccca     60
gagtgcggaa aggggaacgg cgttccgtat cggtcaaggt gcaagcttcg gaaccggagg    120
acgaccgttg caaggtgcaa ggggcaggta tcttgtattt tcattgtgcg tgtcgacatc    180
taccaaactg agacttggag ttcgatattt tgacgatggg gccgggggcc ggaggcaaaa    240
cgacaaacac aggcaccgtg accgtgttcc ggtccctggc ctgcgttgcc ttacgttcac    300
atcttgttct tgcgctttct ctggttttac gataacccta ctacgagttt agtagagccg    360
atcccgtagc cgaagccaaa gcccaagcgc tccgtatccg agaacgcgga agagcacgaa    420
ctccccaaac ccctccgccc ctcccccgcg cgtatccgaa acacaaatgc agcgggcagt    480
acaggttttg gaaggggacg cgggcagtga gcgcaatgca agtaaatgtg attagctcat    540
ggctacgcag ccctgctttt tcagtttcgg ttcggatcgt taggggggtgt gggattggga  600 gcggattcaa tctggacagg aaacagctat gaccaaggtc acgccaagct ctgaattaac    660
cctcaggaaa gggactagtc cggcaggttg aaacgaactc gccccctaagc agtggtatca   720 gagcacagtg gttttttttt tttgtttttt ttcgtagaaa aaaatatgta ttaagtcaat    780
taattaaatc attggttttc tggcttcaca acaggtggca cgtgctgtgc tcggagaaat    840
ttatgaacta tgttctgttc ttcaatgagg aaagatgaga tgatccattc tcagacacat    900
tcagacagag gacaccaccg taagccctat ccacagtctg tccacgtaag gggatcgtgt    960 cccctttccat gggcagagca gggagagggc cgtaagcttg ttcttgcgtc atcaacatgt   1020
gggggtaatg ttggtcatag cgatgttcgg tacacaagag aaccacctgg tgtaatcatt    1080
acagcacagc aatactctgt gttttgtaag ataacaaaaa aggtacttaa gacgctgaac    1140
cattttctac gatcggaaaa caaaaaaaaa gaaaa                              1175

<210> SEQ ID NO 173
<211> LENGTH: 1023
<212> TYPE: DNA
<213> ORGANISM: Lygus hesperus

<400> SEQUENCE: 173
tcagcgagat ccctaagaca acgcctgcca cgtgggagaa tatcggacac gcctccccag     60
agtgcggaaa ggggaacggc gttccgtatc ggtcaaggtg caagcttcgg aaccggagga    120
```

```
cgaccgttgc aaggtgcaag gggcaggtat cttgtatttt cattgtgcgt gtcgacatct    180
accaaactga gacttggagt tcgatatttt gacgatgggg ccgggggccg gaggcaaaac    240
gacaaacaca ggcaccgtga ccgtgttccg gtccctggcc tgcgttgcct tacgttcaca    300
tcttgttctt gcgctttctc tggttttacg ataaccctac tacgagttta gtagagccga    360
tcccgtagcc gaagccaaag cccaagcgct ccgtatccga gaacgcggaa gagcacgaac    420
tccccaaacc cctccgcccc tccccgcgcg tatccgaaaa cacaaatgca gcgggcagta    480
caggttttgg aaggggacgc gggcagtgag cgcaatgcaa gtaaatgtga ttagctcatg    540
gctacgcagc cctgcttttt cagtttcggt tcggatcgtt aggggtgtg  ggattgggag    600 cggattcaat ctggacagga aacagctatg accaaggtca cgccaagctc tgaattaacc    660
ctcaggaaag ggactagtcc ggcaggttga aacgaactcg cccctaagca gtggtatcag    720
agcacagtgg ttttttttt   ttgttttttt tcgtagaaaa aaatatgtat taagtcaatt    780
aattaaatca ttggttttct ggcttcacaa caggtggcac gtgctgtgct cggagaaatt    840
tatgaactat gttctgttct tcaatgagga aagatgagat gatccattct cagacacatt    900
cagacagagg acaccaccgt aagccctatc cacagtctgt ccacgtaagg ggatcgtgtc    960
cccttccatg ggcagagcag ggagagggcc gtaagcttgt tcttgcgtca tcaacatgtg    1020
ggg                                                                  1023
```

<210> SEQ ID NO 174
<211> LENGTH: 454
<212> TYPE: DNA
<213> ORGANISM: leptinotarsa decemlineata

<400> SEQUENCE: 174

```
ccaagaaggc caagaagggg tttatgaccc ctgagaggaa gaagaaactt aggttattgc     60
tgagaaagaa agcagcagaa gaactgaaaa agaacaaga  acgcaaagct gccgaaagga    120
gacgtattat tgaagagaga tgcggaaaac caaaactcat tgatgaggca aatgaagagc    180
aggtgaggaa ctattgcaag ttatatcacg gtagaatagc taaactggag gaccagaaat    240
ttgatttgga ataccttgtc aaaaagaaag acatggagat cgccgaattg aacagtcaag    300
tcaacgacct caggggtaaa ttcgtcaaac ccactctcaa gaaagtatcc aaatacgaga    360
acaaatttgc taaactccaa aagaaagcag cagaattcaa tttccgtaat caactgaaag    420
ttgtaaagaa gaaggagttc accctggagg agga                                454
```

<210> SEQ ID NO 175
<211> LENGTH: 431
<212> TYPE: DNA
<213> ORGANISM: leptinotarsa decemlineata

<400> SEQUENCE: 175

```
ggtttatgac ccctgagagg aagaagaaac ttaggttatt gctgagaaag aaagcagcag     60
aagaactgaa aaagaacaa  gaacgcaaag ctgccgaaag gagacgtatt attgaagaga    120
gatgcggaaa accaaaactc attgatgagg caaatgaaga gcaggtgagg aactattgca    180
agttatatca cggtagaata gctaaactgg aggaccagaa atttgatttg gaataccttg    240
tcaaaaagaa agacatggag atcgccgaat tgaacagtca agtcaacgac ctcaggggta    300
aattcgtcaa acccactctc aagaaagtat ccaaatacga gaacaaattt gctaaactcc    360
aaaagaaagc agcagaattc aatttccgta atcaactgaa agttgtaaag aagaaggagt    420
tcaccctgga g                                                         431
```

<210> SEQ ID NO 176
<211> LENGTH: 888
<212> TYPE: DNA
<213> ORGANISM: leptinotarsa decemlineata

<400> SEQUENCE: 176
agcagtggta tcaacgcaga gtacgcgggg acatcgagga gaagaggcaa cgcctcgaag 60
aggctgaaaa gaaacgccag gccatgatgc aggccctcaa ggaccagaac aagaacaagg 120
ggcccaactt caccatcacc aagagggatg cttcatctaa cctttctgcc gctcagttgg 180
aacgcaacaa gaccaaggag caactcgagg aagagaagaa aatttccctt tccatccgca 240
tcaagccctt ggtcgttgat ggtctgggcg tagataaact ccgtctgaaa gcacaagaac 300
tttgggaatg catcgtcaag ttggagactg aaaagtacga cttggaagag aggcagaaac 360
gtcaagacta cgatctcaaa gagctgaaag aaagacagaa acaacagctg agacacaaag 420
ccttgaagaa gggtctagac ccagaagccc taaccggcaa atacccgcct aaaatccaag 480
tagcctccaa atatgaacgt cgtgttgaca cgaggtcgta tggagacaaa aagaagctat 540
tcgaaggggg attagaagaa atcattaaag agaccaatga aaagagctgg aaagagaaat 600
ttggacagtt cgattccaga caaaaggcaa gacttcccaa gtggttcggt gaacgtcctg 660
gcaaaaaacc tggagatccc gaaactccag aaggcgagga ggagggcaaa caagtcattg 720
atgaggatga cgacctcaag gagcctgtaa tcgaagctga aattgaagaa gaggaggaag 780
aagaggaagt cgaggtcgat gaagaagaag aggatgacga agaagaagaa gaagaagagt 840
gaatgccaaa ggcagaagat aatcatgaaa tcaacattag ataacgtc 888

<210> SEQ ID NO 177
<211> LENGTH: 404
<212> TYPE: DNA
<213> ORGANISM: leptinotarsa decemlineata

<400> SEQUENCE: 177
caaggaccag aacaagaaca aggggcccaa cttcaccatc accaagaggg atgcttcatc 60
taacctttct gccgctcagt tggaacgcaa caagaccaag gagcaactcg aggaagagaa 120
gaaaatttcc ctttccatcc gcatcaagcc cttggtcgtt gatggtctgg gcgtagataa 180
actccgtctg aaagcacaag aactttggga atgcatcgtc aagttggaga ctgaaaagta 240
cgacttggaa gagaggcaga aacgtcaaga ctacgatctc aaagagctga aagaaagaca 300
gaaacaacag ctgagacaca aagccttgaa gaagggtcta gacccagaag ccctaaccgg 360
caaatacccg cctaaaatcc aagtagcctc caaatatgaa cgtc 404

<210> SEQ ID NO 178
<211> LENGTH: 1155
<212> TYPE: DNA
<213> ORGANISM: leptinotarsa decemlineata

<400> SEQUENCE: 178
gctcttcaga atgaacttga agaatctcgt acactgttgg aacaagctga ccgtgcccgt 60
cgccaagcag aacaagaatt gggagatgct cacgaacaat tgaatgatct tggtgcacag 120
aatggttctc tgtctgccgc caagaggaaa ctggaaactg aactccaaac tctccattcc 180
gatcttgatg aacttctcaa tgaagccaag aactctgagg agaaggctaa gaaagccatg 240
gtcgatgcag ctcgtcttgc agatgaactg agagcagaac aagatcatgc acaaactcag 300

```
gagaaacttc gtaaagcctt agaatcacaa atcaaggacc ttcaagttcg tctcgacgag    360
gctgaagcta acgccctcaa aggaggtaag aaagcaatcg ctaaacttga caacgcgtc     420 agggaattgg agaatgagtt agatggtgaa caaagacgac acgccgatgc tcaaaagaat    480
ttgagaaagt ccgaacgtcg catcaaggag ctcagcctcc aagctgaaga gaccgtaag    540 aaccacgaaa aaatgcaaga cttagtcgac aaacttcaac agaaaatcaa gacccacaag    600
aggcaaatag aagaagctga gaaatagcg gctctcaatt tggccaaatt ccgtaaagca     660
caacaggaat tggaagaagc agaagagcgt gcagaccttg ctgaacaagc aattgtcaaa    720
ttccgtacca agggacgttc tggatcagca gctaggggag ccagccctgc gcctcagcga    780
cagcgtccca cattcggaat gggagattca cttggaggtg ccttccctcc aaggttcgat    840
cttgcacccg actttgaatg aatctgacat tgtgttataa gtgtaaggtg aacattctat    900
cgcagtgtaa atatcatccc aatgcgaatc aattctacat tcagtttaag tcattctatc    960
tctcaaaata ataatagtgt catccattct cactatcaaa tcaagacaag agatgatgat   1020
cagagaacac gtatcacatc tacagcaaac cctcagtcct cggcatctct gataatattt   1080
tcaattatcg agattgatga tatcgggtgt tgaatgctga tgaatagaag gcgccctatg   1140
gaaataagag agaag                                                   1155

<210> SEQ ID NO 179
<211> LENGTH: 523
<212> TYPE: DNA
<213> ORGANISM: leptinotarsa decemlineata

<400> SEQUENCE: 179
gaatctcgta cactgttgga acaagctgac cgtgcccgtc gccaagcaga acaagaattg     60
ggagatgctc acgaacaatt gaatgatctt ggtgcacaga atggttctct gtctgccgcc    120
aagaggaaac tggaaactga actccaaact ctccattccg atcttgatga acttctcaat    180
gaagccaaga actctgagga aaggctaag aaagccatgg tcgatgcagc tcgtcttgca    240
gatgaactga gagcagaaca agatcatgca caaactcagg agaaacttcg taaagcctta    300
gaatcacaaa tcaaggacct tcaagttcgt ctcgacgagg ctgaagctaa cgccctcaaa    360
ggaggtaaga aagcaatcgc taaacttgaa caacgcgtca gggaattgga gaatgagtta    420
gatggtgaac aaagacgaca cgccgatgct caaaagaatt tgagaaagtc cgaacgtcgc    480
atcaaggagc tcagcctcca agctgaagaa gaccgtaaga acc                      523

<210> SEQ ID NO 180
<211> LENGTH: 865
<212> TYPE: DNA
<213> ORGANISM: nilaparvata lugens

<400> SEQUENCE: 180
ctaggagtat ctcctacgta attcggtgct tgagccaact gcagctactc acttttttcc     60
aggttcagtg gtagggacgc aaacacagct aaaatggcgg acgatgaggc aaagaaggca    120
aagcaggcgg aaatcgaccg caagagagcc gaggtccgca agcggatgga ggaagcctcc    180
aaggccaaga aggccaagaa aggtttcatg acgcctgaca gaagaagaa gctcaggttg    240 ttgctgagga aaaaggctgc tgaggaattg aagaaggaac aggagaggaa agccgcggaa    300
aggagaagga tcatcgagga gaggtgtggc aaggctgttg atctcgatga cggaagtgaa    360
gagaaagtca aggcaacttt aaaaacctat cacgacagaa ttgaaaaatt ggaggatgaa    420
aaatttgacc tggaatatat tgtaaaaaag aaagacttcg agatcgctga cctcaacagc    480
```

```
caggtgaatg acctccgtgg taaatttgtc aagccaacct tgaaaaaagt ctccaaatat    540
gagaacaaat tcgccaagct ccagaagaaa gcagctgaat tcaatttcag aaatcagctc    600
aaagttgtca agaagaagga attcaccttg gaagaagaag acaaggagcc gaagaaatcg    660
gagaaagccg aatggcagaa gaaatgaact cacatcacct cttcataata ttgtcccaca    720
cttctacaac cttcatcaaa taacttttat tcgagtaaac ttactgttac taacaaaatt    780
acaaaaccaa actcttatca tcaacgtagg caatgtgctc aacttatttc ttaaacatat    840
tgtccagcta tttattgaaa ttaaa                                          865
```

<210> SEQ ID NO 181
<211> LENGTH: 269
<212> TYPE: DNA
<213> ORGANISM: nilaparvata lugens

<400> SEQUENCE: 181

```
aagaagaagc tcaggttgtt gctgaggaaa aaggctgctg aggaattgaa gaaggaacag     60
gagaggaaag ccgcggaaag gagaaggatc atcgaggaga ggtgtggcaa ggctgttgat    120
ctcgatgacg gaagtgaaga gaaagtcaag gcaactttaa aaacctatca cgacagaatt    180
ggaaaattgg aggatgaaaa atttgacctg gaatatattg taaaaagaa agacttcgag     240 atcgctgacc tcaacagcca ggtgaatga                                      269
```

<210> SEQ ID NO 182
<211> LENGTH: 553
<212> TYPE: DNA
<213> ORGANISM: nilaparvata lugens

<400> SEQUENCE: 182

```
aatgatggcg gctctcaagg accagagcaa atcgaaagga cccaacttca ccgtaaacaa     60
gaaaacagac ttgaacatga cgtcagctca aatggaaagg aacaagacta aggagcagct    120
ggaggaggag aagaagatct ctctgtcgtt ccgcatcaag ccgttggcca tcgagaacat    180
gagcatcaac gcactgcgcg ccaaggccca ggaactgtgg gactgcatcg tcaagctcga    240
aactgagaag tacgatctgg aggaacgcca gaagaggcag gactacgatc tcaaagaatt    300
gaaagaaaga caaaagcaac agctgaggca taaagccctc aaaaaaggtc tagaccctga    360
ggctctcaca ggaaagtacc caccaaaaat ccaagttgcc tccaaatatg aaagacgtgt    420
agatacaagg tcatacgacg acaagaagaa gctcttcgaa ggtggctggg acacattaac    480
atcagaaacc aatgagaaaa tatggaagag cagaaacgat cagttttcaa atcgtagcaa    540
ggctaaactg cca                                                       553
```

<210> SEQ ID NO 183
<211> LENGTH: 470
<212> TYPE: DNA
<213> ORGANISM: nilaparvata lugens

<400> SEQUENCE: 183

```
atgatggcgg ctctcaagga ccagagcaaa tcgaaaggac ccaacttcac cgtaaacaag     60
aaaacagact tgaacatgac gtcagctcaa atggaaagga caagactaa ggagcagctg    120 gaggaggaga agaagatctc tctgtcgttc gcatcaagc cgttggccat cgagaacatg    180
agcatcaacg cactgcgcgc caaggcccag gaactgtggg actgcatcgt caagctcgaa    240
actgagaagt acgatctgga ggaacgccag aagaggcagg actacgatct caaagaattg    300
```

| | |
|---|---|
| aaagaaagac aaaagcaaca gctgaggcat aaagccctca aaaaggtct agaccctgag | 360 |
| gctctcacag gaaagtaccc accaaaaatc caagttgcct ccaaatatga aagacgtgta | 420 |
| gatacaaggt catacgacga caagaagaag ctcttcgaag gtggctggga | 470 |

<210> SEQ ID NO 184
<211> LENGTH: 367
<212> TYPE: DNA
<213> ORGANISM: nilaparvata lugens

<400> SEQUENCE: 184

| | |
|---|---|
| tgccttcgac cgtgaaaggt ctggaagtat cccaacagac atggtcgccg acatcctcag | 60 |
| gctcatggga cagcctttca acaagaagat cctcgacgaa ctcattgagg aagttgatgc | 120 |
| tgacaaatct ggccgtcttg agtttgacga attcgtgact ctggccgcca aattcattgt | 180 |
| tgaggaagac gatgaggcaa tgcagaagga attgaaggaa gctttcagat tatacgacaa | 240 |
| ggaaggtaac ggctacatcc ccacatcatg tctgaaggaa atcttaaggg aacttgacga | 300 |
| tcagctgaca aacgaggaac tcaacatgat gattgatgag atcgactctg acggatcagg | 360 |
| aactgtt | 367 |

<210> SEQ ID NO 185
<211> LENGTH: 204
<212> TYPE: DNA
<213> ORGANISM: nilaparvata lugens

<400> SEQUENCE: 185

| | |
|---|---|
| acatcctcag gctcatggga cagcctttca acaagaagat cctcgacgaa cttattgagg | 60 |
| aggttgatgc tgacaagtct ggccgtctag agtttgacga attcgtgact ctggccgcca | 120 |
| aattcattgt tgaggaagac gatgaggcaa tgcagaagga attgaaggaa gctttcagat | 180 |
| tatacgacaa ggaaggtaac ggct | 204 |

<210> SEQ ID NO 186
<211> LENGTH: 221
<212> TYPE: DNA
<213> ORGANISM: nilaparvata lugens

<400> SEQUENCE: 186

| | |
|---|---|
| cgtaaaaact ctgaccggca agaccatcac cttggaagtg gagccttccg ataccattga | 60 |
| aaacgtgaag gccaagatcc aagacaagga gggaattcct cccgaccagc agagacttat | 120 |
| cttcgctgga aagcaactgg aggatggcag aaccctgtcc gactacaaca tccaaaaaga | 180 |
| atctacactc cacttggttc tcagacttcg tggtggaact a | 221 |

<210> SEQ ID NO 187
<211> LENGTH: 221
<212> TYPE: DNA
<213> ORGANISM: nilaparvata lugens

<400> SEQUENCE: 187

| | |
|---|---|
| cgtaaaaact ctgaccggca agaccatcac cttggaagtg gagccttccg ataccattga | 60 |
| aaacgtgaag gccaagatcc aagacaagga gggaattcct cccgaccagc agagacttat | 120 |
| cttcgctgga aagcaactgg aggatggcag aaccctgtcc gactacaaca tccaaaaaga | 180 |
| atctacactc cacttggttc tcagacttcg tggtggaact a | 221 |

<210> SEQ ID NO 188
<211> LENGTH: 759

```
<212> TYPE: DNA
<213> ORGANISM: Acyrthosiphon pisum

<400> SEQUENCE: 188
atggccgacg atgaagctaa gaaagcaaaa caggcggaaa tcgaccgcaa gagggccgaa      60
gtgcgcaagc gtatggaaga ggcgtccaag gccaagaagg ccaagaaggg tttcatgacc     120
ccagacagaa agaagaaact ccgtctgttg ttgaaaaaaa aggcggccga agagttgaag     180
aaagaacaag aacgcaaagc tgccgaacga aggcggatca tcgaagagcg gtgcggacaa     240
ccgaagaaca tcgacgacgc cggcgaagag gagcttgcgg aaatctgcga agaactatgg     300
aaacgggttt acaccgtaga gggcataaaa tttgacttgg aaagggatat caggatgaaa     360
gttttcgaga tcagcgaatt gaacagccaa gtcaatgact tacgaggaaa attcgtcaaa     420
ccaacattga agaaggtttc caaatacgaa aacaaattcg caaaactcca aaagaaagcg     480
gcggagttca acttcagaaa ccaactgaaa gtagtgaaga aaaaggagtt caccttggaa     540
gaagaagaca aagagaaaaa acccgattgg tccaaaaagg gagacgaaaa gaagggcgaa     600
ggagaagacg gcgacggtac cgaagacgaa aagaccgacg acggtttgac caccgaaggc     660
gaatcggtcg cgggcgatct aacggacgcg acggaagacg cgcagagcga caacgagata     720
ctcgaaccag aacccgtggt tgaacccgaa ccagaacca                            759

<210> SEQ ID NO 189
<211> LENGTH: 759
<212> TYPE: DNA
<213> ORGANISM: Acyrthosiphon pisum

<400> SEQUENCE: 189
atggccgacg atgaagctaa gaaagcaaaa caggcggaaa tcgaccgcaa gagggccgaa      60
gtgcgcaagc gtatggaaga ggcgtccaag gccaagaagg ccaagaaggg tttcatgacc     120
ccagacagaa agaagaaact ccgtctgttg ttgaaaaaaa aggcggccga agagttgaag     180
aaagaacaag aacgcaaagc tgccgaacga aggcggatca tcgaagagcg gtgcggacaa     240
ccgaagaaca tcgacgacgc cggcgaagag gagcttgcgg aaatctgcga agaactatgg     300
aaacgggttt acaccgtaga gggcataaaa tttgacttgg aaagggatat caggatgaaa     360
gttttcgaga tcagcgaatt gaacagccaa gtcaatgact tacgaggaaa attcgtcaaa     420
ccaacattga agaaggtttc caaatacgaa aacaaattcg caaaactcca aaagaaagcg     480
gcggagttca acttcagaaa ccaactgaaa gtagtgaaga aaaaggagtt caccttggaa     540
gaagaagaca aagagaaaaa acccgattgg tccaaaaagg gagacgaaaa gaagggcgaa     600
ggagaagacg gcgacggtac cgaagacgaa aagaccgacg acggtttgac caccgaaggc     660
gaatcggtcg cgggcgatct aacggacgcg acggaagacg cgcagagcga caacgagata     720
ctcgaaccag aacccgtggt tgaacccgaa ccagaacca                            759

<210> SEQ ID NO 190
<211> LENGTH: 759
<212> TYPE: DNA
<213> ORGANISM: Acyrthosiphon pisum

<400> SEQUENCE: 190
atggccgacg atgaagctaa gaaagcaaaa caggcggaaa tcgaccgcaa gagggccgaa      60
gtgcgcaagc gtatggaaga ggcgtccaag gccaagaagg ccaagaaggg tttcatgacc     120
ccagacagaa agaagaaact ccgtctgttg ttgaaaaaaa aggcggccga agagttgaag     180
```

| | | |
|---|---|---|
| aaagaacaag aacgcaaagc tgccgaacga aggcggatca tcgaagagcg gtgcggacaa | 240 | |
| ccgaagaaca tcgacgacgc cggcgaagag gagcttgcgg aaatctgcga agaactatgg | 300 | |
| aaacggggttt acaccgtaga gggcataaaa tttgacttgg aaagggatat caggatgaaa | 360 | |
| gttttcgaga tcagcgaatt gaacagccaa gtcaatgact tacgaggaaa attcgtcaaa | 420 | |
| ccaacattga agaaggtttc caaatacgaa aacaaattcg caaaactcca aagaaagcg | 480 | |
| gcggagttca acttcagaaa ccaactgaaa gtagtgaaga aaaaggagtt caccttggaa | 540 | |
| gaagaagaca aagagaaaaa acccgattgg tccaaaaagg gagacgaaaa gaagggcgaa | 600 | |
| ggagaagacg gcgacggtac cgaagacgaa aagaccgacg acggtttgac cacccgaaggc | 660 | |
| gaatcggtcg cgggcgatct aacggacgcg acggaagacg cgcagagcga caacgagata | 720 | |
| ctcgaaccag aacccgtggt tgaacccgaa ccagaacca | 759 | |

<210> SEQ ID NO 191
<211> LENGTH: 759
<212> TYPE: DNA
<213> ORGANISM: Acyrthosiphon pisum

<400> SEQUENCE: 191

| | | |
|---|---|---|
| atggccgacg atgaagctaa gaaagcaaaa caggcggaaa tcgaccgcaa gagggccgaa | 60 | |
| gtgcgcaagc gtatggaaga ggcgtccaag gccaagaagg ccaagaaggg tttcatgacc | 120 | |
| ccagacagaa agaagaaact ccgtctgttg ttgaaaaaaa aggcggccga agagttgaag | 180 | |
| aaagaacaag aacgcaaagc tgccgaacga aggcggatca tcgaagagcg gtgcggacaa | 240 | |
| ccgaagaaca tcgacgacgc cggcgaagag gagcttgcgg aaatctgcga agaactatgg | 300 | |
| aaacggggttt acaccgtaga gggcataaaa tttgacttgg aaagggatat caggatgaaa | 360 | |
| gttttcgaga tcagcgaatt gaacagccaa gtcaatgact tacgaggaaa attcgtcaaa | 420 | |
| ccaacattga agaaggtttc caaatacgaa aacaaattcg caaaactcca aagaaagcg | 480 | |
| gcggagttca acttcagaaa ccaactgaaa gtagtgaaga aaaaggagtt caccttggaa | 540 | |
| gaagaagaca aagagaaaaa acccgattgg tccaaaaagg gagacgaaaa gaagggcgaa | 600 | |
| ggagaagacg gcgacggtac cgaagacgaa aagaccgacg acggtttgac cacccgaaggc | 660 | |
| gaatcggtcg cgggcgatct aacggacgcg acggaagacg cgcagagcga caacgagata | 720 | |
| ctcgaaccag aacccgtggt tgaacccgaa ccagaacca | 759 | |

<210> SEQ ID NO 192
<211> LENGTH: 759
<212> TYPE: DNA
<213> ORGANISM: Acyrthosiphon pisum

<400> SEQUENCE: 192

| | | |
|---|---|---|
| atggccgacg atgaagctaa gaaagcaaaa caggcggaaa tcgaccgcaa gagggccgaa | 60 | |
| gtgcgcaagc gtatggaaga ggcgtccaag gccaagaagg ccaagaaggg tttcatgacc | 120 | |
| ccagacagaa agaagaaact ccgtctgttg ttgaaaaaaa aggcggccga agagttgaag | 180 | |
| aaagaacaag aacgcaaagc tgccgaacga aggcggatca tcgaagagcg gtgcggacaa | 240 | |
| ccgaagaaca tcgacgacgc cggcgaagag gagcttgcgg aaatctgcga agaactatgg | 300 | |
| aaacggggttt acaccgtaga gggcataaaa tttgacttgg aaagggatat caggatgaaa | 360 | |
| gttttcgaga tcagcgaatt gaacagccaa gtcaatgact tacgaggaaa attcgtcaaa | 420 | |
| ccaacattga agaaggtttc caaatacgaa aacaaattcg caaaactcca aagaaagcg | 480 | |
| gcggagttca acttcagaaa ccaactgaaa gtagtgaaga aaaaggagtt caccttggaa | 540 | |

```
gaagaagaca aagagaaaaa acccgattgg tccaaaaagg gagacgaaaa gaagggcgaa    600
ggagaagacg gcgacggtac cgaagacgaa agaccgacg acggtttgac caccgaaggc     660
gaatcggtcg cgggcgatct aacggacgcg acggaagacg cgcagagcga caacgagata    720
ctcgaaccag aacccgtggt tgaacccgaa ccagaacca                           759
```

<210> SEQ ID NO 193
<211> LENGTH: 759
<212> TYPE: DNA
<213> ORGANISM: Acyrthosiphon pisum

<400> SEQUENCE: 193

```
atggccgacg atgaagctaa gaaagcaaaa caggcggaaa tcgaccgcaa gagggccgaa    60
gtgcgcaagc gtatggaaga ggcgtccaag gccaagaagg ccaagaaggg tttcatgacc    120
ccagacagaa agaagaaact ccgtctgttg ttgaaaaaaa aggcggccga agagttgaag    180
aaagaacaag aacgcaaagc tgccgaacga aggcggatca tcgaagagcg gtgcggacaa    240
ccgaagaaca tcgacgacgc cggcgaagag gagcttgcgg aaatctgcga agaactatgg    300
aaacgggttt acaccgtaga gggcataaaa tttgacttgg aaagggatat caggatgaaa    360
gttttcgaga tcagcgaatt gaacagccaa gtcaatgact tacgaggaaa attcgtcaaa    420
ccaacattga gaaggtttc caaatacgaa aacaaattcg caaaactcca aaagaaagcg    480
gcggagttca acttcagaaa ccaactgaaa gtagtgaaga aaaaggagtt caccttggaa    540
gaagaagaca aagagaaaaa acccgattgg tccaaaaagg gagacgaaaa gaagggcgaa    600
ggagaagacg gcgacggtac cgaagacgaa agaccgacg acggtttgac caccgaaggc     660
gaatcggtcg cgggcgatct aacggacgcg acggaagacg cgcagagcga caacgagata    720
ctcgaaccag aacccgtggt tgaacccgaa ccagaacca                           759
```

<210> SEQ ID NO 194
<211> LENGTH: 759
<212> TYPE: DNA
<213> ORGANISM: Acyrthosiphon pisum

<400> SEQUENCE: 194

```
atggccgacg atgaagctaa gaaagcaaaa caggcggaaa tcgaccgcaa gagggccgaa    60
gtgcgcaagc gtatggaaga ggcgtccaag gccaagaagg ccaagaaggg tttcatgacc    120
ccagacagaa agaagaaact ccgtctgttg ttgaaaaaaa aggcggccga agagttgaag    180
aaagaacaag aacgcaaagc tgccgaacga aggcggatca tcgaagagcg gtgcggacaa    240
ccgaagaaca tcgacgacgc cggcgaagag gagcttgcgg aaatctgcga agaactatgg    300
aaacgggttt acaccgtaga gggcataaaa tttgacttgg aaagggatat caggatgaaa    360
gttttcgaga tcagcgaatt gaacagccaa gtcaatgact tacgaggaaa attcgtcaaa    420
ccaacattga gaaggtttc caaatacgaa aacaaattcg caaaactcca aaagaaagcg    480
gcggagttca acttcagaaa ccaactgaaa gtagtgaaga aaaaggagtt caccttggaa    540
gaagaagaca aagagaaaaa acccgattgg tccaaaaagg gagacgaaaa gaagggcgaa    600
ggagaagacg gcgacggtac cgaagacgaa agaccgacg acggtttgac caccgaaggc     660
gaatcggtcg cgggcgatct aacggacgcg acggaagacg cgcagagcga caacgagata    720
ctcgaaccag aacccgtggt tgaacccgaa ccagaacca                           759
```

<210> SEQ ID NO 195

<211> LENGTH: 759
<212> TYPE: DNA
<213> ORGANISM: Acyrthosiphon pisum

<400> SEQUENCE: 195

| | | | | | |
|---|---|---|---|---|---|
| atggccgacg | atgaagctaa | gaaagcaaaa | caggcggaaa | tcgaccgcaa | gagggccgaa | 60 |
| gtgcgcaagc | gtatggaaga | ggcgtccaag | gccaagaagg | ccaagaaggg | tttcatgacc | 120 |
| ccagacagaa | agaagaaact | ccgtctgttg | ttgaaaaaaa | aggcggccga | agagttgaag | 180 |
| aaagaacaag | aacgcaaagc | tgccgaacga | aggcggatca | tcgaagagcg | gtgcggacaa | 240 |
| ccgaagaaca | tcgacgacgc | cggcgaagag | gagcttgcgg | aaatctgcga | agaactatgg | 300 |
| aaacggguttt | acaccgtaga | gggcataaaa | tttgacttgg | aaagggatat | caggatgaaa | 360 |
| gtttcgaga | tcagcgaatt | gaacagccaa | gtcaatgact | tacgaggaaa | attcgtcaaa | 420 |
| ccaacattga | agaaggtttc | caaatacgaa | aacaaattcg | caaaactcca | aaagaaagcg | 480 |
| gcggagttca | acttcagaaa | ccaactgaaa | gtagtgaaga | aaaaggagtt | caccttggaa | 540 |
| gaagaagaca | agagaaaaa | acccgattgg | tccaaaaagg | gagacgaaaa | gaagggcgaa | 600 |
| ggagaagacg | gcgacggtac | cgaagacgaa | aagaccgacg | acggtttgac | caccgaaggc | 660 |
| gaatcggtcg | cggcgatct | aacggacgcg | acggaagacg | cgcagagcga | caacgagata | 720 |
| ctcgaaccag | aacccgtggt | tgaacccgaa | ccagaacca | | | 759 |

<210> SEQ ID NO 196
<211> LENGTH: 759
<212> TYPE: DNA
<213> ORGANISM: Acyrthosiphon pisum

<400> SEQUENCE: 196

| | | | | | |
|---|---|---|---|---|---|
| atggccgacg | atgaagctaa | gaaagcaaaa | caggcggaaa | tcgaccgcaa | gagggccgaa | 60 |
| gtgcgcaagc | gtatggaaga | ggcgtccaag | gccaagaagg | ccaagaaggg | tttcatgacc | 120 |
| ccagacagaa | agaagaaact | ccgtctgttg | ttgaaaaaaa | aggcggccga | agagttgaag | 180 |
| aaagaacaag | aacgcaaagc | tgccgaacga | aggcggatca | tcgaagagcg | gtgcggacaa | 240 |
| ccgaagaaca | tcgacgacgc | cggcgaagag | gagcttgcgg | aaatctgcga | agaactatgg | 300 |
| aaacggguttt | acaccgtaga | gggcataaaa | tttgacttgg | aaagggatat | caggatgaaa | 360 |
| gtttcgaga | tcagcgaatt | gaacagccaa | gtcaatgact | tacgaggaaa | attcgtcaaa | 420 |
| ccaacattga | agaaggtttc | caaatacgaa | aacaaattcg | caaaactcca | aaagaaagcg | 480 |
| gcggagttca | acttcagaaa | ccaactgaaa | gtagtgaaga | aaaaggagtt | caccttggaa | 540 |
| gaagaagaca | agagaaaaa | acccgattgg | tccaaaaagg | gagacgaaaa | gaagggcgaa | 600 |
| ggagaagacg | gcgacggtac | cgaagacgaa | aagaccgacg | acggtttgac | caccgaaggc | 660 |
| gaatcggtcg | cgggcgatct | aacggacgcg | acggaagacg | cgcagagcga | caacgagata | 720 |
| ctcgaaccag | aacccgtggt | tgaacccgaa | ccagaacca | | | 759 |

<210> SEQ ID NO 197
<211> LENGTH: 759
<212> TYPE: DNA
<213> ORGANISM: Acyrthosiphon pisum

<400> SEQUENCE: 197

| | | | | | |
|---|---|---|---|---|---|
| atggccgacg | atgaagctaa | gaaagcaaaa | caggcggaaa | tcgaccgcaa | gagggccgaa | 60 |
| gtgcgcaagc | gtatggaaga | ggcgtccaag | gccaagaagg | ccaagaaggg | tttcatgacc | 120 |
| ccagacagaa | agaagaaact | ccgtctgttg | ttgaaaaaaa | aggcggccga | agagttgaag | 180 |

| aaagaacaag aacgcaaagc tgccgaacga aggcggatca tcgaagagcg gtgcggacaa | 240 |
| ccgaagaaca tcgacgacgc cggcgaagag gagcttgcgg aaatctgcga agaactatgg | 300 |
| aaacgggttt acaccgtaga gggcataaaa tttgacttgg aaagggatat caggatgaaa | 360 |
| gttttcgaga tcagcgaatt gaacagccaa gtcaatgact tacgaggaaa attcgtcaaa | 420 |
| ccaacattga agaaggtttc caaatacgaa aacaaattcg caaaactcca aaagaaagcg | 480 |
| gcggagttca acttcagaaa ccaactgaaa gtagtgaaga aaaaggagtt caccttggaa | 540 |
| gaagaagaca aagagaaaaa acccgattgg tccaaaaagg gagacgaaaa gaagggcgaa | 600 |
| ggagaagacg gcgacggtac cgaagacgaa aagaccgacg acggtttgac caccgaaggc | 660 |
| gaatcggtcg cgggcgatct aacggacgcg acggaagacg cgcagagcga caacgagata | 720 |
| ctcgaaccag aacccgtggt tgaacccgaa ccagaacca | 759 |

<210> SEQ ID NO 198
<211> LENGTH: 759
<212> TYPE: DNA
<213> ORGANISM: Acyrthosiphon pisum

<400> SEQUENCE: 198

| atggccgacg atgaagctaa gaaagcaaaa caggcggaaa tcgaccgcaa gagggccgaa | 60 |
| gtgcgcaagc gtatggaaga ggcgtccaag gccaagaagg ccaagaaggg tttcatgacc | 120 |
| ccagacagaa agaagaaact ccgtctgttg ttgaaaaaaa aggcggccga agagttgaag | 180 |
| aaagaacaag aacgcaaagc tgccgaacga aggcggatca tcgaagagcg gtgcggacaa | 240 |
| ccgaagaaca tcgacgacgc cggcgaagag gagcttgcgg aaatctgcga agaactatgg | 300 |
| aaacgggttt acaccgtaga gggcataaaa tttgacttgg aaagggatat caggatgaaa | 360 |
| gttttcgaga tcagcgaatt gaacagccaa gtcaatgact tacgaggaaa attcgtcaaa | 420 |
| ccaacattga agaaggtttc caaatacgaa aacaaattcg caaaactcca aaagaaagcg | 480 |
| gcggagttca acttcagaaa ccaactgaaa gtagtgaaga aaaaggagtt caccttggaa | 540 |
| gaagaagaca aagagaaaaa acccgattgg tccaaaaagg gagacgaaaa gaagggcgaa | 600 |
| ggagaagacg gcgacggtac cgaagacgaa aagaccgacg acggtttgac caccgaaggc | 660 |
| gaatcggtcg cgggcgatct aacggacgcg acggaagacg cgcagagcga caacgagata | 720 |
| ctcgaaccag aacccgtggt tgaacccgaa ccagaacca | 759 |

<210> SEQ ID NO 199
<211> LENGTH: 759
<212> TYPE: DNA
<213> ORGANISM: Acyrthosiphon pisum

<400> SEQUENCE: 199

| atggccgacg atgaagctaa gaaagcaaaa caggcggaaa tcgaccgcaa gagggccgaa | 60 |
| gtgcgcaagc gtatggaaga ggcgtccaag gccaagaagg ccaagaaggg tttcatgacc | 120 |
| ccagacagaa agaagaaact ccgtctgttg ttgaaaaaaa aggcggccga agagttgaag | 180 |
| aaagaacaag aacgcaaagc tgccgaacga aggcggatca tcgaagagcg gtgcggacaa | 240 |
| ccgaagaaca tcgacgacgc cggcgaagag gagcttgcgg aaatctgcga agaactatgg | 300 |
| aaacgggttt acaccgtaga gggcataaaa tttgacttgg aaagggatat caggatgaaa | 360 |
| gttttcgaga tcagcgaatt gaacagccaa gtcaatgact tacgaggaaa attcgtcaaa | 420 |
| ccaacattga agaaggtttc caaatacgaa aacaaattcg caaaactcca aaagaaagcg | 480 |

```
gcggagttca acttcagaaa ccaactgaaa gtagtgaaga aaaggagtt caccttggaa      540 gaagaagaca aagagaaaaa acccgattgg tccaaaaagg gagacgaaaa gaagggcgaa      600
ggagaagacg gcgacggtac cgaagacgaa aagaccgacg acggtttgac caccgaaggc      660
gaatcggtcg cgggcgatct aacgacgcg acggaagacg cgcagagcga caacgagata      720
ctcgaaccag aacccgtggt tgaacccgaa ccagaacca                            759

<210> SEQ ID NO 200
<211> LENGTH: 541
<212> TYPE: DNA
<213> ORGANISM: Acyrthosiphon pisum

<400> SEQUENCE: 200
cggtaatgcg atgcggtaag aagaaggtat ggttggatcc aaacgaaata atgaaattg       60 ccaacaccaa ttccagacaa atattcgta agttgatcaa agatggtttg atcattaaaa      120
agccagtagc tgtacactct agggctcgtg cacgtaaaaa tgcagatgcc agaagaaaag      180
gtcgtcattg tggttttggt aaaaggaagg gtactgctaa tgctcgaaca cctcaaaaag      240
acctttgggt gaaaagaatg cgagtattaa ggcggttgct taaaaaatac cgtgaagcaa      300
agaaaattga caaccatctt taccatcagt tatacatgaa ggctaagggt aatgttttca      360
agaacaaacg tgtattgatg gagttcatcc acaaaaagaa ggcagagaag gcccgtgcca      420
agatgttgag tgatcaagct gaagctagac gtcaaaaggt taaggaagct aggaaacgta      480
aagaagcaag attttacaa aataggaagg aacttttggc tgcatacgcc cgagaagatg       540
a                                                                     541

<210> SEQ ID NO 201
<211> LENGTH: 541
<212> TYPE: DNA
<213> ORGANISM: Acyrthosiphon pisum

<400> SEQUENCE: 201
cggtaatgcg atgcggtaag aagaaggtat ggttggatcc aaacgaaata atgaaattg       60 ccaacaccaa ttccagacaa atattcgta agttgatcaa agatggtttg atcattaaaa      120
agccagtagc tgtacactct agggctcgtg cacgtaaaaa tgcagatgcc agaagaaaag      180
gtcgtcattg tggttttggt aaaaggaagg gtactgctaa tgctcgaaca cctcaaaaag      240
acctttgggt gaaaagaatg cgagtattaa ggcggttgct taaaaaatac cgtgaagcaa      300
agaaaattga caaccatctt taccatcagt tatacatgaa ggctaagggt aatgttttca      360
agaacaaacg tgtattgatg gagttcatcc acaaaaagaa ggcagagaag gcccgtgcca      420
agatgttgag tgatcaagct gaagctagac gtcaaaaggt taaggaagct aggaaacgta      480
aagaagcaag attttacaa aataggaagg aacttttggc tgcatacgcc cgagaagatg       540
a                                                                     541

<210> SEQ ID NO 202
<211> LENGTH: 823
<212> TYPE: DNA
<213> ORGANISM: Acyrthosiphon pisum

<400> SEQUENCE: 202
gttgtagtcg gaaagggtac gtccgtcttc aagttgtttt ccggcaaaga tcaaacgttg       60
ttggtctggt gggataccct ctttgtcttg gatcttggct tttacatttt caatggaatc      120
agatgattcc acctccaatg taatggtctt tccagtgagg gtctttacaa agatttgcat      180
```

```
accaccacgg agacgcaaca ctaagtgaag ggtagattct ttctggatgt tgtagtcaga    240
aagtgtgcgt ccgtcttcaa gttgctttcc ggcaaagatc aaacgttgtt ggtcaggtgg    300
aataccttct ttgtcttgga tcttagcttt tacattttca atggaatctg atgactcaac    360
ttccaatgta atggtctttc cagtgagggt ctttacaaag atttgcatac caccacggag    420
acgcaacact aagtgaaggg tagattcttt ctggatgttg tagtcggaaa gggtacgtcc    480
gtcttcaagt tgctttccgg caaagatcaa acgttgttgg tctggtggga taccttcttt    540
gtcttggatc ttggctttta cattttcaat ggaatcagat gattccacct ccaatgtaat    600
ggtctttcca gtgagggtct ttacaaagat ttgcatacca ccacggagac gcaacactaa    660 gtgaaggta gattctttct ggatgttgta gtcggaaagg gtacgtccgt cttcaagttg    720 cttttccagca aagatcaaac gttgctggtc tggtgggata ccttccttgt cttggatctt    780
ggccttaaca ttttcaatgg aatctgatga ctcaacttcc aaa    823
```

\<210\> SEQ ID NO 203
\<211\> LENGTH: 823
\<212\> TYPE: DNA
\<213\> ORGANISM: Acyrthosiphon pisum

\<400\> SEQUENCE: 203

```
gttgtagtcg aaagggtac gtccgtcttc aagttgtttt ccggcaaaga tcaaacgttg     60
ttggtctggt gggatacctt ctttgtcttg atcttggct tttacatttt caatggaatc    120
agatgattcc acctccaatg taatggtctt tccagtgagg gtctttacaa agatttgcat    180
accaccacgg agacgcaaca ctaagtgaag ggtagattct ttctggatgt tgtagtcaga    240
aagtgtgcgt ccgtcttcaa gttgctttcc ggcaaagatc aaacgttgtt ggtcaggtgg    300
aataccttct ttgtcttgga tcttagcttt tacattttca atggaatctg atgactcaac    360
ttccaatgta atggtctttc cagtgagggt ctttacaaag atttgcatac caccacggag    420
acgcaacact aagtgaaggg tagattcttt ctggatgttg tagtcggaaa gggtacgtcc    480
gtcttcaagt tgctttccgg caaagatcaa acgttgttgg tctggtggga taccttcttt    540
gtcttggatc ttggctttta cattttcaat ggaatcagat gattccacct ccaatgtaat    600
ggtctttcca gtgagggtct ttacaaagat ttgcatacca ccacggagac gcaacactaa    660 gtgaaggta gattctttct ggatgttgta gtcggaaagg gtacgtccgt cttcaagttg    720 cttttccagca aagatcaaac gttgctggtc tggtgggata ccttccttgt cttggatctt    780
ggccttaaca ttttcaatgg aatctgatga ctcaacttcc aaa    823
```

\<210\> SEQ ID NO 204
\<211\> LENGTH: 172
\<212\> TYPE: DNA
\<213\> ORGANISM: Acyrthosiphon pisum

\<400\> SEQUENCE: 204

```
aagacttgct tcatcctact gcaattgaag aacgcaggaa acacaaatta agcgccttg     60 ttcaacaccc aaactctttt ttcatggatg tcaaatgccc tggatgttat aaaattacaa    120
ctgtattcag tcacgctcag agtgtagtta tatgtaccgg atgttccaca at    172
```

\<210\> SEQ ID NO 205
\<211\> LENGTH: 172
\<212\> TYPE: DNA
\<213\> ORGANISM: Acyrthosiphon pisum

<400> SEQUENCE: 205
aagacttgct tcatcctact gcaattgaag aacgcaggaa acacaaatta aagcgccttg    60
ttcaacaccc aaactctttt ttcatggatg tcaaatgccc tggatgttat aaaattacaa   120
ctgtattcag tcacgctcag agtgtagtta tatgtaccgg atgttccaca at           172

<210> SEQ ID NO 206
<211> LENGTH: 25
<212> TYPE: DNA
<213> ORGANISM: Artificial
<220> FEATURE:
<223> OTHER INFORMATION: Primer

<400> SEQUENCE: 206
cgaaccatct gggaagcttg gaatg                                          25

<210> SEQ ID NO 207
<211> LENGTH: 25
<212> TYPE: DNA
<213> ORGANISM: Artificial
<220> FEATURE:
<223> OTHER INFORMATION: Primer

<400> SEQUENCE: 207
gcagctggag gaagagaaac gtatc                                          25

<210> SEQ ID NO 208
<211> LENGTH: 47
<212> TYPE: DNA
<213> ORGANISM: Artificial
<220> FEATURE:
<223> OTHER INFORMATION: Primer

<400> SEQUENCE: 208
gcgtaatacg actcactata ggcgaaccat ctgggaagct tggaatg                  47

<210> SEQ ID NO 209
<211> LENGTH: 46
<212> TYPE: DNA
<213> ORGANISM: Artificial
<220> FEATURE:
<223> OTHER INFORMATION: Primer

<400> SEQUENCE: 209
gcgtaatacg actcactata ggcagctgga ggaagagaaa cgtatc                   46

<210> SEQ ID NO 210
<211> LENGTH: 20
<212> TYPE: DNA
<213> ORGANISM: Artificial
<220> FEATURE:
<223> OTHER INFORMATION: Primer

<400> SEQUENCE: 210
agttcgagaa caccaggaag                                                20

<210> SEQ ID NO 211
<211> LENGTH: 22
<212> TYPE: DNA
<213> ORGANISM: Artificial
<220> FEATURE:
<223> OTHER INFORMATION: Primer

<400> SEQUENCE: 211
cctgacacgt tgttccagct tg                                             22

<210> SEQ ID NO 212
<211> LENGTH: 45
<212> TYPE: DNA
<213> ORGANISM: Artificial
<220> FEATURE:
<223> OTHER INFORMATION: Primer

<400> SEQUENCE: 212
gcgtaatacg actcactata ggaggagttc gagaacacca ggaag            45

<210> SEQ ID NO 213
<211> LENGTH: 44
<212> TYPE: DNA
<213> ORGANISM: Artificial
<220> FEATURE:
<223> OTHER INFORMATION: Primer

<400> SEQUENCE: 213
gcgtaatacg actcactata ggcctgacac gttgttccag cttg             44

<210> SEQ ID NO 214
<211> LENGTH: 20
<212> TYPE: DNA
<213> ORGANISM: Artificial
<220> FEATURE:
<223> OTHER INFORMATION: Primer

<400> SEQUENCE: 214
gcaggcgatg aagatggaga                                        20

<210> SEQ ID NO 215
<211> LENGTH: 24
<212> TYPE: DNA
<213> ORGANISM: Artificial
<220> FEATURE:
<223> OTHER INFORMATION: Primer

<400> SEQUENCE: 215
ccacctcttt ctgcaacttc ttga                                   24

<210> SEQ ID NO 216
<211> LENGTH: 42
<212> TYPE: DNA
<213> ORGANISM: Artificial
<220> FEATURE:
<223> OTHER INFORMATION: Primer

<400> SEQUENCE: 216
gcgtaatacg actcactata gggcaggcga tgaagatgga ga               42

<210> SEQ ID NO 217
<211> LENGTH: 46
<212> TYPE: DNA
<213> ORGANISM: Artificial
<220> FEATURE:
<223> OTHER INFORMATION: Primer

<400> SEQUENCE: 217
gcgtaatacg actcactata ggccacctct ttctgcaact tcttga           46

<210> SEQ ID NO 218
<211> LENGTH: 25
<212> TYPE: DNA
<213> ORGANISM: Artificial
<220> FEATURE:

<223> OTHER INFORMATION: Primer

<400> SEQUENCE: 218
cagaatccca cagaatctga cgtga                                                    25

<210> SEQ ID NO 219
<211> LENGTH: 20
<212> TYPE: DNA
<213> ORGANISM: Artificial
<220> FEATURE:
<223> OTHER INFORMATION: Primer

<400> SEQUENCE: 219
gcaagtggcg aagctcagct                                                          20

<210> SEQ ID NO 220
<211> LENGTH: 47
<212> TYPE: DNA
<213> ORGANISM: Artificial
<220> FEATURE:
<223> OTHER INFORMATION: Primer

<400> SEQUENCE: 220
gcgtaatacg actcactata ggcagaatcc cacagaatct gacgtga                            47

<210> SEQ ID NO 221
<211> LENGTH: 41
<212> TYPE: DNA
<213> ORGANISM: Artificial
<220> FEATURE:
<223> OTHER INFORMATION: Primer

<400> SEQUENCE: 221
gcgtaatacg actcactata ggcaagtggc gaagctcagc t                                  41

<210> SEQ ID NO 222
<211> LENGTH: 21
<212> TYPE: DNA
<213> ORGANISM: Artificial
<220> FEATURE:
<223> OTHER INFORMATION: Primer

<400> SEQUENCE: 222
cgtgtttgcc atgttcgatc a                                                        21

<210> SEQ ID NO 223
<211> LENGTH: 23
<212> TYPE: DNA
<213> ORGANISM: Artificial
<220> FEATURE:
<223> OTHER INFORMATION: Primer

<400> SEQUENCE: 223
ggtacatttc gtccacgtct tca                                                      23

<210> SEQ ID NO 224
<211> LENGTH: 43
<212> TYPE: DNA
<213> ORGANISM: Artificial
<220> FEATURE:
<223> OTHER INFORMATION: Primer

<400> SEQUENCE: 224
gcgtaatacg actcactata ggcgtgtttg ccatgttcga tca                                43

```
<210> SEQ ID NO 225
<211> LENGTH: 43
<212> TYPE: DNA
<213> ORGANISM: Artificial
<220> FEATURE:
<223> OTHER INFORMATION: Primer

<400> SEQUENCE: 225
gcgtaatacg actcactata ggtacatttc gtccacgtct tca              43

<210> SEQ ID NO 226
<211> LENGTH: 23
<212> TYPE: DNA
<213> ORGANISM: Artificial
<220> FEATURE:
<223> OTHER INFORMATION: Primer

<400> SEQUENCE: 226
gacttgatct tcagccgacc att                                    23

<210> SEQ ID NO 227
<211> LENGTH: 23
<212> TYPE: DNA
<213> ORGANISM: Artificial
<220> FEATURE:
<223> OTHER INFORMATION: Primer

<400> SEQUENCE: 227
ccattgccag ttcctcaact tca                                    23

<210> SEQ ID NO 228
<211> LENGTH: 44
<212> TYPE: DNA
<213> ORGANISM: Artificial
<220> FEATURE:
<223> OTHER INFORMATION: Primer

<400> SEQUENCE: 228
gcgtaatacg actcactata ggacttgatc ttcagccgac catt             44

<210> SEQ ID NO 229
<211> LENGTH: 45
<212> TYPE: DNA
<213> ORGANISM: Artificial
<220> FEATURE:
<223> OTHER INFORMATION: Primer

<400> SEQUENCE: 229
gcgtaatacg actcactata ggccattgcc agttcctcaa cttca            45

<210> SEQ ID NO 230
<211> LENGTH: 21
<212> TYPE: DNA
<213> ORGANISM: Artificial
<220> FEATURE:
<223> OTHER INFORMATION: Primer

<400> SEQUENCE: 230
cgcaatgatc tcctccagga t                                      21

<210> SEQ ID NO 231
<211> LENGTH: 24
<212> TYPE: DNA
<213> ORGANISM: Artificial
<220> FEATURE:
<223> OTHER INFORMATION: Primer
```

```
<400> SEQUENCE: 231
ggtcatcatc tccatgaact cgtc                                         24

<210> SEQ ID NO 232
<211> LENGTH: 43
<212> TYPE: DNA
<213> ORGANISM: Artificial
<220> FEATURE:
<223> OTHER INFORMATION: Primer

<400> SEQUENCE: 232
gcgtaatacg actcactata ggcgcaatga tctcctccag gat                    43

<210> SEQ ID NO 233
<211> LENGTH: 45
<212> TYPE: DNA
<213> ORGANISM: Artificial
<220> FEATURE:
<223> OTHER INFORMATION: Primer

<400> SEQUENCE: 233
gcgtaatacg actcactata gggtcatcat ctccatgaac tcgtc                  45

<210> SEQ ID NO 234
<211> LENGTH: 26
<212> TYPE: DNA
<213> ORGANISM: Artificial
<220> FEATURE:
<223> OTHER INFORMATION: Primer

<400> SEQUENCE: 234
cgtcactaat cggactggtc taacag                                       26

<210> SEQ ID NO 235
<211> LENGTH: 24
<212> TYPE: DNA
<213> ORGANISM: Artificial
<220> FEATURE:
<223> OTHER INFORMATION: Primer

<400> SEQUENCE: 235
ggtcatcatc tccatgaact cgtc                                         24

<210> SEQ ID NO 236
<211> LENGTH: 48
<212> TYPE: DNA
<213> ORGANISM: Artificial
<220> FEATURE:
<223> OTHER INFORMATION: Primer

<400> SEQUENCE: 236
gcgtaatacg actcactata ggcgtcacta atcggactgg tctaacag               48

<210> SEQ ID NO 237
<211> LENGTH: 45
<212> TYPE: DNA
<213> ORGANISM: Artificial
<220> FEATURE:
<223> OTHER INFORMATION: Primer

<400> SEQUENCE: 237
gcgtaatacg actcactata gggtcatcat ctccatgaac tcgtc                  45

<210> SEQ ID NO 238
<211> LENGTH: 23
```

```
<212> TYPE: DNA
<213> ORGANISM: Artificial
<220> FEATURE:
<223> OTHER INFORMATION: Primer

<400> SEQUENCE: 238
ggtgaaggag ggtgcctgct cag                                        23

<210> SEQ ID NO 239
<211> LENGTH: 25
<212> TYPE: DNA
<213> ORGANISM: Artificial
<220> FEATURE:
<223> OTHER INFORMATION: Primer

<400> SEQUENCE: 239
cagggtgaat agaacgaggt actcg                                      25

<210> SEQ ID NO 240
<211> LENGTH: 40
<212> TYPE: DNA
<213> ORGANISM: Artificial
<220> FEATURE:
<223> OTHER INFORMATION: Primer

<400> SEQUENCE: 240
aatacgactc actatagggc gctatgaaat tccaagcaca                      40

<210> SEQ ID NO 241
<211> LENGTH: 47
<212> TYPE: DNA
<213> ORGANISM: Artificial
<220> FEATURE:
<223> OTHER INFORMATION: Primer

<400> SEQUENCE: 241
gcgtaatacg actcactata ggcagggtga atagaacgag gtactcg              47

<210> SEQ ID NO 242
<211> LENGTH: 29
<212> TYPE: DNA
<213> ORGANISM: Artificial
<220> FEATURE:
<223> OTHER INFORMATION: Primer

<400> SEQUENCE: 242
ctcaacgaag gtcttgtcag tggctttgg                                  29

<210> SEQ ID NO 243
<211> LENGTH: 20
<212> TYPE: DNA
<213> ORGANISM: Artificial
<220> FEATURE:
<223> OTHER INFORMATION: Primer

<400> SEQUENCE: 243
ttcgcctggc ttcttcgtga                                            20

<210> SEQ ID NO 244
<211> LENGTH: 44
<212> TYPE: DNA
<213> ORGANISM: Artificial
<220> FEATURE:
<223> OTHER INFORMATION: Primer

<400> SEQUENCE: 244
```
gcgtaatacg actcactata ggccacgccg acttaattca ttcc                44

<210> SEQ ID NO 245
<211> LENGTH: 42
<212> TYPE: DNA
<213> ORGANISM: Artificial
<220> FEATURE:
<223> OTHER INFORMATION: Primer

<400> SEQUENCE: 245
gcgtaatacg actcactata ggttcgcctg gcttcttcgt ga                  42

<210> SEQ ID NO 246
<211> LENGTH: 22
<212> TYPE: DNA
<213> ORGANISM: Artificial
<220> FEATURE:
<223> OTHER INFORMATION: Primer

<400> SEQUENCE: 246
tgtcgatggc ggtcttaaca tc                                        22

<210> SEQ ID NO 247
<211> LENGTH: 24
<212> TYPE: DNA
<213> ORGANISM: Artificial
<220> FEATURE:
<223> OTHER INFORMATION: Primer

<400> SEQUENCE: 247
tctccagctt ccactttctt gaga                                      24

<210> SEQ ID NO 248
<211> LENGTH: 44
<212> TYPE: DNA
<213> ORGANISM: Artificial
<220> FEATURE:
<223> OTHER INFORMATION: Primer

<400> SEQUENCE: 248
gcgtaatacg actcactata ggtgtcgatg gcggtcttaa catc                44

<210> SEQ ID NO 249
<211> LENGTH: 46
<212> TYPE: DNA
<213> ORGANISM: Artificial
<220> FEATURE:
<223> OTHER INFORMATION: Primer

<400> SEQUENCE: 249
gcgtaatacg actcactata ggtctccagc ttccactttc ttgaga              46

<210> SEQ ID NO 250
<211> LENGTH: 20
<212> TYPE: DNA
<213> ORGANISM: Artificial
<220> FEATURE:
<223> OTHER INFORMATION: Primer

<400> SEQUENCE: 250
aacgtgcatt tcgcgtaccc                                           20

<210> SEQ ID NO 251
<211> LENGTH: 20
<212> TYPE: DNA
<213> ORGANISM: Artificial

```
<220> FEATURE:
<223> OTHER INFORMATION: Primer

<400> SEQUENCE: 251
tgatgggcat aactggcagg                                             20

<210> SEQ ID NO 252
<211> LENGTH: 42
<212> TYPE: DNA
<213> ORGANISM: Artificial
<220> FEATURE:
<223> OTHER INFORMATION: Primer

<400> SEQUENCE: 252
gcgtaatacg actcactata ggaacgtgca tttcgcgtac cc                    42

<210> SEQ ID NO 253
<211> LENGTH: 42
<212> TYPE: DNA
<213> ORGANISM: Artificial
<220> FEATURE:
<223> OTHER INFORMATION: Primer

<400> SEQUENCE: 253
gcgtaatacg actcactata ggtgatgggc ataactggca gg                    42

<210> SEQ ID NO 254
<211> LENGTH: 22
<212> TYPE: DNA
<213> ORGANISM: Artificial
<220> FEATURE:
<223> OTHER INFORMATION: Primer

<400> SEQUENCE: 254
ccttattgaa cgtggtcgac ag                                          22

<210> SEQ ID NO 255
<211> LENGTH: 20
<212> TYPE: DNA
<213> ORGANISM: Artificial
<220> FEATURE:
<223> OTHER INFORMATION: Primer

<400> SEQUENCE: 255
ctgatgtagt ccttgaggag                                             20

<210> SEQ ID NO 256
<211> LENGTH: 44
<212> TYPE: DNA
<213> ORGANISM: Artificial
<220> FEATURE:
<223> OTHER INFORMATION: Primer

<400> SEQUENCE: 256
gcgtaatacg actcactata ggccttattg aacgtggtcg acag                  44

<210> SEQ ID NO 257
<211> LENGTH: 42
<212> TYPE: DNA
<213> ORGANISM: Artificial
<220> FEATURE:
<223> OTHER INFORMATION: Primer

<400> SEQUENCE: 257
gcgtaatacg actcactata ggctgatgta gtccttgagg ag                    42
```

<210> SEQ ID NO 258
<211> LENGTH: 26
<212> TYPE: DNA
<213> ORGANISM: Artificial
<220> FEATURE:
<223> OTHER INFORMATION: Primer

<400> SEQUENCE: 258
gtacggacgg gtagtttagt tgtgtc                                              26

<210> SEQ ID NO 259
<211> LENGTH: 20
<212> TYPE: DNA
<213> ORGANISM: Artificial
<220> FEATURE:
<223> OTHER INFORMATION: Primer

<400> SEQUENCE: 259
ttgccaagtg ccaagtcacg                                                     20

<210> SEQ ID NO 260
<211> LENGTH: 48
<212> TYPE: DNA
<213> ORGANISM: Artificial
<220> FEATURE:
<223> OTHER INFORMATION: Primer

<400> SEQUENCE: 260
gcgtaatacg actcactata gggtacggac gggtagttta gttgtgtc                      48

<210> SEQ ID NO 261
<211> LENGTH: 42
<212> TYPE: DNA
<213> ORGANISM: Artificial
<220> FEATURE:
<223> OTHER INFORMATION: Primer

<400> SEQUENCE: 261
gcgtaatacg actcactata ggttgccaag tgccaagtca cg                            42

<210> SEQ ID NO 262
<211> LENGTH: 22
<212> TYPE: DNA
<213> ORGANISM: Artificial
<220> FEATURE:
<223> OTHER INFORMATION: Primer

<400> SEQUENCE: 262
ctgttgtcgg ctggtcatat cc                                                  22

<210> SEQ ID NO 263
<211> LENGTH: 20
<212> TYPE: DNA
<213> ORGANISM: Artificial
<220> FEATURE:
<223> OTHER INFORMATION: Primer

<400> SEQUENCE: 263
taacgtaacg catcgccacc                                                     20

<210> SEQ ID NO 264
<211> LENGTH: 44
<212> TYPE: DNA
<213> ORGANISM: Artificial
<220> FEATURE:
<223> OTHER INFORMATION: Primer

<400> SEQUENCE: 264
gcgtaatacg actcactata ggctgttgtc ggctggtcat atcc     44

<210> SEQ ID NO 265
<211> LENGTH: 42
<212> TYPE: DNA
<213> ORGANISM: Artificial
<220> FEATURE:
<223> OTHER INFORMATION: Primer

<400> SEQUENCE: 265
gcgtaatacg actcactata ggtaacgtaa cgcatcgcca cc     42

<210> SEQ ID NO 266
<211> LENGTH: 20
<212> TYPE: DNA
<213> ORGANISM: Artificial
<220> FEATURE:
<223> OTHER INFORMATION: Primer

<400> SEQUENCE: 266
agccctcatc cgtgatttgg     20

<210> SEQ ID NO 267
<211> LENGTH: 20
<212> TYPE: DNA
<213> ORGANISM: Artificial
<220> FEATURE:
<223> OTHER INFORMATION: Primer

<400> SEQUENCE: 267
gatccggcct caatttgacg     20

<210> SEQ ID NO 268
<211> LENGTH: 42
<212> TYPE: DNA
<213> ORGANISM: Artificial
<220> FEATURE:
<223> OTHER INFORMATION: Primer

<400> SEQUENCE: 268
gcgtaatacg actcactata ggagccctca tccgtgattt gg     42

<210> SEQ ID NO 269
<211> LENGTH: 42
<212> TYPE: DNA
<213> ORGANISM: Artificial
<220> FEATURE:
<223> OTHER INFORMATION: Primer

<400> SEQUENCE: 269
gcgtaatacg actcactata gggatccggc ctcaatttga cg     42

<210> SEQ ID NO 270
<211> LENGTH: 22
<212> TYPE: DNA
<213> ORGANISM: Artificial
<220> FEATURE:
<223> OTHER INFORMATION: Primer

<400> SEQUENCE: 270
acgtttctct gctcattcgt gc     22

<210> SEQ ID NO 271

```
<211> LENGTH: 20
<212> TYPE: DNA
<213> ORGANISM: Artificial
<220> FEATURE:
<223> OTHER INFORMATION: Primer

<400> SEQUENCE: 271
cttgtacaaa gtgtgcaggg                                              20

<210> SEQ ID NO 272
<211> LENGTH: 44
<212> TYPE: DNA
<213> ORGANISM: Artificial
<220> FEATURE:
<223> OTHER INFORMATION: Primer

<400> SEQUENCE: 272
gcgtaatacg actcactata ggacgtttct ctgctcattc gtgc                   44

<210> SEQ ID NO 273
<211> LENGTH: 42
<212> TYPE: DNA
<213> ORGANISM: Artificial
<220> FEATURE:
<223> OTHER INFORMATION: Primer

<400> SEQUENCE: 273
gcgtaatacg actcactata ggcttgtaca aagtgtgcag gg                     42

<210> SEQ ID NO 274
<211> LENGTH: 22
<212> TYPE: DNA
<213> ORGANISM: Artificial
<220> FEATURE:
<223> OTHER INFORMATION: Primer

<400> SEQUENCE: 274
ggttttcttc ttgcccgaat cg                                           22

<210> SEQ ID NO 275
<211> LENGTH: 20
<212> TYPE: DNA
<213> ORGANISM: Artificial
<220> FEATURE:
<223> OTHER INFORMATION: Primer

<400> SEQUENCE: 275
tttggggttc ggcttggttg                                              20

<210> SEQ ID NO 276
<211> LENGTH: 44
<212> TYPE: DNA
<213> ORGANISM: Artificial
<220> FEATURE:
<223> OTHER INFORMATION: Primer

<400> SEQUENCE: 276
gcgtaatacg actcactata ggggttttct tcttgcccga atcg                   44

<210> SEQ ID NO 277
<211> LENGTH: 42
<212> TYPE: DNA
<213> ORGANISM: Artificial
<220> FEATURE:
<223> OTHER INFORMATION: Primer

<400> SEQUENCE: 277
```

-continued gcgtaatacg actcactata ggtttggggt tcggcttggt tg                42

<210> SEQ ID NO 278
<211> LENGTH: 23
<212> TYPE: DNA
<213> ORGANISM: Artificial
<220> FEATURE:
<223> OTHER INFORMATION: Primer

<400> SEQUENCE: 278
tcagcgagat ccctaagaca acg                                    23

<210> SEQ ID NO 279
<211> LENGTH: 20
<212> TYPE: DNA
<213> ORGANISM: Artificial
<220> FEATURE:
<223> OTHER INFORMATION: Primer

<400> SEQUENCE: 279
ccccacatgt tgatgacgca                                        20

<210> SEQ ID NO 280
<211> LENGTH: 45
<212> TYPE: DNA
<213> ORGANISM: Artificial
<220> FEATURE:
<223> OTHER INFORMATION: Primer

<400> SEQUENCE: 280
gcgtaatacg actcactata ggtcagcgag atccctaaga caacg            45

<210> SEQ ID NO 281
<211> LENGTH: 42
<212> TYPE: DNA
<213> ORGANISM: Artificial
<220> FEATURE:
<223> OTHER INFORMATION: Primer

<400> SEQUENCE: 281
gcgtaatacg actcactata ggccccacat gttgatgacg ca               42

<210> SEQ ID NO 282
<211> LENGTH: 23
<212> TYPE: DNA
<213> ORGANISM: Artificial
<220> FEATURE:
<223> OTHER INFORMATION: Primer

<400> SEQUENCE: 282
ggtttatgac ccctgagagg aag                                    23

<210> SEQ ID NO 283
<211> LENGTH: 22
<212> TYPE: DNA
<213> ORGANISM: Artificial
<220> FEATURE:
<223> OTHER INFORMATION: Primer

<400> SEQUENCE: 283
ctccagggtg aactccttct tc                                     22

<210> SEQ ID NO 284
<211> LENGTH: 43
<212> TYPE: DNA

```
<213> ORGANISM: Artificial
<220> FEATURE:
<223> OTHER INFORMATION: Primer

<400> SEQUENCE: 284
gcgtaatacg actcactata ggtttatgac ccctgagagg aag            43

<210> SEQ ID NO 285
<211> LENGTH: 44
<212> TYPE: DNA
<213> ORGANISM: Artificial
<220> FEATURE:
<223> OTHER INFORMATION: Primer

<400> SEQUENCE: 285
gcgtaatacg actcactata ggctccaggg tgaactcctt cttc           44

<210> SEQ ID NO 286
<211> LENGTH: 24
<212> TYPE: DNA
<213> ORGANISM: Artificial
<220> FEATURE:
<223> OTHER INFORMATION: Primer

<400> SEQUENCE: 286
caaggaccag aacaagaaca aggg                                 24

<210> SEQ ID NO 287
<211> LENGTH: 26
<212> TYPE: DNA
<213> ORGANISM: Artificial
<220> FEATURE:
<223> OTHER INFORMATION: Primer

<400> SEQUENCE: 287
gacgttcata tttggaggct acttgg                               26

<210> SEQ ID NO 288
<211> LENGTH: 46
<212> TYPE: DNA
<213> ORGANISM: Artificial
<220> FEATURE:
<223> OTHER INFORMATION: Primer

<400> SEQUENCE: 288
gcgtaatacg actcactata ggcaaggacc agaacaagaa caaggg         46

<210> SEQ ID NO 289
<211> LENGTH: 47
<212> TYPE: DNA
<213> ORGANISM: Artificial
<220> FEATURE:
<223> OTHER INFORMATION: Primer

<400> SEQUENCE: 289
gcgtaatacg actcactata ggacgttcat atttggaggc tacttgg        47

<210> SEQ ID NO 290
<211> LENGTH: 25
<212> TYPE: DNA
<213> ORGANISM: Artificial
<220> FEATURE:
<223> OTHER INFORMATION: Primer

<400> SEQUENCE: 290
aatctcgtac actgttggaa caagc                                25
```

<210> SEQ ID NO 291
<211> LENGTH: 25
<212> TYPE: DNA
<213> ORGANISM: Artificial
<220> FEATURE:
<223> OTHER INFORMATION: Primer

<400> SEQUENCE: 291
ggttcttacg gtcttcttca gcttg                                        25

<210> SEQ ID NO 292
<211> LENGTH: 47
<212> TYPE: DNA
<213> ORGANISM: Artificial
<220> FEATURE:
<223> OTHER INFORMATION: Primer

<400> SEQUENCE: 292
gcgtaatacg actcactata ggaatctcgt acactgttgg aacaagc                47

<210> SEQ ID NO 293
<211> LENGTH: 45
<212> TYPE: DNA
<213> ORGANISM: Artificial
<220> FEATURE:
<223> OTHER INFORMATION: Primer

<400> SEQUENCE: 293
gcgtaatacg actcactata ggttcttacg gtcttcttca gcttg                  45

<210> SEQ ID NO 294
<211> LENGTH: 22
<212> TYPE: DNA
<213> ORGANISM: Artificial
<220> FEATURE:
<223> OTHER INFORMATION: Primer

<400> SEQUENCE: 294
aagaagaagc tcaggttgtt gc                                           22

<210> SEQ ID NO 295
<211> LENGTH: 20
<212> TYPE: DNA
<213> ORGANISM: Artificial
<220> FEATURE:
<223> OTHER INFORMATION: Primer

<400> SEQUENCE: 295
tcattcacct ggctgttgag                                              20

<210> SEQ ID NO 296
<211> LENGTH: 44
<212> TYPE: DNA
<213> ORGANISM: Artificial
<220> FEATURE:
<223> OTHER INFORMATION: Primer

<400> SEQUENCE: 296
gcgtaatacg actcactata ggaagaagaa gctcaggttg ttgc                   44

<210> SEQ ID NO 297
<211> LENGTH: 42
<212> TYPE: DNA
<213> ORGANISM: Artificial
<220> FEATURE:

<223> OTHER INFORMATION: Primer

<400> SEQUENCE: 297
gcgtaatacg actcactata ggtcattcac ctggctgttg ag                42

<210> SEQ ID NO 298
<211> LENGTH: 20
<212> TYPE: DNA
<213> ORGANISM: Artificial
<220> FEATURE:
<223> OTHER INFORMATION: Primer

<400> SEQUENCE: 298
acatcctcag gctcatggga                                         20

<210> SEQ ID NO 299
<211> LENGTH: 20
<212> TYPE: DNA
<213> ORGANISM: Artificial
<220> FEATURE:
<223> OTHER INFORMATION: Primer

<400> SEQUENCE: 299
agccgttacc ttccttgtcg                                         20

<210> SEQ ID NO 300
<211> LENGTH: 42
<212> TYPE: DNA
<213> ORGANISM: Artificial
<220> FEATURE:
<223> OTHER INFORMATION: Primer

<400> SEQUENCE: 300
gcgtaatacg actcactata ggacatcctc aggctcatgg ga                42

<210> SEQ ID NO 301
<211> LENGTH: 42
<212> TYPE: DNA
<213> ORGANISM: Artificial
<220> FEATURE:
<223> OTHER INFORMATION: Primer

<400> SEQUENCE: 301
gcgtaatacg actcactata ggagccgtta ccttccttgt cg                42

<210> SEQ ID NO 302
<211> LENGTH: 20
<212> TYPE: DNA
<213> ORGANISM: Artificial
<220> FEATURE:
<223> OTHER INFORMATION: Primer

<400> SEQUENCE: 302
acatcctcag gctcatggga                                         20

<210> SEQ ID NO 303
<211> LENGTH: 20
<212> TYPE: DNA
<213> ORGANISM: Artificial
<220> FEATURE:
<223> OTHER INFORMATION: Primer

<400> SEQUENCE: 303
agccgttacc ttccttgtcg                                         20

```
<210> SEQ ID NO 304
<211> LENGTH: 42
<212> TYPE: DNA
<213> ORGANISM: Artificial
<220> FEATURE:
<223> OTHER INFORMATION: Primer

<400> SEQUENCE: 304
gcgtaatacg actcactata ggacatcctc aggctcatgg ga                42

<210> SEQ ID NO 305
<211> LENGTH: 42
<212> TYPE: DNA
<213> ORGANISM: Artificial
<220> FEATURE:
<223> OTHER INFORMATION: Primer

<400> SEQUENCE: 305
gcgtaatacg actcactata ggagccgtta ccttccttgt cg                42

<210> SEQ ID NO 306
<211> LENGTH: 24
<212> TYPE: DNA
<213> ORGANISM: Artificial
<220> FEATURE:
<223> OTHER INFORMATION: Primer

<400> SEQUENCE: 306
cgtaaaaact ctgaccggca agac                                    24

<210> SEQ ID NO 307
<211> LENGTH: 26
<212> TYPE: DNA
<213> ORGANISM: Artificial
<220> FEATURE:
<223> OTHER INFORMATION: Primer

<400> SEQUENCE: 307
tagttccacc acgaagtctg agaacc                                  26

<210> SEQ ID NO 308
<211> LENGTH: 46
<212> TYPE: DNA
<213> ORGANISM: Artificial
<220> FEATURE:
<223> OTHER INFORMATION: Primer

<400> SEQUENCE: 308
gcgtaatacg actcactata ggcgtaaaaa ctctgaccgg caagac            46

<210> SEQ ID NO 309
<211> LENGTH: 48
<212> TYPE: DNA
<213> ORGANISM: Artificial
<220> FEATURE:
<223> OTHER INFORMATION: Primer

<400> SEQUENCE: 309
gcgtaatacg actcactata ggtagttcca ccacgaagtc tgagaacc          48

<210> SEQ ID NO 310
<211> LENGTH: 21
<212> TYPE: DNA
<213> ORGANISM: Artificial
<220> FEATURE:
<223> OTHER INFORMATION: Primer
```

```
<400> SEQUENCE: 310
atggccgacg atgaagctaa g                                      21

<210> SEQ ID NO 311
<211> LENGTH: 20
<212> TYPE: DNA
<213> ORGANISM: Artificial
<220> FEATURE:
<223> OTHER INFORMATION: Primer

<400> SEQUENCE: 311
tggttgtggt tctggttcgg                                        20

<210> SEQ ID NO 312
<211> LENGTH: 43
<212> TYPE: DNA
<213> ORGANISM: Artificial
<220> FEATURE:
<223> OTHER INFORMATION: Primer

<400> SEQUENCE: 312
gcgtaatacg actcactata ggatggccga cgatgaagct aag              43

<210> SEQ ID NO 313
<211> LENGTH: 42
<212> TYPE: DNA
<213> ORGANISM: Artificial
<220> FEATURE:
<223> OTHER INFORMATION: Primer

<400> SEQUENCE: 313
gcgtaatacg actcactata ggtggttctg gttcgggttc aa               42

<210> SEQ ID NO 314
<211> LENGTH: 20
<212> TYPE: DNA
<213> ORGANISM: Artificial
<220> FEATURE:
<223> OTHER INFORMATION: Primer

<400> SEQUENCE: 314
cggtaatgcg atgcggtaag                                        20

<210> SEQ ID NO 315
<211> LENGTH: 20
<212> TYPE: DNA
<213> ORGANISM: Artificial
<220> FEATURE:
<223> OTHER INFORMATION: Primer

<400> SEQUENCE: 315
tcatcttctc gggcgtatgc                                        20

<210> SEQ ID NO 316
<211> LENGTH: 42
<212> TYPE: DNA
<213> ORGANISM: Artificial
<220> FEATURE:
<223> OTHER INFORMATION: Primer

<400> SEQUENCE: 316
gcgtaatacg actcactata ggcggtaatg cgatgcggta ag               42

<210> SEQ ID NO 317
<211> LENGTH: 42
```

```
<212> TYPE: DNA
<213> ORGANISM: Artificial
<220> FEATURE:
<223> OTHER INFORMATION: Primer

<400> SEQUENCE: 317
gcgtaatacg actcactata ggtcatcttc tcgggcgtat gc                    42

<210> SEQ ID NO 318
<211> LENGTH: 25
<212> TYPE: DNA
<213> ORGANISM: Artificial
<220> FEATURE:
<223> OTHER INFORMATION: Primer

<400> SEQUENCE: 318
tttggaagtt gagtcatcag attcc                                       25

<210> SEQ ID NO 319
<211> LENGTH: 24
<212> TYPE: DNA
<213> ORGANISM: Artificial
<220> FEATURE:
<223> OTHER INFORMATION: Primer

<400> SEQUENCE: 319
gttgtagtcg gaaagggtac gtcc                                        24

<210> SEQ ID NO 320
<211> LENGTH: 47
<212> TYPE: DNA
<213> ORGANISM: Artificial
<220> FEATURE:
<223> OTHER INFORMATION: Primer

<400> SEQUENCE: 320
gcgtaatacg actcactata ggtttggaag ttgagtcatc agattcc                47

<210> SEQ ID NO 321
<211> LENGTH: 46
<212> TYPE: DNA
<213> ORGANISM: Artificial
<220> FEATURE:
<223> OTHER INFORMATION: Primer

<400> SEQUENCE: 321
gcgtaatacg actcactata gggttgtagt cggaaagggt acgtcc                 46

<210> SEQ ID NO 322
<211> LENGTH: 23
<212> TYPE: DNA
<213> ORGANISM: Artificial
<220> FEATURE:
<223> OTHER INFORMATION: Primer

<400> SEQUENCE: 322
aagacttgct tcatcctact gca                                         23

<210> SEQ ID NO 323
<211> LENGTH: 20
<212> TYPE: DNA
<213> ORGANISM: Artificial
<220> FEATURE:
<223> OTHER INFORMATION: Primer

<400> SEQUENCE: 323
```

-continued

```
attgtggaac atccggtaca                                          20
```

<210> SEQ ID NO 324
<211> LENGTH: 45
<212> TYPE: DNA
<213> ORGANISM: Artificial
<220> FEATURE:
<223> OTHER INFORMATION: Primer

<400> SEQUENCE: 324

```
gcgtaatacg actcactata ggaagacttg cttcatccta ctgca             45
```

<210> SEQ ID NO 325
<211> LENGTH: 42
<212> TYPE: DNA
<213> ORGANISM: Artificial
<220> FEATURE:
<223> OTHER INFORMATION: Primer

<400> SEQUENCE: 325

```
gcgtaatacg actcactata ggattgtgga acatccggta ca                42
```

<210> SEQ ID NO 326
<211> LENGTH: 424
<212> TYPE: PRT
<213> ORGANISM: Lygus hesperus

<400> SEQUENCE: 326

Met Ile Pro Pro Thr Ser Arg Pro Gln Val Thr Val Tyr Ser Asp Lys
1               5                   10                  15

Asn Glu Ala Thr Gly Thr Leu Leu Asn Leu Pro Ala Val Phe Asn Ala
            20                  25                  30

Pro Ile Arg Pro Asp Val Val Asn Phe Val His Gln Asn Val Ala Lys
        35                  40                  45

Asn His Arg Gln Pro Tyr Cys Val Ser Ala Gln Ala Gly His Gln Thr
    50                  55                  60

Ser Ala Glu Ser Trp Gly Thr Gly Arg Ala Val Ala Arg Ile Pro Arg
65                  70                  75                  80

Val Arg Gly Gly Thr His Arg Ser Gly Gln Gly Ala Phe Gly Asn
                85                  90                  95

Met Cys Arg Gly Gly Arg Met Phe Ala Pro Thr Arg Pro Trp Arg Arg
            100                 105                 110

Trp His Arg Lys Ile Asn Val Asn Gln Lys Arg Tyr Ala Val Val Ser
        115                 120                 125

Ala Ile Ala Ala Ser Gly Val Pro Ala Leu Val Met Ser Lys Gly His
    130                 135                 140

Met Val Gln Ser Val Pro Glu Phe Pro Leu Val Val Ser Asp Lys Val
145                 150                 155                 160

Gln Glu Tyr Thr Lys Thr Lys Gln Ala Val Ile Phe Leu His Arg Ile
                165                 170                 175

Lys Ala Trp Gln Asp Ile Gln Lys Val Tyr Lys Ser Lys Arg Phe Arg
            180                 185                 190

Ala Gly Lys Gly Lys Met Arg Asn Arg Arg Ile Gln Arg Arg Gly
        195                 200                 205

Pro Leu Ile Ile Tyr Asp Gln Asp Gln Gly Leu Asn Arg Ala Phe Arg
    210                 215                 220

Asn Ile Pro Gly Val Asp Leu Ile Glu Val Ser Arg Leu Asn Leu Leu
225                 230                 235                 240

```
Lys Leu Ala Pro Gly Gly His Ile Gly Arg Phe Val Ile Trp Thr Gln
            245                 250                 255

Ser Ala Phe Glu Lys Leu Asp Ala Leu Tyr Gly Thr Trp Lys Lys
        260                 265                 270

Ser Thr Leu Lys Ala Gly Tyr Asn Leu Pro Met Pro Lys Met Ala Asn
        275                 280                 285

Thr Asp Leu Ser Arg Leu Phe Lys Ala Pro Glu Ile Lys Ala Val Leu
    290                 295                 300

Arg Asn Pro Lys Lys Thr Ile Val Arg Val Arg Lys Leu Asn Pro
305                 310                 315                 320

Leu Arg Asn Thr Arg Ala Met Leu Arg Leu Asn Pro Tyr Ala Ala Val
            325                 330                 335

Leu Lys Arg Lys Ala Ile Leu Asp Gln Arg Lys Leu Lys Leu Gln Lys
        340                 345                 350

Leu Val Glu Ala Ala Lys Lys Gly Asp Thr Lys Leu Ser Pro Arg Val
        355                 360                 365

Glu Arg His Leu Lys Met Ile Glu Arg Lys Ala Leu Ile Lys Lys
        370                 375                 380

Ala Lys Ala Ala Lys Pro Lys Lys Pro Lys Thr Ala Lys Lys Pro Lys
385                 390                 395                 400

Thr Ala Glu Lys Ala Pro Ala Pro Ala Lys Lys Ala Ala Pro Lys
            405                 410                 415

Lys Ala Thr Thr Pro Ala Lys Lys
            420

<210> SEQ ID NO 327
<211> LENGTH: 242
<212> TYPE: PRT
<213> ORGANISM: Lygus hesperus

<400> SEQUENCE: 327

Met Ala Asn Ala Lys Pro Ile Ser Lys Lys Lys Phe Val Ser Asp
1               5                   10                  15

Gly Val Phe Lys Ala Glu Leu Asn Glu Phe Leu Thr Arg Glu Leu Ala
            20                  25                  30

Glu Glu Gly Tyr Ser Gly Val Glu Val Arg Val Thr Pro Asn Lys Thr
        35                  40                  45

Glu Ile Ile Ile Met Ala Thr Arg Thr Gln Ser Val Leu Gly Asp Lys
    50                  55                  60

Gly Arg Arg Ile Arg Glu Leu Thr Ser Val Val Gln Lys Arg Phe Asn
65                  70                  75                  80

Phe Lys Pro Gln Thr Leu Asp Leu Tyr Ala Glu Lys Val Ala Thr Arg
                85                  90                  95

Gly Leu Cys Ala Ile Ala Gln Ala Glu Ser Leu Arg Tyr Lys Leu Ile
            100                 105                 110

Gly Gly Leu Ala Val Arg Gly Ala Cys Tyr Gly Val Leu Arg Phe Ile
        115                 120                 125

Met Glu Asn Gly Ala Lys Gly Cys Glu Val Val Ser Gly Lys Leu
    130                 135                 140

Arg Gly Gln Arg Ala Lys Ser Met Lys Phe Val Asp Gly Leu Met Ile
145                 150                 155                 160

His Ser Gly Asp Pro Cys Asn Glu Tyr Val Asp Thr Ala Thr Arg His
                165                 170                 175

Val Leu Leu Arg Gln Gly Val Leu Gly Ile Lys Val Lys Ile Met Leu
            180                 185                 190
```

```
Pro Trp Asp Val Thr Gly Lys Asn Gly Pro Lys Asn Pro Leu Pro Asp
        195                 200                 205

His Val Ser Val Leu Pro Lys Glu Glu Leu Pro Asn Leu Ala Val
    210                 215                 220

Ser Val Pro Gly Ser Asp Ile Lys Pro Lys Pro Glu Val Pro Ala Pro
225                 230                 235                 240

Ala Leu

<210> SEQ ID NO 328
<211> LENGTH: 262
<212> TYPE: PRT
<213> ORGANISM: Lygus hesperus

<400> SEQUENCE: 328

Met Ala Val Gly Lys Asn Lys Gly Leu Ser Gly Gly Lys Lys Gly
1               5                   10                  15

Val Lys Lys Lys Val Val Asp Pro Phe Thr Arg Lys Asp Trp Tyr Asp
            20                  25                  30

Val Lys Ala Pro Ser Met Phe Lys Arg Gln Val Gly Lys Thr Leu
        35                  40                  45

Val Asn Arg Thr Gln Gly Thr Lys Ile Ala Ser Glu Gly Leu Lys Gly
    50                  55                  60

Arg Val Phe Glu Val Ser Leu Ala Asp Ile Gln Glu Asp Thr Asp Ala
65                  70                  75                  80

Glu Arg Ser Phe Arg Lys Phe Arg Leu Ile Ala Glu Asp Val Gln Ala
                85                  90                  95

Arg Asn Val Leu Thr Asn Phe His Gly Met Asp Leu Thr Thr Asp Lys
            100                 105                 110

Leu Arg Ser Met Val Lys Lys Trp Gln Thr Leu Ile Glu Ala Asn Val
        115                 120                 125

Asp Val Lys Thr Thr Asp Gly Tyr Leu Leu Arg Val Phe Cys Ile Gly
    130                 135                 140

Phe Thr Asn Lys Asp Gln Leu Ser Gln Arg Lys Thr Cys Tyr Ala Gln
145                 150                 155                 160

His Asn Gln Val Arg Glu Ile Arg Lys Lys Met Val Lys Asn Ile Ser
                165                 170                 175

Asp Ser Ile Ser Ser Cys Asp Leu Arg Ser Val Val Asn Lys Leu Ile
            180                 185                 190

Pro Asp Ser Ile Ala Lys Asp Ile Glu Lys Asn Cys Gln Gly Ile Tyr
        195                 200                 205

Pro Leu His Asp Val Tyr Ile Arg Lys Val Leu Val Leu Lys Lys Pro
    210                 215                 220

Arg Phe Glu Leu Ser Lys Leu Leu Glu Leu His Val Asp Gly Lys Gly
225                 230                 235                 240

Ile Asp Glu Pro Gly Ala Lys Val Thr Arg Thr Asp Ala Tyr Glu Pro
                245                 250                 255

Pro Val Gln Glu Ser Val
            260

<210> SEQ ID NO 329
<211> LENGTH: 152
<212> TYPE: PRT
<213> ORGANISM: Lygus hesperus

<400> SEQUENCE: 329
```

Met Ser Leu Met Leu Pro Glu Lys Phe Gln His Ile Leu Arg Ile Met
1               5                   10                  15

Gly Thr Asn Ile Asp Gly Lys Arg Lys Val Met Phe Ala Met Thr Ala
            20                  25                  30

Ile Lys Gly Val Gly Arg Arg Tyr Ala Asn Ile Val Leu Lys Lys Ala
        35                  40                  45

Asp Val Asn Leu Asp Lys Arg Ala Gly Glu Cys Ser Glu Glu Glu Val
50                  55                  60

Glu Lys Ile Val Thr Ile Met Gln Asn Pro Arg Gln Tyr Lys Ile Pro
65                  70                  75                  80

Asn Trp Phe Leu Asn Arg Gln Lys Asp Thr Val Glu Gly Lys Tyr Ser
                85                  90                  95

Gln Leu Thr Ser Ser Leu Leu Asp Ser Lys Leu Arg Asp Asp Leu Glu
            100                 105                 110

Arg Leu Lys Lys Ile Arg Ala His Arg Gly Met Arg His Tyr Trp Gly
        115                 120                 125

Leu Arg Val Arg Gly Gln His Thr Lys Thr Thr Gly Arg Arg Gly Arg
130                 135                 140

Thr Val Gly Val Ser Lys Lys Lys
145                 150

<210> SEQ ID NO 330
<211> LENGTH: 381
<212> TYPE: PRT
<213> ORGANISM: Lygus hesperus

<400> SEQUENCE: 330

Met Ser Asp Glu Glu Tyr Ser Glu Ser Glu Glu Thr Gln Pro Glu
1               5                   10                  15

Pro Gln Lys Lys Pro Glu Ala Glu Gly Gly Gly Asp Pro Glu Phe Val
            20                  25                  30

Lys Arg Lys Glu Ala Gln Thr Ser Ala Leu Asp Glu Gln Leu Lys Asp
        35                  40                  45

Tyr Ile Ala Glu Trp Arg Lys Gln Arg Ala Arg Glu Glu Glu Asp Leu
50                  55                  60

Lys Lys Leu Lys Glu Lys Gln Ala Lys Arg Lys Val Ala Arg Ala Glu
65                  70                  75                  80

Glu Glu Lys Arg Leu Ala Glu Lys Lys Gln Glu Glu Glu Arg Arg
                85                  90                  95

Val Arg Glu Ala Glu Glu Lys Lys Gln Arg Glu Ile Glu Glu Lys Arg
            100                 105                 110

Arg Arg Leu Glu Glu Ala Glu Lys Lys Arg Gln Ala Met Met Ala Ala
        115                 120                 125

Leu Lys Asp Gln Ser Lys Thr Lys Gly Pro Asn Phe Val Val Asn Lys
130                 135                 140

Lys Ala Glu Thr Leu Gly Met Ser Ser Ala Gln Ile Glu Arg Asn Lys
145                 150                 155                 160

Thr Lys Glu Gln Leu Glu Glu Lys Arg Ile Ser Leu Ser Ile Arg
            165                 170                 175

Leu Lys Pro Leu Ala Ile Glu Asn Met Ser Ile Asp Arg Leu Arg Ile
        180                 185                 190

Lys Ala Gln Glu Leu Trp Glu Ala Ile Val Lys Leu Glu Thr Glu Lys
        195                 200                 205

Tyr Asp Leu Glu Glu Arg Gln Lys Arg Gln Asp Tyr Asp Leu Lys Glu
210                 215                 220

-continued

Leu Lys Glu Arg Gln Lys Gln Leu Arg His Lys Ala Leu Lys Lys
225                 230                 235                 240

Gly Leu Asp Pro Glu Ala Leu Thr Gly Lys Tyr Pro Pro Lys Ile Gln
            245                 250                 255

Val Ala Ser Lys Tyr Glu Arg Arg Val Asp Thr Arg Ser Tyr Asp Asp
        260                 265                 270

Lys Lys Lys Leu Phe Glu Gly Gly Ile Leu Glu Arg Tyr Lys Glu Leu
        275                 280                 285

Ile Glu Lys Val Trp Thr Glu Lys Val Asp Gln Phe Gly Ser Arg Ala
290                 295                 300

His Ser Lys Leu Pro Arg Trp Phe Gly Glu Arg Pro Gly Lys Lys Lys
305                 310                 315                 320

Asp Ala Pro Glu Ser Pro Glu Glu Glu Val Lys Val Glu Asp Glu
            325                 330                 335

Pro Glu Ala Glu Pro Ser Phe Met Leu Asp Glu Glu Glu Glu Ala
            340                 345                 350

Glu Glu Glu Glu Ala Glu Glu Glu Glu Ala Glu Glu Glu Glu
        355                 360                 365

Glu Glu Glu Glu Glu Glu Glu Glu Glu Glu Glu
        370                 375                 380

<210> SEQ ID NO 331
<211> LENGTH: 1689
<212> TYPE: PRT
<213> ORGANISM: Lygus hesperus

<400> SEQUENCE: 331

Ser Gly Lys Leu Ala Gly Ala Asp Ile Glu Thr Tyr Leu Leu Glu Lys
1               5                   10                  15

Ala Arg Val Ile Ser Gln Gln Thr Leu Glu Arg Ser Tyr His Ile Phe
            20                  25                  30

Tyr Gln Met Met Ser Gly Ala Val Lys Gly Val Lys Glu Met Cys Leu
        35                  40                  45

Leu Val Asp Asp Ile Tyr Thr Tyr Asn Phe Ile Ser Gln Gly Lys Val
50                  55                  60

Ser Ile Ala Gly Val Asp Asp Gly Glu Glu Met Val Leu Thr Asp Gln
65                  70                  75                  80

Ala Phe Asp Ile Leu Gly Phe Thr Lys Gln Glu Lys Glu Asp Ile Tyr
            85                  90                  95

Lys Ile Thr Ala Ala Val Ile His Met Gly Thr Met Lys Phe Lys Gln
        100                 105                 110

Arg Gly Arg Glu Glu Gln Ala Glu Ala Asp Gly Thr Glu Glu Gly Gly
        115                 120                 125

Lys Val Gly Val Leu Gly Ile Asp Gly Asp Leu Tyr Lys Asn
        130                 135                 140

Met Cys Lys Pro Arg Ile Lys Val Gly Thr Glu Phe Val Thr Gln Gly
145                 150                 155                 160

Lys Asn Val Asn Gln Val Ser Tyr Ser Leu Gly Ala Met Ser Lys Gly
            165                 170                 175

Met Phe Asp Arg Leu Phe Lys Phe Leu Val Lys Lys Cys Asn Glu Thr
        180                 185                 190

Leu Asp Thr Lys Gln Lys Arg Gln His Phe Ile Gly Val Leu Asp Ile
        195                 200                 205

Ala Gly Phe Glu Ile Phe Asp Phe Asn Gly Phe Glu Gln Leu Cys Ile

```
              210                 215                 220
Asn Phe Thr Asn Glu Lys Leu Gln Gln Phe Phe Asn His His Met Phe
225                 230                 235                 240

Val Leu Glu Gln Glu Glu Tyr Lys Arg Glu Gly Ile Asn Trp Ala Phe
                    245                 250                 255

Ile Asp Phe Gly Met Asp Leu Leu Ala Cys Ile Glu Leu Ile Glu Lys
                260                 265                 270

Pro Met Gly Ile Leu Ser Ile Leu Glu Glu Ser Met Phe Pro Lys
            275                 280                 285

Ala Thr Asp Lys Thr Phe Glu Asp Lys Leu Ile Thr Asn His Leu Gly
        290                 295                 300

Lys Ser Pro Asn Phe Arg Lys Pro Ala Val Pro Lys Pro Gly Gln Gln
305                 310                 315                 320

Ala Gly His Phe Ala Ile Ala His Tyr Ala Gly Cys Val Ser Tyr Asn
                325                 330                 335

Ile Thr Gly Trp Leu Glu Lys Asn Lys Asp Pro Leu Asn Asp Thr Val
                340                 345                 350

Val Asp Gln Tyr Lys Lys Gly Thr Asn Lys Leu Leu Cys Glu Ile Phe
                355                 360                 365

Ala Asp His Pro Gly Gln Ser Gly Ala Pro Gly Gly Asp Ala Gly Gly
        370                 375                 380

Lys Gly Gly Arg Gly Lys Lys Gly Gly Gly Phe Ala Thr Val Ser Ser
385                 390                 395                 400

Ser Tyr Lys Glu Gln Leu Asn Asn Leu Met Thr Thr Leu Lys Ser Thr
                405                 410                 415

Gln Pro His Phe Val Arg Cys Ile Ile Pro Asn Glu Leu Lys Gln Pro
                420                 425                 430

Gly Val Ile Asp Ser His Leu Val Met His Gln Leu Thr Cys Asn Gly
                435                 440                 445

Val Leu Glu Gly Ile Arg Ile Cys Arg Lys Gly Phe Pro Asn Arg Met
        450                 455                 460

Asn Tyr Pro Asp Phe Lys Leu Arg Tyr Lys Ile Leu Asn Pro Ala Ala
465                 470                 475                 480

Val Asp Arg Glu Ser Asp Ile Leu Lys Ala Ala Gly Leu Val Leu Glu
                485                 490                 495

Ser Thr Gly Leu Asp Pro Asp Met Tyr Arg Leu Gly His Thr Lys Val
                500                 505                 510

Phe Phe Arg Ala Gly Val Leu Gly Gln Leu Glu Glu Leu Arg Asp Asp
                515                 520                 525

Arg Leu Ser Lys Ile Ile Gly Trp Met Gln Ala Phe Met Arg Gly Tyr
        530                 535                 540

Leu Val Arg Lys Glu Tyr Lys Lys Leu Gln Glu Gln Arg Leu Ala Leu
545                 550                 555                 560

Gln Val Val Gln Arg Asn Leu Arg Arg Tyr Leu Gln Leu Arg Thr Trp
                565                 570                 575

Pro Trp Trp Lys Met Trp Ser Arg Val Lys Pro Leu Leu Asn Val Ala
                580                 585                 590

Asn Val Glu Glu Glu Met Arg Lys Leu Glu Glu Leu Val Ala Glu Thr
                595                 600                 605

Gln Ala Ala Leu Glu Lys Glu Glu Lys Leu Arg Lys Glu Ala Glu Ala
        610                 615                 620

Leu Asn Ala Lys Leu Leu Gln Glu Lys Thr Asp Leu Leu Arg Asn Leu
625                 630                 635                 640
```

```
Glu Gly Glu Lys Gly Ser Ile Ser Gly Ile Gln Arg Cys Ala Lys
            645                 650                 655

Leu Gln Ala Gln Lys Ala Asp Leu Glu Ser Gln Leu Met Asp Thr Gln
            660                 665                 670

Glu Arg Leu Gln Asn Glu Glu Asp Ala Arg Asn Gln Leu Phe Gln Gln
            675                 680                 685

Lys Lys Lys Leu Glu Gln Glu Ala Ala Ala Leu Lys Lys Asp Ile Glu
        690                 695                 700

Asp Leu Glu Leu Ser Asn Gln Lys Thr Asp Gln Asp Lys Ala Ser Lys
705                 710                 715                 720

Glu His Gln Ile Arg Asn Leu Asn Asp Glu Ile Ala His Gln Asp Asp
                725                 730                 735

Leu Ile Asn Lys Leu Asn Lys Glu Lys Lys Ile Gln Ser Glu Leu Asn
            740                 745                 750

Gln Lys Thr Ala Glu Glu Leu Gln Ala Ala Glu Asp Lys Ile Asn His
            755                 760                 765

Leu Thr Lys Val Lys Val Lys Leu Glu Gln Thr Leu Asp Glu Leu Glu
            770                 775                 780

Asp Thr Leu Glu Arg Glu Lys Lys Leu Arg Gly Asp Val Glu Lys Ala
785                 790                 795                 800

Lys Arg Lys Thr Glu Gly Asp Leu Lys Leu Thr Gln Glu Ala Val Ala
                805                 810                 815

Asp Leu Glu Arg Asn Lys Lys Glu Leu Glu Gln Thr Ile Gln Arg Lys
            820                 825                 830

Asp Lys Glu Ile Ala Ser Leu Thr Ala Lys Leu Glu Asp Glu Gln Ser
            835                 840                 845

Ile Val Asn Lys Thr Gly Lys Gln Ile Lys Glu Leu Gln Ser Arg Ile
850                 855                 860

Glu Glu Leu Glu Glu Glu Val Glu Ala Glu Arg Gln Ala Arg Gly Lys
865                 870                 875                 880

Ala Glu Lys Gln Arg Ala Asp Leu Ala Arg Glu Leu Glu Glu Leu Gly
                885                 890                 895

Glu Arg Leu Glu Glu Ala Gly Gly Ala Thr Ser Ala Gln Ile Glu Leu
            900                 905                 910

Asn Lys Lys Arg Glu Ala Glu Met Ser Lys Leu Arg Arg Asp Leu Glu
            915                 920                 925

Glu Ala Asn Ile Gln His Glu Gly Thr Leu Ala Asn Leu Arg Lys Lys
        930                 935                 940

His Asn Asp Ala Val Ser Glu Met Gly Asp Gln Ile Asp Gln Leu Asn
945                 950                 955                 960

Lys Leu Lys Thr Lys Val Glu Lys Glu Lys Ser Gln Tyr Leu Gly Glu
                965                 970                 975

Leu Asn Asp Val Arg Ala Ser Ile Asp His Leu Thr Asn Glu Lys Ala
            980                 985                 990

Ala Thr Glu Lys Val Ala Lys Gln Leu Gln His Gln Ile Asn Glu Val
            995                 1000                1005

Gln Gly Lys Leu Asp Glu Ala Asn Arg Thr Leu Asn Asp Phe Asp
        1010                1015                1020

Ala Ala Lys Lys Lys Leu Ser Ile Glu Asn Ser Asp Leu Leu Arg
        1025                1030                1035

Gln Leu Glu Glu Ala Glu Ser Gln Val Ser Gln Leu Ser Lys Ile
        1040                1045                1050
```

```
Lys Ile Ser Leu Thr Thr Gln Leu Glu Asp Thr Lys Arg Leu Ala
1055                1060                1065

Asp Glu Glu Ala Arg Glu Arg Ala Thr Leu Leu Gly Lys Phe Arg
1070                1075                1080

Asn Leu Glu His Asp Leu Asp Asn Leu Arg Glu Gln Val Glu Glu
1085                1090                1095

Glu Ala Glu Ala Lys Ala Asp Ile Gln Arg Gln Leu Ser Lys Ala
1100                1105                1110

Asn Ala Glu Ala Gln Leu Trp Arg Ser Lys Tyr Glu Ser Glu Gly
1115                1120                1125

Val Ala Arg Ala Glu Glu Leu Glu Glu Ala Lys Arg Lys Leu Gln
1130                1135                1140

Ala Arg Leu Ala Glu Ala Glu Glu Thr Ile Glu Ser Leu Asn Gln
1145                1150                1155

Lys Val Ile Ala Leu Glu Lys Thr Lys Gln Arg Leu Ala Thr Glu
1160                1165                1170

Val Glu Asp Leu Gln Leu Glu Val Asp Arg Ala Asn Ala Ile Ala
1175                1180                1185

Asn Ala Ala Glu Lys Lys Ala Lys Ala Ile Asp Lys Ile Ile Gly
1190                1195                1200

Glu Trp Lys Leu Lys Val Asp Asp Leu Ala Ala Glu Leu Asp Ala
1205                1210                1215

Ser Gln Lys Glu Cys Arg Asn Tyr Ser Thr Glu Leu Phe Arg Leu
1220                1225                1230

Lys Gly Ala Tyr Glu Glu Gly Gln Glu Gln Leu Glu Ala Val Arg
1235                1240                1245

Arg Glu Asn Lys Asn Leu Ala Asp Glu Val Lys Asp Leu Leu Asp
1250                1255                1260

Gln Ile Gly Glu Gly Gly Arg Asn Ile His Glu Ile Glu Lys Gln
1265                1270                1275

Arg Lys Arg Leu Glu Val Glu Lys Asp Glu Leu Gln Ala Ala Leu
1280                1285                1290

Glu Glu Ala Glu Ala Ala Leu Glu Gln Glu Glu Asn Lys Val Leu
1295                1300                1305

Arg Ala Gln Leu Glu Leu Ser Gln Val Arg Gln Glu Ile Asp Arg
1310                1315                1320

Arg Ile Gln Glu Lys Glu Glu Glu Phe Glu Asn Thr Arg Lys Asn
1325                1330                1335

His Gln Arg Ala Leu Asp Ser Met Gln Ala Ser Leu Glu Ala Glu
1340                1345                1350

Ala Lys Gly Lys Ala Glu Ala Leu Arg Met Lys Lys Lys Leu Glu
1355                1360                1365

Ala Asp Ile Asn Glu Leu Glu Ile Ala Leu Asp His Ala Asn Lys
1370                1375                1380

Ala Asn Ala Glu Ala Gln Lys Thr Ile Lys Lys Tyr Gln Gln Gln
1385                1390                1395

Leu Lys Asp Val Gln Thr Ala Leu Glu Glu Glu Gln Arg Ala Arg
1400                1405                1410

Asp Asp Ala Arg Glu Gln Leu Gly Ile Ala Glu Arg Arg Ala Asn
1415                1420                1425

Ala Leu Gly Asn Glu Leu Glu Glu Ser Arg Thr Leu Leu Glu Gln
1430                1435                1440

Ala Asp Arg Gly Arg Arg Gln Ala Glu Gln Glu Leu Gly Asp Ala
```

His Glu Gln Ile Asn Glu Leu Ala Ala Gln Ala Thr Ser Ala Ser
            1460                1465                1470

Ala Ala Lys Arg Lys Leu Glu Gly Glu Leu Gln Thr Leu His Ala
    1475                1480                1485

Asp Leu Asp Glu Leu Leu Asn Glu Ala Lys Asn Ser Glu Glu Lys
    1490                1495                1500

Ala Lys Lys Ala Met Val Asp Ala Ala Arg Leu Ala Asp Glu Leu
    1505                1510                1515

Arg Ala Glu Gln Asp His Ala Gln Thr Gln Glu Lys Leu Arg Lys
    1520                1525                1530

Ala Leu Glu Thr Gln Ile Lys Glu Leu Gln Val Arg Leu Asp Glu
    1535                1540                1545

Ala Glu Asn Asn Ala Leu Lys Gly Gly Lys Lys Ala Ile Ala Lys
    1550                1555                1560

Leu Glu Gln Arg Val Arg Glu Leu Glu Asn Glu Leu Asp Gly Glu
    1565                1570                1575

Gln Arg Arg His Ala Asp Ala Gln Lys Asn Leu Arg Lys Ser Glu
    1580                1585                1590

Arg Arg Ile Lys Glu Leu Ser Phe Gln Ser Asp Glu Asp Arg Lys
    1595                1600                1605

Asn His Glu Arg Met Gln Asp Leu Val Asp Lys Leu Gln Gln Lys
    1610                1615                1620

Ile Lys Thr Tyr Lys Arg Gln Ile Glu Glu Ala Glu Glu Ile Ala
    1625                1630                1635

Ala Leu Asn Leu Ala Lys Phe Arg Lys Ala Gln Gln Glu Leu Glu
    1640                1645                1650

Glu Ala Glu Glu Arg Ala Asp Leu Ala Glu Gln Ala Val Ser Lys
    1655                1660                1665

Phe Arg Thr Lys Gly Gly Arg Ala Gly Ser Ala Ala Arg Ala Met
    1670                1675                1680

Ser Pro Val Gly Gln Lys
    1685

<210> SEQ ID NO 332
<211> LENGTH: 256
<212> TYPE: PRT
<213> ORGANISM: Lygus hesperus

<400> SEQUENCE: 332

Asp Ala Ile Lys Lys Lys Met Gln Ala Met Lys Met Glu Lys Asp Thr
1               5                   10                  15

Ala Met Asp Lys Ala Asp Thr Cys Glu Gly Gln Ala Lys Asp Ala Asn
            20                  25                  30

Thr Arg Ala Asp Lys Ile Leu Glu Asp Val Arg Asp Leu Gln Lys Lys
        35                  40                  45

Leu Asn Gln Val Glu Ser Asp Leu Glu Arg Thr Lys Arg Glu Leu Glu
    50                  55                  60

Thr Lys Thr Thr Glu Leu Glu Glu Lys Glu Lys Ala Asn Thr Asn Ala
65                  70                  75                  80

Glu Ser Glu Val Ala Ser Leu Asn Arg Lys Val Gln Met Val Glu Glu
                85                  90                  95

Asp Leu Glu Arg Ser Glu Glu Arg Ser Gly Thr Ala Gln Gln Lys Leu
            100                 105                 110

Ser Glu Ala Ser His Ala Ala Asp Glu Ala Ser Arg Met Cys Lys Val
     115                        120                     125

Leu Glu Asn Arg Ser Gln Gln Asp Glu Arg Met Asp Gln Leu Thr
130                   135                     140

Asn Gln Leu Lys Glu Ala Arg Leu Leu Ala Glu Asp Ala Asp Gly Lys
145                   150                   155                   160

Ser Asp Glu Val Ser Arg Lys Leu Ala Phe Val Asp Glu Leu Glu
                165                   170                   175

Val Ala Glu Asp Arg Val Lys Ser Gly Asp Ser Lys Ile Met Glu Leu
            180                   185                   190

Glu Glu Glu Leu Lys Val Val Gly Asn Ser Leu Lys Ser Leu Glu Val
     195                       200                   205

Ser Glu Glu Lys Ala Asn Gln Arg Val Glu Glu Tyr Lys Arg Gln Ile
210                   215                   220

Lys Gln Leu Thr Val Lys Leu Lys Glu Ala Glu Ala Arg Ala Glu Phe
225                   230                   235                   240

Ala Glu Lys Thr Val Lys Lys Leu Gln Lys Glu Val Asp Arg Leu Glu
            245                   250                   255

<210> SEQ ID NO 333
<211> LENGTH: 85
<212> TYPE: PRT
<213> ORGANISM: Lygus hesperus

<400> SEQUENCE: 333

Arg Ala Leu Gly Gln Asn Pro Thr Glu Ser Asp Val Lys Lys Phe Thr
1               5                   10                   15

His Gln His Lys Pro Asp Glu Arg Ile Ser Phe Glu Val Phe Leu Pro
               20                   25                   30

Ile Tyr Gln Ala Ile Ser Lys Gly Arg Thr Ser Asp Thr Ala Glu Asp
            35                   40                   45

Phe Ile Glu Gly Leu Arg His Phe Asp Lys Asp Gly Asn Gly Phe Ile
50                   55                   60

Ser Thr Ala Glu Leu Arg His Leu Leu Thr Thr Leu Gly Glu Lys Leu
65                   70                   75                   80

Thr Asp Asp Glu Val
            85

<210> SEQ ID NO 334
<211> LENGTH: 174
<212> TYPE: PRT
<213> ORGANISM: Lygus hesperus

<400> SEQUENCE: 334

Met Ser Ser Arg Lys Thr Ala Gly Arg Ala Thr Thr Lys Lys Arg
1               5                   10                   15

Ala Gln Arg Ala Thr Ser Asn Val Phe Ala Met Phe Asp Gln Ala Gln
            20                   25                   30

Ile Gln Glu Phe Lys Glu Ala Phe Asn Met Ile Asp Gln Asn Arg Asp
            35                   40                   45

Gly Phe Val Asp Lys Glu Asp Leu His Asp Met Leu Ala Ser Leu Gly
50                   55                   60

Lys Asn Pro Ser Asp Glu Tyr Leu Glu Gly Met Met Asn Glu Ala Pro
65                   70                   75                   80

Gly Pro Ile Asn Phe Thr Met Phe Leu Thr Leu Phe Gly Glu Arg Leu
                 85                   90                   95

```
Gln Gly Thr Asp Pro Glu Glu Val Ile Lys Asn Ala Phe Gly Cys Phe
            100                 105                 110

Asp Glu Asp Asn Asn Gly Phe Ile Asn Glu Glu Arg Leu Arg Glu Leu
            115                 120                 125

Leu Thr Ser Met Gly Asp Arg Phe Thr Asp Glu Asp Val Asp Glu Met
        130                 135                 140

Tyr Arg Glu Ala Pro Ile Lys Asn Gly Met Phe Asp Tyr Ile Glu Phe
145                 150                 155                 160

Thr Arg Ile Leu Lys His Gly Ala Lys Asp Lys Asp Glu Gln
                165                 170

<210> SEQ ID NO 335
<211> LENGTH: 1881
<212> TYPE: PRT
<213> ORGANISM: Lygus hesperus

<400> SEQUENCE: 335

Asp Leu Thr Cys Leu Asn Glu Ala Ser Val Leu His Asn Ile Lys Asp
1               5                   10                  15

Arg Tyr Tyr Ser Gly Leu Ile Tyr Thr Tyr Ser Gly Leu Phe Cys Val
            20                  25                  30

Val Val Asn Pro Tyr Lys Lys Leu Pro Ile Tyr Thr Glu Arg Ile Met
        35                  40                  45

Glu Lys Tyr Lys Gly Val Lys Arg His Asp Leu Pro Pro His Val Phe
50                  55                  60

Ala Ile Thr Asp Thr Ala Tyr Arg Ser Met Leu Gln Asp Arg Glu Asp
65                  70                  75                  80

Gln Ser Ile Leu Cys Thr Gly Glu Ser Gly Ala Gly Lys Thr Glu Asn
                85                  90                  95

Thr Lys Lys Val Ile Gln Tyr Leu Ala Tyr Val Ala Ala Ser Lys Pro
            100                 105                 110

Lys Ser Ser Ala Ser Pro His Thr Ala Gln Ser Gln Ala Leu Ile Ile
        115                 120                 125

Gly Glu Leu Glu Gln Gln Leu Leu Gln Ala Asn Pro Ile Leu Glu Ala
        130                 135                 140

Phe Gly Asn Ala Lys Thr Val Lys Asn Asp Asn Ser Ser Arg Phe Gly
145                 150                 155                 160

Lys Phe Ile Arg Ile Asn Phe Asp Ala Ser Gly Tyr Ile Ala Gly Ala
                165                 170                 175

Asn Ile Glu Thr Tyr Leu Leu Glu Lys Ser Arg Ala Ile Arg Gln Ala
            180                 185                 190

Lys Asp Glu Arg Thr Phe His Ile Phe Tyr Gln Leu Leu Ala Gly Ala
        195                 200                 205

Ser Ala Glu Gln Arg Lys Glu Phe Ile Leu Glu Asp Pro Lys Asn Tyr
    210                 215                 220

Pro Phe Leu Ser Ser Gly Met Val Ser Val Pro Gly Val Asp Asp Gly
225                 230                 235                 240

Val Asp Phe Gln Ala Thr Ile Ala Ser Met Ser Ile Met Gly Met Thr
                245                 250                 255

Asn Asp Asp Leu Ser Ala Leu Phe Arg Ile Val Ser Ala Val Met Leu
            260                 265                 270

Phe Gly Ser Met Gln Phe Lys Gln Glu Arg Asn Ser Asp Gln Ala Thr
        275                 280                 285

Leu Pro Asp Asn Thr Val Ala Gln Lys Ile Ala His Leu Leu Gly Leu
    290                 295                 300
```

Ser Ile Thr Glu Met Thr Lys Ala Phe Leu Arg Pro Arg Ile Lys Val
305                 310                 315                 320

Gly Arg Asp Phe Val Thr Lys Ala Gln Thr Lys Glu Gln Val Glu Phe
            325                 330                 335

Ala Val Glu Ala Ile Ser Lys Ala Cys Tyr Glu Arg Met Phe Arg Trp
            340                 345                 350

Leu Val Asn Arg Ile Asn Arg Ser Leu Asp Arg Thr Lys Arg Gln Gly
            355                 360                 365

Ala Ser Phe Ile Gly Ile Leu Asp Met Ala Gly Phe Glu Ile Phe Glu
370                 375                 380

Ile Asn Ser Phe Glu Gln Leu Cys Ile Asn Tyr Thr Asn Glu Lys Leu
385                 390                 395                 400

Gln Gln Leu Phe Asn His Thr Met Phe Ile Leu Glu Gln Glu Glu Tyr
            405                 410                 415

Gln Arg Glu Gly Ile Glu Trp Lys Phe Ile Asp Phe Gly Leu Asp Leu
            420                 425                 430

Gln Pro Thr Ile Asp Leu Ile Asp Lys Pro Met Gly Val Met Ala Leu
            435                 440                 445

Leu Asp Glu Glu Cys Trp Phe Pro Lys Ala Thr Asp Lys Thr Phe Val
450                 455                 460

Glu Lys Leu Val Gly Ala His Ser Val His Pro Lys Phe Ile Lys Thr
465                 470                 475                 480

Asp Phe Arg Gly Val Ala Asp Phe Ala Val Val His Tyr Ala Gly Lys
            485                 490                 495

Val Asp Tyr Ser Ala Ala Gln Trp Leu Met Lys Asn Met Asp Pro Leu
            500                 505                 510

Asn Glu Asn Val Val Gln Leu Leu Gln Asn Ser Gln Asp Pro Phe Val
            515                 520                 525

Ile His Ile Trp Lys Asp Ala Glu Ile Val Gly Met Ala His Gln Ala
530                 535                 540

Leu Ser Asp Thr Gln Phe Gly Ala Arg Thr Arg Lys Gly Met Phe Arg
545                 550                 555                 560

Thr Val Ser Gln Leu Tyr Lys Asp Gln Leu Ser Lys Leu Met Ile Thr
            565                 570                 575

Leu Arg Asn Thr Asn Pro Asn Phe Val Arg Cys Ile Leu Pro Asn His
            580                 585                 590

Glu Lys Arg Ala Gly Lys Ile Asp Ala Pro Leu Val Leu Asp Gln Leu
            595                 600                 605

Arg Cys Asn Gly Val Leu Glu Gly Ile Arg Ile Cys Arg Gln Gly Phe
            610                 615                 620

Pro Asn Arg Ile Pro Phe Gln Glu Phe Arg Gln Arg Tyr Glu Leu Leu
625                 630                 635                 640

Thr Pro Asn Val Ile Pro Lys Gly Phe Met Asp Gly Lys Lys Ala Cys
            645                 650                 655

Glu Lys Met Ile Asn Ala Leu Glu Leu Asp Pro Asn Leu Tyr Arg Val
            660                 665                 670

Gly Gln Ser Lys Ile Phe Phe Arg Ala Gly Val Leu Ala His Leu Glu
            675                 680                 685

Glu Glu Arg Asp Tyr Lys Ile Thr Asp Leu Ile Ala Asn Phe Arg Ala
            690                 695                 700

Phe Cys Arg Gly Tyr Leu Ala Arg Arg Asn Tyr Gln Lys Arg Leu Gln
705                 710                 715                 720

```
Gln Leu Asn Ala Ile Arg Ile Ile Gln Arg Asn Cys Ser Ala Tyr Leu
            725                 730                 735

Lys Leu Arg Asn Trp Gln Trp Trp Arg Leu Tyr Thr Lys Val Lys Pro
            740                 745                 750

Leu Leu Glu Val Thr Lys Gln Glu Lys Leu Thr Gln Lys Glu Asp
            755                 760                 765

Glu Leu Lys Gln Val Arg Glu Lys Leu Asp Asn Gln Val Arg Ser Lys
            770                 775                 780

Glu Glu Tyr Glu Lys Arg Leu Gln Asp Ala Leu Glu Lys Ala Ala
785                 790                 795                 800

Leu Ala Glu Gln Leu Gln Ala Glu Val Glu Leu Cys Ala Glu Ala Glu
            805                 810                 815

Glu Met Arg Ala Arg Leu Ala Val Arg Lys Gln Glu Leu Glu Glu Ile
            820                 825                 830

Leu His Asp Leu Glu Ala Arg Ile Glu Glu Glu Gln Arg Asn Thr
            835                 840                 845

Val Leu Ile Asn Glu Lys Lys Lys Leu Thr Leu Asn Ile Ala Asp Leu
            850                 855                 860

Glu Glu Gln Leu Glu Glu Glu Gly Ala Arg Gln Lys Leu Gln Leu
865                 870                 875                 880

Glu Lys Val Gln Ile Glu Ala Arg Leu Lys Lys Met Glu Glu Asp Leu
            885                 890                 895

Ala Leu Ala Glu Asp Thr Asn Thr Lys Val Val Lys Glu Lys Lys Val
            900                 905                 910

Leu Glu Glu Arg Ala Ser Asp Leu Ala Gln Thr Leu Ala Glu Glu Glu
            915                 920                 925

Glu Lys Ala Lys His Leu Ala Lys Leu Lys Thr Lys His Glu Thr Thr
            930                 935                 940

Ile Ala Glu Leu Glu Glu Arg Leu Leu Lys Asp Asn Gln Arg Gln
945                 950                 955                 960

Glu Met Asp Arg Asn Lys Arg Lys Ile Glu Ser Glu Val Asn Asp Leu
            965                 970                 975

Lys Glu Gln Ile Asn Glu Lys Lys Val Gln Val Glu Glu Leu Gln Leu
            980                 985                 990

Gln Leu Gly Lys Arg Glu Glu Glu Ile Ala Gln Ala Leu Met Arg Ile
            995                 1000                1005

Asp Glu Glu Gly Ala Gly Lys Ala Gln Thr Gln Lys Ala Leu Arg
            1010                1015                1020

Glu Leu Glu Ser Gln Leu Ala Glu Leu Gln Glu Asp Leu Glu Ala
            1025                1030                1035

Glu Lys Ala Ala Arg Ala Lys Ala Glu Lys Gln Lys Arg Asp Leu
            1040                1045                1050

Asn Glu Glu Leu Glu Ser Leu Lys Asn Glu Leu Leu Asp Ser Leu
            1055                1060                1065

Asp Thr Thr Ala Ala Gln Gln Glu Leu Arg Thr Lys Arg Glu His
            1070                1075                1080

Glu Leu Ala Thr Leu Lys Lys Thr Leu Glu Glu Glu Thr His Ile
            1085                1090                1095

His Glu Val Ser Leu Thr Glu Met Arg His Lys His Thr Gln Glu
            1100                1105                1110

Val Ala Ala Leu Asn Glu Gln Leu Glu Gln Leu Lys Lys Ala Lys
            1115                1120                1125

Ser Ala Leu Glu Lys Ser Lys Ala Gln Leu Glu Gly Glu Ala Ala
```

-continued

|  |  |  |  |  |  |  |  |  |  |
|--|--|--|--|--|--|--|--|--|--|
| | | 1130 | | | 1135 | | | 1140 | |
| Glu | Leu | Ala | Asn | Glu | Leu | Glu | Thr | Ala | Gly | Thr | Ser | Lys | Gly | Glu |
| | | 1145 | | | | 1150 | | | | 1155 | | | | |
| Ser | Glu | Arg | Lys | Arg | Lys | Gln | Ala | Glu | Ser | Ser | Leu | Gln | Glu | Leu |
| | | 1160 | | | | 1165 | | | | 1170 | | | | |
| Ser | Ser | Arg | Leu | Leu | Glu | Met | Glu | Arg | Thr | Lys | Ala | Glu | Leu | Gln |
| | | 1175 | | | | 1180 | | | | 1185 | | | | |
| Glu | Arg | Val | Gln | Lys | Leu | Ser | Ala | Glu | Ala | Asp | Ser | Val | Asn | Gln |
| | | 1190 | | | | 1195 | | | | 1200 | | | | |
| Gln | Leu | Glu | Ala | Ala | Glu | Leu | Lys | Ala | Ser | Ala | Ala | Leu | Lys | Ala |
| | | 1205 | | | | 1210 | | | | 1215 | | | | |
| Ser | Gly | Thr | Leu | Glu | Thr | Gln | Leu | Gln | Glu | Ala | Gln | Val | Leu | Leu |
| | | 1220 | | | | 1225 | | | | 1230 | | | | |
| Glu | Glu | Glu | Thr | Arg | Gln | Lys | Leu | Ser | Leu | Thr | Thr | Lys | Leu | Lys |
| | | 1235 | | | | 1240 | | | | 1245 | | | | |
| Gly | Leu | Glu | Ser | Glu | Arg | Asp | Ala | Leu | Lys | Glu | Gln | Leu | Tyr | Glu |
| | | 1250 | | | | 1255 | | | | 1260 | | | | |
| Glu | Asp | Glu | Gly | Arg | Lys | Asn | Leu | Glu | Lys | Gln | Met | Ala | Ile | Leu |
| | | 1265 | | | | 1270 | | | | 1275 | | | | |
| Asn | Gln | Gln | Val | Ala | Glu | Ser | Lys | Lys | Lys | Ser | Glu | Glu | Glu | Thr |
| | | 1280 | | | | 1285 | | | | 1290 | | | | |
| Glu | Lys | Ile | Thr | Glu | Leu | Glu | Glu | Ser | Arg | Lys | Lys | Leu | Leu | Lys |
| | | 1295 | | | | 1300 | | | | 1305 | | | | |
| Asp | Ile | Glu | Ile | Leu | Gln | Arg | Gln | Val | Glu | Glu | Leu | Gln | Val | Thr |
| | | 1310 | | | | 1315 | | | | 1320 | | | | |
| Asn | Asp | Lys | Leu | Glu | Lys | Gly | Lys | Lys | Lys | Leu | Gln | Ser | Glu | Leu |
| | | 1325 | | | | 1330 | | | | 1335 | | | | |
| Glu | Asp | Leu | Thr | Ile | Asp | Leu | Glu | Ser | Gln | Arg | Thr | Lys | Val | Val |
| | | 1340 | | | | 1345 | | | | 1350 | | | | |
| Glu | Leu | Glu | Lys | Lys | Gln | Arg | Asn | Phe | Asp | Lys | Val | Leu | Ala | Glu |
| | | 1355 | | | | 1360 | | | | 1365 | | | | |
| Glu | Lys | Ala | Leu | Ser | Gln | Gln | Ile | Thr | His | Glu | Arg | Asp | Ala | Ala |
| | | 1370 | | | | 1375 | | | | 1380 | | | | |
| Glu | Arg | Glu | Ala | Arg | Glu | Lys | Glu | Thr | Arg | Val | Leu | Ser | Leu | Thr |
| | | 1385 | | | | 1390 | | | | 1395 | | | | |
| Arg | Glu | Leu | Asp | Glu | Phe | Met | Glu | Lys | Ile | Glu | Glu | Leu | Glu | Arg |
| | | 1400 | | | | 1405 | | | | 1410 | | | | |
| Ser | Lys | Arg | Gln | Leu | Gln | Ala | Glu | Leu | Asp | Glu | Leu | Val | Asn | Asn |
| | | 1415 | | | | 1420 | | | | 1425 | | | | |
| Gln | Gly | Thr | Thr | Asp | Lys | Ser | Val | His | Glu | Leu | Glu | Arg | Ala | Lys |
| | | 1430 | | | | 1435 | | | | 1440 | | | | |
| Arg | Val | Leu | Glu | Ser | Gln | Leu | Ala | Glu | Gln | Lys | Ala | Gln | Asn | Glu |
| | | 1445 | | | | 1450 | | | | 1455 | | | | |
| Glu | Leu | Glu | Asp | Glu | Leu | Gln | Met | Thr | Glu | Asp | Ala | Lys | Leu | Arg |
| | | 1460 | | | | 1465 | | | | 1470 | | | | |
| Leu | Glu | Val | Asn | Met | Gln | Ala | Leu | Arg | Ala | Gln | Phe | Glu | Arg | Asp |
| | | 1475 | | | | 1480 | | | | 1485 | | | | |
| Leu | Gln | Gly | Lys | Glu | Glu | Ser | Gly | Glu | Glu | Lys | Arg | Arg | Gly | Leu |
| | | 1490 | | | | 1495 | | | | 1500 | | | | |
| Leu | Lys | Gln | Leu | Arg | Asp | Ile | Glu | Ala | Glu | Leu | Glu | Asp | Glu | Arg |
| | | 1505 | | | | 1510 | | | | 1515 | | | | |
| Lys | Gln | Arg | Thr | Ala | Ala | Val | Ala | Ser | Arg | Lys | Lys | Ile | Glu | Ala |
| | | 1520 | | | | 1525 | | | | 1530 | | | | |

```
Asp Phe Lys Asp Val Glu Gln Gln Leu Glu Met His Thr Lys Val
1535                1540                1545

Lys Glu Asp Leu Gln Lys Gln Leu Lys Lys Cys Gln Val Gln Leu
1550                1555                1560

Lys Asp Ala Ile Arg Asp Ala Glu Glu Ala Arg Leu Gly Arg Glu
1565                1570                1575

Glu Leu Gln Ala Ala Ala Lys Glu Ala Glu Arg Lys Trp Lys Gly
1580                1585                1590

Leu Glu Thr Glu Leu Ile Gln Val Gln Glu Asp Leu Met Ala Ser
1595                1600                1605

Glu Arg Gln Arg Arg Ala Ala Glu Ala Glu Arg Asp Glu Val Val
1610                1615                1620

Glu Glu Ala Asn Lys Asn Val Lys Ser Leu Ser Asn Leu Leu Asp
1625                1630                1635

Glu Lys Lys Arg Leu Glu Ala Gln Cys Ser Gly Leu Glu Glu Glu
1640                1645                1650

Leu Glu Glu Glu Leu Ser Asn Asn Glu Ala Leu Gln Asp Lys Ala
1655                1660                1665

Arg Lys Ala Gln Leu Ser Val Glu Gln Leu Asn Ala Glu Leu Ala
1670                1675                1680

Ala Glu Arg Ser Asn Val Gln Lys Leu Glu Gly Thr Arg Leu Ser
1685                1690                1695

Met Glu Arg Gln Asn Lys Glu Leu Lys Ala Lys Leu Asn Glu Leu
1700                1705                1710

Glu Thr Leu Gln Arg Asn Lys Phe Lys Ala Asn Ala Ser Leu Glu
1715                1720                1725

Ala Lys Ile Thr Asn Leu Glu Gln Leu Glu Asn Glu Ala Lys
1730                1735                1740

Glu Lys Leu Leu Leu Gln Lys Gly Asn Arg Lys Leu Asp Lys Lys
1745                1750                1755

Ile Lys Asp Leu Leu Val Gln Leu Glu Asp Glu Arg Arg His Ala
1760                1765                1770

Asp Gln Tyr Lys Glu Gln Val Glu Lys Ile Asn Val Arg Val Lys
1775                1780                1785

Thr Leu Lys Arg Thr Leu Asp Asp Ala Glu Glu Glu Met Ser Arg
1790                1795                1800

Glu Lys Thr Gln Lys Arg Lys Ala Leu Arg Glu Leu Glu Asp Leu
1805                1810                1815

Arg Glu Asn Tyr Asp Ser Leu Leu Arg Glu Asn Asp Asn Leu Lys
1820                1825                1830

Asn Lys Leu Arg Arg Gly Gly Gly Ile Ser Gly Ile Ser Ser Arg
1835                1840                1845

Leu Gly Gly Ser Lys Arg Gly Ser Ile Pro Gly Glu Asp Ser Gln
1850                1855                1860

Gly Leu Asn Asn Thr Thr Asp Glu Ser Val Asp Gly Asp Asp Ile
1865                1870                1875

Ser Asn Pro
1880

<210> SEQ ID NO 336
<211> LENGTH: 108
<212> TYPE: PRT
<213> ORGANISM: Lygus hesperus
```

<400> SEQUENCE: 336

Lys Lys Ile Leu Glu Glu Ile Ile Ala Glu Val Asp Ala Asp Gly Ser
1               5                   10                  15

Gly Gln Leu Glu Phe Glu Glu Phe Val Ala Leu Ala Ala Gly Phe Leu
            20                  25                  30

Thr Glu Asp Glu Thr Gln Asp Ala Glu Ala Met Gln Gln Glu Leu Arg
        35                  40                  45

Glu Ala Phe Arg Leu Tyr Asp Lys Gly Asn Gly Tyr Ile Thr Thr
    50                  55                  60

Asp Val Leu Arg Glu Ile Leu Lys Glu Leu Asp Lys Ile Thr Ser
65                  70                  75                  80

Gln Glu Leu Asp Met Met Ile Ala Glu Ile Asp Ser Asp Gly Ser Gly
            85                  90                  95

Thr Val Asp Phe Asp Glu Phe Met Glu Met Met Thr
            100                 105

<210> SEQ ID NO 337
<211> LENGTH: 141
<212> TYPE: PRT
<213> ORGANISM: Lygus hesperus

<400> SEQUENCE: 337

Ile Pro Ile Met Thr Ile Ala Leu Asn Ala Phe Asp Arg Asp His Ser
1               5                   10                  15

Gly Ser Ile Pro Thr Asp Met Val Ala Asp Ile Leu Arg Leu Met Gly
            20                  25                  30

Gln Pro Phe Asn Lys Lys Ile Leu Asp Glu Leu Ile Glu Glu Val Asp
        35                  40                  45

Ala Asp Lys Ser Gly Arg Leu Glu Phe Glu Glu Phe Ile Thr Leu Ala
    50                  55                  60

Ala Lys Phe Ile Val Glu Glu Asp Asp Glu Ala Met Gln Lys Glu Leu
65                  70                  75                  80

Arg Glu Ala Phe Arg Leu Tyr Asp Lys Glu Gly Asn Gly Tyr Ile Pro
            85                  90                  95

Thr Ser Cys Leu Lys Glu Ile Leu His Glu Leu Asp Glu Gln Leu Thr
            100                 105                 110

Asn Glu Glu Leu Asp Met Ile Ile Glu Glu Ile Asp Ser Asp Gly Ser
            115                 120                 125

Gly Thr Val Asp Phe Asp Glu Phe Met Glu Met Met Thr
        130                 135                 140

<210> SEQ ID NO 338
<211> LENGTH: 58
<212> TYPE: PRT
<213> ORGANISM: Lygus hesperus

<400> SEQUENCE: 338

Trp Val Lys Glu Gly Ala Cys Ser Glu Gln Ser Ser Arg Met Thr Ala
1               5                   10                  15

Met Asp Asn Ala Ser Lys Asn Ala Ala Glu Met Ile Asp Lys Leu Thr
            20                  25                  30

Leu Thr Phe Asn Arg Thr Arg Gln Ala Val Ile Thr Arg Glu Leu Ile
            35                  40                  45

Glu Ile Ile Ser Gly Ala Ser Ala Leu Glu
        50                  55

```
<210> SEQ ID NO 339
<211> LENGTH: 130
<212> TYPE: PRT
<213> ORGANISM: Lygus hesperus

<400> SEQUENCE: 339

Met Val Arg Met Asn Val Leu Ser Asp Ala Leu Lys Ser Ile Asn Asn
1               5                   10                  15

Ala Glu Lys Arg Gly Lys Arg Gln Val Leu Arg Pro Cys Ser Lys
            20                  25                  30

Val Ile Ile Lys Phe Leu Thr Val Met Met Lys Lys Gly Tyr Ile Gly
        35                  40                  45

Glu Phe Glu Ile Val Asp Asp His Arg Ser Gly Lys Ile Val Val Asn
    50                  55                  60

Leu Asn Gly Arg Leu Asn Lys Cys Gly Val Ile Ser Pro Arg Phe Asp
65                  70                  75                  80

Val Pro Ile Thr Gln Ile Glu Lys Trp Thr Asn Asn Leu Leu Pro Ser
                85                  90                  95

Arg Gln Phe Gly Tyr Val Val Leu Thr Thr Ser Gly Gly Ile Met Asp
            100                 105                 110

His Glu Glu Ala Arg Arg Lys His Leu Gly Gly Lys Ile Leu Gly Phe
        115                 120                 125

Phe Phe
    130

<210> SEQ ID NO 340
<211> LENGTH: 131
<212> TYPE: PRT
<213> ORGANISM: Lygus hesperus

<400> SEQUENCE: 340

Val Asp Gly Gly Leu Asn Ile Pro His Ser Thr Lys Arg Phe Pro Gly
1               5                   10                  15

Tyr Asp Ser Glu Ser Lys Glu Phe Asn Ala Glu Val His Arg Lys His
            20                  25                  30

Ile Phe Gly Ile His Val Ala Asp Tyr Met Arg Gln Leu Ala Glu Glu
        35                  40                  45

Asp Asp Asp Ala Tyr Lys Lys Gln Phe Ser Gln Tyr Val Lys Asn Gly
    50                  55                  60

Val Thr Ala Asp Ser Ile Glu Ser Ile Tyr Lys Lys Ala His Glu Ala
65                  70                  75                  80

Ile Arg Ala Asp Pro Thr Arg Lys Pro Leu Glu Lys Lys Glu Val Lys
                85                  90                  95

Lys Lys Arg Trp Asn Arg Ala Lys Leu Ser Leu Ser Glu Arg Lys Asn
            100                 105                 110

Thr Ile Asn Gln Lys Lys Ala Thr Tyr Leu Lys Lys Val Glu Ala Gly
        115                 120                 125

Glu Ile Glu
    130

<210> SEQ ID NO 341
<211> LENGTH: 214
<212> TYPE: PRT
<213> ORGANISM: Lygus hesperus

<400> SEQUENCE: 341

Met Ala Pro Lys Gly Asn Asn Met Ile Pro Asn Gly His Phe His Lys
1               5                   10                  15
```

-continued

Asp Trp Gln Arg Phe Ile Lys Thr Trp Phe Asn Gln Pro Ala Arg Lys
            20                  25                  30

Leu Arg Arg Arg Asn Lys Arg Leu Glu Lys Ala Gln Arg Leu Ala Pro
        35                  40                  45

Arg Pro Ala Gly Pro Leu Arg Pro Ala Val Arg Cys Pro Thr Val Arg
    50                  55                  60

Tyr His Thr Lys Leu Arg Pro Gly Arg Gly Phe Thr Leu Glu Glu Ile
65                  70                  75                  80

Lys Arg Ala Gly Leu Cys Lys Gly Phe Ala Met Ser Ile Gly Ile Ala
                85                  90                  95

Val Asp Pro Arg Arg Asn Lys Ser Ile Glu Ser Leu Gln Leu Asn
            100                 105                 110

Val Gln Arg Leu Lys Glu Tyr Arg Ala Lys Leu Ile Leu Phe Pro His
        115                 120                 125

Lys Asn Ala Lys Lys Leu Lys Lys Gly Glu Ala Thr Glu Glu Glu Arg
    130                 135                 140

Lys Val Ala Thr Gln Gln Pro Leu Pro Val Met Pro Ile Lys Gln Pro
145                 150                 155                 160

Val Ile Lys Phe Lys Ala Arg Val Ile Thr Asp Asp Glu Lys Lys Tyr
                165                 170                 175

Ser Ala Phe Thr Ala Leu Arg Lys Gly Arg Ala Asp Gln Arg Leu Val
            180                 185                 190

Gly Ile Arg Ala Lys Arg Ala Lys Glu Ala Ala Glu Asn Ala Glu Asp
        195                 200                 205

Pro Ser Lys Ala Pro Lys
    210

<210> SEQ ID NO 342
<211> LENGTH: 134
<212> TYPE: PRT
<213> ORGANISM: Lygus hesperus

<400> SEQUENCE: 342

Met Asp Ile Glu Glu Pro Ala Ala Pro Thr Glu Pro Ser Asp Val
1               5                   10                  15

Asn Thr Ala Leu Gln Glu Val Leu Lys Ala Ala Leu Gln His Gly Val
            20                  25                  30

Val Val His Gly Ile His Glu Ser Ala Lys Ala Leu Asp Lys Arg Gln
        35                  40                  45

Ala Leu Leu Cys Val Leu Ala Glu Asn Cys Asp Glu Pro Met Tyr Lys
    50                  55                  60

Lys Leu Val Gln Ala Leu Cys Ser Glu His His Ile Pro Leu Val Lys
65                  70                  75                  80

Val Asp Ser Asn Lys Lys Leu Gly Glu Trp Thr Gly Leu Cys Lys Ile
                85                  90                  95

Asp Lys Thr Gly Lys Ser Arg Lys Ile Val Gly Cys Ser Cys Val Val
            100                 105                 110

Ile Lys Asp Trp Gly Glu Asp Thr Pro His Leu Asp Leu Leu Lys Asp
        115                 120                 125

Tyr Ile Arg Asp Val Phe
    130

<210> SEQ ID NO 343
<211> LENGTH: 148
<212> TYPE: PRT

<213> ORGANISM: Lygus hesperus

<400> SEQUENCE: 343

Met Lys Met Asn Lys Leu Val Thr Ser Ser Arg Arg Lys Asn Arg Lys
1               5                   10                  15

Arg His Phe Thr Ala Pro Ser His Ile Arg Arg Lys Leu Met Ser Ala
            20                  25                  30

Pro Leu Ser Lys Glu Leu Arg Gln Lys Tyr Asn Val Arg Thr Met Pro
        35                  40                  45

Val Arg Lys Asp Asp Glu Val Gln Val Val Arg Gly His Tyr Lys Gly
    50                  55                  60

Gln Gln Val Gly Lys Val Leu Gln Val Tyr Arg Lys Lys Phe Ile Ile
65                  70                  75                  80

Tyr Ile Glu Arg Ile Gln Arg Glu Lys Ala Asn Gly Ala Ser Val Tyr
                85                  90                  95

Val Gly Ile His Pro Ser Lys Cys Val Ile Val Lys Leu Lys Val Asp
            100                 105                 110

Lys Asp Arg Lys Glu Ile Leu Asp Arg Arg Ser Lys Gly Arg Asp Leu
        115                 120                 125

Ala Leu Gly Lys Asp Lys Gly Leu Tyr Thr Glu Asp Ser Thr Thr Ala
    130                 135                 140

Met Asp Thr Ser
145

<210> SEQ ID NO 344
<211> LENGTH: 65
<212> TYPE: PRT
<213> ORGANISM: Lygus hesperus

<400> SEQUENCE: 344

Met Glu Lys Pro Val Val Leu Ala Arg Val Ile Lys Ile Leu Gly Arg
1               5                   10                  15

Thr Gly Ser Gln Gly Gln Cys Thr Gln Val Lys Val Glu Phe Ile Gly
            20                  25                  30

Glu Gln Asn Arg Gln Ile Ile Arg Asn Val Lys Gly Pro Val Arg Glu
        35                  40                  45

Gly Asp Ile Leu Thr Leu Leu Glu Ser Glu Arg Glu Ala Arg Arg Leu
    50                  55                  60

Arg
65

<210> SEQ ID NO 345
<211> LENGTH: 229
<212> TYPE: PRT
<213> ORGANISM: Lygus hesperus

<400> SEQUENCE: 345

Leu Phe Tyr Phe Pro Phe Ser Arg Lys Trp Gly Asp Val Gln Arg Gly
1               5                   10                  15

Val Ile Gly Thr Val Lys Thr Ser His Thr Pro Lys Ser Arg Phe Cys
            20                  25                  30

Arg Gly Val Pro Asp Pro Lys Ile Arg Ile Phe Asp Leu Gly Lys Lys
        35                  40                  45

Lys Ala Arg Val Glu Asp Phe Pro Leu Cys Val His Leu Val Ser Asp
    50                  55                  60

Glu Tyr Glu Gln Leu Ser Ser Glu Ala Leu Glu Ala Gly Arg Ile Cys
65                  70                  75                  80

```
Cys Asn Lys Tyr Leu Val Lys Asn Cys Gly Lys Asp Gln Phe His Ile
                85                  90                  95

Arg Met Arg Leu His Pro Phe His Val Ile Arg Ile Asn Lys Met Leu
            100                 105                 110

Ser Cys Ala Gly Ala Asp Arg Leu Gln Thr Gly Met Arg Gly Ala Phe
        115                 120                 125

Gly Lys Pro Gln Gly Thr Val Ala Arg Val Arg Ile Gly Gln Pro Ile
    130                 135                 140

Met Ser Val Arg Ser Ser Asp Arg Tyr Lys Ala Ala Val Ile Lys Ala
145                 150                 155                 160

Leu Arg Arg Ala Lys Phe Lys Phe Pro Gly Arg Gln Lys Ile Tyr Val
                165                 170                 175

Ser Lys Lys Trp Gly Phe Thr Lys Phe Asp Arg Glu Glu Tyr Glu Gly
            180                 185                 190

Leu Arg Asn Asp Asn Lys Leu Ala Asn Asp Gly Cys Asn Val Lys Leu
        195                 200                 205

Arg Pro Asp His Gly Pro Leu Gln Ala Trp Arg Lys Ala Gln Leu Asp
    210                 215                 220

Ile Ala Ala Gly Leu
225

<210> SEQ ID NO 346
<211> LENGTH: 220
<212> TYPE: PRT
<213> ORGANISM: Lygus hesperus

<400> SEQUENCE: 346

Met Gly Arg Arg Pro Ala Arg Cys Tyr Arg Tyr Cys Lys Asn Lys Pro
1               5                   10                  15

Tyr Pro Lys Ser Arg Phe Cys Arg Gly Val Pro Asp Pro Lys Ile Arg
            20                  25                  30

Ile Phe Asp Leu Gly Lys Lys Lys Ala Arg Val Glu Asp Phe Pro Leu
        35                  40                  45

Cys Val His Leu Val Ser Asp Glu Tyr Glu Gln Leu Ser Ser Glu Ala
50                  55                  60

Leu Glu Ala Gly Arg Ile Cys Cys Asn Lys Tyr Leu Val Lys Asn Cys
65                  70                  75                  80

Gly Lys Asp Gln Phe His Ile Arg Met Arg Leu His Pro Phe His Val
                85                  90                  95

Ile Arg Ile Asn Lys Met Leu Ser Cys Ala Gly Ala Asp Arg Leu Gln
            100                 105                 110

Thr Gly Met Arg Gly Ala Phe Gly Lys Pro Gln Gly Thr Val Ala Arg
        115                 120                 125

Val Arg Ile Gly Gln Pro Ile Met Ser Val Arg Ser Ser Asp Arg Tyr
    130                 135                 140

Lys Ala Ala Val Ile Glu Ala Leu Arg Arg Ala Lys Phe Lys Phe Pro
145                 150                 155                 160

Gly Arg Gln Lys Ile Tyr Val Ser Lys Lys Trp Gly Phe Thr Lys Phe
                165                 170                 175

Asp Arg Glu Glu Tyr Glu Gly Leu Arg Asn Asp Asn Lys Leu Ala Asn
            180                 185                 190

Gly Gly Cys Asn Val Lys Leu Arg Pro Asp His Gly Pro Leu Gln Ala
        195                 200                 205

Trp Arg Lys Ala Gln Leu Asp Ile Ala Ala Gly Leu
```

-continued

<210> SEQ ID NO 347
<211> LENGTH: 159
<212> TYPE: PRT
<213> ORGANISM: Lygus hesperus

<400> SEQUENCE: 347

```
Met Thr Asn Ser Lys Gly Tyr Arg Arg Gly Thr Arg Asp Leu Phe Ser
1               5                   10                  15
Arg Pro Phe Arg His His Gly Val Ile Pro Leu Ser Thr Tyr Met Lys
            20                  25                  30
Val Tyr Arg Val Gly Asp Ile Val Ser Ile Lys Gly Asn Gly Ala Val
        35                  40                  45
Gln Lys Gly Met Pro His Lys Val Tyr His Gly Lys Thr Gly Arg Val
    50                  55                  60
Tyr Asn Val Thr Pro Arg Ala Leu Gly Val Ile Val Asn Lys Arg Val
65                  70                  75                  80
Arg Gly Lys Ile Leu Pro Lys Arg Ile Asn Ile Arg Ile Glu His Val
                85                  90                  95
Asn His Ser Lys Cys Arg Glu Asp Phe Leu Lys Val Arg Glu Asn
            100                 105                 110
Glu Arg Leu Arg Lys Phe Ala Lys Glu Thr Gly Thr Arg Val Glu Leu
        115                 120                 125
Lys Arg Gln Pro Ala Gln Pro Arg Pro Ala His Phe Val Gln Ala Lys
    130                 135                 140
Glu Val Pro Glu Leu Leu Ala Pro Ile Pro Tyr Glu Phe Ile Ala
145                 150                 155
```

<210> SEQ ID NO 348
<211> LENGTH: 131
<212> TYPE: PRT
<213> ORGANISM: Lygus hesperus

<400> SEQUENCE: 348

```
Thr Tyr Met Lys Val Tyr Arg Val Gly Asp Ile Val Ser Ile Lys Gly
1               5                   10                  15
Asn Gly Ala Val Gln Lys Gly Met Pro His Lys Val Tyr His Gly Lys
            20                  25                  30
Thr Gly Arg Val Tyr Asn Val Thr Pro Arg Ala Leu Gly Val Ile Val
        35                  40                  45
Asn Lys Arg Val Arg Gly Lys Ile Leu Pro Lys Arg Ile Asn Ile Arg
    50                  55                  60
Ile Glu His Val Asn His Ser Lys Cys Arg Glu Asp Phe Leu Lys Arg
65                  70                  75                  80
Val Arg Glu Asn Glu Arg Leu Arg Lys Phe Ala Lys Glu Thr Gly Thr
                85                  90                  95
Arg Val Glu Leu Lys Arg Gln Pro Ala Gln Pro Arg Pro Ala His Phe
            100                 105                 110
Val Gln Ala Lys Glu Val Pro Glu Leu Leu Ala Pro Ile Pro Tyr Glu
        115                 120                 125
Phe Ile Ala
    130
```

<210> SEQ ID NO 349
<211> LENGTH: 150
<212> TYPE: PRT

<213> ORGANISM: leptinotarsa decemlineata

<400> SEQUENCE: 349

Lys Lys Ala Lys Lys Gly Phe Met Thr Pro Glu Arg Lys Lys Lys Leu
1 5 10 15

Arg Leu Leu Leu Arg Lys Lys Ala Ala Glu Glu Leu Lys Lys Glu Gln
20 25 30

Glu Arg Lys Ala Ala Glu Arg Arg Arg Ile Ile Glu Glu Arg Cys Gly
35 40 45

Lys Pro Lys Leu Ile Asp Glu Ala Asn Glu Glu Gln Val Arg Asn Tyr
50 55 60

Cys Lys Leu Tyr His Gly Arg Ile Ala Lys Leu Glu Asp Gln Lys Phe
65 70 75 80

Asp Leu Glu Tyr Leu Val Lys Lys Lys Asp Met Glu Ile Ala Glu Leu
85 90 95

Asn Ser Gln Val Asn Asp Leu Arg Gly Lys Phe Val Lys Pro Thr Leu
100 105 110

Lys Lys Val Ser Lys Tyr Glu Asn Lys Phe Ala Lys Leu Gln Lys Lys
115 120 125

Ala Ala Glu Phe Asn Phe Arg Asn Gln Leu Lys Val Val Lys Lys Lys
130 135 140

Glu Phe Thr Leu Glu Glu
145 150

<210> SEQ ID NO 350
<211> LENGTH: 279
<212> TYPE: PRT
<213> ORGANISM: leptinotarsa decemlineata

<400> SEQUENCE: 350

Gln Trp Tyr Gln Arg Arg Val Arg Gly Asp Ile Glu Glu Lys Arg Gln
1 5 10 15

Arg Leu Glu Glu Ala Glu Lys Lys Arg Gln Ala Met Met Gln Ala Leu
20 25 30

Lys Asp Gln Asn Lys Asn Lys Gly Pro Asn Phe Thr Ile Thr Lys Arg
35 40 45

Asp Ala Ser Ser Asn Leu Ser Ala Ala Gln Leu Glu Arg Asn Lys Thr
50 55 60

Lys Glu Gln Leu Glu Glu Glu Lys Lys Ile Ser Leu Ser Ile Arg Ile
65 70 75 80

Lys Pro Leu Val Val Asp Gly Leu Gly Val Asp Lys Leu Arg Leu Lys
85 90 95

Ala Gln Glu Leu Trp Glu Cys Ile Val Lys Leu Glu Thr Glu Lys Tyr
100 105 110

Asp Leu Glu Glu Arg Gln Lys Arg Gln Asp Tyr Asp Leu Lys Glu Leu
115 120 125

Lys Glu Arg Gln Lys Gln Gln Leu Arg His Lys Ala Leu Lys Lys Gly
130 135 140

Leu Asp Pro Glu Ala Leu Thr Gly Lys Tyr Pro Pro Lys Ile Gln Val
145 150 155 160

Ala Ser Lys Tyr Glu Arg Arg Val Asp Thr Arg Ser Tyr Gly Asp Lys
165 170 175

Lys Lys Leu Phe Glu Gly Gly Leu Glu Glu Ile Ile Lys Glu Thr Asn
180 185 190

Glu Lys Ser Trp Lys Glu Lys Phe Gly Gln Phe Asp Ser Arg Gln Lys

```
            195                 200                 205
Ala Arg Leu Pro Lys Trp Phe Gly Glu Arg Pro Gly Lys Lys Pro Gly
210                 215                 220

Asp Pro Glu Thr Pro Glu Gly Glu Glu Gly Lys Gln Val Ile Asp
225                 230                 235                 240

Glu Asp Asp Asp Leu Lys Glu Pro Val Ile Glu Ala Glu Ile Glu Glu
                245                 250                 255

Glu Glu Glu Glu Glu Glu Val Glu Val Asp Glu Glu Glu Asp Asp
                260                 265                 270

Glu Glu Glu Glu Glu Glu Glu
                275

<210> SEQ ID NO 351
<211> LENGTH: 286
<212> TYPE: PRT
<213> ORGANISM: leptinotarsa decemlineata

<400> SEQUENCE: 351

Ala Leu Gln Asn Glu Leu Glu Ser Arg Thr Leu Leu Glu Gln Ala
1               5                   10                  15

Asp Arg Ala Arg Arg Gln Ala Glu Gln Glu Leu Gly Asp Ala His Glu
                20                  25                  30

Gln Leu Asn Asp Leu Gly Ala Gln Asn Gly Ser Leu Ser Ala Ala Lys
            35                  40                  45

Arg Lys Leu Glu Thr Glu Leu Gln Thr Leu His Ser Asp Leu Asp Glu
50                  55                  60

Leu Leu Asn Glu Ala Lys Asn Ser Glu Glu Lys Ala Lys Lys Ala Met
65                  70                  75                  80

Val Asp Ala Ala Arg Leu Ala Asp Glu Leu Arg Ala Glu Gln Asp His
                85                  90                  95

Ala Gln Thr Gln Glu Lys Leu Arg Lys Ala Leu Glu Ser Gln Ile Lys
            100                 105                 110

Asp Leu Gln Val Arg Leu Asp Glu Ala Glu Ala Asn Ala Leu Lys Gly
        115                 120                 125

Gly Lys Lys Ala Ile Ala Lys Leu Glu Gln Arg Val Arg Glu Leu Glu
    130                 135                 140

Asn Glu Leu Asp Gly Glu Gln Arg Arg His Ala Asp Ala Gln Lys Asn
145                 150                 155                 160

Leu Arg Lys Ser Glu Arg Arg Ile Lys Glu Leu Ser Leu Gln Ala Glu
                165                 170                 175

Glu Asp Arg Lys Asn His Glu Lys Met Gln Asp Leu Val Asp Lys Leu
            180                 185                 190

Gln Gln Lys Ile Lys Thr His Lys Arg Gln Ile Glu Glu Ala Glu Glu
        195                 200                 205

Ile Ala Ala Leu Asn Leu Ala Lys Phe Arg Lys Ala Gln Gln Glu Leu
    210                 215                 220

Glu Glu Ala Glu Glu Arg Ala Asp Leu Ala Glu Gln Ala Ile Val Lys
225                 230                 235                 240

Phe Arg Thr Lys Gly Arg Ser Gly Ser Ala Ala Arg Gly Ala Ser Pro
                245                 250                 255

Ala Pro Gln Arg Gln Arg Pro Thr Phe Gly Met Gly Asp Ser Leu Gly
            260                 265                 270

Gly Ala Phe Pro Pro Arg Phe Asp Leu Ala Pro Asp Phe Glu
        275                 280                 285
```

<210> SEQ ID NO 352
<211> LENGTH: 197
<212> TYPE: PRT
<213> ORGANISM: nilaparvata lugens

<400> SEQUENCE: 352

Met Ala Asp Asp Glu Ala Lys Lys Ala Lys Gln Ala Glu Ile Asp Arg
1               5                   10                  15

Lys Arg Ala Glu Val Arg Lys Arg Met Glu Glu Ala Ser Lys Ala Lys
            20                  25                  30

Lys Ala Lys Lys Gly Phe Met Thr Pro Asp Arg Lys Lys Lys Leu Arg
        35                  40                  45

Leu Leu Leu Arg Lys Lys Ala Ala Glu Glu Leu Lys Lys Glu Gln Glu
    50                  55                  60

Arg Lys Ala Ala Glu Arg Arg Ile Ile Glu Arg Cys Gly Lys
65                  70                  75                  80

Ala Val Asp Leu Asp Asp Gly Ser Glu Glu Lys Val Lys Ala Thr Leu
                85                  90                  95

Lys Thr Tyr His Asp Arg Ile Gly Lys Leu Glu Asp Glu Lys Phe Asp
            100                 105                 110

Leu Glu Tyr Ile Val Lys Lys Asp Phe Glu Ile Ala Asp Leu Asn
        115                 120                 125

Ser Gln Val Asn Asp Leu Arg Gly Lys Phe Val Lys Pro Thr Leu Lys
    130                 135                 140

Lys Val Ser Lys Tyr Glu Asn Lys Phe Ala Lys Leu Gln Lys Lys Ala
145                 150                 155                 160

Ala Glu Phe Asn Phe Arg Asn Gln Leu Lys Val Val Lys Lys Glu
                165                 170                 175

Phe Thr Leu Glu Glu Asp Lys Glu Pro Lys Lys Ser Glu Lys Ala
            180                 185                 190

Glu Trp Gln Lys Lys
        195

<210> SEQ ID NO 353
<211> LENGTH: 184
<212> TYPE: PRT
<213> ORGANISM: nilaparvata lugens

<400> SEQUENCE: 353

Met Met Ala Ala Leu Lys Asp Gln Ser Lys Ser Lys Gly Pro Asn Phe
1               5                   10                  15

Thr Val Asn Lys Lys Thr Asp Leu Asn Met Thr Ser Ala Gln Met Glu
            20                  25                  30

Arg Asn Lys Thr Lys Glu Gln Leu Glu Glu Lys Lys Ile Ser Leu
        35                  40                  45

Ser Phe Arg Ile Lys Pro Leu Ala Ile Glu Asn Met Ser Ile Asn Ala
    50                  55                  60

Leu Arg Ala Lys Ala Gln Glu Leu Trp Asp Cys Ile Val Lys Leu Glu
65                  70                  75                  80

Thr Glu Lys Tyr Asp Leu Glu Glu Arg Gln Lys Arg Gln Asp Tyr Asp
                85                  90                  95

Leu Lys Glu Leu Lys Glu Arg Gln Gln Leu Arg His Lys Ala
            100                 105                 110

Leu Lys Lys Gly Leu Asp Pro Glu Ala Leu Thr Gly Lys Tyr Pro Pro
        115                 120                 125

```
Lys Ile Gln Val Ala Ser Lys Tyr Glu Arg Arg Val Asp Thr Arg Ser
        130                 135                 140

Tyr Asp Asp Lys Lys Leu Phe Glu Gly Gly Trp Asp Thr Leu Thr
145                 150                 155                 160

Ser Glu Thr Asn Glu Lys Ile Trp Lys Ser Arg Asn Asp Gln Phe Ser
                165                 170                 175

Asn Arg Ser Lys Ala Lys Leu Pro
            180
```

<210> SEQ ID NO 354
<211> LENGTH: 122
<212> TYPE: PRT
<213> ORGANISM: nilaparvata lugens

<400> SEQUENCE: 354

```
Ala Phe Asp Arg Glu Arg Ser Gly Ser Ile Pro Thr Asp Met Val Ala
1               5                   10                  15

Asp Ile Leu Arg Leu Met Gly Gln Pro Phe Asn Lys Lys Ile Leu Asp
            20                  25                  30

Glu Leu Ile Glu Glu Val Asp Ala Asp Lys Ser Gly Arg Leu Glu Phe
        35                  40                  45

Asp Glu Phe Val Thr Leu Ala Ala Lys Phe Ile Val Glu Glu Asp Asp
    50                  55                  60

Glu Ala Met Gln Lys Glu Leu Lys Glu Ala Phe Arg Leu Tyr Asp Lys
65                  70                  75                  80

Glu Gly Asn Gly Tyr Ile Pro Thr Ser Cys Leu Lys Glu Ile Leu Arg
                85                  90                  95

Glu Leu Asp Asp Gln Leu Thr Asn Glu Glu Leu Asn Met Met Ile Asp
            100                 105                 110

Glu Ile Asp Ser Asp Gly Ser Gly Thr Val
        115                 120
```

<210> SEQ ID NO 355
<211> LENGTH: 73
<212> TYPE: PRT
<213> ORGANISM: nilaparvata lugens

<400> SEQUENCE: 355

```
Val Lys Thr Leu Thr Gly Lys Thr Ile Thr Leu Glu Val Glu Pro Ser
1               5                   10                  15

Asp Thr Ile Glu Asn Val Lys Ala Lys Ile Gln Asp Lys Glu Gly Ile
            20                  25                  30

Pro Pro Asp Gln Gln Arg Leu Ile Phe Ala Gly Lys Gln Leu Glu Asp
        35                  40                  45

Gly Arg Thr Leu Ser Asp Tyr Asn Ile Gln Lys Glu Ser Thr Leu His
    50                  55                  60

Leu Val Leu Arg Leu Arg Gly Gly Thr
65                  70
```

<210> SEQ ID NO 356
<211> LENGTH: 253
<212> TYPE: PRT
<213> ORGANISM: Acyrthosiphon pisum

<400> SEQUENCE: 356

```
Met Ala Asp Asp Glu Ala Lys Lys Ala Lys Gln Ala Glu Ile Asp Arg
1               5                   10                  15

Lys Arg Ala Glu Val Arg Lys Arg Met Glu Glu Ala Ser Lys Ala Lys
```

```
                20                  25                  30
Lys Ala Lys Lys Gly Phe Met Thr Pro Asp Arg Lys Lys Lys Leu Arg
            35                  40                  45

Leu Leu Leu Lys Lys Lys Ala Ala Glu Glu Leu Lys Lys Glu Gln Glu
        50                  55                  60

Arg Lys Ala Ala Glu Arg Arg Ile Ile Glu Arg Cys Gly Gln
65                  70                  75                  80

Pro Lys Asn Ile Asp Asp Ala Gly Glu Glu Leu Ala Glu Ile Cys
                85                  90                  95

Glu Glu Leu Trp Lys Arg Val Tyr Thr Val Glu Gly Ile Lys Phe Asp
            100                 105                 110

Leu Glu Arg Asp Ile Arg Met Lys Val Phe Glu Ile Ser Glu Leu Asn
            115                 120                 125

Ser Gln Val Asn Asp Leu Arg Gly Lys Phe Val Lys Pro Thr Leu Lys
        130                 135                 140

Lys Val Ser Lys Tyr Glu Asn Lys Phe Ala Lys Leu Gln Lys Lys Ala
145                 150                 155                 160

Ala Glu Phe Asn Phe Arg Asn Gln Leu Lys Val Val Lys Lys Glu
            165                 170                 175

Phe Thr Leu Glu Glu Glu Asp Lys Glu Lys Lys Pro Asp Trp Ser Lys
            180                 185                 190

Lys Gly Asp Glu Lys Lys Gly Glu Gly Glu Asp Gly Asp Gly Thr Glu
            195                 200                 205

Asp Glu Lys Thr Asp Asp Gly Leu Thr Thr Glu Gly Glu Ser Val Ala
        210                 215                 220

Gly Asp Leu Thr Asp Ala Thr Glu Asp Ala Gln Ser Asp Asn Glu Ile
225                 230                 235                 240

Leu Glu Pro Glu Pro Val Val Glu Pro Glu Pro
                245                 250

<210> SEQ ID NO 357
<211> LENGTH: 179
<212> TYPE: PRT
<213> ORGANISM: Acyrthosiphon pisum

<400> SEQUENCE: 357

Val Met Arg Cys Gly Lys Lys Val Trp Leu Asp Pro Asn Glu Ile
1               5                   10                  15

Asn Glu Ile Ala Asn Thr Asn Ser Arg Gln Asn Ile Arg Lys Leu Ile
            20                  25                  30

Lys Asp Gly Leu Ile Ile Lys Lys Pro Val Ala Val His Ser Arg Ala
        35                  40                  45

Arg Ala Arg Lys Asn Ala Asp Ala Arg Arg Lys Gly Arg His Cys Gly
    50                  55                  60

Phe Gly Lys Arg Lys Gly Thr Ala Asn Ala Arg Thr Pro Gln Lys Asp
65                  70                  75                  80

Leu Trp Val Lys Arg Met Arg Val Leu Arg Arg Leu Leu Lys Lys Tyr
                85                  90                  95

Arg Glu Ala Lys Lys Ile Asp Asn His Leu Tyr His Gln Leu Tyr Met
            100                 105                 110

Lys Ala Lys Gly Asn Val Phe Lys Asn Lys Arg Val Leu Met Glu Phe
        115                 120                 125

Ile His Lys Lys Lys Ala Glu Lys Ala Arg Ala Lys Met Leu Ser Asp
    130                 135                 140
```

```
Gln Ala Glu Ala Arg Arg Gln Lys Val Lys Glu Ala Arg Lys Arg Lys
145                 150                 155                 160

Glu Ala Arg Phe Leu Gln Asn Arg Lys Glu Leu Leu Ala Ala Tyr Ala
                165                 170                 175

Arg Glu Asp

<210> SEQ ID NO 358
<211> LENGTH: 275
<212> TYPE: PRT
<213> ORGANISM: Acyrthosiphon pisum

<400> SEQUENCE: 358

Gly Leu Glu Val Glu Ser Ser Asp Ser Ile Glu Asn Val Lys Ala Lys
1               5                   10                  15

Ile Gln Asp Lys Glu Gly Ile Pro Pro Asp Gln Gln Arg Leu Ile Phe
                20                  25                  30

Ala Gly Lys Gln Leu Glu Asp Gly Arg Thr Leu Ser Asp Tyr Asn Ile
                35                  40                  45

Gln Lys Glu Ser Thr Leu His Leu Val Leu Arg Leu Arg Gly Gly Met
    50                  55                  60

Gln Ile Phe Val Lys Thr Leu Thr Gly Lys Thr Ile Thr Leu Glu Val
65                  70                  75                  80

Glu Ser Ser Asp Ser Ile Glu Asn Val Lys Ala Lys Ile Gln Asp Lys
                85                  90                  95

Glu Gly Ile Pro Pro Asp Gln Gln Arg Leu Ile Phe Ala Gly Lys Gln
                100                 105                 110

Leu Glu Asp Gly Arg Thr Leu Ser Asp Tyr Asn Ile Gln Lys Glu Ser
                115                 120                 125

Thr Leu His Leu Val Leu Arg Leu Arg Gly Gly Met Gln Ile Phe Val
            130                 135                 140

Lys Thr Leu Thr Gly Lys Thr Ile Thr Leu Glu Val Glu Ser Ser Asp
145                 150                 155                 160

Ser Ile Glu Asn Val Lys Ala Lys Ile Gln Asp Lys Glu Gly Ile Pro
                165                 170                 175

Pro Asp Gln Gln Arg Leu Ile Phe Ala Gly Lys Gln Leu Glu Asp Gly
                180                 185                 190

Arg Thr Leu Ser Asp Tyr Asn Ile Gln Lys Glu Ser Thr Leu His Leu
                195                 200                 205

Val Leu Arg Leu Arg Gly Gly Met Gln Ile Phe Val Lys Thr Leu Thr
            210                 215                 220

Gly Lys Thr Ile Thr Leu Glu Val Glu Ser Ser Asp Ser Ile Glu Asn
225                 230                 235                 240

Val Lys Ala Lys Ile Gln Asp Lys Glu Gly Ile Pro Pro Asp Gln Gln
                245                 250                 255

Arg Leu Ile Phe Ala Gly Lys Gln Leu Glu Asp Gly Arg Thr Leu Ser
                260                 265                 270

Asp Tyr Asn
        275

<210> SEQ ID NO 359
<211> LENGTH: 56
<212> TYPE: PRT
<213> ORGANISM: Acyrthosiphon pisum

<400> SEQUENCE: 359

Asp Leu Leu His Pro Thr Ala Ile Glu Glu Arg Arg Lys His Lys Leu
```

```
  1               5                  10                  15
Lys Arg Leu Val Gln His Pro Asn Ser Phe Phe Met Asp Val Lys Cys
         20                  25                  30

Pro Gly Cys Tyr Lys Ile Thr Thr Val Phe Ser His Ala Gln Ser Val
         35                  40                  45

Val Ile Cys Thr Gly Cys Ser Thr
         50                  55
```

<210> SEQ ID NO 360  
<211> LENGTH: 20  
<212> TYPE: DNA  
<213> ORGANISM: Artificial  
<220> FEATURE:  
<223> OTHER INFORMATION: Primer

<400> SEQUENCE: 360
atcatgcagg cgtacgcccg                                                        20

<210> SEQ ID NO 361  
<211> LENGTH: 19  
<212> TYPE: DNA  
<213> ORGANISM: Artificial  
<220> FEATURE:  
<223> OTHER INFORMATION: Primer

<400> SEQUENCE: 361 cggaggggc gagatcact                                                       19

<210> SEQ ID NO 362  
<211> LENGTH: 62  
<212> TYPE: DNA  
<213> ORGANISM: Artificial  
<220> FEATURE:  
<223> OTHER INFORMATION: Amplicon

<400> SEQUENCE: 362
atcatgcagg cgtacgcccg agaagacgag gctgccgtca aaaagtgatc tcgccccctc      60
cg                                                                                                                                             62

<210> SEQ ID NO 363  
<211> LENGTH: 22  
<212> TYPE: DNA  
<213> ORGANISM: Artificial  
<220> FEATURE:  
<223> OTHER INFORMATION: Primer

<400> SEQUENCE: 363
tgtgttggct actggtggct ac                                                     22

<210> SEQ ID NO 364  
<211> LENGTH: 25  
<212> TYPE: DNA  
<213> ORGANISM: Artificial  
<220> FEATURE:  
<223> OTHER INFORMATION: Primer

<400> SEQUENCE: 364
tcggatggaa ctggacaaat tcaag                                        25

<210> SEQ ID NO 365  
<211> LENGTH: 137  
<212> TYPE: DNA  
<213> ORGANISM: Artificial  
<220> FEATURE:

-continued

<223> OTHER INFORMATION: Amplicon

<400> SEQUENCE: 365
tgtgttggct actggtggct acggcagagc ttacttttca tgcacttcag ctcacacttg    60
cacgggagat ggccaagcaa tggtttcacg agctgggctt cccaacgaag atcttgaatt   120
tgtccagttc catccga                                                  137

<210> SEQ ID NO 366
<211> LENGTH: 21
<212> TYPE: DNA
<213> ORGANISM: Artificial
<220> FEATURE:
<223> OTHER INFORMATION: Primer

<400> SEQUENCE: 366
gcaacccgtg ttctccaaag c                                              21

<210> SEQ ID NO 367
<211> LENGTH: 28
<212> TYPE: DNA
<213> ORGANISM: Artificial
<220> FEATURE:
<223> OTHER INFORMATION: Primer

<400> SEQUENCE: 367
tcaactcgta ttctcgtact ttcaaacc                                       28

<210> SEQ ID NO 368
<211> LENGTH: 146
<212> TYPE: DNA
<213> ORGANISM: Artificial
<220> FEATURE:
<223> OTHER INFORMATION: Amplicon

<400> SEQUENCE: 368
gcaacccgtg ttctccaaag ccagatacac tgtgcgatcc ttcggtatca ggcgtaacga    60
aaaaatcgcc gttcactgca ctgtcagggg cgccaaagca gaggaaattc tggagcgtgg   120
tttgaaagta cgagaatacg agttga                                        146

<210> SEQ ID NO 369
<211> LENGTH: 21
<212> TYPE: DNA
<213> ORGANISM: Artificial
<220> FEATURE:
<223> OTHER INFORMATION: Primer

<400> SEQUENCE: 369
atggccgacg atgaagctaa g                                              21

<210> SEQ ID NO 370
<211> LENGTH: 20
<212> TYPE: DNA
<213> ORGANISM: Artificial
<220> FEATURE:
<223> OTHER INFORMATION: Primer

<400> SEQUENCE: 370
tggttctggt tcgggttcaa                                                20

<210> SEQ ID NO 371
<211> LENGTH: 20
<212> TYPE: DNA
<213> ORGANISM: Artificial

<220> FEATURE:
<223> OTHER INFORMATION: Primer

<400> SEQUENCE: 371
cggtaatgcg atgcggtaag                                              20

<210> SEQ ID NO 372
<211> LENGTH: 20
<212> TYPE: DNA
<213> ORGANISM: Artificial
<220> FEATURE:
<223> OTHER INFORMATION: Primer

<400> SEQUENCE: 372
tcatcttctc gggcgtatgc                                              20

<210> SEQ ID NO 373
<211> LENGTH: 25
<212> TYPE: DNA
<213> ORGANISM: Artificial
<220> FEATURE:
<223> OTHER INFORMATION: Primer

<400> SEQUENCE: 373
tttggaagtt gagtcatcag attcc                                        25

<210> SEQ ID NO 374
<211> LENGTH: 24
<212> TYPE: DNA
<213> ORGANISM: Artificial
<220> FEATURE:
<223> OTHER INFORMATION: Primer

<400> SEQUENCE: 374
gttgtagtcg gaaagggtac gtcc                                         24

<210> SEQ ID NO 375
<211> LENGTH: 20
<212> TYPE: DNA
<213> ORGANISM: Artificial
<220> FEATURE:
<223> OTHER INFORMATION: Primer

<400> SEQUENCE: 375
attgtggaac atccggtaca                                              20

<210> SEQ ID NO 376
<211> LENGTH: 23
<212> TYPE: DNA
<213> ORGANISM: Artificial
<220> FEATURE:
<223> OTHER INFORMATION: Primer

<400> SEQUENCE: 376
aagacttgct tcatcctact gca                                          23

<210> SEQ ID NO 377
<211> LENGTH: 28
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (20)..(20)
<223> OTHER INFORMATION: n is a, c, g, or t

```
<400> SEQUENCE: 377
ccaagaaggc caagaagggn ttyatgac                                          28

<210> SEQ ID NO 378
<211> LENGTH: 29
<212> TYPE: DNA
<213> ORGANISM: Artificial
<220> FEATURE:
<223> OTHER INFORMATION: Primer

<400> SEQUENCE: 378
tcctcctcca gggtgaactc yttyttytt                                         29

<210> SEQ ID NO 379
<211> LENGTH: 26
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 379
gccaagaagg gcttcatgac nccnga                                            26

<210> SEQ ID NO 380
<211> LENGTH: 27
<212> TYPE: DNA
<213> ORGANISM: Artificial
<220> FEATURE:
<223> OTHER INFORMATION: Primer

<400> SEQUENCE: 380
gaagttgaac tcggcggcyt tyttytg                                           27

<210> SEQ ID NO 381
<211> LENGTH: 26
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (24)..(24)
<223> OTHER INFORMATION: n is a, c, g, or t

<400> SEQUENCE: 381
ctggaggagg ccgagaaraa rmgnca                                            26

<210> SEQ ID NO 382
<211> LENGTH: 22
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (14)..(14)
<223> OTHER INFORMATION: n is a, c, g, or t

<400> SEQUENCE: 382
tgccgggccg ctcnccraac ca                                                22
```

<210> SEQ ID NO 383
<211> LENGTH: 28
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t

<400> SEQUENCE: 383
agatcgccat cctgaggaan gcnttyra                                28

<210> SEQ ID NO 384
<211> LENGTH: 31
<212> TYPE: DNA
<213> ORGANISM: Artificial
<220> FEATURE:
<223> OTHER INFORMATION: Primer

<400> SEQUENCE: 384
cggtcatcat ctccatgaac tcrtcraart c                            31

<210> SEQ ID NO 385
<211> LENGTH: 170
<212> TYPE: DNA
<213> ORGANISM: Artificial
<220> FEATURE:
<223> OTHER INFORMATION: Intron

<400> SEQUENCE: 385
tctagaaggt aagtgtacac actacatttt catgaacatt attgcgaccg ttgagattct    60
cattgtttgg tgattgatta ctaaagtag aagcatgaat agatataaca taaactagta   120
actaatgggt tagttatggg tatacttcat gcttttctct caggctcgag              170

<210> SEQ ID NO 386
<211> LENGTH: 521
<212> TYPE: DNA
<213> ORGANISM: leptinotarsa decemlineata

<400> SEQUENCE: 386 tcgattttc atttttcttt tattatttgg agtgggcctg ttgtggtcgt tatcaaaatg    60
ggtaaaataa tgaaatctgg taaagtcgta ttggtccttg gaggccgata cgctggaaga   120
aaggcagtag tcataaaaaa ttacgatgat gggacgtcag ataaacaata tggacatgcc   180
gtggtggctg gaatcgatag gtaccctaga aaaatccaca aacgtatggg caaaggaaaa   240
atgcacaaga ggtccaaaat caagcccttc cttaaggtgc tcaactataa ccatttgatg   300
cctacaagat attcagtgga tttgacttcg gacttgaaag tggcgcccaa agacctcaag   360
gatccagtga agaggaagaa gattaggttc caaaccagag ttaaattcga agagagatac   420
aagcaaggaa aacacaaatg gttttttccag aaattgaggt tctagattct ataaatttaa   480 ccatttgta atccacccac cttttttgttc aaataaattg t                       521

<210> SEQ ID NO 387
<211> LENGTH: 475
<212> TYPE: DNA

<213> ORGANISM: leptinotarsa decemlineata

<400> SEQUENCE: 387
tatcgcgaaa aatatacaac ttacaaaatg aggaacacgt atgagttgag ccctaaagaa 60
gcagcaaatt tcactcgtcg aaatttagca gatactcttc gaagcaggag tccatatcat 120
gttaatcttc tcttggctgg atatgacaag aaagacgggg ctcagttgta ttacatggat 180
tatctagcgt ctgttgctag tgttgattac gctgcccatg gatacggagg atatttctcc 240
ctttccataa tggatcgcaa ttatttgaaa accctgtcga aagatcaagg atacgaactt 300
ctgaaggaat gtgttaaaga agttcaaaag agacttgcta taaatttacc aaatttcaaa 360
gttcaggtta ttgataaaga tggtattaag gatatgccta atataacttc aaaaggtttg 420
aattgattaa gcaacttcag tttcagattt ttttctaaat aaacatttaa agtgt 475

<210> SEQ ID NO 388
<211> LENGTH: 467
<212> TYPE: DNA
<213> ORGANISM: leptinotarsa decemlineata

<400> SEQUENCE: 388
gcggggactg gatacatctc taaaacacag aaaaatgaaa ttcttcaagt caggaatata 60
ttctgttgta tttttggcaa ttatattttc tttggtcact gaggaagtgg aaggtcgaag 120
gactatttta agagggcgta aaacactgac gagaacctat tttcgtgaca atgcagtccc 180
agcatacgtc atagtgatac tcgttggaat aggagaaatc attttgggag ctatcctgta 240
tgttataatg aggaaaacga taatagattt tcctttatca gggagttacg cagtggcccc 300
tactcaagaa gcataaatcc cattgaaatt gtgactgttt actttctttg gaaaaatgtg 360
tataataaat acaattcatt tataatattt atatttggaa cttaaaatac ttacaaaatt 420
accatttaca tgatcaaata actaataaag ttctgtctca attataa 467

<210> SEQ ID NO 389
<211> LENGTH: 906
<212> TYPE: DNA
<213> ORGANISM: leptinotarsa decemlineata

<400> SEQUENCE: 389
ggattggaag taaaaatata caattcatgc tgtagctgta gtgtaaaaac tgaactgaaa 60
gccataaaat aaagaccttg caagaaacat gtccaagatt aatgaggtgt ctaatttgta 120
caaacaactg aaatcagaat ggaacacatc caatccaaat ttaagcaaat gtgaaaagct 180
tttgtcagat ttgaagcttg agctaacaca cttaatgttc cttccaactt caaacgccac 240
tgcttcaaaa caagaacttc ttctggcaag agatgttctg gaaattgggg tacaatggag 300
tatagctgca aatgatatac ctgcctttga aagatacatg gcacagttga aatgttatta 360
tttcgattat aagaatcaac ttcccgaatc ttctttcaaa tatcagttac tgggtctgaa 420
tttactattt ttgttatcac aaaatagagt ggcagagttc cacacagaat tagaattgtt 480
gcctgctgac cacattcaga atgatgtata catcaggcac cctccatcta ttgaacagta 540
ccttatggaa ggaagttata ataagatatt tctggcaaag ggaaatgtcc cagcaacaaa 600
ttacaatttt tttatggata tacttctaga tactatcaga ggggagattg cagattgtct 660
agagaaagca tatgaaaaaa tatcaattaa agatgttgct aggatgctat acttgggcag 720
tgaagaatcg gccaaggcct ttgtaacaaa gagtaagaca tggaaattag aaaaggacaa 780
cttctttcac ttcacgcccg aggttaaaaa gacacatgag ccaattctat ccaaagaatt 840

```
ggcacaacaa gctattgaat atgcaaaaga actggaaatg attgtttaaa gtaataaagt    900
ttttca                                                               906
```

<210> SEQ ID NO 390
<211> LENGTH: 135
<212> TYPE: PRT
<213> ORGANISM: leptinotarsa decemlineata

<400> SEQUENCE: 390

```
Met Gly Lys Ile Met Lys Ser Gly Lys Val Val Leu Val Leu Gly Gly
1               5                  10                  15

Arg Tyr Ala Gly Arg Lys Ala Val Val Ile Lys Asn Tyr Asp Asp Gly
                20                  25                  30

Thr Ser Asp Lys Gln Tyr Gly His Ala Val Val Ala Gly Ile Asp Arg
            35                  40                  45

Tyr Pro Arg Lys Ile His Lys Arg Met Gly Lys Gly Lys Met His Lys
        50                  55                  60

Arg Ser Lys Ile Lys Pro Phe Leu Lys Val Leu Asn Tyr Asn His Leu
65                  70                  75                  80

Met Pro Thr Arg Tyr Ser Val Asp Leu Thr Ser Asp Leu Lys Val Ala
                85                  90                  95

Pro Lys Asp Leu Lys Asp Pro Val Lys Arg Lys Lys Ile Arg Phe Gln
            100                 105                 110

Thr Arg Val Lys Phe Glu Glu Arg Tyr Lys Gln Gly Lys His Lys Trp
        115                 120                 125

Phe Phe Gln Lys Leu Arg Phe
    130                 135
```

<210> SEQ ID NO 391
<211> LENGTH: 141
<212> TYPE: PRT
<213> ORGANISM: leptinotarsa decemlineata

<400> SEQUENCE: 391

```
Tyr Arg Glu Lys Tyr Thr Thr Tyr Lys Met Arg Asn Thr Tyr Glu Leu
1               5                  10                  15

Ser Pro Lys Glu Ala Ala Asn Phe Thr Arg Arg Asn Leu Ala Asp Thr
                20                  25                  30

Leu Arg Ser Arg Ser Pro Tyr His Val Asn Leu Leu Leu Ala Gly Tyr
            35                  40                  45

Asp Lys Lys Asp Gly Ala Gln Leu Tyr Tyr Met Asp Tyr Leu Ala Ser
        50                  55                  60

Val Ala Ser Val Asp Tyr Ala Ala His Gly Tyr Gly Gly Tyr Phe Ser
65                  70                  75                  80

Leu Ser Ile Met Asp Arg Asn Tyr Leu Lys Thr Leu Ser Lys Asp Gln
                85                  90                  95

Gly Tyr Glu Leu Leu Lys Glu Cys Val Lys Glu Val Gln Lys Arg Leu
            100                 105                 110

Ala Ile Asn Leu Pro Asn Phe Lys Val Gln Val Ile Asp Lys Asp Gly
        115                 120                 125

Ile Lys Asp Met Pro Asn Ile Thr Ser Lys Gly Leu Asn
        130                 135                 140
```

<210> SEQ ID NO 392
<211> LENGTH: 104
<212> TYPE: PRT

<213> ORGANISM: leptinotarsa decemlineata

<400> SEQUENCE: 392

```
Arg Gly Leu Asp Thr Ser Leu Lys His Arg Lys Met Lys Phe Phe Lys
1               5                   10                  15

Ser Gly Ile Tyr Ser Val Val Phe Leu Ala Ile Ile Phe Ser Leu Val
            20                  25                  30

Thr Glu Glu Val Glu Gly Arg Arg Thr Ile Leu Arg Gly Arg Lys Thr
        35                  40                  45

Leu Thr Arg Thr Tyr Phe Arg Asp Asn Ala Val Pro Ala Tyr Val Ile
    50                  55                  60

Val Ile Leu Val Gly Ile Gly Glu Ile Ile Leu Gly Ala Ile Leu Tyr
65                  70                  75                  80

Val Ile Met Arg Lys Thr Ile Ile Asp Phe Pro Leu Ser Gly Ser Tyr
                85                  90                  95

Ala Val Ala Pro Thr Gln Glu Ala
            100
```

<210> SEQ ID NO 393
<211> LENGTH: 266
<212> TYPE: PRT
<213> ORGANISM: leptinotarsa decemlineata

<400> SEQUENCE: 393

```
Met Ser Lys Ile Asn Glu Val Ser Asn Leu Tyr Lys Gln Leu Lys Ser
1               5                   10                  15

Glu Trp Asn Thr Ser Asn Pro Asn Leu Ser Lys Cys Glu Lys Leu Leu
            20                  25                  30

Ser Asp Leu Lys Leu Glu Leu Thr His Leu Met Phe Leu Pro Thr Ser
        35                  40                  45

Asn Ala Thr Ala Ser Lys Gln Glu Leu Leu Leu Ala Arg Asp Val Leu
    50                  55                  60

Glu Ile Gly Val Gln Trp Ser Ile Ala Ala Asn Asp Ile Pro Ala Phe
65                  70                  75                  80

Glu Arg Tyr Met Ala Gln Leu Lys Cys Tyr Tyr Phe Asp Tyr Lys Asn
                85                  90                  95

Gln Leu Pro Glu Ser Ser Phe Lys Tyr Gln Leu Leu Gly Leu Asn Leu
            100                 105                 110

Leu Phe Leu Leu Ser Gln Asn Arg Val Ala Glu Phe His Thr Glu Leu
        115                 120                 125

Glu Leu Leu Pro Ala Asp His Ile Gln Asn Asp Val Tyr Ile Arg His
    130                 135                 140

Pro Pro Ser Ile Glu Gln Tyr Leu Met Glu Gly Ser Tyr Asn Lys Ile
145                 150                 155                 160

Phe Leu Ala Lys Gly Asn Val Pro Ala Thr Asn Tyr Asn Phe Phe Met
                165                 170                 175

Asp Ile Leu Leu Asp Thr Ile Arg Gly Glu Ile Ala Asp Cys Leu Glu
            180                 185                 190

Lys Ala Tyr Glu Lys Ile Ser Ile Lys Asp Val Ala Arg Met Leu Tyr
        195                 200                 205

Leu Gly Ser Glu Glu Ser Ala Lys Ala Phe Val Thr Lys Ser Lys Thr
    210                 215                 220

Trp Lys Leu Glu Lys Asp Asn Phe Phe His Phe Thr Pro Glu Val Lys
225                 230                 235                 240

Lys Thr His Glu Pro Ile Leu Ser Lys Glu Leu Ala Gln Gln Ala Ile
```

245             250             255
Glu Tyr Ala Lys Glu Leu Glu Met Ile Val
            260             265

<210> SEQ ID NO 394
<211> LENGTH: 750
<212> TYPE: DNA
<213> ORGANISM: Leptinotarsa decemlineata

<400> SEQUENCE: 394
cgcccagcag tggtatcaac gcagagtacg cgggagacat tcaagtcttg tgatagtgca      60
ggcacggcag ttcaaataaa ctggtgcctt caatttattt atatatttat acttttttac     120
tagaaaccaa atactaacca atcaacatgt gtgacgaaga ggttgccgca ttagtcgtag     180
acaatggatc tggtatgtgc aaagctggat ttgctgggga tgatgccccc cgtgcagttt     240
tcccatccat tgttggtcgt ccaagacatc aaggagttat ggtaggaatg ggccaaaagg     300
actcgtatgt aggagatgaa gcccaaagca aagaggtat ccttaccttg aaataccccca     360 ttgaacacgg tattgtcaca aactgggatg atatggagaa aatctggcac catacctict     420 acaatgaact tcgagttgcc cccgaagagc accctgtttt gttgacagag gcaccattga     480
accccaaagc caacagggag aagatgaccc agatcatgtt tgaaaccttc aatacccccg     540
ccatgtacgc cgccatccaa gctgtattgt ctctgtatgc ttctggtcgt acaactggta     600
ttgtgctgga ttctggagat ggtgtttctc acacagtacc aatctatgaa ggttatgccc     660
ttcctcatgc catccttcgt ttggacttgg ctggtagaga cttgactgat taccttatga     720
aaattctgac tgaacgtggt tactcttttca                                     750

<210> SEQ ID NO 395
<211> LENGTH: 204
<212> TYPE: PRT
<213> ORGANISM: Leptinotarsa decemlineata

<400> SEQUENCE: 395

Pro Ile Asn Met Cys Asp Glu Glu Val Ala Ala Leu Val Val Asp Asn
1               5                   10                  15

Gly Ser Gly Met Cys Lys Ala Gly Phe Ala Gly Asp Asp Ala Pro Arg
            20                  25                  30

Ala Val Phe Pro Ser Ile Val Gly Arg Pro Arg His Gln Gly Val Met
        35                  40                  45

Val Gly Met Gly Gln Lys Asp Ser Tyr Val Gly Asp Glu Ala Gln Ser
    50                  55                  60

Lys Arg Gly Ile Leu Thr Leu Lys Tyr Pro Ile Glu His Gly Ile Val
65                  70                  75                  80

Thr Asn Trp Asp Asp Met Glu Lys Ile Trp His His Thr Phe Tyr Asn
                85                  90                  95

Glu Leu Arg Val Ala Pro Glu Glu His Pro Val Leu Leu Thr Glu Ala
            100                 105                 110

Pro Leu Asn Pro Lys Ala Asn Arg Glu Lys Met Thr Gln Ile Met Phe
        115                 120                 125

Glu Thr Phe Asn Thr Pro Ala Met Tyr Val Ala Ile Gln Ala Val Leu
    130                 135                 140

Ser Leu Tyr Ala Ser Gly Arg Thr Thr Gly Ile Val Leu Asp Ser Gly
145                 150                 155                 160

Asp Gly Val Ser His Thr Val Pro Ile Tyr Glu Gly Tyr Ala Leu Pro
                165                 170                 175

His Ala Ile Leu Arg Leu Asp Leu Ala Gly Arg Asp Leu Thr Asp Tyr
            180                 185                 190

Leu Met Lys Ile Leu Thr Glu Arg Gly Tyr Ser Phe
        195                 200

```
<210> SEQ ID NO 396
<211> LENGTH: 44
<212> TYPE: DNA
<213> ORGANISM: Artificial
<220> FEATURE:
<223> OTHER INFORMATION: Primer

<400> SEQUENCE: 396
gcgtaatacg actcactata ggatgtgtga cgaagaggtt gccg          44

<210> SEQ ID NO 397
<211> LENGTH: 24
<212> TYPE: DNA
<213> ORGANISM: Artificial
<220> FEATURE:
<223> OTHER INFORMATION: Primer

<400> SEQUENCE: 397
gtcaacaaaa cagggtgctc ttcg                                24

<210> SEQ ID NO 398
<211> LENGTH: 22
<212> TYPE: DNA
<213> ORGANISM: Artificial
<220> FEATURE:
<223> OTHER INFORMATION: Primer

<400> SEQUENCE: 398
atgtgtgacg aagaggttgc cg                                  22

<210> SEQ ID NO 399
<211> LENGTH: 46
<212> TYPE: DNA
<213> ORGANISM: Artificial
<220> FEATURE:
<223> OTHER INFORMATION: Primer

<400> SEQUENCE: 399
gcgtaatacg actcactata gggtcaacaa aacagggtgc tcttcg        46

<210> SEQ ID NO 400
<211> LENGTH: 320
<212> TYPE: DNA
<213> ORGANISM: Leptinotarsa decemlineata

<400> SEQUENCE: 400
atgtgtgacg aagaggttgc cgcattagtc gtagacaatg gatctggtat gtgcaaagct    60
ggatttgctg gggatgatgc ccccgtgca gttttcccat ccattgttgg tcgtccaaga   120
catcaaggag ttatggtagg aatgggccaa aaggactcgt atgtaggaga tgaagcccaa   180
agcaaaagag gtatccttac cttgaaatac cccattgaac acggtattgt cacaaactgg   240
gatgatatgg agaaaatctg gcaccatacc ttctacaatg aacttcgagt tgcccccgaa   300
gagcaccctg ttttgttgac                                              320

<210> SEQ ID NO 401
<211> LENGTH: 1152
<212> TYPE: DNA
```

<400> SEQUENCE: 401

```
tgacgacctt gagttggttt ctgaagttga actcggcagc cttcttctgg agcttggcga      60
atttgttttc gtacttggaa acctttttca aggtaggttt gacgaattta ccacggaggt     120
cgttgacctg gctgttgagg tcggcgatct caaggtcacg tctctccact tcgaattcga     180
tgtcaatttt actcctctcc agagcgtcaa ttcgcttatg gtagtctgtg cagagtttct     240
tcaaggttgc ttcattggcg ttgtcgacgt cggcaatttg cccgcagcgc tcctcaatcg     300
ttcgcctcct ctcagctgct ttgcgttcct gctccttctt cagttcctca gcggcttttt     360
tcctcagcag gagtcggagt ttcttcttcc tttccggggt catgaaaccc ttcttggctt     420
tcttcgcctt agaggcttcc tccatcctct tgcgcacttc agcgcgcttc ctctcgattt     480
cggcctgttt gtctagaagg taagtgtaca cactacattt tcatgaacat tattgcgacc     540
gttgagattc tcattgtttg gtgattgatt atctaaagta gaagcatgaa tagatataac     600
ataaactagt aactaatggg ttagttatgg gtatacttca tgcttttctc tcaggctcga     660
gcaaacaggc cgaaatcgag aggaagcgcg ctgaagtgcg caagaggatg gaggaagcct     720
ctaaggcgaa gaaagccaag aagggtttca tgaccccgga aaggaagaag aaactccgac     780
tcctgctgag gaaaaaagcc gctgaggaac tgaagaagga gcaggaacgc aaagcagctg     840
agaggaggcg aacgattgag gagcgctgcg ggcaaattgc cgacgtcgac aacgccaatg     900
aagcaacctt gaagaaactc tgcacagact accataagcg aattgacgct ctggagagga     960
gtaaaattga catcgaattc gaagtggaga gacgtgacct tgagatcgcc gacctcaaca    1020
gccaggtcaa cgacctccgt ggtaaaattcg tcaaacctac cttgaaaaag gtttccaagt    1080
acgaaaacaa attcgccaag ctccagaaga aggctgccga gttcaacttc agaaaccaac    1140
tcaaggtcgt ca                                                         1152
```

<210> SEQ ID NO 402
<211> LENGTH: 1192
<212> TYPE: DNA
<213> ORGANISM: Artificial
<220> FEATURE:
<223> OTHER INFORMATION: Hairpin

<400> SEQUENCE: 402

```
ctcttgcttc ttggtggcga tcctctcctc gcgcctcttc ttcgcctcct tgaccttgag      60
acgtctcgcc tctgcctggt ccttcaacat ctttgatctc gccttttcag ccttcttctt     120
gtgaatgaag tccatcagta ccctcttgtt tttgaagacg ttacctttgg ctttcatgta     180
aaggtcgtgg tacatttgcc tatcgatctt cttggcttct ctgtattttt taaggagccg     240
tcgcaggact ctcattctgt tgacccacag gaccttcaca ggcattctgg cgttggcggt     300
accccttcctc ttaccgaagc cacagtgacg acccttccgt ctggcttctg tgtttttacg     360
gacgcgggct ctggagtgga cagccacagg cttttttgatg atcaaaccat ccttgatcag     420
cttacggatg ttttgcctag agttggtgtt ggcgatttcg ttgatttcat tagggtccaa     480
ccacactttc ttcttgccgc atctcatcac ctctagaagg taagtgtaca cactacattt     540
tcatgaacat tattgcgacc gttgagattc tcattgtttg gtgattgatt atctaaagta     600
gaagcatgaa tagatataac ataaactagt aactaatggg ttagttatgg gtatacttca     660
tgcttttctc tcaggctcga gggtgatgag atgcggcaag aagaaagtgt ggttggaccc     720
```

```
taatgaaatc aacgaaatcg ccaacaccaa ctctaggcaa acatccgta agctgatcaa     780 ggatggtttg atcatcaaaa agcctgtggc tgtccactcc agagcccgcg tccgtaaaaa     840
cacagaagcc agacggaagg gtcgtcactg tggcttcggt aagaggaagg gtaccgccaa     900
cgccagaatg cctgtgaagg tcctgtgggt caacagaatg agagtcctgc gacggctcct     960
taaaaaatac agagaagcca agaagatcga taggcaaatg taccacgacc tttacatgaa    1020
agccaaaggt aacgtcttca aaacaagag ggtactgatg gacttcattc acaagaagaa    1080
ggctgaaaag gcgagatcaa agatgttgaa ggaccaggca gaggcgagac gtctcaaggt    1140
caaggaggcg aagaagaggc gcgaggagag gatcgccacc aagaagcaag ag           1192

<210> SEQ ID NO 403
<211> LENGTH: 792
<212> TYPE: DNA
<213> ORGANISM: Artificial
<220> FEATURE:
<223> OTHER INFORMATION: Hairpin

<400> SEQUENCE: 403
actctgtctg gcttttggct gtgacgcaca gttcatagag ataaccttca cccgaatatg      60
ccttgcgagg tcgcaaaatc ggcgaaattc catacctgtt caccgacgac ggcgctggat     120
caattccaca gttttcgcga tccagactga atgcccacag gccgtcgagt ttttgatttt     180
cagatacgta cacttttccc ggcaataaca tacggcgtga catcggcttc aaatggcgta     240
tagccgccct gatgctccat cacactttgc cgtaatgagt gaccgcatcg aaacgcagca     300
cgatacgctg gtctagaagg taagtgtaca cactacattt tcatgaacat tattgcgacc     360
gttgagattc tcattgtttg gtgattgatt atctaaagta gaagcatgaa tagatataac     420
ataaactagt aactaatggg ttagttatgg gtatacttca tgcttttctc tcaggctcga     480
gccagcgtat cgtgctgcgt ttcgatgcgt tcactcatta cggcaaagtg tgatggagca     540
tcagggcggc tatacgccat ttgaagccga tgtcacgccg tatgttattg ccgggaaaag     600
tgtacgtatc tgaaatcaaa aaactcgacg gcctgtgggc attcagtctg gatcgcgaaa     660
actgtggaat tgatccagcg ccgtcgtcgg tgaacaggta tggaatttcg ccgattttgc     720
gacctcgcaa ggcatattcg ggtgaaggtt atctctatga actgtgcgtc acagccaaaa     780
gccagacaga gt                                                        792

<210> SEQ ID NO 404
<211> LENGTH: 839
<212> TYPE: DNA
<213> ORGANISM: leptinotarsa decemlineata

<400> SEQUENCE: 404
cagtcagcac cgagtccttg ttgactgctc acattttcca tcgtttctac cagaacaaca      60
gcaacaactt tcatcatggc ggacgacgag gaaaagagga ggaaacaagc ggaaattgaa     120
cgcaagaggg ctgaggtcag ggctcgcatg gaagaggcct ccaaggccaa aaaagccaag     180
aaaggtttca tgaccctga gaggaagaag aaacttaggt tattgctgag aaagaaagca     240
gcagaagaac tgaaaaaaga acaagaacgc aaagctgccg aaaggcgtat tattgaagag     300
agatgcggaa aaccaaaact cattgatgag gcaaatgaag agcaggtgag gaactattgc     360
aagttatatc acggtagaat agctaaactg gaggaccaga aatttgattt ggaataccct     420
gtcaaaaaga aagacatgga gatcgccgaa ttgaacagtc aagtcaacga cctcagggt     480
```

-continued

```
aaattcgtca aacccactct caagaaagta tccaaatacg agaacaaatt tgctaaactc      540
caaaagaaag cagcagaatt caatttccgt aatcaactga aagttgtaaa gaagaaggag      600
ttcaccctgg aggaggaaga caaagaaaag aagcccgatt ggtcgaagaa gggagacgaa      660
aagaaggtac aagaagtgga agcatgatct gtccctacaa tttaatattt cccttcgtcc      720
gtggaaattt tacaacttaa gatatattta ttttattcgc ttcttatgag actatgaaag      780
tgatgtctgc atgtatatta ttcgttttat gtatgtatta aaaaaagaac ttgattgaa       839
```

<210> SEQ ID NO 405
<211> LENGTH: 203
<212> TYPE: PRT
<213> ORGANISM: leptinotarsa decemlineata

<400> SEQUENCE: 405

```
Met Ala Asp Asp Glu Glu Lys Arg Arg Lys Gln Ala Glu Ile Glu Arg
1               5                  10                  15

Lys Arg Ala Glu Val Arg Ala Arg Met Glu Glu Ala Ser Lys Ala Lys
            20                  25                  30

Lys Ala Lys Lys Gly Phe Met Thr Pro Glu Arg Lys Lys Lys Leu Arg
        35                  40                  45

Leu Leu Leu Arg Lys Lys Ala Ala Glu Glu Leu Lys Lys Glu Gln Glu
    50                  55                  60

Arg Lys Ala Ala Glu Arg Arg Ile Ile Glu Glu Arg Cys Gly Lys Pro
65                  70                  75                  80

Lys Leu Ile Asp Glu Ala Asn Glu Glu Gln Val Arg Asn Tyr Cys Lys
                85                  90                  95

Leu Tyr His Gly Arg Ile Ala Lys Leu Glu Asp Gln Lys Phe Asp Leu
            100                 105                 110

Glu Tyr Leu Val Lys Lys Lys Asp Met Glu Ile Ala Glu Leu Asn Ser
        115                 120                 125

Gln Val Asn Asp Leu Arg Gly Lys Phe Val Lys Pro Thr Leu Lys Lys
    130                 135                 140

Val Ser Lys Tyr Glu Asn Lys Phe Ala Lys Leu Gln Lys Lys Ala Ala
145                 150                 155                 160

Glu Phe Asn Phe Arg Asn Gln Leu Lys Val Val Lys Lys Lys Glu Phe
                165                 170                 175

Thr Leu Glu Glu Glu Asp Lys Gly Lys Lys Pro Asp Trp Ser Lys Lys
            180                 185                 190

Gly Asp Glu Lys Lys Val Gln Gly Val Glu Ala
        195                 200
```

DOWN-REGULATING GENE EXPRESSION IN INSECT PESTS

RELATED APPLICATIONS

This application is a divisional application of U.S. application Ser. No. 14/930,753, filed Nov. 3, 2015, which application is a divisional application of U.S. application Ser. No. 13/462,636, filed May 2, 2012, which application is a continuation-in-part of PCT/EP2012/057332, filed Apr. 20, 2012, which claims the benefit under 35 U.S.C. § 119(e) of U.S. provisional application 61/477,371 filed Apr. 20, 2011, and U.S. provisional application 61/508,826 filed Jul. 18, 2011, each of which is incorporated by reference in its entirety herein.

SEQUENCE LISTING

The instant application contains a Sequence Listing which has been submitted in ASCII format via EFS-Web and is hereby incorporated by reference in its entirety.

FIELD OF THE INVENTION

The present invention relates generally to genetic control of infestation by insect pest species, particularly prevention and/or control of pest infestation of plants. More specifically, the invention relates to down-regulation of expression of target genes in insect pest species by interfering ribonucleic acid (RNA) molecules. Compositions and combinations containing the interfering RNA molecules of the invention for use in topical applications, for example in the form of insecticides, are also provided.

BACKGROUND TO THE INVENTION

There exists an abundance of insect pest species that can infect or infest a wide variety of environments and host organisms. Insect pests include a variety of species from the insect Orders Hemiptera (true bugs), Coleoptera (beetles), Siphonaptera (fleas), Dichyoptera (cockroaches and mantids), Lepidoptera (moths and butterflies), Orthoptera (e.g. grasshoppers) and Diptera (true flies). Pest infestation can lead to significant damage. Insect pests that infest plant species are particularly problematic in agriculture as they can cause serious damage to crops and significantly reduce plant yields. A wide variety of different types of plant are susceptible to pest infestation including commercial crops such as rice, cotton, soybean, potato and corn.

Traditionally, infestation with insect pests has been prevented or controlled through the use of chemical pesticides. However, these chemicals are not always suitable for use in the treatment of crops as they can be toxic to other species and can cause significant environmental damage. Over more recent decades, researchers have developed more environmentally-friendly methods of controlling pest infestation. For example, microorganisms such as *Bacillus thuringiensis* bacteria that naturally express proteins toxic to insect pests have been used. Scientists have also isolated the genes encoding these insecticidal proteins and used them to generate transgenic crops resistant to insect pests e.g. corn and cotton plants genetically engineered to produce proteins of the Cry family. Although bacterial toxins have been highly successful in controlling certain types of pest, they are not effective against all pest species. Researchers have therefore looked for other more targeted approaches to pest control and in particular to RNA interference or 'gene silencing' as a means to control pests at the genetic level.

RNA interference or 'RNAi' is a process whereby the expression of genes in the context of a cell or whole organism is down-regulated in a sequence-specific manner. RNAi is now a well-established technique in the art for inhibiting or down-regulating gene expression in a wide variety of organisms including pest organisms such as fungi, nematodes and insects. Furthermore, previous studies have shown that down-regulation of target genes in insect pest species can be used as a means to control pest infestation. WO2007/074405 describes methods of inhibiting expression of target genes in invertebrate pests including Colorado potato beetle. Furthermore, WO2009/091864 describes compositions and methods for the suppression of target genes from insect pest species including pests from the *Lygus* genus.

Although the use of RNAi for down-regulating gene expression in pest species is known in the art, the success of this technique for use as a pest control measure depends on selection of the most appropriate target genes, namely those wherein loss of function results in significant disruption of an essential biological process and/or death of the organism. The present invention is thus directed towards the down-regulation of particular target genes in insect pests as a means to achieve more effective prevention and/or control of insect pest infestation, particularly of plants.

SUMMARY OF THE INVENTION

The current inventors sought to identify improved means for preventing and/or controlling insect pest infestation using genetic approaches. In particular, they investigated the use of RNAi to down-regulate genes in such a way as to impair the ability of the insect pest to survive, grow, colonize specific environments and/or infest host organisms and thus limit the damage caused by the pest. Therefore, in accordance with one aspect of the invention, there is provided an interfering ribonucleic acid (RNA or double stranded RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or having a nucleotide sequence that, when the two sequences are optimally aligned and compared, is at least 75%, preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (ii) is selected from the group of genes having a nucleotide sequence consisting of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (iii) is selected from the group of genes having a nucleotide sequence comprising a fragment of at least 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100, 1200, 1300, 1400, 1500, 2000 or 3000 contiguous nucleotides of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or having a nucleotide sequence that, when said gene comprising said fragment is optimally aligned and compared with any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, said nucleotide sequence is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (iv) is selected from the group of genes having a nucleotide sequence comprising a fragment of at least 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100, 1200, 1300, 1400, 1500, 2000 or 3000 contiguous nucleotides of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, and wherein when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, said nucleotide sequence of said fragment is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (v) is an insect pest orthologue of a gene having a nucleotide sequence comprising any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or (vi) is selected from the group of genes having a nucleotide sequence encoding an amino acid sequence that, when the two amino acid sequences are optimally aligned and compared, is at least 70% preferably at least 75%, 80%, 85%, 90%, 95%, 98% or 99% identical to the amino acid sequence encoded by any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389.

In a particular aspect of the invention, interfering RNA molecules of the current invention comprise at least one double-stranded region, typically the silencing element of the interfering RNA, comprising a sense RNA strand annealed by complementary basepairing to an antisense RNA strand wherein the sense strand of the dsRNA molecule comprises a sequence of nucleotides complementary to a sequence of nucleotides located within the RNA transcript of the target gene.

In one embodiment, the present invention relates to an interfering ribonucleic acid (RNA or double stranded RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233 or the complement thereof, or having a nucleotide sequence so that, when the two sequences are optimally aligned and compared, is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or (ii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or having a nucleotide sequence so that, when said gene comprising said fragment is optimally aligned and compared with any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, said nucleotide sequence is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or (iii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, and wherein when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, said nucleotide sequence of said fragment is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or (iv) is an insect pest orthologue of a gene having a nucleotide sequence comprising any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233 or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233.

These target genes encode proteins within the troponin/myofilament complex.

In a further embodiment, the present invention relates to an interfering ribonucleic acid (RNA or double stranded RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or having a nucleotide sequence so that, when the two sequences are optimally aligned and compared, is at least 75% preferably at least 80%, 85%, 90%, 95%, 98% or 99% identical to any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or (ii) is selected from the group of genes having a nucleotide sequence comprising a fragment of at least 21 contiguous nucleotides of any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or having a nucleotide sequence so that, when said gene comprising said fragment is optimally aligned and compared with any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, said nucleotide sequence is at least 75% preferably at least 80%, 85%, 90%, 95%, 98% or 99% identical to any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or (iii) is selected from the group of genes having a nucleotide sequence comprising a fragment of at least 21 contiguous nucleotides of any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, and wherein when said fragment is optimally aligned and compared with the corresponding fragment in any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, said nucleotide sequence of said fragment is at least 75% preferably at least 80%, 85%, 90%, 95%, 98% or 99% identical to said corresponding fragment of any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or (iv) is an insect pest orthologue of a gene having a nucleotide sequence comprising any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273.

These target genes encode insect ribosomal proteins.

In certain embodiments, the present invention relates to an interfering RNA molecule which comprises at least one double-stranded region, typically the silencing element of the interfering RNA molecule, comprising a sense RNA strand annealed by complementary basepairing to an antisense RNA strand wherein the sense strand of the dsRNA molecule comprises a sequence of at least 17, 18, 19, 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100, 1200, 1300, 1400, 1500, 2000 or 3000 contiguous nucleotides, that is at least 75% preferably at least 80%, 85%, 90%, 95%, 98%, 99% or 100% complementary to a sequence of nucleotides located within the RNA transcript of a target gene from the troponin/myofilament complex.

In one embodiment, the target gene encodes an insect wings up A (troponin I) protein (e.g. an insect orthologue of the CG7178 Dm protein), said target gene being represented by SEQ ID NOs 1, 2, 174, 404, 175, 180, 181, 188 and 189. In a preferred embodiment, the insect orthologue has at least 85%, 90%, 92%, 94%, 96%, 98%, 99% or 100% amino acid sequence identity to one or more of SEQ ID NOs. 79, 349, 405, 352 or 356.

In one embodiment, the target gene encodes an upheld protein (e.g. an insect orthologue of the CG7107 Dm protein), said target gene being represented by SEQ ID NOs 121, 130, 142, 143, 176, 177, 182 and 183. In a preferred embodiment, the insect orthologue has at least 85%, 90%, 92%, 94%, 96%, 98%, 99% or 100% amino acid sequence identity to one or more of SEQ ID NOs. 330, 350 or 353.

In one embodiment, the target gene encodes the tropomyosin 1 protein (e.g. an insect orthologue of the CG4898 Dm protein), or the tropomyosin 2 protein (e.g. an insect orthologue of the CG4843 Dm protein), said target gene being represented by SEQ ID NOs 123 and 132. In a preferred embodiment, the insect orthologue has at least 85%, 90%, 92%, 94%, 96%, 98%, 99% or 100% amino acid sequence identity to SEQ ID NO. 332.

In one embodiment, the target gene encodes the myosin heavy chain (e.g. an insect orthologue of the CG17927 Dm protein), said target gene being represented by SEQ ID NOs 122, 131, 144, 145, 178 and 179. In a preferred embodiment, the insect orthologue has at least 85%, 90%, 92%, 94%, 96%, 98%, 99% or 100% amino acid sequence identity to one or more of SEQ ID NOs. 331 or 351.

In one embodiment, the target gene encodes the myosin light chain cytoplasmic protein (e.g. an insect orthologue of the CG3201 Dm protein), said target gene being represented by SEQ ID NOs 124 and 133. In a preferred embodiment, the insect orthologue has at least 85%, 90%, 92%, 94%, 96%, 98%, 99% or 100% amino acid sequence identity to SEQ ID NO. 333.

In one embodiment, the target gene encodes the spaghetti squash protein (e.g. an insect orthologue of the CG3595 Dm protein), said target gene being represented by SEQ ID NOs 125 and 134. In a preferred embodiment, the insect orthologue has at least 85%, 90%, 92%, 94%, 96%, 98%, 99% or 100% identity to SEQ ID NO. 334.

In one embodiment, the target gene encodes the zipper protein (e.g. an insect orthologue of the CG15792 Dm protein), said target gene being represented by SEQ ID NOs 126 and 135. In a preferred embodiment, the insect orthologue has at least 85%, 90%, 92%, 94%, 96%, 98%, 99% or 100% identity to SEQ ID NO. 335.

In one embodiment, the target gene encodes the troponin C (e.g. an insect orthologue of the CG2981, CG7930, CG9073, CG6514, CG12408, CG9073, CG7930, CG2981, CG12408 or CG6514 Dm protein), said target gene being represented by SEQ ID NOs 127 and 136, or 128 and 137, or 184 and 185. In a preferred embodiment, the insect orthologue has at least 85%, 90%, 92%, 94%, 96%, 98%, 99% or 100% amino acid sequence identity to one or more of SEQ ID NOs. 336, 337 and 354.

According to another embodiment the present invention relates to an interfering RNA molecule which comprises at least one double-stranded region, typically the silencing element of the interfering RNA molecule, comprising a sense RNA strand annealed by complementary basepairing to an antisense RNA strand wherein the sense strand of the dsRNA molecule comprises a sequence of at least 17, 18, 19, 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100, 1200, 1300, 1400, 1500, 2000 or 3000 contiguous nucleotides, that is at least 75% preferably at least 80%, 85%, 90%, 95%, 98%, 99% or 100% complementary to a sequence of nucleotides located within the RNA transcript of a target gene that encodes an insect ribosomal protein.

In one embodiment, the target gene encodes ribosomal protein S3A (e.g. an insect orthologue of the CG2168 Dm protein), said target gene being represented by SEQ ID NOs 11, 12 and 141. In a preferred embodiment, the insect orthologue has at least 85%, 90%, 92%, 94%, 96%, 98%, 99% or 100% amino acid sequence identity to one or both of SEQ ID NO. 84 or 328.

In one embodiment, the target gene encodes the ribosomal protein LP1 (e.g. an insect orthologue of the CG4087 Dm protein), said target gene being represented by SEQ ID NO 3 and 4. In a preferred embodiment, the insect orthologue has at least 85%, 90%, 92%, 94%, 96%, 98%, 99% or 100% amino acid sequence identity to SEQ ID NO.80.

In one embodiment, the target gene encodes the ribosomal protein S3 (e.g. an insect orthologue of the CG6779 Dm protein), said target gene being represented by SEQ ID NOs 7 and 8. In a preferred embodiment, the insect orthologue has at least 85%, 90%, 92%, 94%, 96%, 98%, 99% or 100% amino acid sequence identity to SEQ ID NO.82.

In one embodiment, the target gene encodes the ribosomal protein L10Ab (e.g. an insect orthologue of the CG7283 Dm protein) represented by SEQ ID NOs 9 and 10. In a preferred embodiment, the insect orthologue has at least 85%, 90%, 92%, 94%, 96%, 98%, 99% or 100% amino acid sequence identity to SEQ ID NO. 83.

In one embodiment, the target gene encodes the ribosomal protein S18 (e.g. an insect orthologue of the CG8900 Dm protein), said target gene being represented by SEQ ID NO 13 and 14. In a preferred embodiment, the insect orthologue has at least 85%, 90%, 92%, 94%, 96%, 98%, 99% or 100% amino acid sequence identity to SEQ ID NO.85.

In one embodiment, the target gene encodes the ribosomal protein L4 (e.g. an insect orthologue of the CG5502 Dm protein), said target gene represented by SEQ ID NO 5 and 6. In a preferred embodiment, the insect orthologue has at least 85%, 90%, 92%, 94%, 96%, 98%, 99% or 100% amino acid sequence identity to SEQ ID NO.81.

In one embodiment, the target gene encodes the ribosomal protein S27 (e.g. an insect orthologue of the CG10423 Dm protein), said target gene being represented by SEQ ID NO 15 and 16, 204 and 205. In a preferred embodiment, the insect orthologue has at least 85%, 90%, 92%, 94%, 96%, 98%, 99% or 100% amino acid sequence identity to one or both of SEQ ID NOs.86 and 359.

In one embodiment, the target gene encodes the ribosomal protein L6 (e.g. an insect orthologue of the CG11522 Dm protein), said target gene being represented by SEQ ID NO 17 and 18. In a preferred embodiment, the insect orthologue has at least 85%, 90%, 92%, 94%, 96%, 98%, 99% or 100% amino acid sequence identity to SEQ ID NO. 87.

In one embodiment, the target gene encodes the ribosomal protein S13 (e.g. an insect orthologue of the CG13389 Dm protein), said target gene being represented by SEQ ID NO 19 and 20. In a preferred embodiment, the insect orthologue has at least 85%, 90%, 92%, 94%, 96%, 98%, 99% or 100% amino acid sequence identity to SEQ ID NO. 88.

In one embodiment, the target gene encodes the ribosomal protein L12 (e.g. an insect orthologue of the CG3195 Dm protein), said target gene being represented by SEQ ID NOs 21 and 22. In a preferred embodiment, the insect orthologue has at least 85%, 90%, 92%, 94%, 96%, 98%, 99% or 100% amino acid sequence identity to SEQ ID NO.89.

In one embodiment, the target gene encodes the ribosomal protein L26 (e.g. an insect orthologue of the CG6846 Dm protein), said target gene being represented by SEQ ID NOs 158 and 159. In a preferred embodiment, the insect orthologue has at least 85%, 90%, 92%, 94%, 96%, 98%, 99% or 100% amino acid sequence identity to SEQ ID NO. 343.

In one embodiment, the target gene encodes the ribosomal protein L21 (e.g. an insect orthologue of the CG12775 Dm protein), said target gene being represented by SEQ ID NO 165, 166 and 167. In a preferred embodiment, the insect orthologue has at least 85%, 90%, 92%, 94%, 96%, 98%, 99% or 100% amino acid sequence identity to SEQ ID NOs 347 and 348.

In one embodiment, the target gene encodes the ribosomal protein S12 (e.g. an insect orthologue of the CG11271 Dm protein), said target gene being represented by SEQ ID NOs 156 and 157. In a preferred embodiment, the insect orthologue has at least 85%, 90%, 92%, 94%, 96%, 98%, 99% or 100% amino acid sequence identity to SEQ ID NO. 342.

In one embodiment, the target gene encodes the ribosomal protein S28b (e.g. an insect orthologue of the CG2998 Dm protein), said target gene being represented by SEQ ID NOs 160 and 161. In a preferred embodiment, the insect orthologue has at least 85%, 90%, 92%, 94%, 96%, 98%, 99% or 100% amino acid sequence identity to SEQ ID NO. 344.

In one embodiment, the target gene encodes the ribosomal protein L13 (e.g. an insect orthologue of the CG4651 Dm protein), said target gene being represented by SEQ ID NOs. 154 and 155. In a preferred embodiment, the insect orthologue has at least 85%, 90%, 92%, 94%, 96%, 98%, 99% or 100% amino acid sequence identity to SEQ ID NO. 341.

In one embodiment, the target gene encodes the ribosomal protein L10 (e.g. an insect orthologue of the CG17521 Dm protein), said target gene being represented by SEQ ID NOs. 163 and 164. In a preferred embodiment, the insect orthologue has at least 85%, 90%, 92%, 94%, 96%, 98%, 99% or 100% amino acid sequence identity to SEQ ID NO. 345.

In one embodiment, the target gene encodes the ribosomal protein L5 (e.g. an insect orthologue of the CG17489 Dm protein), said target gene being represented by SEQ ID NOs. 152 and 153. In a preferred embodiment, the insect orthologue has at least 85%, 90%, 92%, 94%, 96%, 98%, 99% or 100% amino acid sequence identity to SEQ ID NO. 340.

In one embodiment, the target gene encodes the ribosomal protein S15Aa (e.g. an insect orthologue of the CG2033 Dm protein), said target gene being represented by SEQ ID NOs. 150 and 151. In a preferred embodiment, the insect orthologue has at least 85%, 90%, 92%, 94%, 96%, 98%, 99% or 100% amino acid sequence identity to SEQ ID NO. 339.

In one embodiment, the target gene encodes the ribosomal protein L19 (e.g. an insect orthologue of the CG2746 Dm protein), said target gene being represented by SEQ ID NOs. 200 and 201. In a preferred embodiment, the insect orthologue has at least 85%, 90%, 92%, 94%, 96%, 98%, 99% or 100% amino acid sequence identity to SEQ ID NO.357.

In one embodiment, the target gene encodes the ribosomal protein L27 (e.g. an insect orthologue of the CG4759 Dm protein), said target gene being represented by SEQ ID NO. 386. In a preferred embodiment, the insect orthologue has at least 85%, 90%, 92%, 94%, 96%, 98%, 99% or 100% amino acid sequence identity to SEQ ID NO.390.

In one embodiment, the target gene encodes the mitochondrial cytochrome c oxidase subunit II protein (e.g. an insect orthologue of the CG34069 Dm protein), said target gene being represented by SEQ ID NO 25 and 26. In a preferred embodiment, the insect orthologue has at least 85%, 90%, 92%, 94%, 96%, 98%, 99% or 100% amino acid sequence identity to SEQ ID NO. 91.

In one embodiment, the target gene encodes the ATP synthase-γ chain (e.g. an insect orthologue of the CG7610 Dm protein), said target gene being represented by SEQ ID NOs 129 and 138. In a preferred embodiment, the insect orthologue has at least 85%, 90%, 92%, 94%, 96%, 98%, 99% or 100% amino acid sequence identity to SEQ ID NO. 338.

In one embodiment, the target gene encodes the ubiquitin-5E (e.g. an insect orthologue of the CG32744 Dm protein) said target gene being represented by SEQ ID NOs. 186 and 187, 202 and 203. In a preferred embodiment, the insect orthologue has at least 85%, 90%, 92%, 94%, 96%, 98%, 99% or 100% amino acid sequence identity to one or both of SEQ ID NOs.355 and 358.

In one embodiment, the target gene encodes the proteasome beta-type subunit (e.g. an insect orthologue of the CG17331 Dm protein) said target gene being represented by SEQ ID NO. 387. In a preferred embodiment, the insect orthologue has at least 85%, 90%, 92%, 94%, 96%, 98%, 99% or 100% amino acid sequence identity to SEQ ID NO.391.

In one embodiment, the target gene encodes the protein which is an insect orthologue of the CG13704 Dm protein, said target gene being represented by SEQ ID NO.388. In a preferred embodiment, the insect orthologue has at least 85%, 90%, 92%, 94%, 96%, 98%, 99% or 100% amino acid sequence identity to SEQ ID NO.392.

In one embodiment, the target gene encodes the Rpn12 protein (e.g. an insect orthologue of the CG4157 Dm protein) said target gene being represented by SEQ ID NO. 389. In a preferred embodiment, the insect orthologue has at least 85%, 90%, 92%, 94%, 96%, 98%, 99% or 100% amino acid sequence identity to SEQ ID NO.393.

In accordance with a second aspect of the invention, there is provided a composition for preventing and/or controlling insect pest infestation comprising at least one interfering ribonucleic acid (RNA) and at least one suitable carrier, excipient or diluent, wherein the interfering RNA functions upon uptake by the pest to down-regulate the expression of a target gene within said pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or having a nucleotide sequence so that, when the two sequences are optimally aligned and compared, is at least 75% identical to any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (ii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or having a nucleotide sequence so that, when said gene comprising said fragment is optimally aligned and compared with any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, said nucleotide sequence is at least 75% identical to any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (iii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, and wherein when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, said nucleotide sequence of said fragment is at least 75% identical to said corresponding fragment of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (iv) is an insect pest orthologue of a gene having a nucleotide sequence comprising any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, wherein the two orthologous genes are similar in sequence to such a degree that when the two genes are optimally aligned and compared, the orthologue has a sequence that is at least 75% identical to any of the sequences represented by SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or (v) is selected from the group of genes having a nucleotide sequence encoding an amino acid sequence that, when the two amino acid sequences are optimally aligned and compared, is at least 85% identical to the amino acid sequence encoded by any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389.

The composition of the invention may be used for the prevention and/or control of pest infestation. In certain embodiments, the composition may be used as a pesticide for a plant or for propagation or reproductive material of a plant. In a further aspect, provided herein is a combination for preventing and/or controlling pest infestation comprising the composition of the invention and at least one other active agent.

In a further aspect, provided herein is a method for down-regulating expression of a target gene in an insect pest species in order to prevent and/or control pest infestation, comprising contacting said pest species with an effective amount of at least one interfering ribonucleic acid (RNA), wherein the interfering RNA functions upon uptake by the pest to down-regulate the expression of a target gene within said pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or having a nucleotide sequence so that, when the two sequences are optimally aligned and compared, is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (ii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or having a nucleotide sequence so that, when said gene comprising said fragment is optimally aligned and compared with any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, said nucleotide sequence is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (iii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, and wherein when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, said nucleotide sequence of said fragment is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (iv) is an insect pest orthologue of a gene having a nucleotide sequence comprising any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs. SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389.

In accordance with a further aspect of the invention, there is provided an isolated polynucleotide selected from the group consisting of:

(i) a polynucleotide which comprises at least 21, preferably at least 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide sequence as represented by any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (ii) a polynucleotide which consists of at least 21, preferably at least 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide sequence as represented by any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (iii) a polynucleotide which comprises at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide sequence as represented in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, that, when the two sequences are optimally aligned and compared, said polynucleotide is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (iv) a polynucleotide which comprises a fragment of at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide as represented in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, and wherein said fragment or said complement has a nucleotide sequence that, when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, said nucleotide sequence is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389 or the complement thereof, or (v) a polynucleotide which consists of a fragment of at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide as represented in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, and wherein said fragment or said complement has a nucleotide sequence that, when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, said nucleotide sequence is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389 or the complement thereof, or (vi) a polynucleotide encoding an amino acid sequence that, when the two amino acid sequences are optimally aligned and compared, is at least 70% preferably at least 75%, 80%, 85%, 90%, 95%, 98% or 99% identical to the amino acid sequence encoded by any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, and wherein said polynucleotide is no longer than 10000, 9000, 8000, 7000, 6000, 5000, 4000, 3000, 2000 or 1500 nucleotides.

The amino acid sequences encoded by the target genes of the present invention are represented by SEQ ID NOs 79, 349, 405, 352, 356, 80, 326, 81, 327, 82, 83, 328, 84, 329, 85, 86, 359, 87 to 91, 330, 350, 353, 331, 351, 332 to 336, 337, 354, 338 to 344, 346, 345, 347, 348, 357, 355, 358, 390 to 393, respectively.

In a particular aspect of the invention, the isolated polynucleotide is part of an interfering RNA molecule, typically part of the silencing element, comprising at least one double-stranded region comprising a sense RNA strand annealed by complementary basepairing to an antisense RNA strand wherein the sense strand of the dsRNA molecule comprises a sequence of nucleotides complementary to a sequence of nucleotides located within the RNA transcript of the target gene. More particularly, the isolated polynucleotide is cloned in a DNA construct in a sense and antisense orientation so that the upon transcription of the sense and antisense polynucleotide a dsRNA molecule is formed, which functions upon uptake by a pest to inhibit or down-regulate the expression of a target gene within said pest.

In one embodiment the present invention relates to an isolated polynucleotide that is cloned in a DNA construct in a sense and antisense orientation so that the upon transcription of the sense and antisense polynucleotide a dsRNA molecule is formed, which functions upon uptake by an insect to inhibit or down-regulate the expression of a target gene within the troponin/myofilament complex.

In one embodiment, the target gene encodes an insect wings up A (troponin I) protein (e.g. an insect orthologue of the CG7178 Dm protein), said target gene being represented by SEQ ID NOs 1, 2, 174, 404, 175, 180, 181, 188 and 189. In a preferred embodiment, the insect orthologue has at least 85%, 90%, 92%, 94%, 96%, 98%, 99% or 100% amino acid sequence identity to one or more of SEQ ID NOs. 79, 349, 405, 352 or 356.

In one embodiment, the target gene encodes an upheld protein (e.g. an insect orthologue of the CG7107 Dm protein), said target gene being represented by SEQ ID NOs 121, 130, 142, 143, 176, 177, 182 and 183. In a preferred embodiment, the insect orthologue has at least 85%, 90%, 92%, 94%, 96%, 98%, 99% or 100% amino acid sequence identity to one or more of SEQ ID NOs. 330, 350 or 353.

In one embodiment, the target gene encodes the tropomyosin 1 protein (e.g. an insect orthologue of the CG4898 Dm protein), or the tropomyosin 2 protein (e.g. an insect orthologue of the CG4843 Dm protein), said target gene being represented by SEQ ID NOs 123 and 132. In a preferred embodiment, the insect orthologue has at least 85%, 90%, 92%, 94%, 96%, 98%, 99% or 100% amino acid sequence identity to SEQ ID NO. 332.

In one embodiment, the target gene encodes the myosin heavy chain (e.g. an insect orthologue of the CG17927 Dm protein), said target gene being represented by SEQ ID NOs 122, 131, 144, 145, 178 and 179. In a preferred embodiment, the insect orthologue has at least 85%, 90%, 92%, 94%, 96%, 98%, 99% or 100% amino acid sequence identity to one or more of SEQ ID NOs. 331 or 351.

In one embodiment, the target gene encodes the myosin light chain cytoplasmic protein (e.g. an insect orthologue of the CG3201 Dm protein), said target gene being represented by SEQ ID NOs 124 and 133. In a preferred embodiment, the insect orthologue has at least 85%, 90%, 92%, 94%, 96%, 98%, 99% or 100% amino acid sequence identity to SEQ ID NO. 333.

In one embodiment, the target gene encodes the spaghetti squash protein (e.g. an insect orthologue of the CG3595 Dm protein), said target gene being represented by SEQ ID NOs 125 and 134. In a preferred embodiment, the insect orthologue has at least 85%, 90%, 92%, 94%, 96%, 98%, 99% or 100% identity to SEQ ID NO. 334.

In one embodiment, the target gene encodes the zipper protein (e.g. an insect orthologue of the CG15792 Dm protein), said target gene being represented by SEQ ID NOs 126 and 135. In a preferred embodiment, the insect orthologue has at least 85%, 90%, 92%, 94%, 96%, 98%, 99% or 100% identity to SEQ ID NO. 335.

In one embodiment, the target gene encodes the troponin C (e.g. an insect orthologue of the CG2981, CG7930, CG9073, CG6514, CG12408, CG9073, CG7930, CG2981, CG12408 or CG6514 Dm protein), said target gene being represented by SEQ ID NOs 127 and 136, or 128 and 137, or 184 and 185. In a preferred embodiment, the insect orthologue has at least 85%, 90%, 92%, 94%, 96%, 98%, 99% or 100% amino acid sequence identity to one or more of SEQ ID NOs. 336, 337 and 354.

According to other embodiments, the present invention relates to an isolated polynucleotide that is cloned in a DNA construct in a sense and antisense orientation so that the upon transcription of the sense and antisense polynucleotide a dsRNA molecule is formed, which functions upon uptake by an insect to inhibit or down-regulate the expression of a target gene that encodes an insect ribosomal protein.

In one embodiment, the target gene encodes ribosomal protein S3A (e.g. an insect orthologue of the CG2168 Dm protein), said target gene being represented by SEQ ID NOs 11, 12 and 141. In a preferred embodiment, the insect orthologue has at least 85%, 90%, 92%, 94%, 96%, 98%, 99% or 100% amino acid sequence identity to one or both of SEQ ID NO. 84 or 328.

In one embodiment, the target gene encodes the ribosomal protein LP1 (e.g. an insect orthologue of the CG4087 Dm protein), said target gene being represented by SEQ ID NO 3 and 4. In a preferred embodiment, the insect orthologue has at least 85%, 90%, 92%, 94%, 96%, 98%, 99% or 100% amino acid sequence identity to SEQ ID NO.80.

In one embodiment, the target gene encodes the ribosomal protein S3 (e.g. an insect orthologue of the CG6779 Dm protein), said target gene being represented by SEQ ID NOs 7 and 8. In a preferred embodiment, the insect orthologue has at least 85%, 90%, 92%, 94%, 96%, 98%, 99% or 100% amino acid sequence identity to SEQ ID NO.82.

In one embodiment, the target gene encodes the ribosomal protein L10Ab (e.g. an insect orthologue of the CG7283 Dm protein) represented by SEQ ID NOs 9 and 10. In a preferred embodiment, the insect orthologue has at least 85%, 90%, 92%, 94%, 96%, 98%, 99% or 100% amino acid sequence identity to SEQ ID NO. 83.

In one embodiment, the target gene encodes the ribosomal protein S18 (e.g. an insect orthologue of the CG8900 Dm protein), said target gene being represented by SEQ ID NO 13 and 14. In a preferred embodiment, the insect orthologue has at least 85%, 90%, 92%, 94%, 96%, 98%, 99% or 100% amino acid sequence identity to SEQ ID NO.85.

In one embodiment, the target gene encodes the ribosomal protein L4 (e.g. an insect orthologue of the CG5502 Dm protein), said target gene represented by SEQ ID NO 5 and 6. In a preferred embodiment, the insect orthologue has at least 85%, 90%, 92%, 94%, 96%, 98%, 99% or 100% amino acid sequence identity to SEQ ID NO.81.

In one embodiment, the target gene encodes the ribosomal protein S27 (e.g. an insect orthologue of the CG10423 Dm protein), said target gene being represented by SEQ ID NO 15 and 16, 204 and 205. In a preferred embodiment, the insect orthologue has at least 85%, 90%, 92%, 94%, 96%, 98%, 99% or 100% amino acid sequence identity to one or both of SEQ ID NOs.86 and 359.

In one embodiment, the target gene encodes the ribosomal protein L6 (e.g. an insect orthologue of the CG11522 Dm protein), said target gene being represented by SEQ ID NO 17 and 18. In a preferred embodiment, the insect orthologue has at least 85%, 90%, 92%, 94%, 96%, 98%, 99% or 100% amino acid sequence identity to SEQ ID NO. 87.

In one embodiment, the target gene encodes the ribosomal protein S13 (e.g. an insect orthologue of the CG13389 Dm protein), said target gene being represented by SEQ ID NO 19 and 20. In a preferred embodiment, the insect orthologue has at least 85%, 90%, 92%, 94%, 96%, 98%, 99% or 100% amino acid sequence identity to SEQ ID NO. 88.

In one embodiment, the target gene encodes the ribosomal protein L12 (e.g. an insect orthologue of the CG3195 Dm protein), said target gene being represented by SEQ ID NOs 21 and 22. In a preferred embodiment, the insect orthologue has at least 85%, 90%, 92%, 94%, 96%, 98%, 99% or 100% amino acid sequence identity to SEQ ID NO.89.

In one embodiment, the target gene encodes the ribosomal protein L26 (e.g. an insect orthologue of the CG6846 Dm protein), said target gene being represented by SEQ ID NOs 158 and 159. In a preferred embodiment, the insect orthologue has at least 85%, 90%, 92%, 94%, 96%, 98%, 99% or 100% amino acid sequence identity to SEQ ID NO. 343.

In one embodiment, the target gene encodes the ribosomal protein L21 (e.g. an insect orthologue of the CG12775 Dm protein), said target gene being represented by SEQ ID NO 165, 166 and 167. In a preferred embodiment, the insect orthologue has at least 85%, 90%, 92%, 94%, 96%, 98%, 99% or 100% amino acid sequence identity to SEQ ID NOs 347 and 348.

In one embodiment, the target gene encodes the ribosomal protein S12 (e.g. an insect orthologue of the CG11271 Dm protein), said target gene being represented by SEQ ID NOs 156 and 157. In a preferred embodiment, the insect orthologue has at least 85%, 90%, 92%, 94%, 96%, 98%, 99% or 100% amino acid sequence identity to SEQ ID NO. 342.

In one embodiment, the target gene encodes the ribosomal protein S28b (e.g. an insect orthologue of the CG2998 Dm protein), said target gene being represented by SEQ ID NOs 160 and 161. In a preferred embodiment, the insect orthologue has at least 85%, 90%, 92%, 94%, 96%, 98%, 99% or 100% amino acid sequence identity to SEQ ID NO. 344.

In one embodiment, the target gene encodes the ribosomal protein L13 (e.g. an insect orthologue of the CG4651 Dm protein), said target gene being represented by SEQ ID NOs. 154 and 155. In a preferred embodiment, the insect orthologue has at least 85%, 90%, 92%, 94%, 96%, 98%, 99% or 100% amino acid sequence identity to SEQ ID NO. 341.

In one embodiment, the target gene encodes the ribosomal protein L10 (e.g. an insect orthologue of the CG17521 Dm protein), said target gene being represented by SEQ ID NOs. 163 and 164. In a preferred embodiment, the insect orthologue has at least 85%, 90%, 92%, 94%, 96%, 98%, 99% or 100% amino acid sequence identity to SEQ ID NO. 345.

In one embodiment, the target gene encodes the ribosomal protein L5 (e.g. an insect orthologue of the CG17489 Dm protein), said target gene being represented by SEQ ID NOs. 152 and 153. In a preferred embodiment, the insect orthologue has at least 85%, 90%, 92%, 94%, 96%, 98%, 99% or 100% amino acid sequence identity to SEQ ID NO. 340.

In one embodiment, the target gene encodes the ribosomal protein S15Aa (e.g. an insect orthologue of the CG2033 Dm protein), said target gene being represented by SEQ ID NOs. 150 and 151. In a preferred embodiment, the insect orthologue has at least 85%, 90%, 92%, 94%, 96%, 98%, 99% or 100% amino acid sequence identity to SEQ ID NO. 339.

In one embodiment, the target gene encodes the ribosomal protein L19 (e.g. an insect orthologue of the CG2746 Dm protein), said target gene being represented by SEQ ID NOs. 200 and 201. In a preferred embodiment, the insect orthologue has at least 85%, 90%, 92%, 94%, 96%, 98%, 99% or 100% amino acid sequence identity to SEQ ID NO.357.

In one embodiment, the target gene encodes the ribosomal protein L27 (e.g. an insect orthologue of the CG4759 Dm protein), said target gene being represented by SEQ ID NO. 386. In a preferred embodiment, the insect orthologue has at least 85%, 90%, 92%, 94%, 96%, 98%, 99% or 100% amino acid sequence identity to SEQ ID NO.390.

Preferably, the methods of the invention find practical application in the prevention and/or control of insect pest infestation, in particular, control of pest infestation of crop plants such as but not limited to cotton, potato, rice, strawberries, alfalfa, soy, tomato, canola, sunflower, sorghum, pearl millet, corn, eggplant, pepper and tobacco. In addition, the interfering RNA of the invention may be introduced into the plants to be protected by routine genetic engineering techniques.

In all aspects of the invention, in preferred embodiments the target gene (i) is selected from the group of genes having a nucleotide sequence comprising any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or having a nucleotide sequence so that, when the two sequences are optimally aligned and compared, is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or (ii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or having a nucleotide sequence so that, when said gene comprising said fragment is optimally aligned and compared with any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, said nucleotide sequence is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or (iii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233 or the complement thereof, and wherein when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233 said nucleotide sequence of said fragment is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233 or the complement thereof, or (iv) is an insect pest orthologue of a gene having a nucleotide sequence comprising any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233.

These target genes encode proteins within the troponin/myofilament complex.

In all aspects of the invention, in preferred embodiments, the target gene (i) is selected from the group of genes having a nucleotide sequence comprising any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or having a nucleotide sequence so that, when the two sequences are optimally aligned and compared, is at least 75% preferably at least 80%, 85%, 90%, 95%, 98% or 99% identical to any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or (ii) is selected from the group of genes having a nucleotide sequence comprising a fragment of at least 21 contiguous nucleotides of any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or having a nucleotide sequence so that, when said gene comprising said fragment is optimally aligned and compared with any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, said nucleotide sequence is at least 75% preferably at least 80%, 85%, 90%, 95%, 98% or 99% identical to any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or (iii) is selected from the group of genes having a nucleotide sequence comprising a fragment of at least 21 contiguous nucleotides of any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, and wherein when said fragment is optimally aligned and compared with the corresponding fragment in any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, said nucleotide sequence of said fragment is at least 75% preferably at least 80%, 85%, 90%, 95%, 98% or 99% identical to said corresponding fragment of any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or (iv) is an insect pest orthologue of a gene having a nucleotide sequence comprising any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or (v) is selected from the group of genes having a nucleotide sequence encoding an amino acid sequence that, when the two amino acid sequences are optimally aligned and compared, is at least 85% identical to the amino acid sequence encoded by any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273.

These target genes encode insect ribosomal proteins.

In all aspects of the invention, in preferred embodiments, the target gene (i) is selected from the group of genes having a nucleotide sequence comprising any of SEQ ID NOs 1, 174, 404, 180, 188, 2, 175, 181, 189, 27 to 30, 282 to 285, 294 to 297, 310 to 313, or the complement thereof, or having a nucleotide sequence so that, when the two sequences are optimally aligned and compared, is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, or the complement thereof, or (ii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, or the complement thereof, or having a nucleotide sequence so that, when said gene comprising said fragment is optimally aligned and compared with any of SEQ ID NOs 1, 174, 404, 180, 188, 2, 175, 181, 189, 27 to 30, 282 to 285, 294 to 297, 310 to 313, said nucleotide sequence is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, or the complement thereof, or (iii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, or the complement thereof, and wherein when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, said nucleotide sequence of said fragment is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, or the complement thereof, or (iv) is an insect pest orthologue of a gene having a nucleotide sequence comprising any of SEQ ID NOs 1, 174, 404, 180, 188, 2, 175, 181, 189, 27 to 30, 282 to 285, 294 to 297, 310 to 313, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 1, 174, 404, 180, 188, 2, 175, 181, 189, 27 to 30, 282 to 285, 294 to 297, 310 to 313, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 1, 174, 404, 180, 188, 2, 175, 181, 189, 27 to 30, 282 to 285, 294 to 297, 310 to 313.

In preferred embodiments, this target gene may encode an insect the troponin I protein (e.g. an insect orthologue of the CG7178 Dm protein). The insect troponin I protein may have an amino acid sequence which is at least 85%, 90%, 92%, 94%, 96%, 98%, 99% identical to the amino acid sequence as presented in any of SEQ ID NOs 79, 349, 405, 352 or 356 (when said encoded proteins are optimally aligned).

BRIEF DESCRIPTION OF THE TABLES AND FIGURES

Table 1 *Lygus hesperus* novel targets identified from first screen.

Table 1B *Lygus hesperus* novel targets in Lh594 pathway.

Table 1C *Lygus hesperus* novel targets identified from second round screen.

Table 2 Polynucleotide sequences of target genes identified in *Lygus hesperus*.

Table 3 Amino acid sequences of target genes identified in *Lygus hesperus*.

Table 4 dsRNAs (sense strand represented by equivalent DNA sequence) corresponding to *Lygus hesperus* target genes and primers for producing the dsRNAs.

Table 5 *Lygus hesperus* targets ranking according to dose response curves (DRCs) and compared to bench mark targets Lh423 & Lh105.

Table 6 *Lygus hesperus* targets from second round screen-ranking according to DRCs and compared to bench mark targets Lh423 & Lh594.

Table 7 Polynucleotide sequences of target genes identified in Colorado potato beetle (CPB).

Table 8 Amino acid sequences of target genes identified in CPB.

Table 9 dsRNAs (sense strand represented by equivalent DNA sequence) corresponding to CPB target genes and primers for producing the dsRNAs.

Table 10 Polynucleotide sequences of target genes identified in brown plant hopper (BPH).

Table 11 Amino acid sequences of target genes identified in BPH.

Table 12 dsRNAs (sense strand represented by equivalent DNA sequence) corresponding to BPH target genes and primers for producing the dsRNAs.

Table 13 Primers used for amplification of aphid cDNAs, based on pea aphid genomic sequence.

Table 14 Polynucleotide sequences of target genes identified in aphids.

Table 15 Amino acid sequences of target genes identified in aphids.

Table 16 dsRNAs (sense strand represented by equivalent DNA sequence) corresponding to aphid target genes and primers for producing the dsRNAs.

Table 17 Degenerate primers used for amplification of CPB Ld594 cDNA

Table 18 Degenerate primers used for amplification of BPH cDNAs

Table 19: *Leptinotarsa decemlineata* novel targets from the screen.

Table 20: *Nilaparvata lugens* novel identified target.

Table 21: *Acyrthosiphon pisum* novel identified targets.

FIG. 1: Plates Lh001_009 second confirmation assay. Dark bars: mortality at day 3 to 6, light bars: mortality at day 6 to 8. Candidate clones are named using the "Lygxxx" screening codes and the "Lhxxx" target nomenclature codes.

Figure 2:
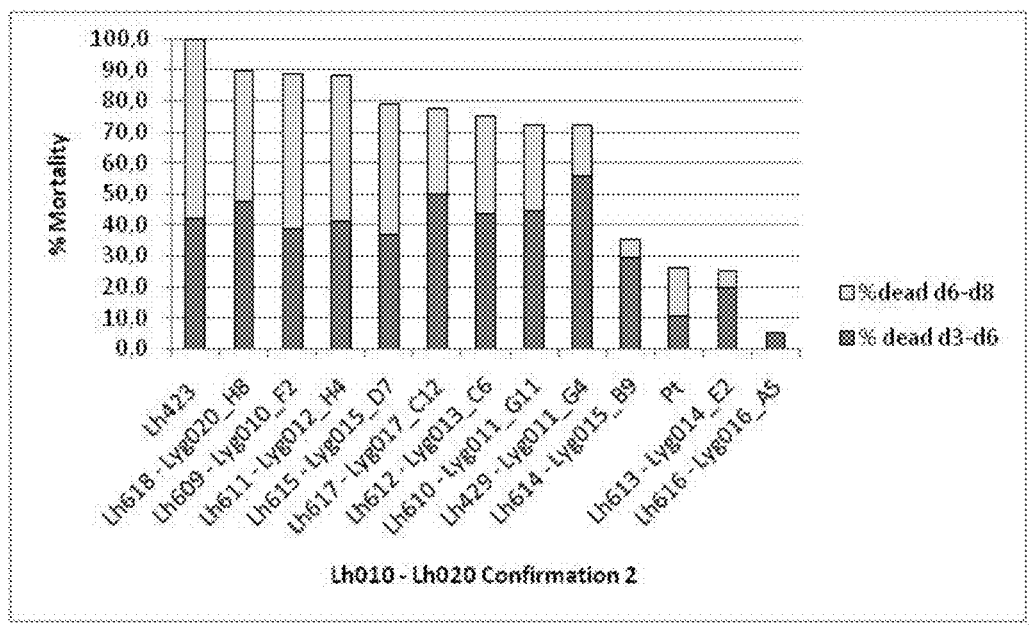

FIG. 2: Plates Lh010_020 second confirmation assay. Dark bars: mortality at day 3 to 6, light bars: mortality at day 6 to 8. Candidate clones are named using the "Lygxxx" screening codes and the "Lhxxx" target nomenclature codes.

Figure 3:
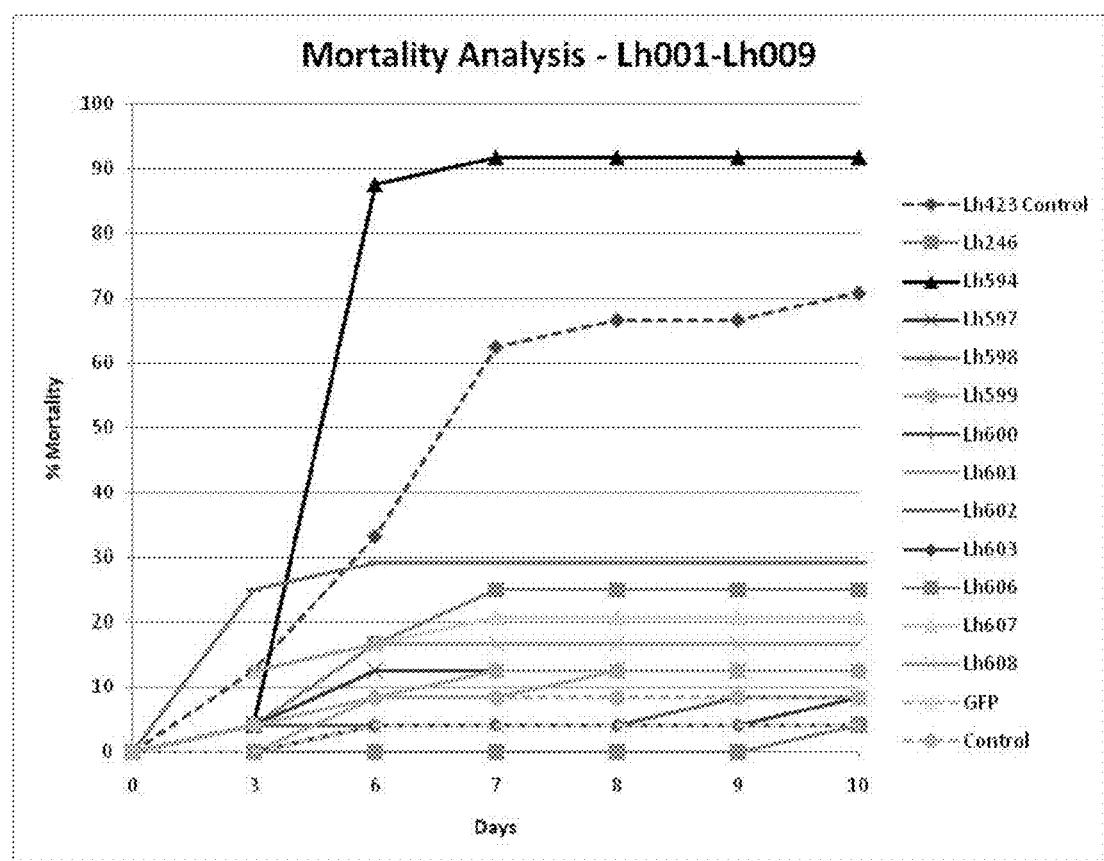

FIG. 3: Mortality analysis of *Lygus* novel targets from plates Lh001 to Lh009, expressed as % mortality over a 10 day period. Controls are indicated in dotted lines. Positive control: Lh423 dsRNA (RpL19). Negative controls: GFP dsRNA and diet only (Control).

Figure 4:
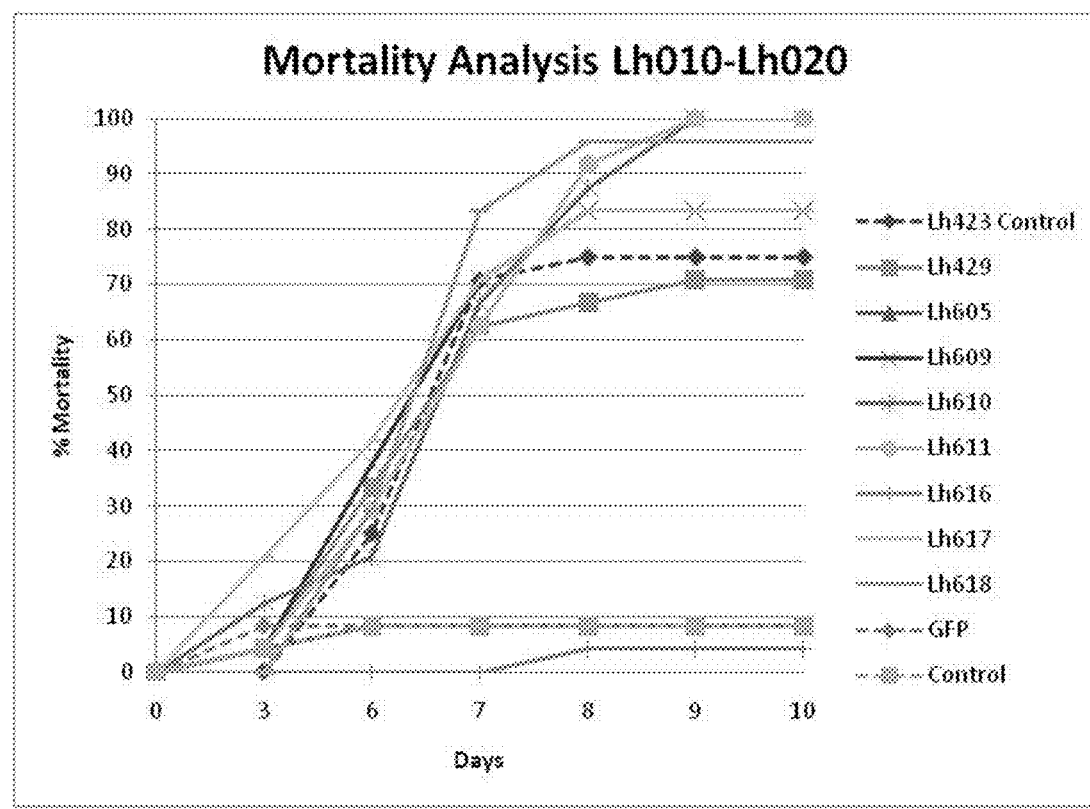
Figure 5:
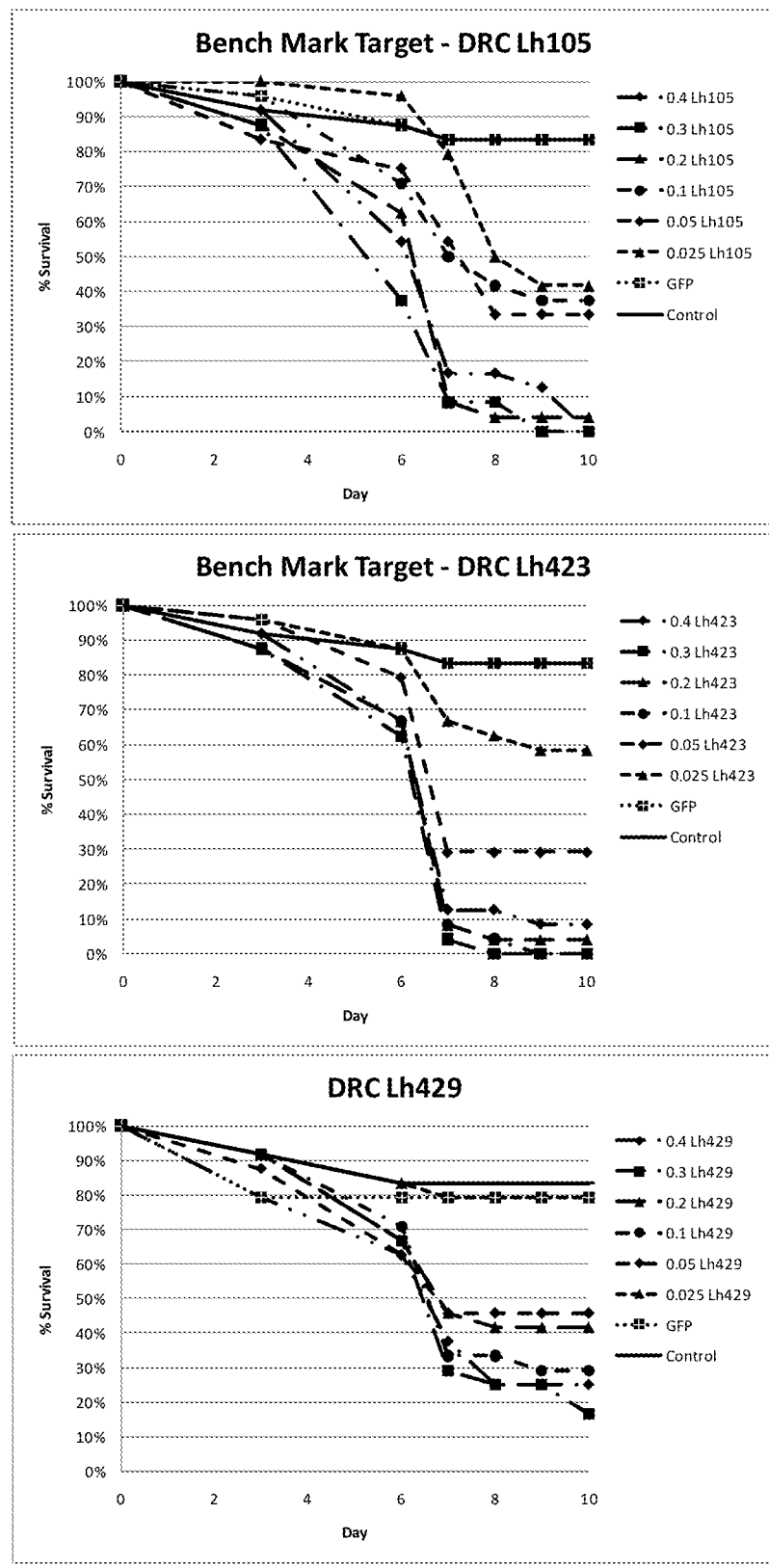
Figure 6:
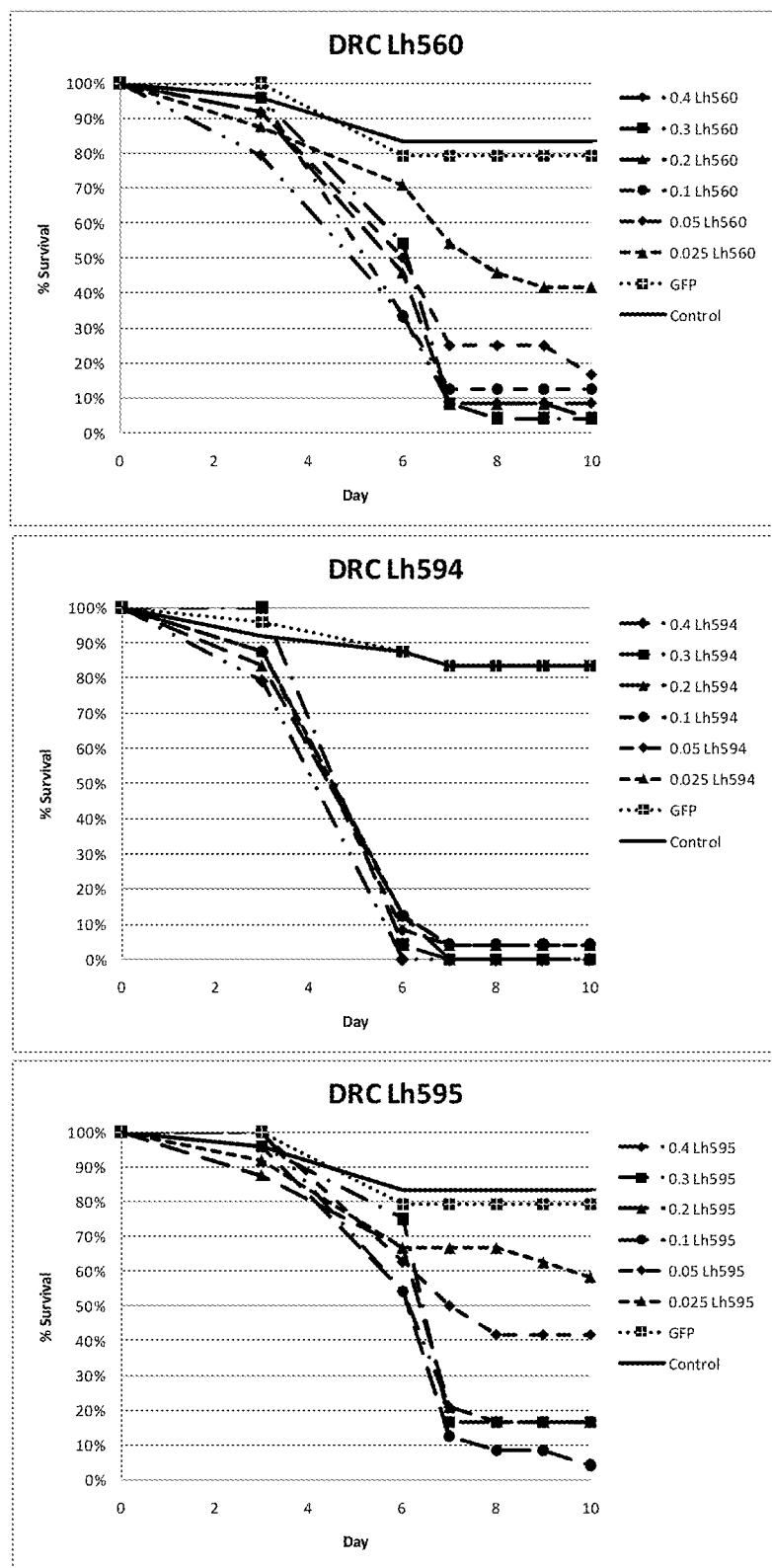
Figure 7:
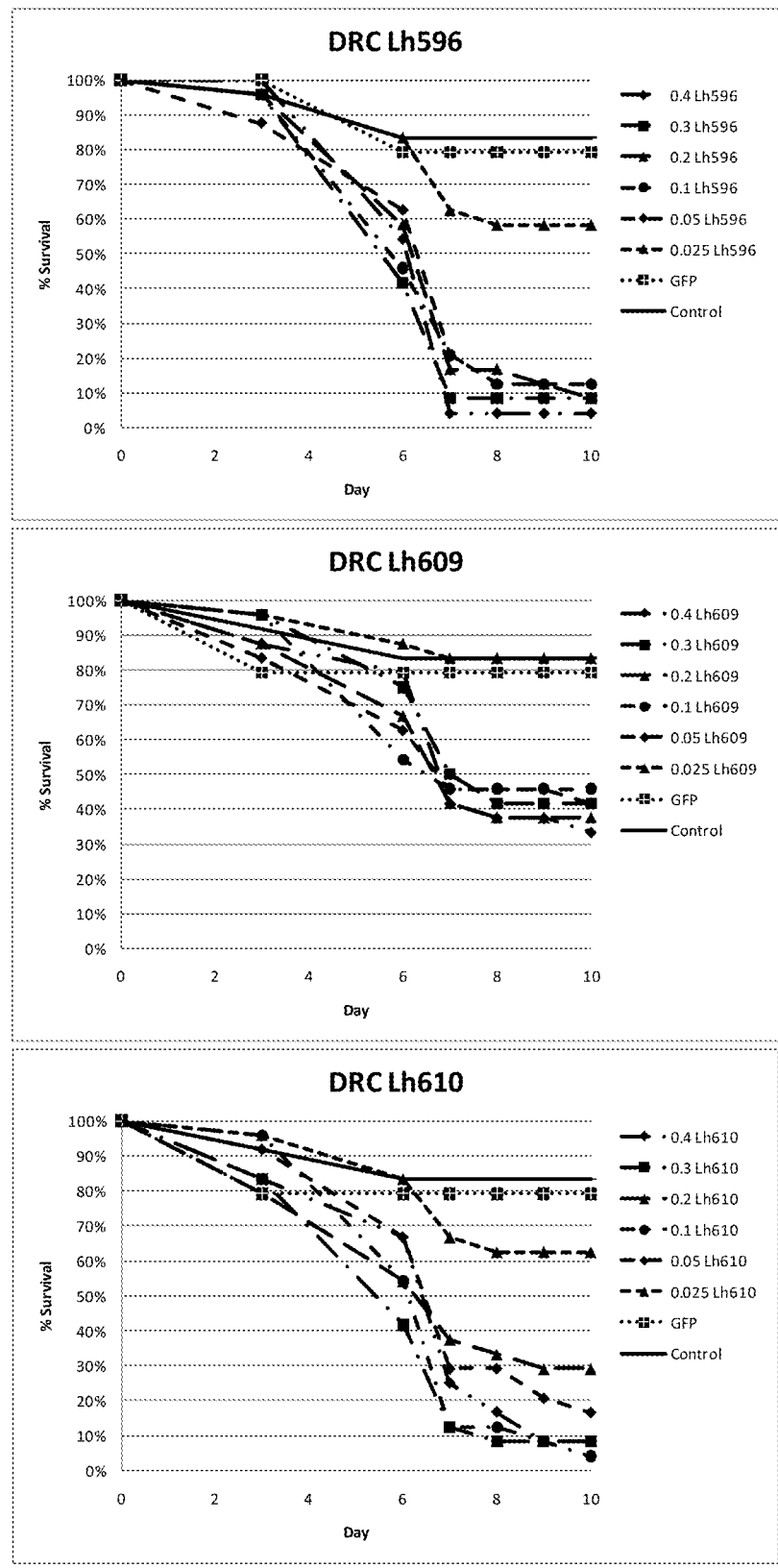
Figure 8:
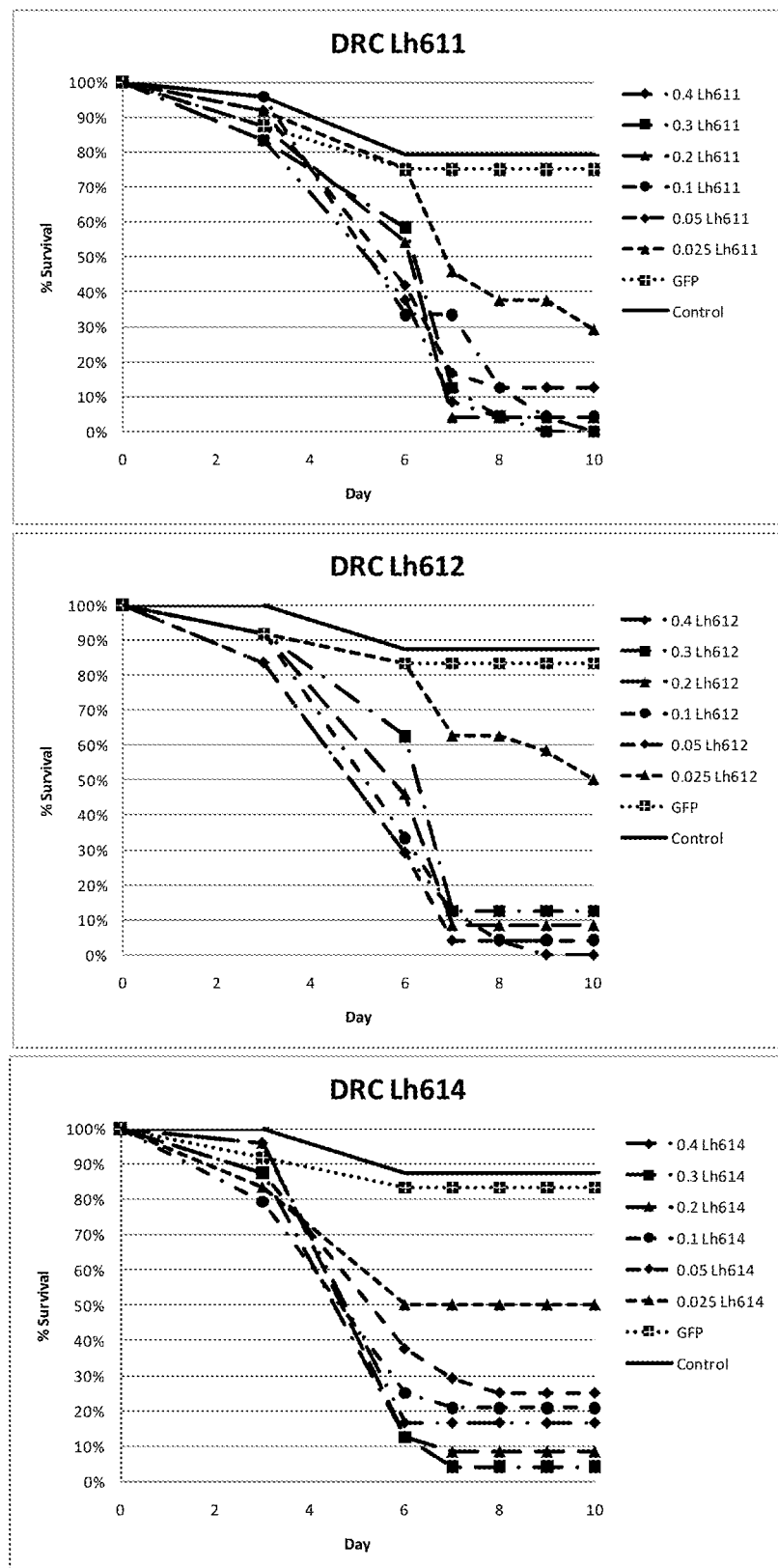
Figure 9:
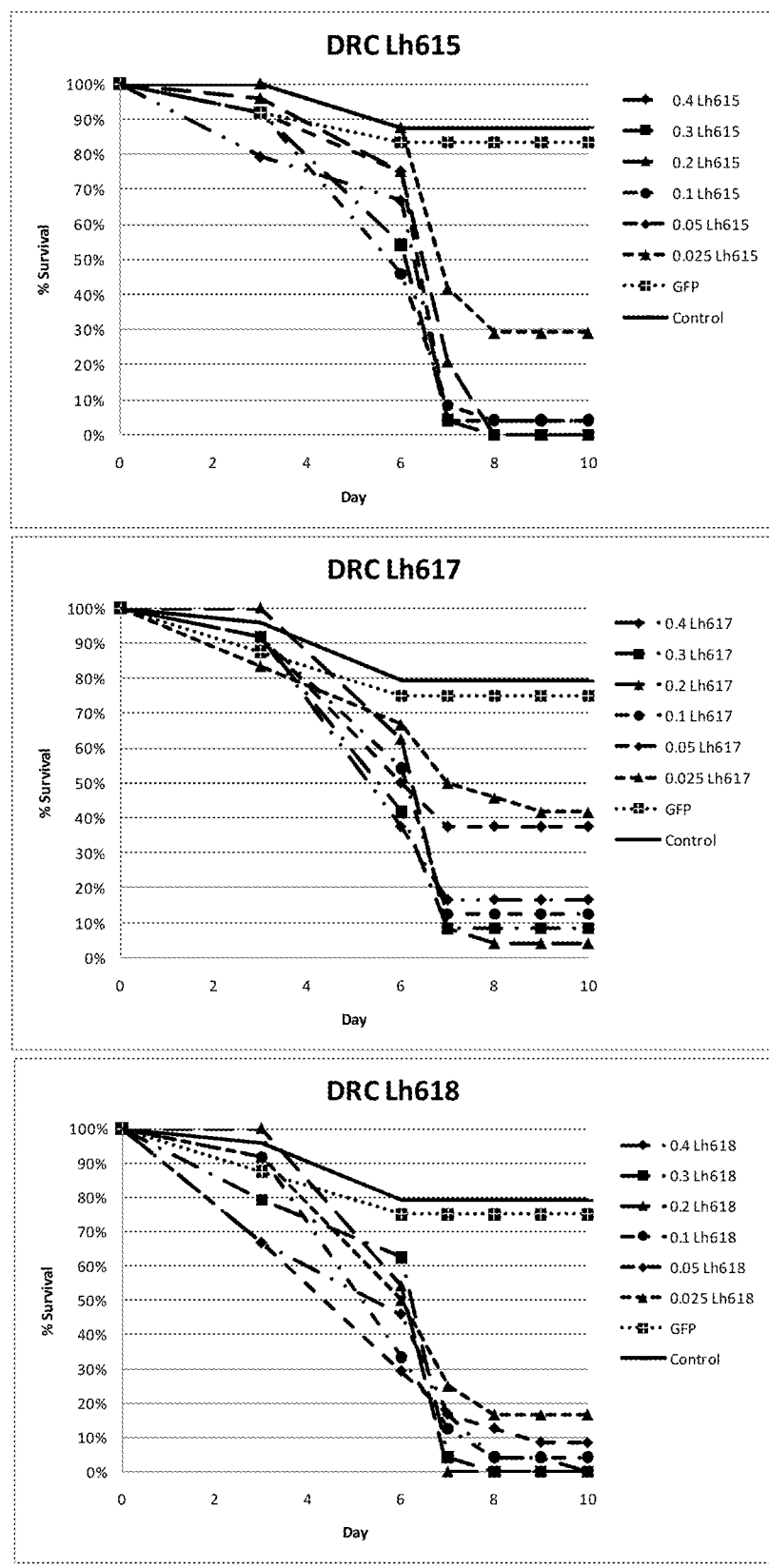

FIG. 4: Mortality analysis of *Lygus* novel targets from plates Lh010 to Lh020, expressed as % mortality over a 10 day period. Controls are indicated in dotted lines. Positive control: Lh423 (RpL19). Negative controls: GFP and diet only (Control).

FIGS. 5 to 9 *Lygus hesperus* novel targets-dose response curves at concentrations of purified synthetic dsRNA ranging from 0.4 to 0.025 µg/µl (in the figure, the unit "µ/µl" is not displayed). GFP dsRNA and milliQ water were used negative controls. dsRNA of targets were produced using the primers as described in the example section 1.1.

Figure 10:
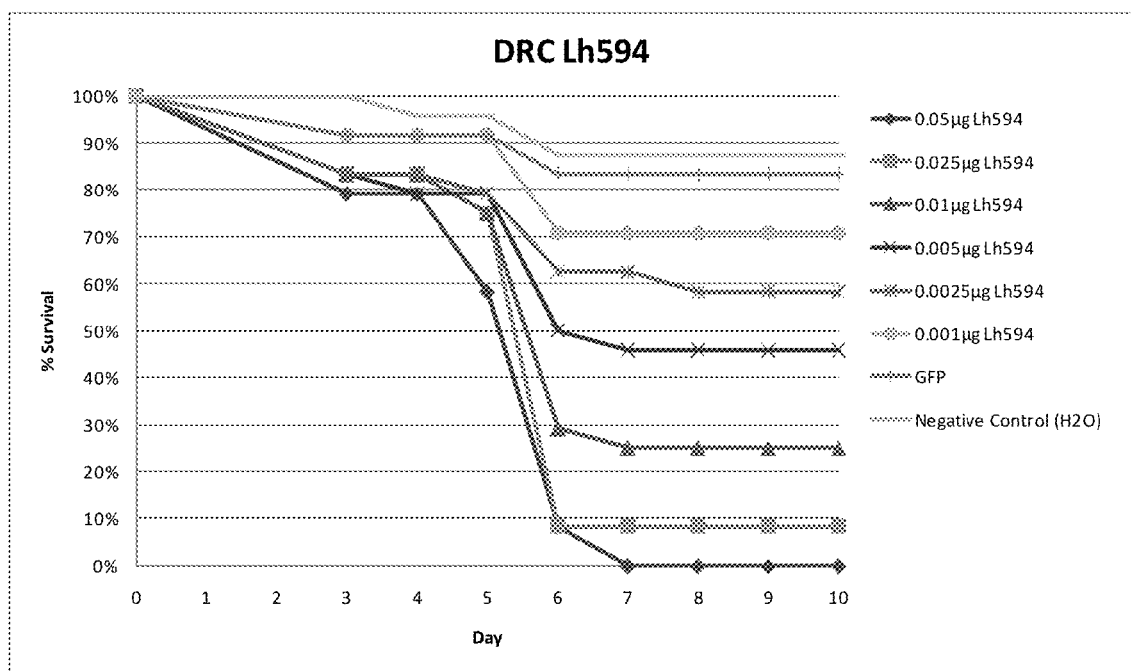

FIG. 10 Lh594 dose response curve, at dsRNA concentrations ranging from 0.05 to 0.001 µg/µl. GFP dsRNA and milliQ water were used negative controls.

Figure 11:
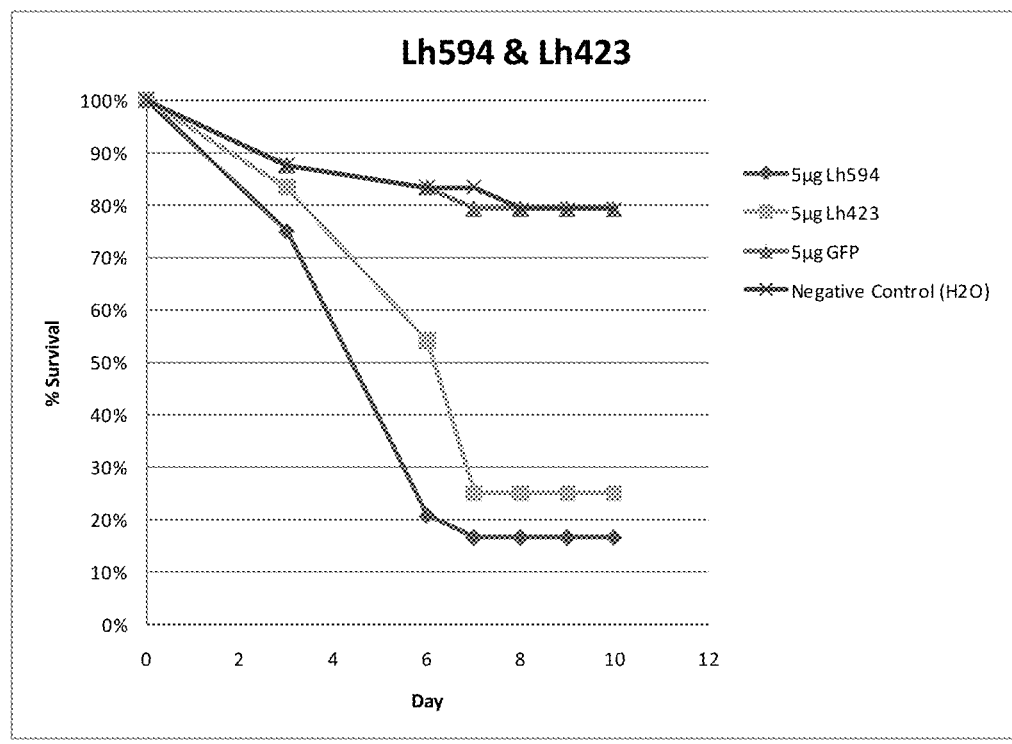
Figure 11:
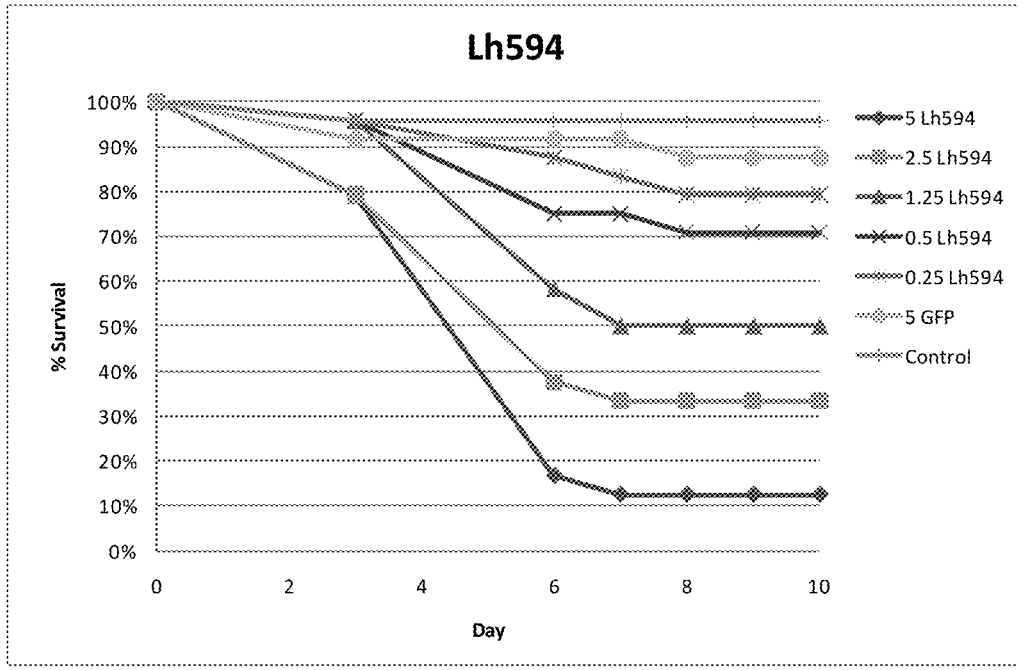

FIG. 11 A dsRNA activity in *Lygus hesperus* bioassay in absence of tRNA. Lh594 (544); positive control: Lh423 (5 µg/µl); negative controls: GFP dsRNA (5 µg/µl) and milliQ water; B Identification of Lh594 limit of activity using decreasing concentration of dsRNA (from 5 µg to 0.25 µg). Negative controls: GFP dsRNA (5µ/µl) and milliQ water.

Figure 12:
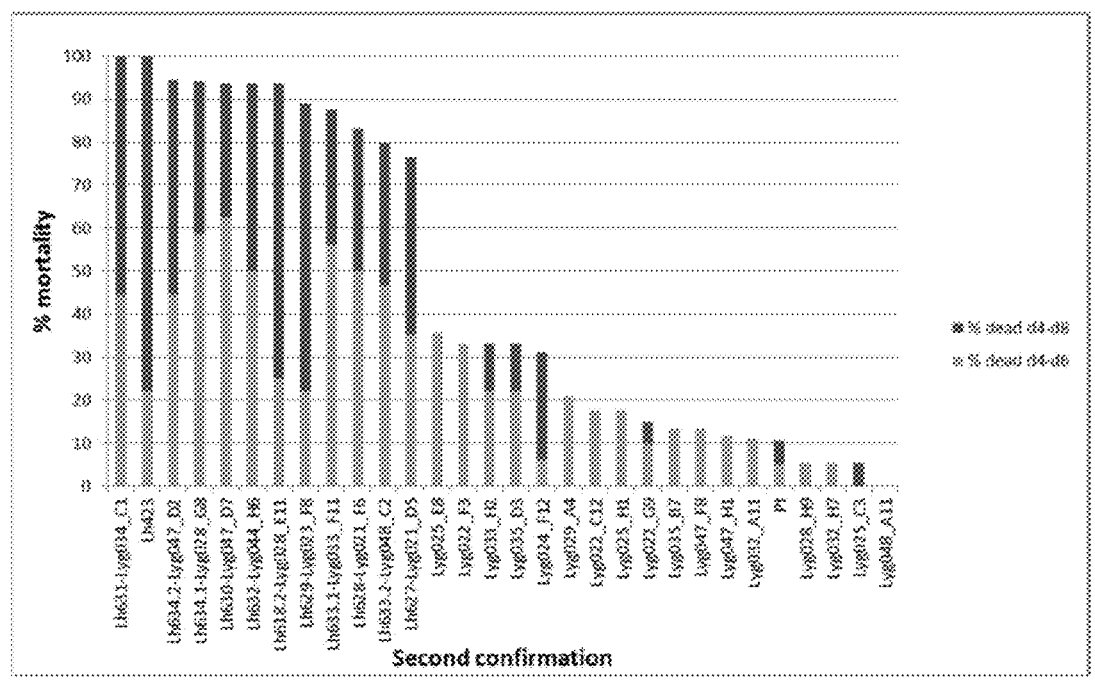

FIG. 12 Plates Lh010 to Lh020 second confirmation assay of second screen targets. Dark bars: mortality at day 4 to 8, light bars: mortality at day 4 to 6. Candidate clones are named using the "Lygxxx" screening codes and the "Lhxxx" target nomenclature codes.

Figure 13:
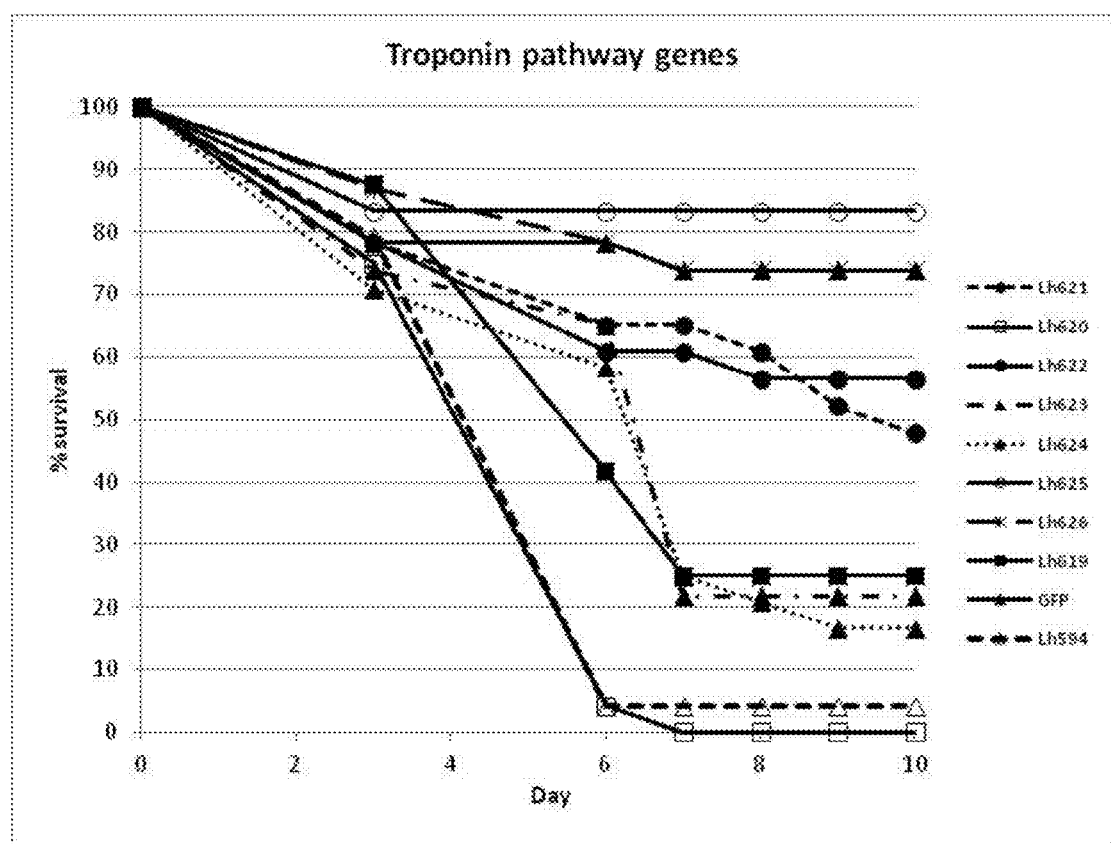

FIG. 13 Assay results for *Lygus* troponin pathway targets, tested at 0.5 µg/µl fixed.

Figure 14:
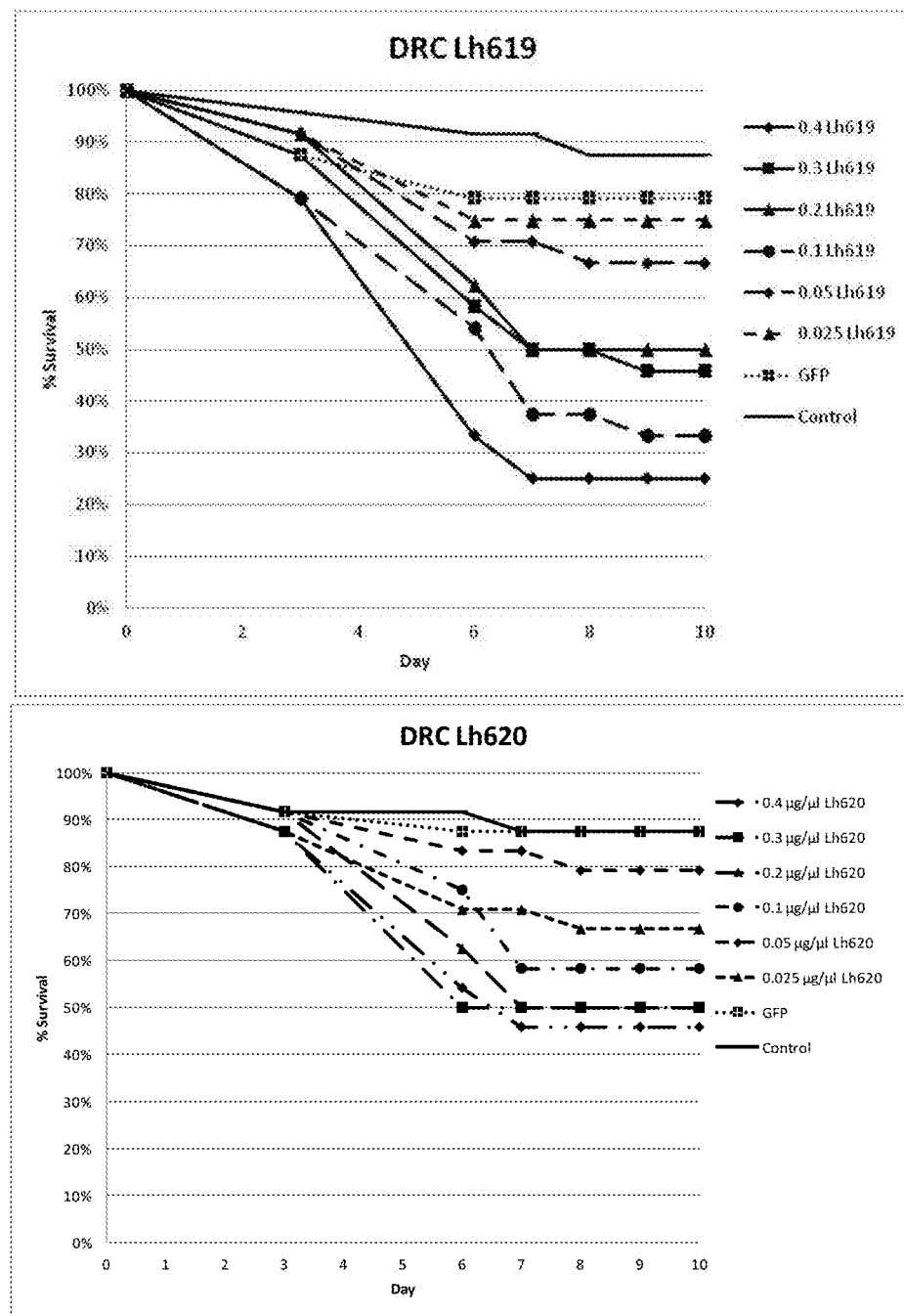
Figure 14:
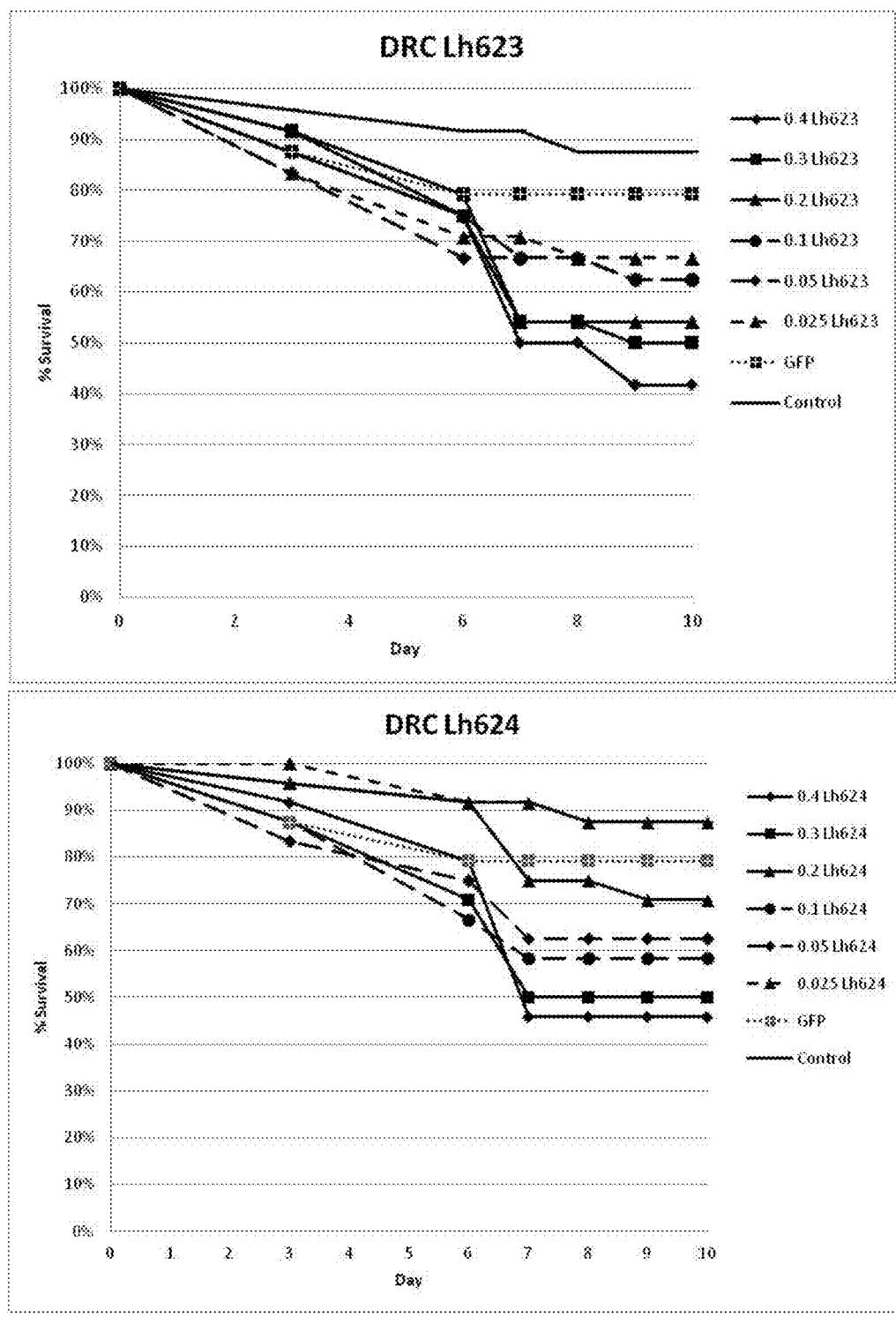

FIGS. 14 A-B *Lygus hesperus* novel targets from troponin pathway-dose response curves at concentrations of purified synthetic dsRNA ranging from 0.4 to 0.025 µg/µl (in the figure, the unit "µg/µl" is not always displayed). GFP dsRNA and milliQ water were used as negative controls.

Figure 15:
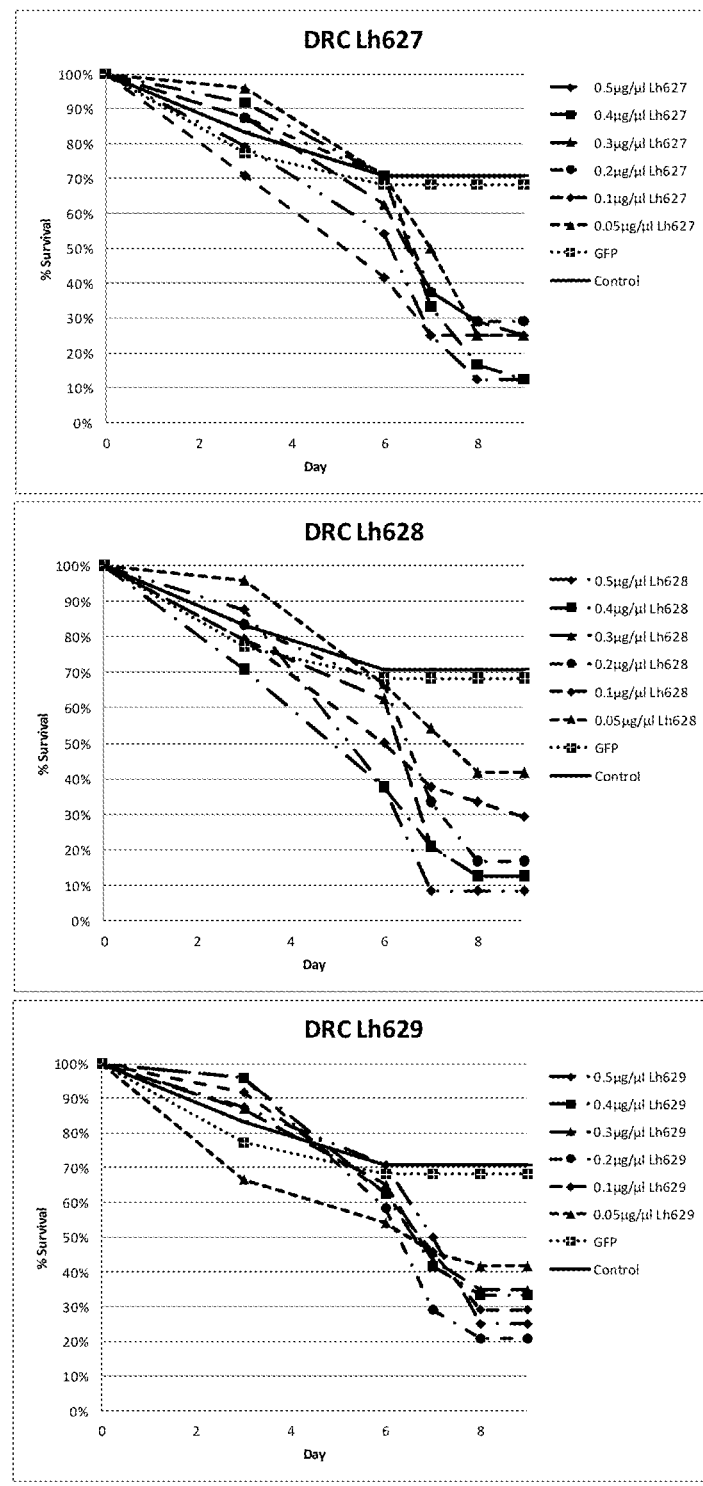
Figure 15:
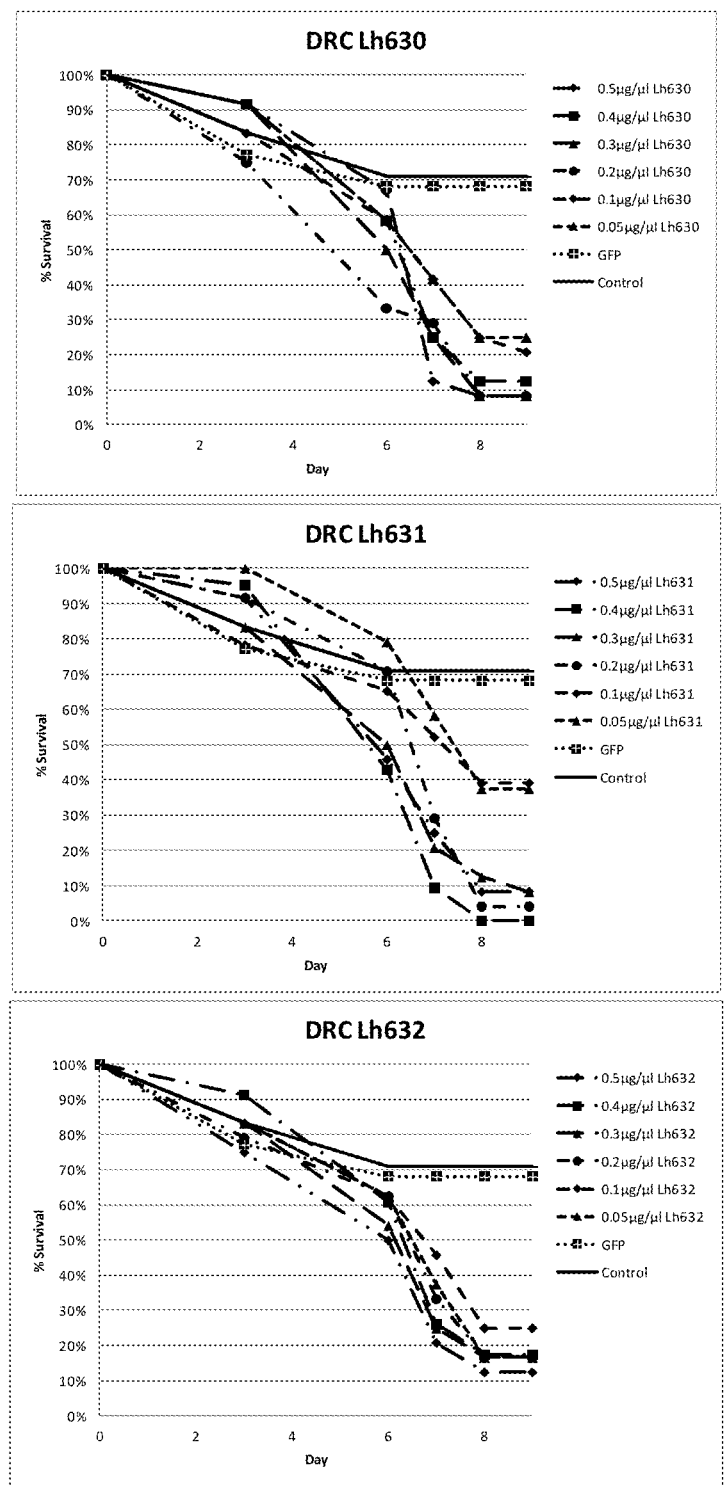
Figure 15:
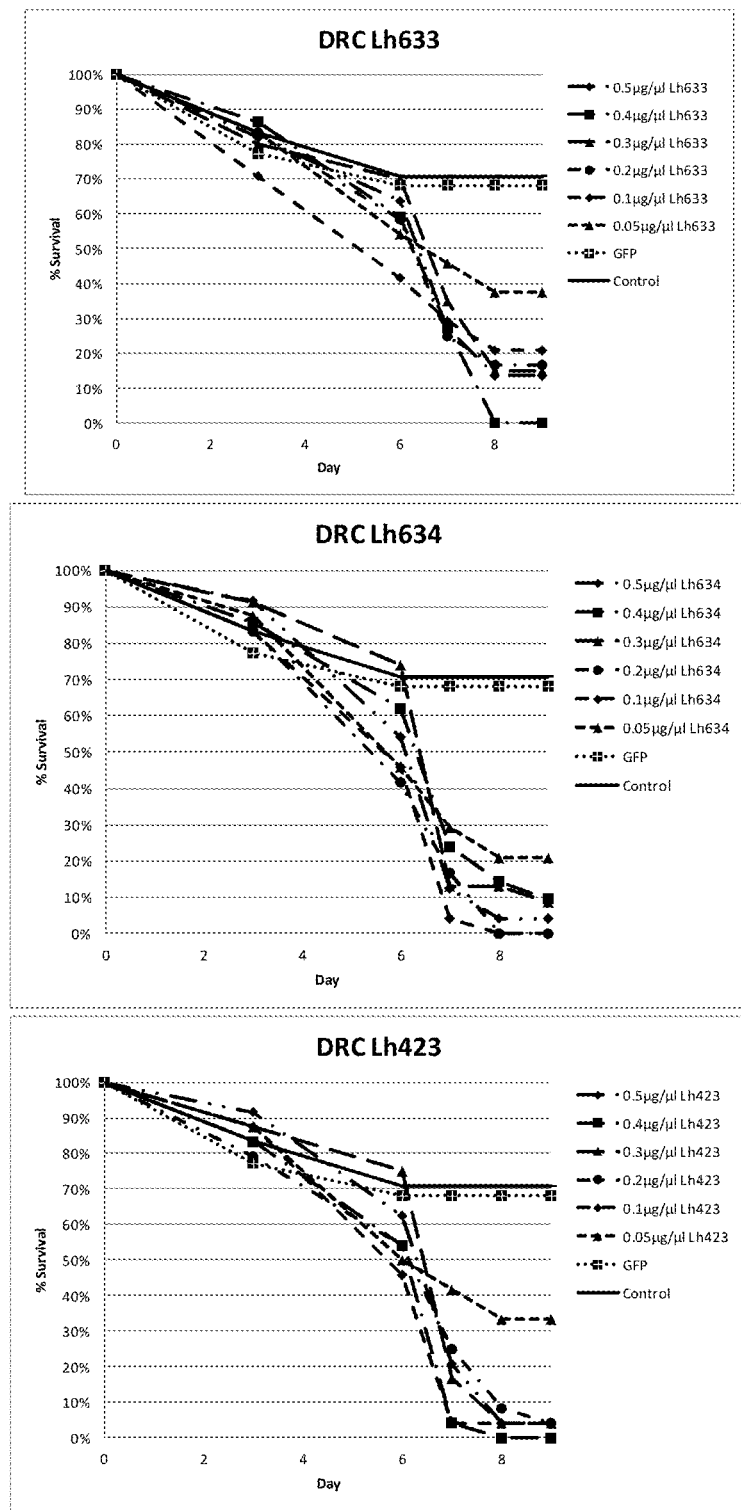
Figure 15:
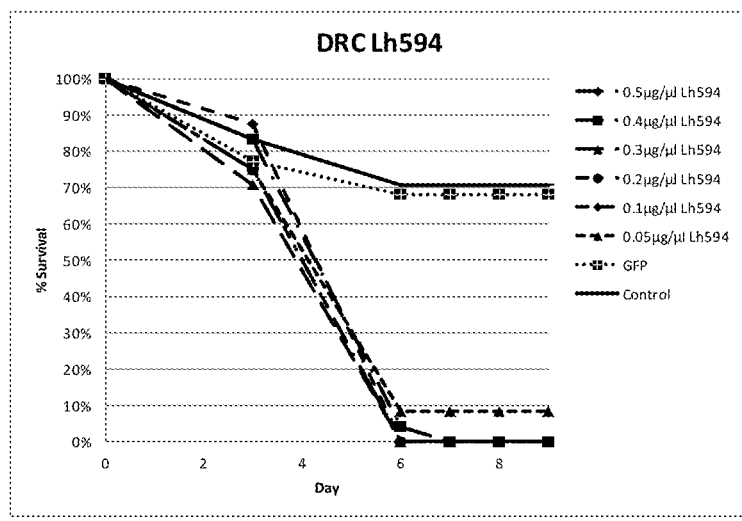

FIGS. 15 A-D *Lygus hesperus* novel targets of second screen targets-dose response curves at concentrations of purified synthetic dsRNA ranging from 0.5 to 0.05 µg/µl. GFP dsRNA and milliQ water were used as negative controls.

Figure 16:
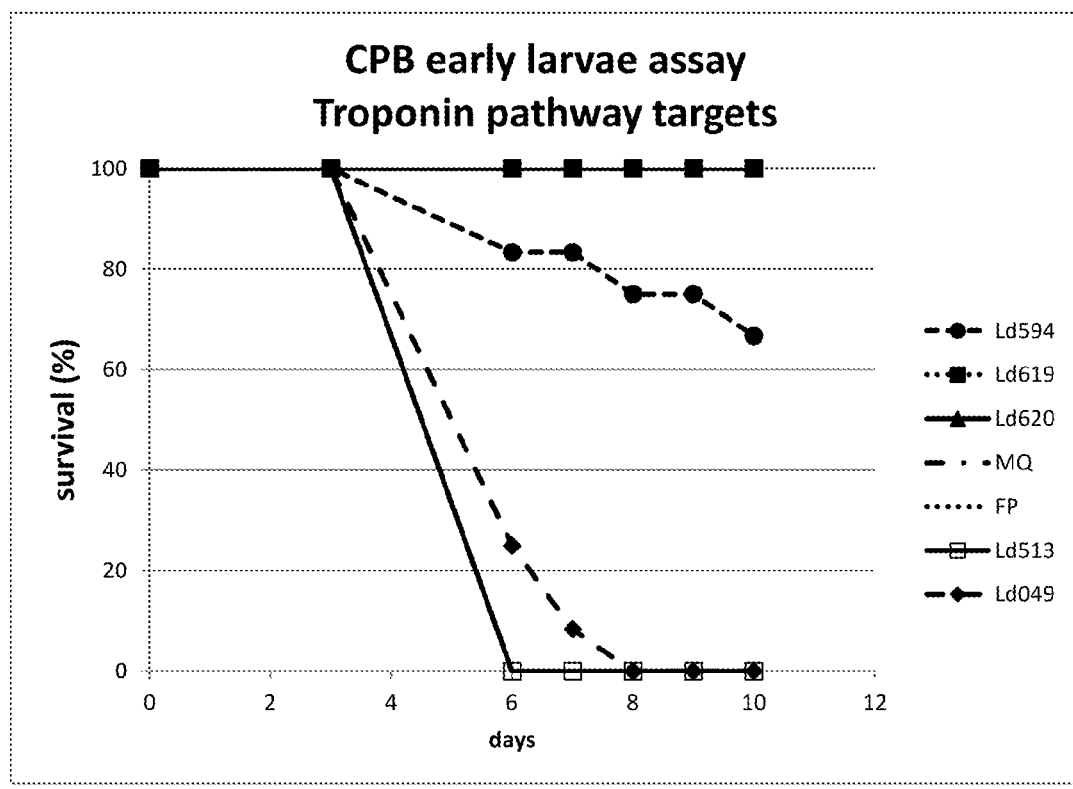

FIG. 16 Survival analysis of CPB larvae treated with 1 µg dsRNA Ld594, Ld619 and Ld620. Positive controls included 1 µg dsRNA of bench mark targets Ld513 and Ld049. Negative controls included milliQ water and FP.

Figure 17:
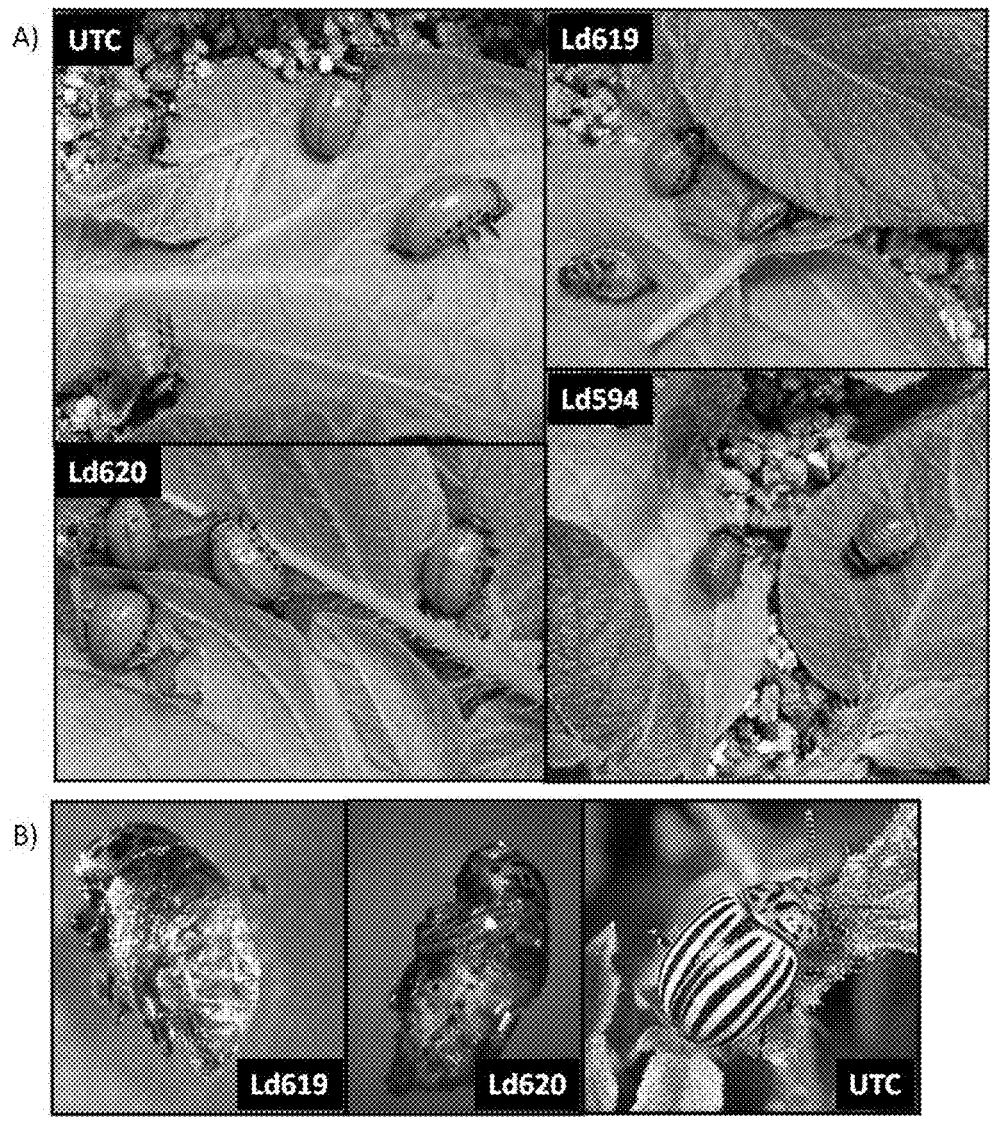

FIG. 17 Effects of Ld594, Ld619 and Ld620 dsRNAs on pupation of CPB 4$^{th}$ instar larvae, compared to untreated control (UTC). Bugs were fed 1 µg dsRNA dispensed in potato leaf disks, then were allowed to feed on untreated potato leaves (A) for 4 days before being placed on vermiculite. To assess the effect of the dsRNA, dead insects were excavated from the vermiculite (because of the strong effects induced by Ld594 dsRNA, no pupae could be recovered from the vermiculite and therefore, no image is available for this target dsRNA) (B).

Figure 18:
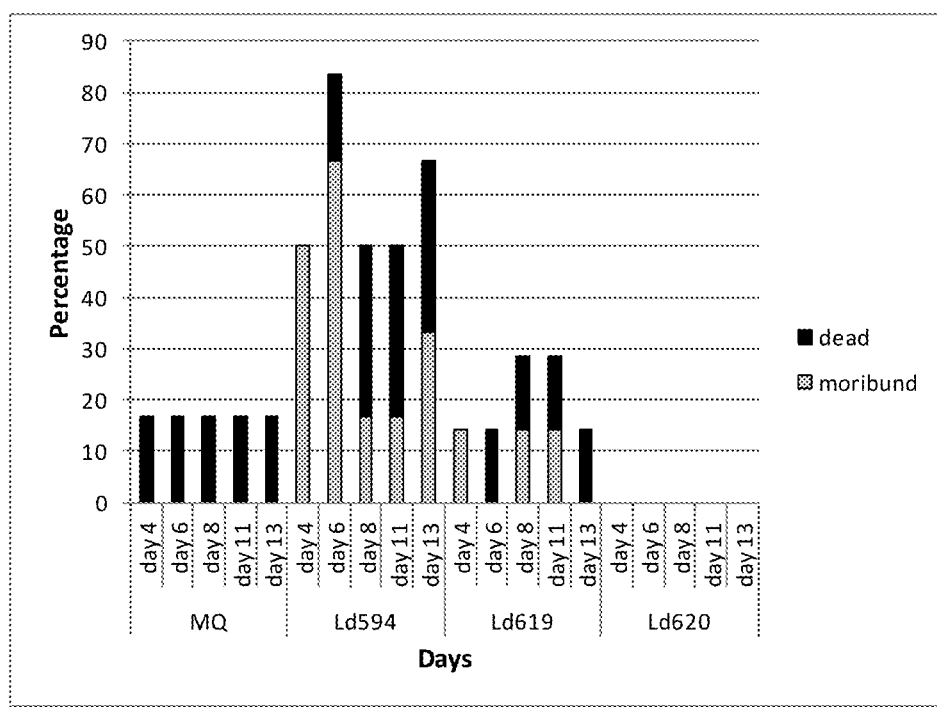

FIG. 18 Effect of CPB Ld594, 619 & 620 dsRNAs on survival and fitness of CPB adults. Assessments were performed on days 4, 6, 7, 8, 11 and 13. Control MQ: milliQ water.

Figure 19:
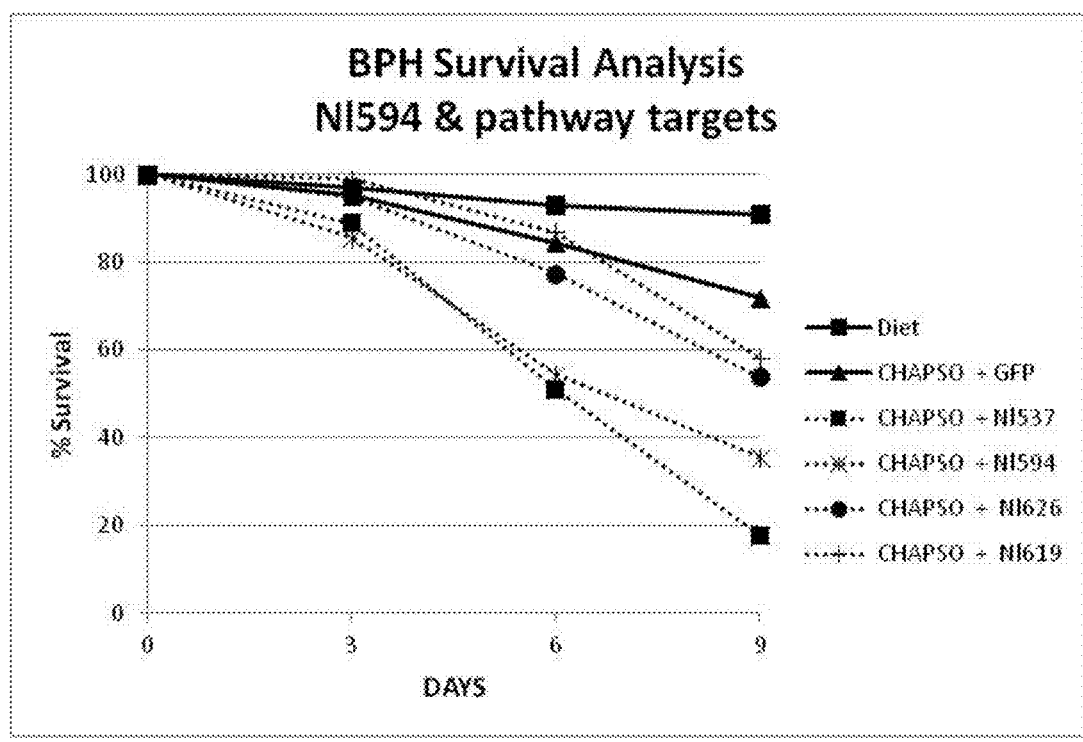

FIG. 19 Activity of dsRNA from Nl594 pathway in brown plant hopper. DsRNAs were tested at 0.5 µg/µl in presence of 0.1% CHAPSO. Positive control: Nl537 dsRNA (0.5 µg/µl), negative controls: GFP dsRNA (0.5 µg/µl) and diet alone.

Figure 20:
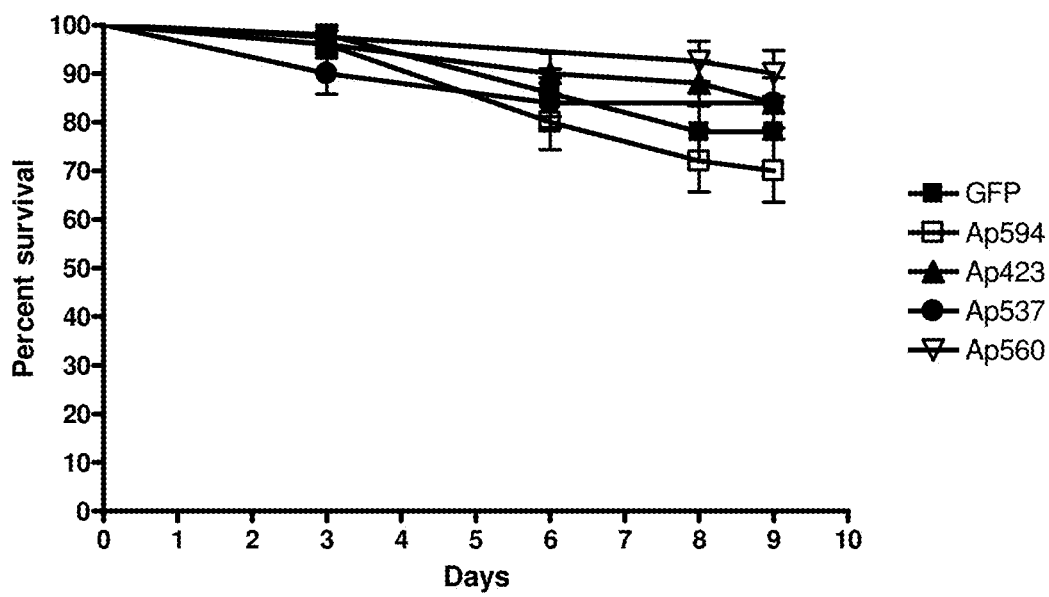

FIG. 20 Activity of dsRNA from Ap594, Ap423, Ap537 and Ap560 on *A. pisum*. DsRNAs were tested at 0.5 µg/µl in presence of 5 µg/µl tRNA. Negative control: GFP dsRNA (0.5 µg/µl).

Figure 21:
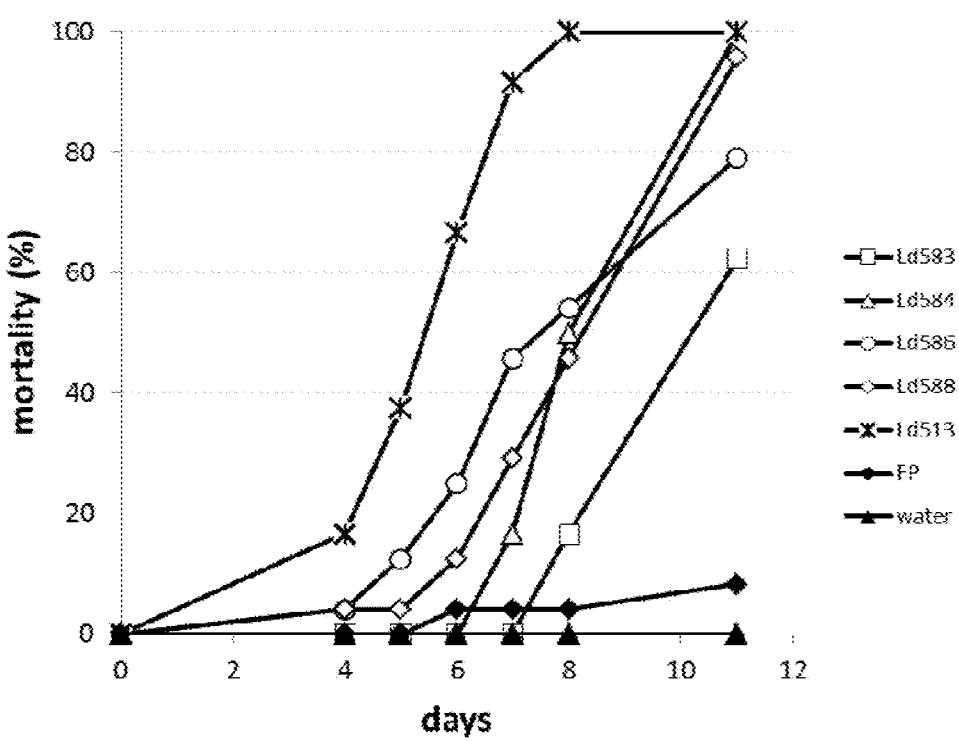

FIG. 21 Mortality percentages of *L. decemlineata* larvae on artificial diet treated with dsRNA. Ld583, Ld584, Ld586 & Ld588 represent target clones. Positive control: Ld513; negative control: FP.

DETAILED DESCRIPTION OF THE INVENTION

The present inventors have discovered that down-regulating the expression of particular target genes in insect pest species by RNAi can be used to effectively prevent and/or control infestation by said insect pest.

As used herein, the term "control" of pest infestation refers to any effect on a pest that serves to limit and/or reduce either the numbers of pest organisms and/or the damage caused by the pest.

Preferred target genes are therefore essential genes that control or regulate one or more essential biological functions within the insect pest, for example, cell division, reproduction, energy metabolism, digestion, neurological function and the like. Down-regulation of these essential genes by RNAi techniques can lead to death of the insect, or otherwise significantly retard growth and development or impair the ability of the pest to colonize an environment or infest host organisms.

The present inventors have now identified superior target genes of insect pest species belonging to the *Lygus*, *Leptinotarsa*, *Nilaparvata* and *Acyrthosiphum* genus, which targets are envisaged for use singly or in combination as an effective means for RNAi-mediated control of insect infestation, for example of agronomically important crops. Orthologues of these newly identified target genes can be used in other insect species to control pest infestation of the corresponding relevant crops.

More specifically, the present inventors describe here that genes encoding for proteins of the troponin/myofilament complex form excellent target genes for suppression by the RNA inhibition machinery. One of these target genes encoded the insect troponin I protein (wings up A) which is an orthologue of the *Drosophila* CG7178 protein. This protein is involved in muscular contraction and belongs to a physiological pathway that was not yet fully explored for (insect) pest control through RNA inhibition. Moreover, since this protein complex is animal specific, no plant genes homologues or orthologues are known, reducing the risk of off-type plant phenotypes when expressing target dsRNA in plants. In addition, in *Drosophila*, troponin I is described as a haplo-insufficient gene, displaying a mutant phenotype in the heterozygote state. Such genes are particularly susceptible to reduced mRNA expression levels and as such can be considered as ideal RNAi targets.

Further interesting target genes in this troponin/myofilament complex are listed below.

| Annotation ID | Cytology | Dm identifier |
| --- | --- | --- |
| up | upheld | CG7107 |
| Tm1 | tropomyosin 1 | CG4898 |
| Tm2 | tropomyosin 2 | CG4843 |
| Mhc | myosin heavy chain | CG17927 |
| Mlc-c | myosin light chain cytoplasmic | CG3201 |
| sqh | spaghetti squash | CG3595 |
| zip | zipper | CG15792 |

Thus, according to one embodiment the present invention relates to an interfering ribonucleic acid (RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233 or the complement thereof, or having a nucleotide sequence so that, when the two sequences are optimally aligned and compared, is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or (ii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or having a nucleotide sequence so that, when said gene comprising said fragment is optimally aligned and compared with any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, said nucleotide sequence is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or (iii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, and wherein when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, said nucleotide sequence of said fragment is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, or (iv) is an insect pest orthologue of a gene having a nucleotide sequence comprising any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 1, 174, 404, 180, 188, 2, 175, 181, 189, 27 to 30, 282 to 285, 294 to 297, 310 to 313, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233.

In a preferred embodiment, the target gene encodes an insect protein chosen from the troponin/myofilament complex chosen from the group comprising the troponin I (e.g. an insect orthologue of the CG7178 Dm protein), the upheld protein (e.g. an insect orthologue of the CG7107 Dm protein), the tropomyosin 1 protein (e.g. an insect orthologue of the CG4898 Dm protein), the tropomyosin 2 protein (e.g. an insect orthologue of the CG4843 Dm protein), the myosin heavy chain (e.g. an insect orthologue of the CG17927 Dm protein), the myosin light chain cytoplasmic protein (e.g. an insect orthologue of the CG3201 Dm protein), the spaghetti squash protein (e.g. an insect orthologue of the CG3595 Dm protein), the zipper protein (e.g. an insect orthologue of the CG15792 Dm protein), the troponin C (e.g. an insect orthologue of the CG2981, CG7930, CG9073, CG6514, CG12408, CG9073, CG7930, CG2981, CG12408 or CG6514 Dm protein)

In other embodiments, the present invention relates to an interfering ribonucleic acid (RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or having a nucleotide sequence so that, when the two sequences are optimally aligned and compared, is at least 75% preferably at least 80%, 85%, 90%, 95%, 98% or 99% identical to any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or (ii) is selected from the group of genes having a nucleotide sequence comprising a fragment of at least 21 contiguous nucleotides of any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or having a nucleotide sequence so that, when said gene comprising said fragment is optimally aligned and compared with any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, said nucleotide sequence is at least 75% preferably at least 80%, 85%, 90%, 95%, 98% or 99% identical to any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or (iii) is selected from the group of genes having a nucleotide sequence comprising a fragment of at least 21 contiguous nucleotides of any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, and wherein when said fragment is optimally aligned and compared with the corresponding fragment in any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, said nucleotide sequence of said fragment is at least 75% preferably at least 80%, 85%, 90%, 95%, 98% or 99% identical to said corresponding fragment of any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, or (iv) is an insect pest orthologue of a gene having a nucleotide sequence comprising any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs. 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273.

In a preferred embodiment, the target gene encodes an insect ribosomal protein chosen from the group comprising the ribosomal protein S3A (e.g. an insect orthologue of the CG2168 Dm protein), the ribosomal protein LP1 (e.g. an insect orthologue of the CG4087 Dm protein), the ribosomal protein S3 (e.g. an insect orthologue of the CG6779 Dm protein), the ribosomal protein L10Ab (e.g. an insect orthologue of the CG7283 Dm protein), the ribosomal protein S18 (e.g. an insect orthologue of the CG8900 Dm protein), the ribosomal protein L4 (e.g. an insect orthologue of the CG5502 Dm protein), the ribosomal protein S27 (e.g. an insect orthologue of the CG10423 Dm protein), the ribosomal protein L6 (e.g. an insect orthologue of the CG11522 Dm protein), the ribosomal protein S13 (e.g. an insect orthologue of the CG13389 Dm protein), and the ribosomal protein L12 (e.g. an insect orthologue of the CG3195 Dm protein), the ribosomal protein L26 (e.g. an insect orthologue of the CG6846 Dm protein), the ribosomal protein L21 (e.g. an insect orthologue of the CG12775 Dm protein), the ribosomal protein S12 (e.g. an insect orthologue of the CG11271 Dm protein), the ribosomal protein S28b (e.g. an insect orthologue of the CG2998 Dm protein), the ribosomal protein L13 (e.g. an insect orthologue of the CG4651 Dm protein), the ribosomal protein L10 (e.g. an insect orthologue of the CG17521 Dm protein), the ribosomal protein L5 (e.g. an insect orthologue of the CG17489 Dm protein), the ribosomal protein S15Aa (e.g. an insect orthologue of the CG2033 Dm protein), the ribosomal protein L19 (e.g. an insect orthologue of the CG2746 Dm protein), the ribosomal protein L27 (e.g. an insect orthologue of the CG4759 Dm protein)

In one embodiment, the present invention relates to an interfering ribonucleic acid (RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs 1, 174, 404, 180, 188, 2, 175, 181, 189, 27 to 30, 282 to 285, 294 to 297, 310 to 313, or the complement thereof, or having a nucleotide sequence so that, when the two sequences are optimally aligned and compared, is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, or the complement thereof, or (ii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, or the complement thereof, or having a nucleotide sequence so that, when said gene comprising said fragment is optimally aligned and compared with any of SEQ ID NOs 1, 174, 404, 180, 188, 2, 175, 181, 189, 27 to 30, 282 to 285, 294 to 297, 310 to 313, said nucleotide sequence is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, or the complement thereof, or (iii) is selected from the group of genes having a nucleotide sequence comprising a fragment of at least 21 contiguous nucleotides of any of SEQ ID NOs 1, 174, 404, 180, 188, 2, 175, 181, 189, 27 to 30, 282 to 285, 294 to 297, 310 to 313, or the complement thereof, and wherein when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, said nucleotide sequence of said fragment is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, or the complement thereof, or (iv) is an insect pest orthologue of a gene having a nucleotide sequence comprising any of SEQ ID NOs 1, 174, 404, 180, 188, 2, 175, 181, 189, 27 to 30, 282 to 285, 294 to 297, 310 to 313, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 1, 174, 404, 180, 188, 2, 175, 181, 189, 27 to 30, 282 to 285, 294 to 297, 310 to 313, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 1, 174, 404, 180, 188, 2, 175, 181, 189, 27 to 30, 282 to 285, 294 to 297, 310 to 313.

In one embodiment, the present invention relates to an interfering ribonucleic acid (RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs 141, 11, 12, or the complement thereof, or having a nucleotide sequence so that, when the two sequences are optimally aligned and compared, is at least 75% preferably at least 80%, 85%, 90%, 95%, 98% or 99% identical to any of SEQ ID NOs 141, 11, 12, or the complement thereof, or (ii) is selected from the group of genes having a nucleotide sequence comprising a fragment of at least 21 contiguous nucleotides of any of SEQ ID NOs 141, 11, 12, or the complement thereof, or having a nucleotide sequence so that, when said gene comprising said fragment is optimally aligned and compared with any of SEQ ID NOs 141, 11, 12, said nucleotide sequence is at least 75% preferably at least 80%, 85%, 90%, 95%, 98% or 99% identical to any of SEQ ID NOs 141, 11, 12, or the complement thereof, or (iii) is selected from the group of genes having a nucleotide sequence comprising a fragment of at least 21 contiguous nucleotides of any of SEQ ID NOs 141, 11, 12, or the complement thereof, and wherein when said fragment is optimally aligned and compared with the corresponding fragment in any of SEQ ID NOs 141, 11, 12, said nucleotide sequence of said fragment is at least 75% preferably at least 80%, 85%, 90%, 95%, 98% or 99% identical to said corresponding fragment of any of SEQ ID NOs 141, 11, 12, or the complement thereof, or (iv) is an insect pest orthologue of a gene having a nucleotide sequence comprising any of SEQ ID NOs 141, 11, 12, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 141, 11, 12, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 141, 11, 12.

In one embodiment, the present invention relates to an interfering ribonucleic acid (RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs 17, 18, or the complement thereof, or having a nucleotide sequence so that, when the two sequences are optimally aligned and compared, is at least 75% preferably at least 80%, 85%, 90%, 95%, 98% or 99% identical to any of SEQ ID NOs 17, 18, or the complement thereof, or (ii) is selected from the group of genes having a nucleotide sequence comprising a fragment of at least 21 contiguous nucleotides of any of SEQ ID NOs 17, 18, or the complement thereof, or having a nucleotide sequence so that, when said gene comprising said fragment is optimally aligned and compared with any of SEQ ID NOs 17, 18, said nucleotide sequence is at least 75% preferably at least 80%, 85%, 90%, 95%, 98% or 99% identical to any of SEQ ID NOs 17, 18, or the complement thereof, or (iii) is selected from the group of genes having a nucleotide sequence comprising a fragment of at least 21 contiguous nucleotides of any of SEQ ID NOs 17, 18, or the complement thereof, and wherein when said fragment is optimally aligned and compared with the corresponding fragment in any of SEQ ID NOs 17, 18, said nucleotide sequence of said fragment is at least 75% preferably at least 80%, 85%, 90%, 95%, 98% or 99% identical to said corresponding fragment of any of SEQ ID NOs 17, 18, or the complement thereof, or (iv) is an insect pest orthologue of a gene having a nucleotide sequence comprising any of SEQ ID NOs 17, 18, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 17, 18, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 17, 18.

In one embodiment, the present invention relates to an interfering ribonucleic acid (RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs 19, 20, or the complement thereof, or having a nucleotide sequence so that, when the two sequences are optimally aligned and compared, is at least 75% preferably at least 80%, 85%, 90%, 95%, 98% or 99% identical to any of SEQ ID NOs 19, 20, or the complement thereof, or (ii) is selected from the group of genes having a nucleotide sequence comprising a fragment of at least 21 contiguous nucleotides of any of SEQ ID NOs 19, 20, or the complement thereof, or having a nucleotide sequence so that, when said gene comprising said fragment is optimally aligned and compared with any of SEQ ID NOs 19, 20, said nucleotide sequence is at least 75% preferably at least 80%, 85%, 90%, 95%, 98% or 99% identical to any of SEQ ID NOs 19, 20, or the complement thereof, or (iii) is selected from the group of genes having a nucleotide sequence comprising a fragment of at least 21 contiguous nucleotides of any of SEQ ID NOs 19, 20, or the complement thereof, and wherein when said fragment is optimally aligned and compared with the corresponding fragment in any of SEQ ID NOs 19, 20, said nucleotide sequence of said fragment is at least 75% preferably at least 80%, 85%, 90%, 95%, 98% or 99% identical to said corresponding fragment of any of SEQ ID NOs 19, 20, or the complement thereof, or (iv) is an insect pest orthologue of a gene having a nucleotide sequence comprising any of SEQ ID NOs 19, 20, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 19, 20, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 19, 20.

In one embodiment, the present invention relates to an interfering ribonucleic acid (RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs 165, 166, 167, or the complement thereof, or having a nucleotide sequence so that, when the two sequences are optimally aligned and compared, is at least 75% preferably at least 80%, 85%, 90%, 95%, 98% or 99% identical to any of SEQ ID NOs 165, 166, 167, or the complement thereof, or (ii) is selected from the group of genes having a nucleotide sequence comprising a fragment of at least 21 contiguous nucleotides of any of SEQ ID NOs 165, 166, 167, or the complement thereof, or having a nucleotide sequence so that, when said gene comprising said fragment is optimally aligned and compared with any of SEQ ID NOs 165, 166, 167, said nucleotide sequence is at least 75% preferably at least 80%, 85%, 90%, 95%, 98% or 99% identical to any of SEQ ID NOs 165, 166, 167, or the complement thereof, or (iii) is selected from the group of genes having a nucleotide sequence comprising a fragment of at least 21 contiguous nucleotides of any of SEQ ID NOs 165, 166, 167, or the complement thereof, and wherein when said fragment is optimally aligned and compared with the corresponding fragment in any of SEQ ID NOs 17, 18, said nucleotide sequence of said fragment is at least 75% preferably at least 80%, 85%, 90%, 95%, 98% or 99% identical to said corresponding fragment of any of SEQ ID NOs 165, 166, 167, or the complement thereof, or (iv) is an insect pest orthologue of a gene having a nucleotide sequence comprising any of SEQ ID NOs 165, 166, 167, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 165, 166, 167, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 165, 166, 167.

In one embodiment, the present invention relates to an interfering ribonucleic acid (RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs 143, 121, 142, 176, 182, 130, 177, 183, or the complement thereof, or having a nucleotide sequence so that, when the two sequences are optimally aligned and compared, is at least 75% preferably at least 80%, 85%, 90%, 95%, 98% or 99% identical to any of SEQ ID NOs 143, 121, 142, 176, 182, 130, 177, 183, or the complement thereof, or (ii) is selected from the group of genes having a nucleotide sequence comprising a fragment of at least 21 contiguous nucleotides of any of SEQ ID NOs 143, 121, 142, 176, 182, 130, 177, 183, or the complement thereof, or having a nucleotide sequence so that, when said gene comprising said fragment is optimally aligned and compared with any of SEQ ID NOs 143, 121, 142, 176, 182, 130, 177, 183, said nucleotide sequence is at least 75% preferably at least 80%, 85%, 90%, 95%, 98% or 99% identical to any of SEQ ID NOs 143, 121, 142, 176, 182, 130, 177, 183, or the complement thereof, or (iii) is selected from the group of genes having a nucleotide sequence comprising a fragment of at least 21 contiguous nucleotides of any of SEQ ID NOs 143, 121, 142, 176, 182, 130, 177, 183, or the complement thereof, and wherein when said fragment is optimally aligned and compared with the corresponding fragment in any of SEQ ID NOs 143, 121, 142, 176, 182, 130, 177, 183, said nucleotide sequence of said fragment is at least 75% preferably at least 80%, 85%, 90%, 95%, 98% or 99% identical to said corresponding fragment of any of SEQ ID NOs 143, 121, 142, 176, 182, 130, 177, 183, or the complement thereof, or (iv) is an insect pest orthologue of a gene having a nucleotide sequence comprising any of SEQ ID NOs 143, 121, 142, 176, 182, 130, 177, 183, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 143, 121, 142, 176, 182, 130, 177, 183, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 143, 121, 142, 176, 182, 130, 177, 183.

In one embodiment, the present invention relates to an interfering ribonucleic acid (RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs 145, 122, 144, 178, 131, 179 or the complement thereof, or having a nucleotide sequence so that, when the two sequences are optimally aligned and compared, is at least 75% preferably at least 80%, 85%, 90%, 95%, 98% or 99% identical to any of SEQ ID NOs 145, 122, 144, 178, 131, 179, or the complement thereof, or (ii) is selected from the group of genes having a nucleotide sequence comprising a fragment of at least 21 contiguous nucleotides of any of SEQ ID NOs 145, 122, 144, 178, 131, 179, or the complement thereof, or having a nucleotide sequence so that, when said gene comprising said fragment is optimally aligned and compared with any of SEQ ID NOs 145, 122, 144, 178, 131, 179, said nucleotide sequence is at least 75% preferably at least 80%, 85%, 90%, 95%, 98% or 99% identical to any of SEQ ID NOs 145, 122, 144, 178, 131, 179, or the complement thereof, or (iii) is selected from the group of genes having a nucleotide sequence comprising a fragment of at least 21 contiguous nucleotides of any of SEQ ID NOs 145, 122, 144, 178, 131, 179, or the complement thereof, and wherein when said fragment is optimally aligned and compared with the corresponding fragment in any of SEQ ID NOs 145, 122, 144, 178, 131, 179, said nucleotide sequence of said fragment is at least 75% preferably at least 80%, 85%, 90%, 95%, 98% or 99% identical to said corresponding fragment of any of SEQ ID NOs 145, 122, 144, 178, 131, 179, or the complement thereof, or (iv) is an insect pest orthologue of a gene having a nucleotide sequence comprising any of SEQ ID NOs 145, 122, 144, 178, 131, 179, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 145, 122, 144, 178, 131, 179, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 145, 122, 144, 178, 131, 179.

In one embodiment, the present invention relates to an interfering ribonucleic acid (RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene, and wherein the target gene (i) is selected from the group of genes having a nucleotide sequence comprising any of SEQ ID NOs 128, 149, 184, 137, or the complement thereof, or having a nucleotide sequence so that, when the two sequences are optimally aligned and compared, is at least 75% preferably at least 80%, 85%, 90%, 95%, 98% or 99% identical to any of SEQ ID NOs 128, 149, 184, 137, or the complement thereof, or (ii) is selected from the group of genes having a nucleotide sequence comprising a fragment of at least 21 contiguous nucleotides of any of SEQ ID NOs 128, 149, 184, 137, or the complement thereof, or having a nucleotide sequence so that, when said gene comprising said fragment is optimally aligned and compared with any of SEQ ID NOs 128, 149, 184, 137, said nucleotide sequence is at least 75% preferably at least 80%, 85%, 90%, 95%, 98% or 99% identical to any of SEQ ID NOs 128, 149, 184, 137, or the complement thereof, or (iii) is selected from the group of genes having a nucleotide sequence comprising a fragment of at least 21 contiguous nucleotides of any of SEQ ID NOs 128, 149, 184, 137, or the complement thereof, and wherein when said fragment is optimally aligned and compared with the corresponding fragment in any of SEQ ID NOs 128, 149, 184, 137, said nucleotide sequence of said fragment is at least 75% preferably at least 80%, 85%, 90%, 95%, 98% or 99% identical to said corresponding fragment of any of SEQ ID NOs 128, 149, 184, 137, or the complement thereof, or (iv) is an insect pest orthologue of a gene having a nucleotide sequence comprising any of SEQ ID NOs 128, 149, 184, 137, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 128, 149, 184, 137, or (v) is selected from the group of genes having a nucleotide sequence encoding an amino acid sequence that, when the two amino acid sequences are optimally aligned and compared, is at least 85% preferably at least 90%, 95%, 98% or 99% identical to the amino acid sequence encoded by any of SEQ ID NOs 128, 149, 184, 137.

In yet other embodiments, the present invention relates to an interfering ribonucleic acid (RNA or double stranded RNA) that inhibits or downregulates the expression of a target gene that encodes a mitochondrial cytochrome c oxidase subunit II protein (e.g. an insect orthologue of the CG34069 Dm protein).

Thus, in one aspect, the invention provides an interfering ribonucleic acid (RNA) that functions upon uptake by an insect pest species to down-regulate expression of a target gene in said insect pest.

As used herein, a "target gene" comprises any gene in the insect pest which one intends to down-regulate. In a preferred embodiment, the target gene is down-regulated so as to control pest infestation, for example by disrupting an essential biological process occurring in the pest, or by decreasing the pathogenicity of the pest. Preferred target genes therefore include but are not limited to those that play key roles in regulating feeding, survival, growth, development, reproduction, infestation and infectivity. According to one embodiment, the target gene is such that when its expression is down-regulated or inhibited, the insect pest is killed. According to another embodiment, the target gene is such that when its expression is down-regulated or inhibited, growth of the pest is prevented or retarded or stunted or delayed or impeded, pest reproduction is prevented, or transition through the life cycles of the pest is prevented. According to yet another embodiment of the invention, the target gene is such that when its expression is down-regulated or inhibited, the damage caused by the pest and/or the ability of the pest to infect or infest environments, surfaces and/or plant or crop species is reduced; or the pest stops feeding from its natural food resources such as plants and plant products. The terms "infest" and "infect" or "infestation" and "infection" are generally used interchangeably throughout.

The target genes may be expressed in all or some of the cells of the insect pest. Furthermore, the target genes may only be expressed by the insect pest at a particular stage of its life-cycle, for example, the mature adult phase, immature nymph or larval phase or egg phase.

As used herein "pest" species are preferably insect species that cause infection or infestation, preferably of plants. The insect species may comprise and species belonging to the Orders Coleoptera, Lepidoptera, Diptera, Dichyoptera, Orthoptera, Hemiptera, or Siphonaptera. Preferred plant pathogenic insects according to the invention are plant pest are selected from the group consisting of *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Laodelphax* spp. (e.g. *L. striatellus* (small brown planthopper)); *Nephotettix* spp. (e.g. *N. virescens* or *N. cincticeps* (green leafhopper), or *N.nigropictus* (rice leafhopper)); *Sogatella* spp. (e.g. *S. furcifera* (white-backed planthopper)); *Chilo* spp. (e.g. *C. suppressalis* (rice striped stem borer), *C. auricilius* (gold-fringed stem borer), or *C. polychrysus* (dark-headed stem borer)); *Sesamia* spp. (e.g. *S. inferens* (pink rice borer)); *Tryporyza* spp. (e.g. *T. innotata* (white rice borer), or *T. incertulas* (yellow rice borer)); *Anthonomus* spp. (e.g. *A. grandis* (boll weevil)); *Phaedon* spp. (e.g. *P. cochleariae* (mustard leaf beetle)); *Epilachna* spp. (e.g. *E. varivetis* (mexican bean beetle)); *Tribolium* spp. (e.g. *T. castaneum* (red floor beetle)); *Diabrotica* spp. (e.g. *D. virgifera virgifera* (western corn rootworm), *D. barberi* (northern corn rootworm), *D. undecimpunctata howardi* (southern corn rootworm), *D. virgifera zeae* (Mexican corn rootworm); *Ostrinia* spp. (e.g. *O. nubilalis* (European corn borer)); *Anaphothrips* spp. (e.g. *A. obscurrus* (grass *thrips*)); *Pectinophora* spp. (e.g. *P. gossypiella* (pink bollworm)); *Heliothis* spp. (e.g. *H. virescens* (tobacco budworm)); *Trialeurodes* spp. (e.g. *T. abutiloneus* (banded-winged whitefly) *T. vaporariorum* (greenhouse whitefly)); *Bemisia* spp. (e.g. *B. argentifolii* (silverleaf whitefly)); *Aphis* spp. (e.g. *A. gossypii* (cotton aphid)); *Lygus* spp. (e.g. *L. lineolaris* (tarnished plant bug) or *L. hesperus* (western tarnished plant bug)); *Euschistus* spp. (e.g. *E. conspersus* (consperse stink bug)); *Chlorochroa* spp. (e.g. *C. sayi* (Say stinkbug)); *Nezara* spp. (e.g. *N. viridula* (southern green stinkbug)); *Thrips* spp. (e.g. *T. tabaci* (onion *thrips*)); *Frankliniella* spp. (e.g. *F. fusca* (tobacco *thrips*), or *F. occidentalis* (western flower *thrips*)); *Acheta* spp. (e.g. *A. domesticus* (house cricket)); *Myzus* spp. (e.g. *M. persicae* (green peach aphid)); *Macrosiphum* spp. (e.g. *M. euphorbiae* (potato aphid)); *Blissus* spp. (e.g. *B. leucopterus leucopterus* (chinch bug)); *Acrosternum* spp. (e.g. *A. hilare* (green stink bug)); *Chilotraea* spp. (e.g. *C. polychrysa* (rice stalk borer)); *Lissorhoptrus* spp. (e.g. *L. oryzophilus* (rice water weevil)); *Rhopalosiphum* spp. (e.g. *R. maidis* (corn leaf aphid)); and *Anuraphis* spp. (e.g. *A. maidiradicis* (corn root aphid)).

According to a more specific embodiment, the invention is applicable for species belonging to the family of Chrysomelidae or leaf beatles. Chrysomelid beetles such Colorado potato Beetles, Flea Beetles, Corn Rootworms and Curculionids such as Alfalfa Weevils are particularly important pests. Specific *Leptinotarsa* species to control according to the invention include Colorado Potato Beetle (*Leptinotarsa decemlineata* (Say) and False Potato Beetle (*Leptinotarsa juncta* (Say). CPB is a (serious) pest on our domestic potato, other cultivated and wild tuber bearing and non-tuber bearing potato species and other Solanaceous (nightshades) plant species incuding the crop species tomato, eggplant, peppers, tobacco (*Nicotiana* species including ornamentals), ground cherry, rice, corn or cotton; and the weed/herb species, horse nettle, common nightshade, thorn apple, henbane and buffalo burr. Corn rootworms include species found in the genus *Diabrotica* (e.g., *D. undecimpunctata undecimpunctata, D. undecimpunctata howardii, D. longicornis, D. virgifera* and *D. balteata*). Corn rootworms cause extensive damage to corn and curcubits.

According to a more specific embodiment, the invention is applicable for species belonging to the order of Hemipterans (family of Aphidoidea), such as *Myzus persicae* (green peach aphid, *Aphis fabae* (Black Bean Aphid), *Acyrthosiphum pisum* (Pea Aphid), *Brevicoryne brassicae* (Cabbage Aphid), *Sitobion avenae* (Grain Aphid), *Cavariella aegopodii* (Carrot Aphid), *Aphis craccivora* (Groundnut Aphid), *Aphis gossypii* (Cotton Aphid), *Toxoptera aurantii* (Black Citrus Aphid), *Cavariella* spp (Willow Aphid), *Chaitophorus* spp (Willow Leaf Aphids), *Cinara* spp. (Black Pine Aphids), *Drepanosiphum platanoides* (Sycamore Aphid) *Elatobium* spp (Spruce Aphids) which cause damage to plants such as Prunus trees, particularly peach, apricot and plum; trees that are mainly cultured for wood production such as willows and poplars, to row crops such as corn, cotton, soy, wheat and rice, to vegetable crops of the families Solanaceae, Chenopodiaceae, Compositae, Cruciferae, and Cucurbitaceae, including but not limited to, artichoke, asparagus, bean, beets, broccoli, Brussels sprouts, cabbage, carrot, cauliflower, cantaloupe, celery, corn, cucumber, fennel, kale, kohlrabi, turnip, eggplant, lettuce, mustard, okra, parsley, parsnip, pea, pepper, potato, radish, spinach, squash, tomato, turnip, watercress, and watermelon; or field crops such as, but not limited to, tobacco, sugar beet, and sunflower; a flower crop or other ornamental plant such as pine trees and conifers. Other Hemipterans belong to *Nilaparvata* ssp (eg. *N. lugens, Sogatella furcifera*) and cause damage to rice plants. Other Hemipterans belong to *Lygus* ssp (eg. *Lygus hesperus, Lygus rugulipennis, Lygus lineolaris, Lygus sully*) and other species of plant-feeding insects in the family of the Miridae, and cause damage to cotton, potato plants, strawberries, cotton, alfalfa, canola, peach, plums, grape, lettuce, eggplant, onion, green beans. As well as several Mediterranean trees and several ornamental trees such as elm tree (*Ulmus* spp.) pine nut (*Pinus Pinea*) London plane tree (*Platanus Acerifolia*), white redbud (*Malus* alba). Other Hemipterans belong to the family of the Pentatomoidea, they are commonly referred to as shield bugs, chust bugs, and stink bugs (eg; the brown marmorated stink bug (*Halyomorpha halys*), the Consperse stink bug (*Euschistus conspersus*), southern green stink bug (*Nezara viridula*), forest bug (*Pentatoma rufipes*), harlequin bug (*Murgantia histrionica*), rice stink bug (*Oebalus pugnax*)) and cause damage to fruits including apples, peaches, figs, mulberries, citrus fruits and persimmons, blackberry, and vegetables including sweetcorn, tomatoes, soy beans, lima beans and green peppers, cabbage, cauliflower, turnips, horseradish, collards, mustard, Brussels sprouts, potato, egg plant, okra, beans, asparagus, beets, weeds, fruit trees and field crops such as field corn and soy bean. Stink bugs are also a pest of grasses, sorghum and rice.

A plant to be used in the methods of the invention, or a transgenic plant according to the invention encompasses any plant, but is preferably a plant that is susceptible to infestation by a plant pathogenic insect.

Accordingly, the present invention extends to plants and to methods as described herein wherein the plant is chosen from the following group of plants (or crops): alfalfa, apple, apricot, artichoke, asparagus, avocado, banana, barley, beans, beet, blackberry, blueberry, broccoli, Brussels sprouts, cabbage, canola, carrot, cassava, cauliflower, a cereal, celery, cherry, citrus, clementine, coffee, corn, cotton, cucumber, eggplant, endive, eucalyptus, figs, grape, grapefruit, groundnuts, ground cherry, kiwifruit, lettuce, leek, lemon, lime, pine, maize, mango, melon, millet, mushroom, nut oat, okra, onion, orange, an ornamental plant or flower or tree, papaya, parsley, pea, peach, peanut, peat, pepper, persimmon, pineapple, plantain, plum, pomegranate, potato, pumpkin, radicchio, radish, rapeseed, raspberry, rice, rye, sorghum, soy, soybean, spinach, strawberry, sugar beet, sugarcane, sunflower, sweet potato, tangerine, tea, tobacco, tomato, a vine, watermelon, wheat, yams and zucchini.

In specific embodiments, the present invention provides target genes which encode proteins involved in the function of a wings up A (troponin I), a mitochondrial cytochrome c oxidase subunit II protein, or one of the ribosomal proteins as specified in Table 1.

In preferred embodiments, the present invention provides target genes selected from the group of genes (i) having a nucleotide sequence comprising any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or having a nucleotide sequence so that, when the two sequences are optimally aligned and compared, is at least 75%, preferably at least 80%, 85%, 90%, 95%, 98% or 99% identical any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (ii) having a nucleotide sequence consisting of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (iii) having a nucleotide sequence comprising a fragment of at least 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100, 1200, 1300, 1400, 1500, 2000, or 3000 contiguous nucleotides of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or having a nucleotide sequence so that, when said gene comprising said fragment is optimally aligned and compared with any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, said nucleotide sequence is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (iv) having a nucleotide sequence comprising a fragment of at least 20, 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900 1000, 1100, 1200, 1300, 1400, 1500, 2000, or 3000 contiguous nucleotides of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, and wherein when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, said nucleotide sequence of said fragment is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (v) having a nucleotide sequence encoding an amino acid sequence that, when the two amino acid sequences are optimally aligned and compared, is at least 70% preferably at least 75%, 80%, 85%, 90%, 95%, 98% or 99% identical to the amino acid sequence encoded by any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389 or (vi) which gene is an insect pest orthologue of a gene having a nucleotide sequence comprising any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, wherein the two orthologous genes are similar in sequence to such a degree that when the two genes are optimally aligned and compared, the orthologue has a sequence that is at least 75% preferably at least 80%, 85%, 90%, 95%, 98% or 99% identical to any of the sequences represented by SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389;

and wherein the nucleotide sequence of said gene is no longer than 10000, 9000, 8000, 7000, 6000, 5000, 4000, 3000, 2000 or 1500 nucleotides.

The amino acid sequences encoded by the target genes of the present invention are represented by SEQ ID NOs. SEQ ID NOs 79, 349, 405, 352, 356, 80, 326, 81, 327, 82, 83, 328, 84, 329, 85, 86, 359, 87 to 91, 330, 350, 353, 331, 351, 332 to 336, 337, 354, 338 to 344, 346, 345, 347, 348, 357, 355, 358, 390 to 393.

As used herein, the term "having" has the same meaning as "comprising".

As used herein, the term "sequence identity" is used to describe the sequence relationship between two or more nucleotide or amino acid sequences. The percentage of "sequence identity" between two sequences is determined by comparing two optimally aligned sequences over a comparison window (a defined number of positions), wherein the portion of the sequence in the comparison window may comprise additions or deletions (i.e. gaps) as compared to the reference sequence in order to achieve optimal alignment. The percentage sequence identity is calculated by determining the number of positions at which the identical nucleotide base or amino acid residue occurs in both sequences to yield the number of 'matched' positions, dividing the number of matched positions by the total number of positions in the comparison window and multiplying the result by 100. Methods and software for determining sequence identity are available in the art and include the Blast software and GAP analysis. For nucleic acids, the percent identity is calculated preferably by the BlastN alignment tool whereby the percent identity is calculated over the entire length of the query nucleotide sequence.

A person skilled in the art will recognise that homologues or orthologues (homologues existing in different species) of the target genes represented by any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389 can be identified. These pest homologues and/or orthologues are also within the scope of the current invention. Preferred homologues and/or orthologues are genes similar in nucleotide sequence to such a degree that when the two genes are optimally aligned and compared, the homologue and/or orthologue has a sequence that is at least 75%, preferably at least 80% or 85%, more preferably at least 90% or 95%, and most preferably at least about 99% identical to any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389 or the complement thereof. Similarly, also preferred homologues and/or orthologues are proteins that are similar in amino acid sequence to such a degree that when the two amino acid sequences are optimally aligned and compared, the homologue and/or orthologue has a sequence that is at least 75%, preferably at least 80% or 85%, more preferably at least 90% or 95%, and most preferably at least about 99% identical to any of SEQ ID NOs 79, 349, 405, 352, 356, 80, 326, 81, 327, 82, 83, 328, 84, 329, 85, 86, 359, 87 to 91, 330, 350, 353, 331, 351, 332 to 336, 337, 354, 338 to 344, 346, 345, 347, 348, 357, 355, 358, 390 to 393.

Other homologues are genes which are alleles of a gene comprising a sequence as represented by any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389. Further preferred homologues are genes comprising at least one single nucleotide polymorphism (SNP) compared to a gene comprising a sequence as represented by any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389.

The 'interfering ribonucleic acid (RNA)' of the current invention encompasses any type of RNA molecule capable of down-regulating or 'silencing' expression of a target gene, including but not limited to sense RNA, antisense RNA, short interfering RNA (siRNA), microRNA (miRNA), double-stranded RNA (dsRNA), hairpin RNA (RNA) and the like. Methods to assay for functional interfering RNA molecules are well known in the art and are disclosed elsewhere herein.

The interfering RNA molecules of the current invention effect sequence-specific down-regulation of expression of a target gene by binding to a target nucleotide sequence within the target gene. Binding occurs as a result of base pairing between complementary regions of the interfering RNA and the target nucleotide sequence. As used herein, the term 'silencing element' refers to the portion or region of the interfering RNA comprising or consisting of a sequence of nucleotides which is complementary, or at least partially complementary, to a target nucleotide sequence within the target gene, and which functions as the active portion of the interfering RNA to direct down-regulation of expression of said target gene. In one embodiment of the invention, the silencing element comprises or consists of a sequence of at least 17 contiguous nucleotides, preferably at least 18 or 19 contiguous nucleotides, more preferably at least 21 contiguous nucleotides, even more preferably at least 22, 23, 24 or 25 contiguous nucleotides complementary to a target nucleotide sequence within the target gene.

As used herein, "expression of a target gene" refers to the transcription and accumulation of the RNA transcript encoded by a target gene and/or translation of the mRNA into protein. The term 'down-regulate' is intended to refer to any of the methods known in the art by which interfering RNA molecules reduce the level of primary RNA transcripts, mRNA or protein produced from a target gene.

In certain embodiments, down-regulation refers to a situation whereby the level of RNA or protein produced from a gene is reduced by at least 10%, preferably by at least 33%, more preferably by at least 50%, yet more preferably by at least 80%. In particularly preferred embodiments, down-regulation refers to a reduction in the level of RNA or protein produced from a gene by at least 80%, preferably by at least 90%, more preferably by at least 95%, and most preferably by at least 99% within cells of the insect pest as compared with an appropriate control insect pest which has for example, not been exposed to an interfering RNA or has been exposed to a control interfering RNA molecule. Methods for detecting reductions in RNA or protein levels are well known in the art and include RNA solution hybridization, Northern hybridization, reverse transcription (e.g. quantitative RT-PCR analysis), microarray analysis, antibody binding, enzyme-linked immunosorbent assay (ELISA) and Western blotting. In another embodiment of the invention, down-regulation refers to a reduction in RNA or protein levels sufficient to result in a detectable change in a phenotype of the pest as compared with an appropriate pest control, for example, cell death, cessation of growth, or the like. Down-regulation can thus be measured by phenotypic analysis of the insect pest using techniques routine in the art.

In a preferred embodiment of the invention, the interfering RNA down-regulates gene expression by RNA interference or RNAi. RNAi is a process of sequence-specific gene regulation typically mediated by double-stranded RNA molecules such as short interfering RNAs (siRNAs). siRNAs comprise a sense RNA strand annealed by complementary basepairing to an antisense RNA strand. The sense strand or 'guide strand' of the siRNA molecule comprises a sequence of nucleotides complementary to a sequence of nucleotides located within the RNA transcript of the target gene. The sense strand of the siRNA is therefore able to anneal to the RNA transcript via Watson-Crick-type basepairing and target the RNA for degradation within a cellular complex known as the RNAi-induced silencing complex or RISC. Thus, in the context of preferred interfering RNA molecules of the current invention, the silencing element as referred to herein may be a double-stranded region comprising annealed complementary strands, at least one strand of which comprises or consists of a sequence of nucleotides which is complementary or at least partially complementary to a target nucleotide sequence within a target gene. In one embodiment the double-stranded region has a length of at least 21, 22, 23, 24, 25, 30, 35, 40, 50, 55, 60, 70, 80, 90, 100, 125, 150, 175, 200, 300, 400, 500, 600, 700, 800, 900, 1000, 1100, 1200, 1300, 1400, 1500, 2000 or 3000 base pairs.

Longer double-stranded RNA (dsRNA) molecules comprising one or more functional double-stranded silencing elements as described elsewhere herein, and capable of RNAi-mediated gene silencing are also contemplated within the scope of the current invention. Such longer dsRNA molecules comprise at least 80, 200, 300, 350, 400, 450, 500, 550, 600, 700, 800, 900, 1000, 1100, 1200, 1300, 1400, 1500, 2000 or 3000 base pairs. These dsRNA molecules may serve as precursors for the active siRNA molecules that direct the RNA transcript to the RISC complex for subsequent degradation. dsRNA molecules present in the environment surrounding an organism or the cells thereof may be taken up by the organism and processed by an enzyme called Dicer to yield siRNA molecules.

Alternatively, the dsRNA may be produced in vivo i.e. transcribed from a polynucleotide or polynucleotides encoding the same present within a cell, for instance a bacterial cell or a plant cell, and subsequently processed by Dicer either within the host cell or preferably within the insect pest cells following uptake of the longer precursor dsRNA. The dsRNA may be formed from two separate (sense and antisense) RNA strands that anneal by virtue of complementary basepairing.

Alternatively, the dsRNA may be a single strand that is capable of folding back on itself to form a hairpin RNA (RNA) or stem-loop structure. In the case of a RNA, the double-stranded region or 'stem' is formed from two regions or segments of the RNA that are essentially inverted repeats of one another and possess sufficient complementarity to allow the formation of a double-stranded region. One or more functional double-stranded silencing elements may be present in this 'stem region' of the molecule. The inverted repeat regions are typically separated by a region or segment of the RNA known as the 'loop' region. This region can comprise any nucleotide sequence conferring enough flexibility to allow self-pairing to occur between the flanking complementary regions of the RNA. In general, the loop region is substantially single-stranded and acts as a spacer element between the inverted repeats.

All the interfering RNA molecules of the invention effect sequence-specific down-regulation of expression of a target gene by binding to a target nucleotide sequence within the target gene. Binding occurs as a result of complementary base pairing between the silencing element of the interfering RNA and the target nucleotide sequence. The interfering RNA molecules of the invention comprise at least one or at least two silencing elements. In one embodiment of the current invention, the target nucleotide sequence comprises a sequence of nucleotides as represented by the RNA transcript of the target gene, or a fragment thereof wherein the fragment is preferably at least 17 nucleotides, more preferably at least 18, 19 or 20 nucleotides, or most preferably at least 21, 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 nucleotides. In a preferred embodiment of the current invention, the target nucleotide sequence comprises a sequence of nucleotides equivalent to the RNA transcript encoded by any of the polynucleotides selected from the group consisting of (i) a polynucleotide which comprises at least 21, preferably at least 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100 or 1115 contiguous nucleotides of a nucleotide sequence as represented by any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (ii) a polynucleotide which consists of at least 21, preferably at least 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide sequence as represented by any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (iii) a polynucleotide which comprises at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide sequence as represented in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, so that, when the two sequences are optimally aligned and compared, said polynucleotide is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (iv) a polynucleotide which comprises a fragment of at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide as represented in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, and wherein said fragment or said complement has a nucleotide sequence so that, when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, said nucleotide sequence is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389 or the complement thereof, or (vi) a polynucleotide encoding an amino acid sequence that, when the two amino acid sequences are optimally aligned and compared, is at least 70% preferably at least 75%, 80%, 85%, 90%, 95%, 98% or 99% identical to the amino acid sequence encoded by any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389. In a more preferred embodiment of the above, said polynucleotide is no longer than 10000, 9000, 8000, 7000, 6000, 5000, 4000, 3000, 2000 or 1500 nucleotides.

Preferably, the interfering RNA molecules of the current invention comprise at least one double-stranded region, typically the silencing element of the interfering RNA, comprising a sense RNA strand annealed by complementary basepairing to an antisense RNA strand wherein the sense strand of the dsRNA molecule comprises a sequence of nucleotides complementary to a sequence of nucleotides located within the RNA transcript of the target gene.

The silencing element, or at least one strand thereof wherein the silencing element is double-stranded, may be fully complementary or partially complementary to the target nucleotide sequence of the target gene. As used herein, the term "fully complementary" means that all the bases of the nucleotide sequence of the silencing element are complementary to or 'match' the bases of the target nucleotide sequence. The term "at least partially complementary" means that there is less than a 100% match between the bases of the silencing element and the bases of the target nucleotide sequence. The skilled person will understand that the silencing element need only be at least partially complementary to the target nucleotide sequence in order to mediate down-regulation of expression of the target gene. It is known in the art that RNA sequences with insertions, deletions and mismatches relative to the target sequence can still be effective at RNAi. According to the current invention, it is preferred that the silencing element and the target nucleotide sequence of the target gene share at least 80% or 85% sequence identity, preferably at least 90% or 95% sequence identity, or more preferably at least 97% or 98% sequence identity and still more preferably at least 99% sequence identity. Alternatively, the silencing element may comprise 1, 2 or 3 mismatches as compared with the target nucleotide sequence over every length of 24 partially complementary nucleotides.

It will be appreciated by the person skilled in the art that the degree of complementarity shared between the silencing element and the target nucleotide sequence may vary depending on the target gene to be down-regulated or depending on the insect pest species in which gene expression is to be controlled.

In another embodiment of the current invention, the silencing element comprises a sequence of nucleotides that is the RNA equivalent of any of the polynucleotides selected from the group consisting of a polynucleotide which comprises at least 21, preferably at least 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100 or 1115 contiguous nucleotides of a nucleotide sequence as represented by any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (ii) a polynucleotide which comprises at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide sequence as represented in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, so that, when the two sequences are optimally aligned and compared, said polynucleotide is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (iii) a polynucleotide which comprises a fragment of at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide as represented in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, and wherein said fragment or said complement has a nucleotide sequence so that, when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, said nucleotide sequence is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, wherein said polynucleotide is no longer than 10000, 9000, 8000, 7000, 6000, 5000, 4000, 3000, 2000 or 1500 nucleotides. It will be appreciated that in such embodiments the silencing element may comprise or consist of a region of double-stranded RNA comprising annealed complementary strands, one strand of which, the sense strand, comprises a sequence of nucleotides at least partially complementary to a target nucleotide sequence within a target gene.

The target nucleotide sequence may be selected from any suitable region or nucleotide sequence of the target gene or RNA transcript thereof. For example, the target nucleotide sequence may be located within the 5'UTR or 3'UTR of the target gene or RNA transcript or within exonic or intronic regions of the gene.

The skilled person will be aware of methods of identifying the most suitable target nucleotide sequences within the context of the full-length target gene. For example, multiple silencing elements targeting different regions of the target gene can be synthesised and tested. Alternatively, digestion of the RNA transcript with enzymes such as RNAse H can be used to determine sites on the RNA that are in a conformation susceptible to gene silencing. Target sites may also be identified using in silico approaches, for example, the use of computer algorithms designed to predict the efficacy of gene silencing based on targeting different sites within the full-length gene.

The interfering RNAs of the current invention may comprise one silencing element or multiple silencing elements, wherein each silencing element comprises or consists of a sequence of nucleotides which is at least partially complementary to a target nucleotide sequence within a target gene and that functions upon uptake by an insect pest species to down-regulate expression of said target gene. Concatemeric RNA constructs of this type are described in WO2006/046148 as incorporated herein by reference. In the context of the present invention, the term 'multiple' means at least two, at least three, at least four, etc and up to at least 10, 15, 20 or at least 30. In one embodiment, the interfering RNA comprises multiple copies of a single silencing element i.e. repeats of a silencing element that binds to a particular target nucleotide sequence within a specific target gene. In another embodiment, the silencing elements within the interfering RNA comprise or consist of different sequences of nucleotides complementary to different target nucleotide sequences. It should be clear that combinations of multiple copies of the same silencing element combined with silencing elements binding to different target nucleotide sequences are within the scope of the current invention.

The different target nucleotide sequences may originate from a single target gene in an insect pest species in order to achieve improved down-regulation of a specific target gene in an insect pest species. In this case, the silencing elements may be combined in the interfering RNA in the original order in which the target nucleotide sequences occur in the target gene, or the silencing elements may be scrambled and combined randomly in any rank order in the context of the interfering RNA as compared with the order of the target nucleotide sequences in the target gene.

Alternatively, the different target nucleotide sequences are representing a single target gene but originating from different insect pest species.

Alternatively, the different target nucleotide sequences may originate from different target genes. If the interfering RNA is for use in preventing and/or controlling pest infestation, it is preferred that the different target genes are chosen from the group of genes regulating essential biological functions of insect pest species, including but not limited to survival, growth, development, reproduction and pathogenicity. The target genes may regulate the same or different biological pathways or processes.

In one embodiment, at least one of the silencing elements comprises or consists of a sequence of nucleotides which is at least partially complementary to a target nucleotide sequence within a target gene wherein the target gene is selected from the group of genes as described earlier.

In a further embodiment of the invention, the different genes targeted by the different silencing elements originate from the same insect pest species. This approach is designed to achieve enhanced attack against a single insect pest species. In particular, the different target genes may be expressed differentially in the different stages of the insect's life cycle, for example, the mature adult, immature larval and egg stages. The interfering RNA of the invention may thus be used to prevent and/or control insect pest infestation at more than one stage of the insect's life cycle.

In an alternative embodiment of the invention, the different genes targeted by the different silencing elements originate from different insect pest species. The interfering RNA of the invention can thus be used to prevent and/or control infestation by more than one insect pest species simultaneously. The silencing elements may be arranged as one contiguous region of the interfering RNA or may be separated by the presence of linker sequences. The linker sequence may comprise a short random nucleotide sequence that is not complementary to any target nucleotide sequences or target genes. In one embodiment, the linker is a conditionally self-cleaving RNA sequence, preferably a pH-sensitive linker or a hydrophobic-sensitive linker. In one embodiment, the linker comprises a sequence of nucleotides equivalent to an intronic sequence. Linker sequences of the current invention may range in length from about 1 base pair to about 10000 base pairs, provided that the linker does not impair the ability of the interfering RNA to down-regulate the expression of target gene(s).

In addition to the silencing element(s) and any linker sequences, the interfering RNA of the invention may comprise at least one additional polynucleotide sequence. In different embodiments of the invention, the additional sequence is chosen from (i) a sequence capable of protecting the interfering RNA against RNA processing, (ii) a sequence affecting the stability of the interfering RNA, (iii) a sequence allowing protein binding, for example to facilitate uptake of the interfering RNA by cells of the insect pest species, (iv) a sequence facilitating large-scale production of the interfering RNA, (v) a sequence which is an aptamer that binds to a receptor or to a molecule on the surface of the insect pest cells to facilitate uptake, or (v) a sequence that catalyses processing of the interfering RNA within the insect pest cells and thereby enhances the efficacy of the interfering RNA. Structures for enhancing the stability of RNA molecules are well known in the art and are described further in WO2006/046148 as incorporated herein by reference.

The length of the interfering RNA of the invention needs to be sufficient for uptake by the cells of an insect pest species and down-regulation of target genes within the pest as described elsewhere herein. However, the upper limit on length may be dependent on (i) the requirement for the interfering RNA to be taken up by cells of the pest and (ii) the requirement for the interfering RNA to be processed in the cells of the pest to mediate gene silencing via the RNAi pathway. The length may also be dictated by the method of production and the formulation for delivery of the interfering RNA to cells. Preferably, the interfering RNA of the current invention will be between 21 and 10000 nucleotides in length, preferably between 50 and 5000 nucleotides or between 100 and 2500 nucleotides, more preferably between 80 and 2000 nucleotides in length.

The interfering RNA may contain DNA bases, non-natural bases or non-natural backbone linkages or modifications of the sugar-phosphate backbone, for example to enhance stability during storage or enhance resistance to degradation by nucleases. Furthermore, the interfering RNA may be produced chemically or enzymatically by one skilled in the art through manual or automated reactions. Alternatively, the interfering RNA may be transcribed from a polynucleotide encoding the same. Thus, provided herein is an isolated polynucleotide encoding any of the interfering RNAs of the current invention.

Also provided herein is an isolated polynucleotide selected from the group consisting of (i) a polynucleotide which comprises at least 21, preferably at least 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide sequence as represented by any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (ii) a polynucleotide which consists of at least 21, preferably at least 22, 23, 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100 or 1115 contiguous nucleotides of a nucleotide sequence as represented by any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (iii) a polynucleotide which comprises at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide sequence as represented in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, so that, when the two sequences are optimally aligned and compared, said polynucleotide is at least 75% preferably at least 80%, 85%, 90%, 95%, 98% or 99% identical to any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, or (iv) a polynucleotide which comprises a fragment of at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide as represented in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, and wherein said fragment or said complement has a nucleotide sequence so that, when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, said nucleotide sequence is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389 or the complement thereof, or (v) a polynucleotide which consists of a fragment of at least 21, preferably at least 22, 23 or 24, 25, 26, 27, 28, 29, 30, 35, 40, 45, 50, 55, 60, 70, 80, 90, 100, 110, 125, 150, 175, 200, 225, 250, 300, 350, 400, 450, 500, 550, 600, 700, 800, 900, 1000, 1100, 1200, 1300, 1400, 1500, 2000 or 3000 contiguous nucleotides of a nucleotide as represented in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, or the complement thereof, and wherein said fragment or said complement has a nucleotide sequence so that, when said fragment is optimally aligned and compared with the corresponding fragment in any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, said nucleotide sequence is at least 75% preferably at least 80%, 85%, 90%, 95%, 98% or 99% identical to said corresponding fragment of any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389 or the complement thereof, or (vi) a polynucleotide encoding an amino acid sequence that, when the two amino acid sequences are optimally aligned and compared, is at least 70% preferably at least 75%, 80%, 85%, 90%, 95%, 98% or 99% identical to the amino acid sequence encoded by any of SEQ ID NOs 1, 174, 404, 180, 188, 2, 175, 181, 189, 27 to 30, 282 to 285, 294 to 297, 310 to 313, 3, 4, 31 to 34, 139, 5, 6, 35 to 38, 140, 7, 8, 39 to 42, 9, 10, 43 to 46, 141, 11, 12, 47 to 50, 13, 14, 51 to 54, 15, 204, 16, 205, 55 to 58, 322 to 325, 17, 18, 59 to 62, 19, 20, 63 to 66, 21, 22, 67 to 70, 23, 24, 71 to 74, 25, 26, 75 to 78, 143, 121, 142, 176, 182, 130, 177, 183, 206 to 209, 286 to 289, 298 to 301, 145, 122, 144, 178, 131, 179, 210 to 213, 290 to 293, 123, 132, 214 to 217, 124, 133, 218 to 221, 146, 125, 134, 222 to 225, 147, 126, 135, 226 to 229, 127, 148, 136, 230 to 233, 128, 149, 184, 137, 185, 234 to 237, 302 to 305, 129, 138, 238 to 241, 150, 151, 242 to 245, 152, 153, 246 to 249, 154, 155, 250 to 253, 156, 157, 254 to 257, 158, 159, 258 to 261, 160, 161, 262 to 265, 163, 162, 164, 266 to 269, 165, 167, 166, 270 to 273, 168, 170, 169, 274 to 277, 172, 173, 278 to 281, 200, 201, 314 to 317, 186, 202, 187, 203, 306 to 309, 318 to 321, 386, 387, 388, 389, and wherein said polynucleotide is no longer than 10000, 9000, 8000, 7000, 6000, 5000, 4000, 3000, 2000 or 1500 nucleotides.

In preferred embodiments, the isolated polynucleotide is part of an interfering RNA molecule, typically part of the silencing element, comprising at least one double-stranded region comprising a sense RNA strand annealed by complementary basepairing to an antisense RNA strand wherein the sense strand of the dsRNA molecule comprises a sequence of nucleotides complementary to a sequence of nucleotides located within the RNA transcript of the target gene. The sense strand of the dsRNA is therefore able to anneal to the RNA transcript and target the RNA for degradation within the RNAi-induced silencing complex or RISC.

The polynucleotides of the invention may be inserted via routine molecular cloning techniques into DNA constructs or vectors known in the art. Therefore, according to one embodiment, a DNA construct comprising any of the polynucleotides of the current invention is provided. Preferably, provided herein is a DNA construct comprising a polynucleotide encoding at least one of the interfering RNAs of the current invention. The DNA construct may be a recombinant DNA vector, for example a bacterial, viral or yeast vector. In a preferred embodiment of the invention, the DNA construct is an expression construct and the polynucleotide is operably linked to at least one regulatory sequence capable of driving expression of the polynucleotide sequence. The term 'regulatory sequence' is to be taken in a broad context and is intended to refer to any nucleotide sequence capable of effecting expression of polynucleotides to which it is operably linked including but not limited to promoters, enhancers and other naturally-occurring or synthetic transcriptional activator elements. The regulatory sequence may be located at the 5' or 3' end of the polynucleotide sequence. The term 'operably linked' refers to a functional linkage between the regulatory sequence and the polynucleotide sequence such that the regulatory sequence drives expression of the polynucleotide. Operably linked elements may be contiguous or non-contiguous.

Preferably, the regulatory sequence is a promoter selected from the group comprising but not limited to constitutive promoters, inducible promoters, tissue-specific promoters and growth/developmental stage-specific promoters. In one embodiment, the polynucleotide is placed under the control of a strong constitutive promoter such as any selected from the group comprising the CaMV35S promoter, doubled CaMV35S promoter, ubiquitin promoter, actin promoter, rubisco promoter, GOS2 promoter, Figwort mosaic virus 34S promoter.

Optionally, one or more transcription termination sequences may be incorporated in the expression construct of the invention. The term 'transcription termination sequence' encompasses a control sequence at the end of a transcriptional unit, which signals termination of transcription, 3' processing and poly-adenylation of a primary transcript. Additional regulatory sequences including but not limited to transcriptional or translational enhancers may be incorporated in the expression construct, for instance as with the double enhanced CaMV35S promoter.

The present invention also encompasses a method for generating any of the interfering RNAs of the invention comprising the steps of (i) contacting a polynucleotide encoding said interfering RNA or a DNA construct comprising the same with cell-free components; or (ii) introducing (e.g. by transformation, transfection or injection) a polynucleotide encoding said interfering RNA or a DNA construct comprising the same into a cell.

The invention thus also relates to any double stranded ribonucleotide produced from the expression of a polynucleotide described herein.

Accordingly, also provided herein is a host cell transformed with any of the polynucleotides described herein. Further encompassed by the present invention are host cells comprising any of the interfering RNA's of the current invention, any of the polynucleotides of the current invention or a DNA construct comprising the same. The host cell may be a prokaryotic cell including but not limited to gram-positive and gram-negative bacterial cells, or an eukaryotic cell including but not limited to yeast cells or plant cells. Preferably, said host cell is a bacterial cell or a plant cell. The bacterial cell can be chosen from the group comprising, but not limited to, Gram positive and Gram negative cells comprising *Escherichia* spp. (e.g. *E. coli*), *Bacillus* spp. (e.g. *B. thuringiensis*), *Rhizobium* spp., *Lactobacillus* spp., *Lactococcus* spp., *Pseudomonas* spp. and *Agrobacterium* spp. The polynucleotide or DNA construct of the invention may exist or be maintained in the host cell as an extra-chromosomal element or may be stably incorporated into the genome of the host cell. Characteristics of particular interest in selecting a host cell for the purposes of the current invention include the ease with which the polynucleotide or DNA construct encoding the interfering RNA can be introduced into the host, the availability of compatible expression systems, the efficiency of expression, and the stability of the interfering RNA in the host.

Preferably, the interfering RNAs of the invention are expressed in a plant host cells. Preferred plants of interest include but are not limited to cotton, potato, rice, tomato, canola, soy, sunflower, sorghum, pearl millet, corn, alfalfa, strawberries, eggplant, pepper and tobacco.

In situations wherein the interfering RNA is expressed within a host cell and/or is used to prevent and/or control pest infestation of a host organism, it is preferred that the interfering RNA does not exhibit significant 'off-target' effects i.e. the interfering RNA does not affect expression of genes within the host. Preferably, the silencing element does not exhibit significant complementarity with nucleotide sequences other than the intended target nucleotide sequence of the target gene. In one embodiment of the invention, the silencing element shows less than 30%, more preferably less than 20%, more preferably less than 10% and even more preferably less than 5% sequence identity with any gene of the host cell or organism. If genomic sequence data is available for the host organism, one can cross-check identity with the silencing element using standard bioinformatics tools. In one embodiment, there is no sequence identity between the silencing element and a gene from the host cell or host organism over a region of 17, more preferably over a region of 18 or 19 and most preferably over a region of 20 or 21 contiguous nucleotides.

In the practical application of the invention, the interfering RNAs of the invention may be used for the prevention and/or control of any insect pest belonging to the Orders Coleoptera, Lepidoptera, Diptera, Dichyoptera, Orthoptera, Hemiptera and Siphonaptera.

Furthermore, in accordance with another aspect of the invention, there is provided herein a composition for preventing and/or controlling insect pest infestation comprising at least one interfering ribonucleic acid (RNA) and optionally at least one suitable carrier, excipient or diluent, wherein the interfering RNA functions upon uptake by the pest to down-regulate the expression of a target gene within said pest. The interfering RNA may be any of those as disclosed elsewhere herein. Preferably, the interfering RNA comprises or consists of at least one silencing element and said silencing element is a region of double-stranded RNA comprising annealed complementary strands, one strand of which (the sense strand) comprises a sequence of nucleotides which is at least partially complementary to a target nucleotide sequence within a target gene. The 'target gene' may be any of the pest target genes as disclosed elsewhere herein including but not limited to genes involved in regulating pest survival, growth, development, reproduction and pathogenicity. Alternatively, the composition comprises at least one host cell comprising at least one interfering RNA molecule or DNA construct encoding the same and optionally at least one suitable carrier, excipient or diluent, wherein the interfering RNA functions upon uptake of the host cell by the insect pest to down-regulate the expression of a target gene within said pest.

In the practical application of the invention, the composition may be used for the prevention and/or control of any insect pest belonging to the Orders Coleoptera, Lepidoptera, Diptera, Dichyoptera, Orthoptera, Hemiptera and Siphonaptera. The composition may therefore be in any suitable form for application to insect pests or for application to substrates and/or organisms, in particular plants, susceptible to infestation by said insect pest. In one embodiment, the composition is for use in preventing and/or controlling pest infestation of plants or propagation or reproductive material of plants and is thus directed towards insect pest species that infest plants. The composition of the present invention is particularly effective when the insect pest belongs to the category of 'chewing' insects that cause considerable damage to plants by eating plant tissues such as roots, leaves, flowers, buds, twigs and the like. Examples from this large insect category include beetles and their larvae.

The composition of the invention may be used to control insect pests at all stages of their life cycle, for example, the mature adult stage, the larval and egg stages.

In the context of the composition of the invention, the interfering RNA may be produced from a DNA construct, in particular an expression construct as described elsewhere herein, comprising a polynucleotide encoding the same. In preferred embodiments, the interfering RNA may be produced inside a host cell or organism engineered to express said interfering RNA from a polynucleotide encoding the same.

Suitable host organisms for use in the compositions of the current invention include but are not limited to microorganisms that are known to colonize the environment on and/or around plants or crops of interest i.e. plants or crops susceptible to infestation by insect pest species. Such microorganisms include but are not limited to those that occupy the phylloplane (the surface of plant leaves) and/or the rhizosphere (the soil surrounding plant roots). These microorganisms are selected so as to be capable of successfully competing with any wild-type organisms present in the plant environment. Suitable microorganisms for use as hosts include various species of bacteria, algae and fungi. It is clear that the chosen microorganisms must not be toxic to plants. Such compositions applied to plants susceptible of infestation by insect pest species will be ingested by the insect pests feeding on the treated plants.

Host organisms that do not naturally colonize plants and/or their environment are also within the scope of the current invention. Such organisms may serve only as a means to generate the interfering RNA of the composition. For example, in one embodiment, the interfering RNA is fermented/produced in a bacterial host and the bacteria are subsequently inactivated/killed. The resulting bacteria may be processed and used as an insecticidal spray in the same manner that *Bacillus thuringiensis* strains have been used as an insecticide for a spray application. In certain embodiments, a bacterial extract or lysate may be suitably purified to leave a substantially pure interfering RNA containing extract, which is subsequently formulated into one of the compositions of the invention. Standard extraction/purification techniques would be known by a person skilled in the art.

Compositions of the invention may be in any suitable physical form for application to insects. For example, the composition may be in solid form (powder, pellet or a bait), liquid form (including a form administered as a spray insecticide) or gel form. In a specific embodiment, the composition may be a coating, paste or powder that can be applied to a substrate in order to protect said substrate from infestation by insects. In this embodiment, the composition can be used to protect any substrate or material that is susceptible to infestation by or damage caused by an insect.

The nature of the excipients and the physical form of the composition may vary depending on the nature of the substrate that it is desired to treat. For example, the composition may be a liquid that is brushed or sprayed onto or imprinted into the material or substrate to be treated, or a coating or powder that is applied to the material or substrate to be treated.

In one embodiment, the composition is in the form of a bait. The bait is designed to lure the insect to come into contact with the composition. Upon coming into contact therewith, the composition is then internalised by the insect, by ingestion for example and mediates RNAi to thus kill the insect. Said bait may comprise a food substance, such as a protein based food, for example fish meal. Boric acid may also be used as a bait. The bait may depend on the species being targeted. An attractant may also be used. The attractant may be a pheromone, such as a male or female pheremone for example. As an example, the pheromones referred to in the book "Insect Pheremones and their use in Pest Management" (Howse et al, Chapman and Hall, 1998) may be used in the invention. The attractant acts to lure the insect to the bait, and may be targeted for a particular insect or may attract a whole range of insects. The bait may be in any suitable form, such as a solid, paste, pellet or powdered form.

The bait may also be carried away by the insect back to the colony. The bait may then act as a food source for other members of the colony, thus providing an effective control of a large number of insects and potentially an entire insect pest colony. This is an advantage associated with use of the double stranded RNA of the invention, because the delayed action of the RNAi mediated effects on the pests allows the bait to be carried back to the colony, thus delivering maximal impact in terms of exposure to the insects.

Additionally, compositions which come into contact with the insects may remain on the cuticle of the insect. When cleaning, either an individual insect cleaning itself or insects cleaning one another, the compositions may be ingested and can thus mediate their effects in the insect. This requires that the composition is sufficiently stable such that the interfering RNA remains intact and capable of mediating RNAi even when exposed to external environmental conditions for a length of time, which may be a period of days for example.

The baits may be provided in a suitable "housing" or "trap". Such housings and traps are commercially available and existing traps may be adapted to include the compositions of the invention. Any housing or trap which may attract an insect to enter it is included within the scope of the invention. The housing or trap may be box-shaped for example, and may be provided in pre-formed condition or may be formed of foldable cardboard for example. Suitable materials for a housing or trap include plastics and cardboard, particularly corrugated cardboard. Suitable dimensions for such a housing or trap are, for example, 7-15 cm wide, 15-20 cm long and 1-5 cm high. The inside surfaces of the traps may be lined with a sticky substance in order to restrict movement of the insect once inside the trap. The housing or trap may contain a suitable trough inside which can hold the bait in place. A trap is distinguished from a housing because the insect can not readily leave a trap following entry, whereas a housing acts as a "feeding station" which provides the insect with a preferred environment in which they can feed and feel safe from predators.

Accordingly, in a further aspect the invention provides a housing or trap for insects which contains a composition of the invention, which may incorporate any of the features of the composition described herein.

In a further alternative embodiment, the composition may be provided in the form of a spray. Thus, a human user can spray the pest directly with the composition. The composition is then internalized by the insect, from where it can mediate RNA interference, thus controlling the insect. The spray is preferably a pressurized/aerosolized spray or a pump spray. The particles may be of suitable size such that they adhere to the insect, for example to the exoskeleton, and may be absorbed therefrom. Particle size may be measured by known means, such as by use of a Mastersizer, which is a commercially available device.

In a still further embodiment, the carrier is an electrostatically charged powder or particle which adheres to the insect. Suitable powders and particles which are capable of adhering to an insect and thus delivering the RNA constructs of the invention are described in detail in WO 94/00980 and WO 97/33472, both of which are incorporated herein by reference.

Alternatively, the carrier may comprise magnetic particles which adhere to the insect cuticle. Suitable magnetic particles which are capable of adhering to an insect and thus delivering the RNA constructs of the invention are described in detail in WO 00/01236, which reference is incorporated herein.

In a still further embodiment, the carrier of the composition comprises metallic particles which are initially unmagnetised but which are capable of becoming magnetically polarised when subjected to the electrical field provided by the insect body. This mode of action is described in detail in WO 2004/049807 and is incorporated by reference herein.

Preferably, the composition incorporates a carrier which increases the uptake of the interfering RNA into the insect pest. Such a carrier may be a lipid-based carrier, preferably comprising one or more of, oil-in water emulsions, micelles, cholesterol, lipopolyamines and liposomes. Other agents which promote uptake of the constructs of the invention are well known to those of skill in the art and include polycations, dextrans and (tris) cationic lipids, such as CS096, CS102 etc. Commercially available liposomes include LIPOFECTIN® and CELLFECTIN® etc. A number of suitable carriers are listed under the heading "Transfection promoting agent" in WO 03/004644 and each of the examples provided is hereby incorporated by reference.

In a further preferred embodiment, the carrier is a nucleic acid condensing agent. Preferably, the nucleic acid condensing agent comprises spermidine or protamine sulphate or a derivative thereof. Wherein the composition of the invention is for use in preventing and/or controlling pest infestation of a plant, the composition can contain an agriculturally suitable carrier. Such a carrier may be any material that the plant to be treated can tolerate, which does not cause undue damage to the environment or other organisms therein and, which allows the interfering RNA to remain effective against the insect pest species. In particular, the compositions of the invention may be formulated for delivery to plants in accordance with routine agricultural practices used in the bioinsecticide industry. The composition may contain further components capable of performing other functions including but not limited to (i) enhancement or promotion of uptake of the interfering RNA by cells of the pest and (ii) stabilization of the active components of the composition. Specific examples of such further components contained in the composition comprising the interfering RNA, are yeast tRNA or yeast total RNA.

The compositions may be formulated for direct application or as a concentration of a primary composition that requires dilution prior to use. Alternatively, the composition may be supplied as kit comprising the interfering RNA or the host cell comprising or expressing the same in one container and the suitable diluent or carrier for the RNA or host cell in a separate container. In the practical application of the invention, the composition may be applied to a plant or any part of a plant at any stage of the plant's development. In one embodiment, the composition is applied to the aerial parts of a plant, for example during cultivation of plant crops in a field. In a further embodiment, the composition is applied to the seeds of a plant either while they are in storage or once they are planted in the soil. It is generally important to obtain good control of pests in the early stages of plant growth as this is the time when the plant can be most severely damaged by pest species.

The composition may be applied to the environment of an insect pest by various techniques including but not limited to spraying, atomizing, dusting, scattering, pouring, coating of seeds, seed treatment, introduction into the soil, and introduction into irrigation water. In the treatment of plants susceptible to pest infestation, the composition may be delivered to the plant or part of a plant before the appearance of the pest (for the purposes of prevention), or once signs of pest infestation begin to appear (for the purposes of pest control).

In a further embodiment of the invention, the compositions of the invention may be formulated so as to contain at least one further active agent. Thus, the composition may be provided as a "kit-of-parts" comprising the interfering RNA containing composition in one container and one or more suitable active ingredients, for example a chemical or biological pesticide, in a separate container. Alternatively, the compositions may be provided as a mixture which are stable and to be used in conjunction with one another.

Suitable active ingredients which may act in a complementary manner to the interfering RNA molecules of the present invention include, but are not limited to the following: Chlorpyrifos, Allethrin, Resmethrin, Tetrabromoethyl, Dimethol-cyclopropane carboxylic acid (which are generally included in liquid compostions); and Hydramethylnon, Avermectin, Chlorpyrifos, Sulfuramid, Hydroprene, Fipronil (GABA receptor), Isopropylphenyl methyl carbamate. Indoxacarb (PARA), Noviflumuron (Chitinsynthesis inhibitor), Imiprothrin (PARA), Abamectin (Glutamate-gated Chloride channel), Imidacloprid (Acethylcholin receptor) (which are generally included in bait compositions).

In a preferred embodiment, the active ingredient is known to be a preferred insecticide in terms of health and environmental considerations, such as for instance Hydramethylnon and Avermectin.

In a further embodiment of the invention, the composition is formulated so as to contain at least one further agronomical agent, for example a herbicide or an additional pesticide. As used herein, a 'second pesticide' or 'additional pesticide' refers to a pesticide other than the first or original interfering RNA molecule of the composition. Alternatively, the composition of the invention may be delivered in combination with at least one other agronomical agent, for a example a herbicide or a second pesticide. In one embodiment, the composition is provided in combination with a herbicide selected from any known in the art, for instance glyphosate, imidazolinone, sulphonylurea and bromoxynil. In a further embodiment, the composition is provided in combination with at least one additional pesticide. The additional pesticide may be selected from any pesticides known in the art and/or may comprise an interfering ribonucleic acid that functions upon uptake by a pest to down-regulate expression of a target gene in said pest species. In one embodiment, the target pest is an insect pest species and the interfering RNA is selected from any of the interfering RNAs as described herein. In a further embodiment, the additional pesticide comprises an interfering RNA that functions to down-regulate expression of a known gene in any target pest species, not limited to insect pests. The original interfering RNA molecule of the composition and the second or additional pesticide(s) may target the same insect pest species or may be intended to target different insect pest species. For example, the original interfering RNA and the second pesticide may target different species of insect pest or may target different families or classes of pest organisms, for example, fungi or nematodes or insects. It will be apparent to one skilled in the art how to test combinations of interfering RNA molecules and other agronomical agents for synergistic effects. In a preferred embodiment, the composition contains a first interfering RNA molecule described elsewhere herein and one or more additional pesticides, each toxic to the same insect pest, wherein the one or more additional pesticides are selected from a patatin, a *Bacillus thuringiensis* insecticidal protein, a *Xenorhabdus* insecticidal protein, a *Photorhabdus* insecticidal protein, a *Bacillus laterosporous* insecticidal protein, a *Bacillus spaericus* insecticidal protein, and a lignin, and wherein said *Bacillus thuringiensis* insecticidal protein is selected from the group consisting of a Cry1Ab, a Cry1C, a Cry2Aa, a Cry3, a TIC851, a CryET70, a Cry22, a VIP, a TIC901, a TIC1201, a TIC407, a TIC417, a binary insecticidal protein selected from CryET33 and CryET34, CryET80 and CryET76, TIC100 and TIC101, and PS149B1, and insecticidal chimeras of any of the preceding insecticidal proteins.

The different components of the combinations described herein may be administered, for example to a host organism susceptible to infestation by pest, in any order. The components may be delivered simultaneously or sequentially to the area or organism to be treated.

Also provided herein is a method for preventing and/or controlling pest infestation, comprising contacting an insect pest species with an effective amount of at least one interfering RNA wherein the RNA functions upon uptake by said pest to down-regulate expression of an essential pest target gene. The essential target gene may be any pest gene involved in the regulation of an essential biological process required by the pest to initiate or maintain infestation including but not limited to survival, growth, development, reproduction and pathogenicity. In particular, the target gene may be any of the pest genes as described elsewhere herein.

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides of any of SEQ ID NOs 1, 174, 404, 180, 188, 2, 175, 181, 189, 27 to 30, 282 to 285, 294 to 297 or 310 to 313, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae* (Mexican corn rootworm). In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 1, 174, 404, 180, 188, 2, 175, 181, 189, 27 to 30, 282 to 285, 294 to 297 or 310 to 313, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae* (Mexican corn rootworm), wherein the orthologous genes encode a protein having an amino acid sequence which is at least 85%, 90%, 92%, 94%, 96%, 98%, 99% identical the amino acid sequence as presented in any of SEQ ID NOs 79, 349, 405, 352 or 356 (when said encoded proteins are optimally aligned).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 141, 11, 12, 47 to 50, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae* (Mexican corn rootworm).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 141, 11, 12, 47 to 50, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae* (Mexican corn rootworm), wherein the orthologous genes encode a protein having an amino acid sequence which is at least 85%, 90%, 92%, 94%, 96%, 98%, 99% identical to the amino acid sequence as presented in any of SEQ ID NOs 328 or 84 (when said encoded proteins are optimally aligned).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 17, 18, 59 to 62, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae* (Mexican corn rootworm).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 17, 18, 59 to 62, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae* (Mexican corn rootworm), wherein the orthologous genes encode a protein having an amino acid sequence which is at least 85%, 90%, 92%, 94%, 96%, 98%, 99% identical to the amino acid sequence as presented in SEQ ID NOs 87 (when said encoded proteins are optimally aligned).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 19, 20, 63 to 66, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae* (Mexican corn rootworm).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 19, 20, 63 to 66, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae* (Mexican corn rootworm), wherein the orthologous genes encode a protein having an amino acid sequence which is at least 85%, 90%, 92%, 94%, 96%, 98%, 99% identical to the amino acid sequence as presented in SEQ ID NOs 88 (when said encoded proteins are optimally aligned).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 165, 167, 166, 270 to 273, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae* (Mexican corn rootworm). In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 165, 167, 166, 270 to 273, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae* (Mexican corn rootworm), wherein the orthologous genes encode a protein having an amino acid sequence which is at least 85%, 90%, 92%, 94%, 96%, 98%, 99% identical to the amino acid sequence as presented in any of SEQ ID NOs 347 or 348 (when said encoded proteins are optimally aligned).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 143, 121, 142, 176, 182, 130, 177, 183, 206 to 209, 286 to 289, 298 to 301, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae* (Mexican corn rootworm).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 143, 121, 142, 176, 182, 130, 177, 183, 206 to 209, 286 to 289, 298 to 301, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae* (Mexican corn rootworm), wherein the orthologous genes encode a protein having an amino acid sequence which is at least 85%, 90%, 92%, 94%, 96%, 98%, 99% identical to the amino acid sequence as presented in any of SEQ ID NOs 330, 350 or 353 (when said encoded proteins are optimally aligned).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 145, 122, 144, 178, 131, 179, 210 to 213, 290 to 293, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae* (Mexican corn rootworm).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 145, 122, 144, 178, 131, 179, 210 to 213, 290 to 293, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae* (Mexican corn rootworm), wherein the orthologous genes encode a protein having an amino acid sequence which is at least 85%, 90%, 92%, 94%, 96%, 98%, 99% identical to the amino acid sequence as presented in any of SEQ ID NOs 331 or 351 (when said encoded proteins are optimally aligned).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 128, 149, 184, 137, 185, 234 to 237, 302 to 305, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae* (Mexican corn rootworm).

In the methods described herein to down-regulate expression of a target gene in an insect pest species, double stranded RNA molecules comprising at least 21 bp, one strand of which comprises or consists of a sequence of nucleotides which is complementary to at least 21 contiguous nucleotides in any of SEQ ID NOs 128, 149, 184, 137, 185, 234 to 237, 302 to 305, or the complement thereof, can be used to down-regulate expression of the orthologous target gene in a coleopteran, hemipteran, lepidoteran or dipteran insect chosen from the group comprising but not limited to *Leptinotarsa* spp. (e.g. *L. decemlineata* (Colorado potato beetle), *L. juncta* (false potato beetle), or *L. texana* (Texan false potato beetle)); *Nilaparvata* spp. (e.g. *N. lugens* (brown planthopper)); *Lygus* spp. (e.g. *L. lineolaris* (tarnished plant bug) or *L. hesperus* (western tarnished plant bug)); *Myzus* spp. (e.g. *M. persicae* (green peach aphid)); *Diabrotica* spp. (e.g. *D. virgifera virgifera* (western corn rootworm), *D. barberi* (northern corn rootworm), *D. undecimpunctata howardi* (southern corn rootworm) or *D. virgifera zeae* (Mexican corn rootworm), wherein the orthologous genes encode a protein having an amino acid sequence which is at least 85%, 90%, 92%, 94%, 96%, 98%, 99% identical to the amino acid sequence as presented in any of SEQ ID NOs 337 or 354 (when said encoded proteins are optimally aligned).

Furthermore, there is provided herein a method for preventing and/or controlling insect pest infestation in a field of crop plants, said method comprising expressing in said plants an effective amount of an interfering RNA as described herein.

Wherein the method is for the control of pest infestation, the phrase 'effective amount' extends to the quantity or concentration of interfering RNA required to produce a phenotypic effect on the pest such that the numbers of pest organisms infesting a host organism are reduced and/or the amount of damage caused by the pest is reduced. In one embodiment, the phenotypic effect is death of the pest and the interfering RNA is used to achieve at least 20%, 30%, 40%, preferably at least 50%, 60%, 70%, more preferably at least 80% or 90% pest mortality as compared to control insect pests. In a further embodiment, the phenotypic effects include but are not limited to stunting of pest growth, cessation of feeding and reduced egg-laying. The total numbers of pest organisms infesting a host organism may thus be reduced by at least 20%, 30%, 40%, preferably at least 50%, 60%, 70%, more preferably at least 80% or 90% as compared with control pests. Alternatively, the damage caused by the insect pest may be reduced by at least 20%, 30%, 40%, preferably at least 50%, 60%, 70%, more preferably at least 80% or 90% as compared with control insect pests. Hence, the method of the invention can be used to achieve at least 20%, 30%, 40%, preferably at least 50%, 60%, 70%, more preferably at least 80% or 90% pest control.

As used herein, the term 'plant' may include any reproductive or propagation material for a plant. Reference to a plant may also include plant cells, plant protoplasts, plant tissue cultures, plant calli, plant clumps and plant cells that are intact in plants or parts of plants such as embryos, pollen, ovules, seeds, leaves, flowers, branches, fruit, kernels, ears, cobs, husks, stalks, roots, root tips and the like.

Also provided herein is the use of the interfering ribonucleic acid (RNA) as described herein or the DNA construct as described herein for preventing and/or controlling insect pest infestation, preferably insect pest infestation of plants.

The invention will be further understood with reference to the following non-limiting examples.

EXAMPLES

Example 1

Identification of Target Genes in Insect Pest Species 1.1. *Lygus hesperus* Normalized cDNA Library and Preparation of dsRNAs in Multiwell Plates for the Screening Assays Nucleic acids were isolated from *Lygus hesperus* nymphs of different life stages, including freshly hatched nymphs 2, 4, 6 and 9 days old nymphs and adults. A cDNA library was prepared using the SMARTer™ PCR cDNA Synthesis Kit, following the manufacturer's instructions (Clontech Cat. No 634925). The cDNA library was normalized using the Trimmer kit (Evrogen Cat No NK001) and cloned in the PCR4-TOPO vector (Invitrogen). The normalization of the clones introduced M2 adapters (Trimmer Kit, Evrogen, SEQ ID NO 92: AAGCAGTGGTATCAACGCAG), oppositely oriented at each end of the clones. The recombinant vector constructs were transformed into cells of *Escherichia coli* strain TOP10 (Invitrogen). The transformed cells were subsequently diluted and plated so as to obtain single colonies or clones. The clones were checked to ensure that clone redundancy for the library did not exceed 5%. Single clones were picked in liquid LB (Luria-broth) media, in 96-deep-well plates, and grown overnight at 37° C. The plates also included positive (Lh423) and negative (FP) control clones.

To generate the dsRNA, sense and antisense DNA fragments, containing T7 promoter sequence, were generated by PCR. In brief, per clone, 1 µl of bacterial suspension was dispensed in multiwell PCR plates containing REDTaq® (Sigma Cat No D4309) and primers oGCC2738 (SEQ ID NO 93: AAGCAGTGGTATCAACGCAG) and oGCC2739 (SEQ ID NO 94: GCGTAATACGACTCACTATAG-GAAGCAGTGGTATCAACGCAG) based on the M2 and the T7-M2 sequences respectively. The PCR reaction was followed by in vitro transcription, where per clone, 6 µl PCR product were added to 9 µl RiboMAX™ Large Scale RNA Production System-T7 (Promega Cat No P1300) and incubated overnight at 37° C. The final dsRNA solution was diluted 2 times in *L. hesperus* sucrose diet, containing 15% sucrose and 5 µg/µl yeast tRNA (Invitrogen Cat No 15401-029) and used for screening. The dsRNA corresponding to the positive Lh423 control clone is SEQ ID NO 101 and to the negative FP control clone is SEQ ID NO 104 (see Table 4).

1.2. Screen for Novel and Potent *Lygus hesperus* Target Genes Using a dsRNA Expression cDNA Library A new screening assay for potent *Lygus hesperus* targets has been developed. The assay set-up was as follows: each well of a 96-well plate houses a one-day-old *L. hesperus* nymph exposed to a parafilm sachet containing sucrose diet which includes either test dsRNA or control dsRNA in the presence of tRNA. Each plate contained dsRNA from 90 different clones, 3×Lh423 (positive control) and 3×FP (fluorescent protein; negative control). Each clone (test dsRNA) was replicated over three plates. After three days exposure, the nymphal survival number was recorded and the diet replaced with fresh rearing (complex) diet in absence of dsRNA. The mortality was assessed at days 4, 6 and 8. An identical set up was used for the first and second round confirmation assays, with 8 and 20 insects respectively, with one nymph per well.

The assay system was validated using dsRNA corresponding to Lh423 target as the positive control and a fluorescent protein dsRNA as the negative control: over 90% were true positives and under 5% were false positives, respectively.

Twenty 96 well-plates, named Lh001 to Lh020 (see bottom line in FIGS. 1 & 2), containing 1800 individual clones have been tested. 205 candidates were identified and tested in a first confirmation assay. Setting the threshold at showing ≥50% mortality, 41 independent clones were identified and progressed to a second round of confirmation. In the assay, the clones were compared to the positive controls Lh423 (RpL19) and Lh105.2 (Sec23) and the negative control Pt (encoding a coral fluorescent protein). The dsRNA corresponding to the positive (Lh423) control clone is SEQ ID NO 101, to the positive Lh105.2 control clone is SEQ ID NO 102 and to the negative (Pt) control clone is SEQ ID NO 104 (see Table 4).

Second round confirmation assays, testing 20 insects/test dsRNA, were initiated for all the test dsRNAs displaying ≥50% mortality in the first confirmation (FIGS. 1 and 2). Candidate targets corresponding to the confirmed test dsRNAs were named with an "Lhxxx number" (see Table 1). Using the same cut-off at ≥50% mortality, 15 targets were confirmed in the first screen.

A second screen for identifying more *Lygus hesperus* targets was performed. The results of the second round confirmation assays are represented in FIG. 12. Using the same cut-off at 50% mortality, several targets were confirmed in the second screen (see Table 1 C).

1.3. Identification of *Lygus* Targets

In parallel to the confirmation insect assays, the inserts corresponding to the positive clones were sequenced and BlastX searches against both *Drosophila* and *Tribolium* protein databases were used to confirm the identity of the targets. Table 1 provides a summary of the bio-informatics analysis and current annotation of the novel identified *L. hesperus* target sequences.

Fifteen novel *L. hesperus* targets were identified in the first screen and 11 novel *L. Hesperus* targets were identified in the second screen. All targets exhibit high potency against *L. hesperus* nymphs indicating that the cDNAs encoding double-stranded RNAs contained therein are essential for pest survival and thus represent target genes of interest for the purposes of pest control. The DNA sequences and deduced amino acid sequences of these target genes were therefore determined and are provided in Tables 2 and 3 respectively.

Lh594, the *Lygus hesperus* orthologue of *Drosophila* troponin I, involved in muscle contraction- and therefore absent in plants-, represents a novel class of target belonging to an animal specific physiological pathway not yet explored for GM-RNAi. In the fruit fly, troponin I is described as a haplo-insufficient gene, displaying a mutant phenotype in the heterozygote state. Such genes may be particularly susceptible to reduced mRNA expression levels and as such can be considered as ideal RNAi targets.

In this Lh594 pathway, eight targets were selected (see Table 1B). For each target, up to 4 pairs of degenerated PCR primers were designed based on the alignments of the sequences of various insects, including bee, *Tribolium* and aphid. The primers are being used to amplify fragments from *Lygus hesperus* targets. The DNA sequences and deduced amino acid sequences of these target genes were determined and are provided in Tables 2 and 3 respectively.

TABLE 1

*Lygus hesperus* novel targets ranked in % mortality according to the second confirmation assay results (first screen).

| Target ID | rank 2nd confirmation | Best *Drosophila* hit | NAME | SYMBOL |
|---|---|---|---|---|
| Lh594 | 1 | CG7178 | wings up A (troponin I) | wupA |
| Lh618 | 2 | CG2168 | ribosomal protein S3A | RpS3A |
| Lh609 | 3 | CG4087 | ribosomal protein LP1 | RpLP1 |
| Lh595 | 4 | — | no *Drosophila* hit found, *Lygus* specific target/sequence | |
| Lh611 | 5 | CG6779 | ribosomal protein S3 | RpS3 |
| Lh560 | 6 | CG10423 | ribosomal protein S27 | RpS27 |
| Lh596 | 7 | — | no *Drosophila* hit found, *Lygus* specific target/sequence | RpL34b |

TABLE 1-continued

Lygus hesperus novel targets ranked in % mortality according to the second confirmation assay results (first screen).

| Target ID | rank 2nd confirmation | Best Drosophila hit | NAME | SYMBOL |
|---|---|---|---|---|
| Lh615 | 8 | CG11522 | ribosomal protein L6 | RpL6 |
| Lh617 | 9 | CG7283 | ribosomal protein L10Ab | RpL10Ab |
| Lh612 | 10 | CG13389 | ribosomal protein S13 | RpS13 |
| Lh246 | 11 | CG3195 | ribosomal protein L12 | RpL12 |
| Lh429 | 12 | CG8900 | ribosomal protein S18 | RpS18 |
| Lh610 | 13 | CG5502 | ribosomal protein L4 | RpL4 |
| Lh597 | 14 | no hit found | | |
| Lh598 | 15 | CG34069 | mitochondrial cytochrome c oxidase subunit II | mt: CoII |
| Lh614 | — | CG7610 | ATP synthase-γ chain | ATPsyn-γ |

TABLE 1B

Lygus hesperus novel targets in Lh594 pathway

| Target ID | Best Drosophila hit(s) | NAME | SYMBOL |
|---|---|---|---|
| Lh619 | CG7107 | troponin T (upheld) | up |
| Lh620 | CG17927 | myosin heavy chain | Mhc |
| Lh621 | CG4843 | tropomyosin2 (Tm2) | Tm2 |
| Lh622 | CG3201 | myosin light chain cytoplasmic | Mlc-c |
| Lh623 | CG3595 | spaghetti squash | sqh |
| Lh624 | CG15792 | zipper | zip |
| Lh625 | *CG2981, CG7930, CG9073, CG6514, CG12408 | troponin C | |
| Lh626 | *CG9073, CG7930, CG2981, CG12408, CG6514 | troponin C | |

*unclear: multiple hits in family-ranked according e-value

TABLE 1C

Lygus hesperus novel targets ranked in % mortality according to the second confirmation assay results (second screen).

| Target ID | rank 2nd confirmation | Best Drosophila hit | NAME | SYMBOL |
|---|---|---|---|---|
| Lh631 | 1 | CG6846 | Ribosomal protein L26 | RpL26 |
| Lh634.2 | 2 | CG12775 | Ribosomal protein L21 | RpL21 |
| Lh634.1 | 3 | CG12775 | Ribosomal protein L21 | RpL21 |
| Lh630 | 4 | CG11271 | Ribosomal protein S12 | RpS12 |
| Lh632 | 5 | CG2998 | Ribosomal protein S28b | RpS28b |
| Lh618.2 | 6 | CG2168 | Ribosomal protein S3A | RpS3A |
| Lh629 | 7 | CG4651 | Ribosomal protein L13 | RpL13 |
| Lh633.2 | 8 | CG17521 | Ribosomal protein L10 | RpL10 |
| Lh628 | 9 | CG17489 | Ribosomal protein L5 | RpL5 |
| Lh633 | 10 | CG17521 | Ribosomal protein L10 | RpL10 |
| Lh627 | 11 | CG2033 | Ribosomal protein S15Aa | RpS15A |

1.4. Full Length cDNA Cloning by RACE (Rapid Amplification of cDNA Ends)

In order to clone full length cDNA, starting from a known clone of internal fragment from the most potent targets, the 5'/3' RACE kit was used (Roche, Cat. No. 1 734 792; based on Sambrook, J. & Russell, D.M). The standard protocol, described in the Instruction Manual, was followed. Briefly, for a 5' RACE, a target sequence specific antisense primer was designed on the known sequence and used for a first strand cDNA synthesis, using Lygus RNA as template. A tail was added to the first strand cDNA and used as an anchor for the second strand synthesis and amplification of an unknown end portion of the transcript. For a 3' RACE, an oligo dT anchor primer was used for the first strand cDNA synthesis. For the 5' and 3' RACEs, nested primers, specific to the target sequence were used in a second PCR reaction. The PCR fragments were analysed on agarose gel, purified, cloned and sequenced for confirmation.

Full length cDNA sequences corresponding to the targets were assembled in VectorNTi, a fully integrated sequence analysis software package for DNA sequence analysis (Invitrogen).

Example 2

In Vitro Production of Double-stranded RNAs for Gene Silencing 2.2. Production of dsRNAs Corresponding to the Partial Sequences of the Lygus hesperus Target Genes Double-stranded RNA was synthesized in milligram quantities. First, two separate 5' T7 RNA polymerase promoter templates (a sense template and an antisense template) were generated by PCR. PCRs were designed and carried out so as to produce sense and antisense template polynucleotides, each having the T7 promoter in a different orientation relative to the target sequence to be transcribed.

For each of the target genes, the sense template was generated using a target-specific T7 forward primer and a target-specific reverse primer. The antisense templates were generated using target-specific forward primers and target-specific T7 reverse primers. The sequences of the respective primers for amplifying the sense and antisense templates via PCR for each of the target genes are provided in Table 4. The PCR products were analysed by agarose gel electrophoresis and purified. The resultant T7 sense and antisense templates were mixed and transcribed by the addition of T7 RNA polymerase. The single-stranded RNAs produced by transcription from the templates were allowed to anneal, were treated with DNase and RNase, and were purified by precipitation. The sense strand of the resulting dsRNA produced from each of the target genes is provided in Table 4.

2.2. Survival Analysis Assays for Novel Lygus hesperus Targets

To enable ranking according to potency, in vitro dsRNAs corresponding to the novel targets were synthesized and applied to L. hesperus in 10 days survival analysis bioassays. Briefly, one day old L. hesperus nymphs were placed in 96 well-plates with sucrose seals containing 0.544 target dsRNA, supplemented with 5 µg/µl yeast tRNA. The plates were incubated for 3 days under standard Lygus rearing conditions. At day 3, 6 and 8, the diet seals were refreshed with seals containing Lygus diet only. Lh423 (RpL19) was used as positive control and GFP dsRNA and sucrose diet were used as negative controls.

The results from the survival analyses confirmed the data from the first and second confirmation assays. Lh594 was established as a highly potent target, with activity and speed-to-kill stronger than the strong control Lh423.

So far, the *Lygus* screen for novel targets identified new targets with activities higher or in the range of the positive control Lh423, these include Lh429, Lh594, Lh609, Lh610, Lh611, Lh617 and Lh618. The mortality induced by these targets is show in the FIGS. 3 and 4.

To allow a more precise ranking of the targets according to their activity, dose response concentration analyses were made. The novel targets were tested in in vitro assays, with concentrations ranging from 0.4 to 0.025 µg/µl. Per condition, 24 one day old nymphs were tested in the 96 well-plate set-up, in sucrose diet supplemented with dsRNA and tRNA carrier. The results are presented as % survival over a 10 day experiment (FIGS. 5 to 9) and are summarized in Table 5.

Based on the concentration curve analyses, the targets were ranked by comparison to the bench mark controls Lh423 and Lh105 (Table 5).

TABLE 5

*Lygus* novel targets ranking according to DRCs and compared to bench mark targets Lh423 & Lh105.

| Target ID | Potency expressed as µg/µl dsRNA needed to reach 90% kill at day 7 |
|---|---|
| Lh594 | 0.025 (at day 6) |
| Lh618 | 0.05-0.1 |
| Lh612 | 0.05 |
| Lh615 | 0.05 |
| Lh423 | 0.1 |
| Lh595 | 0.1 |
| Lh560 | 0.1 |
| Lh610 | 0.1 |
| Lh617 | 0.1 |
| Lh105 | 0.2 |
| Lh614 | 0.2 (at day 6) |
| Lh611 | 0.2 |
| Lh596 | 0.3 |
| Lh609 | ND |
| Lh429 | ND |

The potency of Lh594 was further confirmed. This target effect is clearly observed at least one day before the other targets and the bench mark positive control Lh105 and Lh423. Because Lh594 was highly potent, the LD50 was not reached in the standard DRC experiment, with concentration ranging from 0.4 to 0.025 µg/µl dsRNA (FIG. 6), the Lh594 experiment was therefore repeated, including lower concentrations ranging from 0.05 to 0.001 dsRNA (FIG. 10). In conclusion, Lh594 activity was observed at concentration as low as 0.0025 and about 90% kill (corresponding to about 10% survival) was obtained at day 6 with 0.025 µg dsRNA.

To further explore the potency of Lh594 and the role of tRNA carrier in the RNAi response in *Lygus hesperus*, additional in vitro feeding assays were set up in the absence of carrier tRNA. Lh594, Lh423 (bench mark control) and GFP (negative control) dsRNAs were produced in vitro, using the standard method. The dsRNAs were purified and tested at 5 µg/µl in the absence of tRNA (FIG. 11 A).

In absence of tRNA, targets Lh594 and Lh423, induced high lethality in *Lygus* nymphs. The results from this experiment have been since reproduced. Target dsRNA was able to induce RNAi-by-feeding effects in *Lygus* nymphs in the absence of tRNA.

To investigate the activity of dsRNA at lower concentrations in the absence of carrier tRNA, additional experiments were set up, using decreasing amounts of dsRNA (FIG. 11 B).

A similar approach was followed for the *Lygus* targets that were identified in the second screen. To allow a ranking of the targets according to their activity, dose response concentration analyses were made. The novel targets were tested in in vitro assays, with concentrations ranging from 0.5 to 0.05 µg/µl. Per condition, 24 one day old nymphs were tested in the 96 well-plate set-up, in sucrose diet supplemented with dsRNA and tRNA carrier. The results are presented as % survival over a 9 day experiment (FIGS. 15 A-D). Lh594 and Lh423 have been included in the assay as a reference targets. The results are summarized in Table 6. Based on the concentration curve analyses, the targets were ranked by comparison to the bench mark control Lh423.

TABLE 6

*Lygus* novel targets from second screen-ranking according to DRCs and compared to bench mark targets Lh423 & Lh594.

| Target ID | Potency expressed as µg/µl dsRNA needed to reach 90% kill at day 7 |
|---|---|
| Lh594 | 0.025 (at day 6) |
| Lh634 | 0.1 |
| Lh423 | 0.1 |
| Lh631 | 0.4 |
| Lh633 | 0.4 |
| Lh627 | 0.5 |
| Lh628 | 0.5 |
| Lh630 | 0.5 |
| Lh632 | 0.5 |
| Lh629 | ND |

Example 3

Troponin Pathway Screen

To enable testing of the Troponin pathway targets, in vitro produced dsRNAs corresponding to Lh619, Lh620, Lh621, Lh622, Lh622, Lh623, Lh624, Lh625 and Lh626 were synthesized and applied to *L. hesperus* in 10 days survival analysis bioassays. Briefly, one day old *L. hesperus* nymphs were placed in 96 well-plates with sucrose seals containing 0.5 µg/µl target dsRNA, supplemented with 5 µg/µl yeast tRNA. The plates were incubated for 3 days under standard *Lygus* rearing conditions. At day 3, 6 and 8, the diet seals were refreshed with seals containing *Lygus* diet only. Lh594 (Troponin I) was used as positive control and GFP dsRNA and sucrose diet were used as negative controls (FIG. 13). Four targets were then included in dose response curve analyses in an in vitro assay, with concentrations ranging from 0.4 to 0.025 µg/µl. Per condition, 24 one day old nymphs were tested in the 96 well-plate set-up, in sucrose diet supplemented with dsRNA and tRNA carrier. The results are presented as % survival over a 10 day experiment (FIGS. 14 A-B).

Example 4

Identification of Target Genes in *Leptinotarsa decemlineata*

4.1. *Leptinotarsa decemlineata* Normalized cDNA Library and Preparation of dsRNAs in Multiwell Plates for the Screening Assays Nucleic acids were isolated from *Leptinotarsa decemlineata* larvae of different stages. A cDNA library was prepared using the SMARTer™ PCR cDNA Synthesis Kit, following the manufacturer's instructions (Clontech Cat. No 634925).

The cDNA library was normalized using the Trimmer kit (Evrogen Cat No NK001) and cloned in the PCR®-BLUNTII-TOPO® vector (Invitrogen). The normalization of the clones introduced M2 adapters (Trimmer Kit, Evrogen, SEQ ID NO 92: AAGCAGTGGTATCAACGCAG), oppositely oriented at each end of the clones. The recombinant vector constructs were transformed into cells of Escherichia coli strain TOP10 (Invitrogen). The transformed cells were subsequently diluted and plated so as to obtain single colonies or clones. The clones were checked to ensure that clone redundancy for the library did not exceed 5%. Single clones were inoculated into liquid LB (Luria-broth) media, in 96-well plates, and grown overnight at 37° C. The plates also included positive (Ld513) and negative (FP) control clones.

To generate the dsRNA, sense and antisense DNA fragments, containing T7 promoter sequence, were generated by PCR. In brief, per clone, 1 µl of bacterial suspension was dispensed in multiwell PCR plates containing REDTaq® (Sigma Cat No D4309) and primers oGCC2738 (SEQ ID NO 93: AAGCAGTGGTATCAACGCAG) and oGCC2739 (SEQ ID NO 94: GCGTAATACGACTCACTATAG-GAAGCAGTGGTATCAACGCAG) based on the M2 and the T7-M2 sequences, respectively. The PCR reaction was followed by in vitro transcription, where, per clone, 6 µl PCR product was used in a 20 µl reaction volume containing the transcription reagents provided by the RiboMAX™ Large Scale RNA Production System-T7 kit (Promega Cat No P1300) and incubated overnight at 37° C. The final dsRNA solution was diluted in sterile Milli-Q water and used for screening. The dsRNA corresponding to the positive Ld513 control clone is SEQ ID NO 400 (see Table 9) and to the negative FP control clone is SEQ ID NO 104 (see Table 4).

4.2. Screen for Novel and Potent *Leptinotarsa decemlineata* Target Genes Using a dsRNA Expression cDNA Library Each well of a 48-well plate contained 0.5 mL artificial diet pretreated with a topical overlay of 25 μl (or 1 μg) of the test or control dsRNA. One L2 larva was placed in each well and 3 larvae were tested per clone. CPB survival numbers were assessed at days 4, 7 and 10.

In a second bioassay, CPB larvae were fed on diet treated with topically applied test dsRNA generated from clones derived from a normalized cDNA library. One larva was placed in a well of a 48-well multiplate containing 0.5 mL diet pretreated with a topical overlay of 25 μL of a 40 ng/μL dsRNA solution. A total of twenty-four larvae were tested per treatment (clone). The number of surviving insects were assessed at days 4, 5, 6, 7, 8 & 11. The larval mortality percentage was calculated relative to day 0 (start of assay) (see FIG. 21).

4.3. Identification of *L. decemlineata* Beetle Targets

The new target sequences from the screen in 5.2. and the target sequences corresponding to the troponin pathway targets, orthologuous to the *Lygus* Lh594, Lh619 and Lh620 sequences, have been identified in *L. decemlineata*. The primers which provided relevant cDNA fragment for Ld594 are listed in Table 17. The cDNA sequences and deduced amino acid sequences of these target genes were determined and are provided in Tables 7 and 9 respectively.

4.4. Production of dsRNAs Corresponding to the Partial Sequences of the *L. decemlineata* Target Genes dsRNA was synthesized using the primers as provided in Table 9. The sense strand of the resulting dsRNA produced from the target genes is provided in Table 9.

4.5. Survival Analysis Assays for Novel *L. decemlineata* Targets

Early Larval Assay

Synthetic dsRNAs were produced for the 3 targets, Ld594, Ld619 and Ld620, and were tested in a feeding assay on CPB larvae (see FIG. 16). A 10 day assay was performed in 48 well plates, on artificial diet (based on Gelman et al, J Ins Sc, 1:7, 1-10: Artificial diets for rearing the Colorado Potato Beetle), supplemented with 1 μg dsRNA/well, with 12 larvae per condition.

A clear effect on the development of the larvae could be observed. A second assay was set up to investigate the effect of these dsRNAs during the course of pupation and metamorphosis (see pupation assay underneath).

Pupation Assay

A CPB pupation assay was set up to investigate the effect of RNAi knock-down of Ld594, Ld619 and Ld620 during pupation and metamorphosis. Fourth instar larvae were fed 1 μg in vitro synthesized dsRNA dispensed on a potato leaf disk and were then transferred to a box containing untreated fresh potato leaves. Four days later the surviving insects were placed on vermiculite to allow pupation. Lh594 treated insects were slow, smaller and mostly were unable to go through pupation. The hatching of the pupa was assessed at the end of the experiment. For the untreated control 24 larvae pupated and all hatched into healthy adults. For Ld620, a decrease in numbers of larvae progressing into pupation was observed. For the three targets tested, no larvae progressed into healthy pupae and none emerged into adult. Dead insects recovered from the vermiculite showed various degrees of malformations (FIG. 17).

Ld594, Ld619 and Ld620, first appeared as not lethal targets in the CPB larval assay, although a reduction of vitality was clearly observed in the dsRNA treated insects. On the other hand, in the pupation assay, all 3 targets induced strong effects and inhibited the entry in pupation and/or metamorphosis.

Adult Assay

To assess activity of Ld594, Ld619 and Ld620 in CPB adults, a leaf disc assay was set up. A potato leaf disc (1.7 cm diameter) was painted with dsRNA or controls and was placed in a 3.5 cm Petri dish with one adult beetle. The next day a fresh treated leaf disc was provided to the insects. On the third day, the adults were transferred to a box containing enough fresh, untreated potato leaves to sustain the survival of the untreated controls. Per treatment, 6 adults were tested and the numbers of survivors and moribund insects were counted at regular intervals from day 6 to day 13. The insects were considered moribund if they were unable to right themselves after being placed on their back. Despite the relatively high level of background in the negative control in this particular assay, clear effects were observed for the insects that had been exposed to Ld594 or Ld619 dsRNAs (FIG. 18).

Example 5

Identification of Target Genes in *Nilaparvata lugens*

5.1 Identification of *Nilaparvata lugens* Targets

New target sequences, corresponding to Troponin pathway targets and named NI594 (Troponin I), NI619 (Troponin T) and NI626 (Troponin C) have been identified in brown plant hopper, *Nilaparvata lugens*. Orthologous sequences of the *Lygus* genes, named NI594 (Troponin I), NI619 (Troponin T) and NI6251626 (Troponin C), were cloned through degenerated primer PCR, using BPH cDNA as template. In addition, full length cDNA was identified for NI594, using RACE (see above for method). AmpliTaq Gold PCR system (Applied Biosystems) was used following the manufacters' instructions and with standard conditions for the degenerate primer PCR reactions, typically as follows: 1 cycle with 10 minutes at 95° C., followed by 40 cycles with 30 seconds at 95° C., 1 minute at 50° C. and 1 minute at 72° C., followed by 10 minutes at 72° C. To increase the rate of success, up to 10 different degenerated primers, forward and reverse, were designed, based on alignments of orthologous sequences in other species, and used in various combinations. PCR fragments obtained were purified from the gel by gel extraction kit (Qiagen Cat. No 28706) and cloned into a TOPO TA vector (Invitrogen). The clones were sequenced and the consensus sequences were used in Blast searches against various available insect sequence databases to confirm the relevance of the insert. The degenerated primers that resulted in successful amplification are listed in Table 18.

The DNA sequences and deduced amino acid sequences of these target genes and one other target gene (NI537) were determined and are provided in Tables 10 and 11 respectively.

5.2 Production of dsRNAs Corresponding to the Partial Sequences of the *Nilaparvata lugens* Target Genes dsRNA was synthesized using the primers as provided in Table 12. The sense strand of the resulting dsRNA produced from each of the target genes is provided in Table 12.

5.3 Survival Analysis Assays for Novel *Nilaparvata lugens* Targets dsRNAs were synthesized and tested in the previously optimized BPH RNAi-by-feeding assays, in the presence of the zwitterionic detergent, CHAPSO, at 0.1% final concentration. The dsRNAs were tested at 0.5 final concentration. NI537, a potent target in the BPH assays was used as bench mark target in the assay. The insect survival was assessed over the course of 9 days.

The results of the bioassay showed that in BPH NI594, NI619 and NI626 were also potent RNAi targets in BPH (FIG. 19).

Example 6

Identification of Target Genes in *Acyrthosiphon pisum*

6.1 Identification of *Acyrthosiphon pisum* Targets

New target sequences have been identified in aphids and were named Ap423, Ap537, Ap560 and Ap594, following the same nomenclature: "Apxxx", where "Ap" corresponds to *Acyrthosiphon pisum* and "xxx" to the ID of the target. Primers were designed based on public domain gene prediction in AphidBase (ref: found on the World Wide Web at aphidbase.com)(Table 13).

The DNA sequences and deduced amino acid sequences of these target genes were determined and are provided in Tables 14 and 15 respectively.

6.2 Production of dsRNAs Corresponding to the Partial Sequences of the Aphid Target Genes dsRNA was synthesized using the primers as provided in Table 16. The sense strand of the resulting dsRNA produced from each of the target genes is provided in Table 16.

6.3 Survival Analysis Assays for Novel Aphid Targets

RNAi-by-feeding was tested in *Acyrthosiphon pisum* (pea aphid) with 4 targets Ap594, Ap423, Ap560, Ap537. The sequences were amplified by PCR using primers, designed on public domain sequence information (http://www.aphidbase.com), and cDNA prepared from aphids. The synthetic dsRNAs were prepared and tested at a final concentration of 0.5 µg/µl in presence of 5 µg/µl yeast tRNA in a sucrose diet. Ten neonate pea aphid nymphs were placed in a small Petri dish (32 mm). Fifty µl diet (with tRNA and dsRNA) was pipetted on top of the first layer of parafilm. A second layer of parafilm covered the diet and created a feeding sachet where the aphids could feed. Per target five replicates of 10 neonate nymphs were set-up. GFP dsRNA was used as a negative control. The diet was refreshed on day 4 and 7 of the assays and survival was assessed (FIG. 20).

TABLE 2

| Target ID | cDNA Sequence (sense strand) 5' → 3' |
|---|---|
| Lh594 | SEQ ID NO 1 |
| Lh609 | SEQ ID NO 3 |
| Lh610 | SEQ ID NO 5 |
| Lh610 (b) | SEQ ID NO 139 |
| Lh611 | SEQ ID NO 7 |
| Lh611 (b) | SEQ ID NO 140 |
| Lh617 | SEQ ID NO 9 |
| Lh618 | SEQ ID NO 11 |
| Lh618 (b) | SEQ ID NO 141 |
| Lh429 | SEQ ID NO 13 |
| Lh423 | SEQ ID NO 95 |
| Lh105.2 | SEQ ID NO 96 |
| Lh560 | SEQ ID NO 15 |
| Lh615 | SEQ ID NO 17 |
| Lh612 | SEQ ID NO 19 |
| Lh246 | SEQ ID NO 21 |
| Lh597 | SEQ ID NO 23 |
| Lh598 | SEQ ID NO 25 |
| Lh619 | SEQ ID NO 121 |
| Lh619 (b) | SEQ ID NO 142 |
| Lh619 (c) | SEQ ID NO 143 |
| Lh620 | SEQ ID NO 122 |
| Lh620 (b) | SEQ ID NO 144 |
| Lh620 (c) | SEQ ID NO 145 |
| Lh621 | SEQ ID NO 123 |
| Lh622 | SEQ ID NO 124 |
| Lh623 | SEQ ID NO 125 |
| Lh623 (b) | SEQ ID NO 146 |
| Lh624 | SEQ ID NO 126 |
| Lh624 (b) | SEQ ID NO 147 |
| Lh625 | SEQ ID NO 127 |
| Lh625 (b) | SEQ ID NO 148 |
| Lh626 | SEQ ID NO 128 |
| Lh626 (b) | SEQ ID NO 149 |
| Lh614 | SEQ ID NO 129 |
| Lh627 | SEQ ID NO 150 |
| Lh628 | SEQ ID NO 152 |
| Lh629 | SEQ ID NO 154 |
| Lh630 | SEQ ID NO 156 |
| Lh631 | SEQ ID NO 158 |
| Lh632 | SEQ ID NO 160 |
| Lh633.1 | SEQ ID NO 162 |
| Lh633.2 | SEQ ID NO 163 |
| Lh634.1 | SEQ ID NO 165 |
| Lh634.2 | SEQ ID NO 167 |
| Lh595.1 | SEQ ID NO 168 |
| Lh595.2 | SEQ ID NO 170 |
| Lh596 | SEQ ID NO 172 |

TABLE 3

| Target ID | Corresponding amino acid sequence of cDNA clone as represented in Table 2 |
|---|---|
| Lh594 | SEQ ID NO 79 |
| Lh609 | SEQ ID NO 80 |
| Lh610 | SEQ ID NO 81 |
| Lh610 (b) | SEQ ID NO 326 |
| Lh611 | SEQ ID NO 82 |
| Lh611 (b) | SEQ ID NO 327 |
| Lh617 | SEQ ID NO 83 |
| Lh618 | SEQ ID NO 84 |
| Lh618 (b) | SEQ ID NO 328 |

TABLE 3-continued

| Target ID | Corresponding amino acid sequence of cDNA clone as represented in Table 2 |
|---|---|
| Lh429 | SEQ ID NO 85 |
| Lh429 (b) | SEQ ID NO 329 |
| Lh423 | SEQ ID NO 99 |
| Lh105.2 | SEQ ID NO 100 |
| Lh560 | SEQ ID NO 86 |
| Lh615 | SEQ ID NO 87 |
| Lh612 | SEQ ID NO 88 |
| Lh246 | SEQ ID NO 89 |
| Lh597 | SEQ ID NO 90 |
| Lh598 | SEQ ID NO 91 |
| Lh619 | SEQ ID NO 330 |
| Lh620 | SEQ ID NO 331 |
| Lh621 | SEQ ID NO 332 |
| Lh622 | SEQ ID NO 333 |
| Lh623 | SEQ ID NO 334 |
| Lh624 | SEQ ID NO 335 |
| Lh625 | SEQ ID NO 336 |
| Lh626 | SEQ ID NO 337 |
| Lh614 | SEQ ID NO 338 |
| Lh627 | SEQ ID NO 339 |
| Lh628 | SEQ ID NO 340 |
| Lh629 | SEQ ID NO 341 |
| Lh630 | SEQ ID NO 342 |
| Lh631 | SEQ ID NO 343 |
| Lh632 | SEQ ID NO 344 |
| Lh633.1 | SEQ ID NO 345 |
| Lh633.2 | SEQ ID NO 346 |
| Lh634.1 | SEQ ID NO 347 |
| Lh634.2 | SEQ ID NO 348 |

TABLE 4

| Target ID | Primers Forward 5' → 3' | Primers Reverse 5' → 3' | dsRNA: sense strand represented by equivalent DNA Sequence 5' → 3' |
|---|---|---|---|
| Lh594 | SEQ ID NO 27<br>SEQ ID NO 29 | SEQ ID NO 28<br>SEQ ID NO 30 | SEQ ID NO 2 |
| Lh609 | SEQ ID NO 31<br>SEQ ID NO 33 | SEQ ID NO 32<br>SEQ ID NO 34 | SEQ ID NO 4 |
| Lh610 | SEQ ID NO 35<br>SEQ ID NO 37 | SEQ ID NO 36<br>SEQ ID NO 38 | SEQ ID NO 6 |
| Lh611 | SEQ ID NO 39<br>SEQ ID NO 41 | SEQ ID NO 40<br>SEQ ID NO 42 | SEQ ID NO 8 |
| Lh617 | SEQ ID NO 43<br>SEQ ID NO 45 | SEQ ID NO 44<br>SEQ ID NO 46 | SEQ ID NO 10 |
| Lh618 | SEQ ID NO 47<br>SEQ ID NO 49 | SEQ ID NO 48<br>SEQ ID NO 50 | SEQ ID NO 12 |
| Lh429 | SEQ ID NO 51<br>SEQ ID NO 53 | SEQ ID NO 52<br>SEQ ID NO 54 | SEQ ID NO 14 |
| Lh423 | SEQ ID NO 105<br>SEQ ID NO 107 | SEQ ID NO 106<br>SEQ ID NO 108 | SEQ ID NO 101 |
| Lh105.2 | SEQ ID NO 109<br>SEQ ID NO 111 | SEQ ID NO 110<br>SEQ ID NO 112 | SEQ ID NO 102 |
| GFP | SEQ ID NO 113<br>SEQ ID NO 115 | SEQ ID NO 114<br>SEQ ID NO 116 | SEQ ID NO 103 |
| Pt | SEQ ID NO 117<br>SEQ ID NO 119 | SEQ ID NO 118<br>SEQ ID NO 120 | SEQ ID NO 104 |
| Lh560 | SEQ ID NO 55<br>SEQ ID NO 57 | SEQ ID NO 56<br>SEQ ID NO 58 | SEQ ID NO 16 |
| Lh615 | SEQ ID NO 59<br>SEQ ID NO 61 | SEQ ID NO 60<br>SEQ ID NO 62 | SEQ ID NO 18 |
| Lh612 | SEQ ID NO 63<br>SEQ ID NO 65 | SEQ ID NO 64<br>SEQ ID NO 66 | SEQ ID NO 20 |
| Lh246 | SEQ ID NO 67<br>SEQ ID NO 69 | SEQ ID NO 68<br>SEQ ID NO 70 | SEQ ID NO 22 |
| Lh597 | SEQ ID NO 71<br>SEQ ID NO 73 | SEQ ID NO 72<br>SEQ ID NO 74 | SEQ ID NO 24 |
| Lh598 | SEQ ID NO 75<br>SEQ ID NO 77 | SEQ ID NO 76<br>SEQ ID NO 78 | SEQ ID NO 26 |
| Lh619 | SEQ ID NO 206<br>SEQ ID NO 208 | SEQ ID NO 207<br>SEQ ID NO 209 | SEQ ID NO 130 |
| Lh620 | SEQ ID NO 210<br>SEQ ID NO 212 | SEQ ID NO 211<br>SEQ ID NO 213 | SEQ ID NO 131 |
| Lh621 | SEQ ID NO 214<br>SEQ ID NO 216 | SEQ ID NO 215<br>SEQ ID NO 217 | SEQ ID NO 132 |
| Lh622 | SEQ ID NO 218<br>SEQ ID NO 220 | SEQ ID NO 219<br>SEQ ID NO 221 | SEQ ID NO 133 |
| Lh623 | SEQ ID NO 222<br>SEQ ID NO 224 | SEQ ID NO 223<br>SEQ ID NO 225 | SEQ ID NO 134 |
| Lh624 | SEQ ID NO 226<br>SEQ ID NO 228 | SEQ ID NO 227<br>SEQ ID NO 229 | SEQ ID NO 135 |
| Lh625 | SEQ ID NO 230<br>SEQ ID NO 232 | SEQ ID NO 231<br>SEQ ID NO 233 | SEQ ID NO 136 |
| Lh626 | SEQ ID NO 234<br>SEQ ID NO 236 | SEQ ID NO 235<br>SEQ ID NO 237 | SEQ ID NO 137 |
| Lh614 | SEQ ID NO 238<br>SEQ ID NO 240 | SEQ ID NO 239<br>SEQ ID NO 241 | SEQ ID NO 138 |
| Lh627 | SEQ ID NO 242<br>SEQ ID NO 244 | SEQ ID NO 243<br>SEQ ID NO 245 | SEQ ID NO 151 |
| Lh628 | SEQ ID NO 246<br>SEQ ID NO 248 | SEQ ID NO 247<br>SEQ ID NO 249 | SEQ ID NO 153 |
| Lh629 | SEQ ID NO 250<br>SEQ ID NO 25 | SEQ ID NO 251<br>SEQ ID NO 253 | SEQ ID NO 155 |
| Lh630 | SEQ ID NO 254<br>SEQ ID NO 256 | SEQ ID NO 255<br>SEQ ID NO 257 | SEQ ID NO 157 |
| Lh631 | SEQ ID NO 258<br>SEQ ID NO 260 | SEQ ID NO 259<br>SEQ ID NO 261 | SEQ ID NO 159 |
| Lh632 | SEQ ID NO 262<br>SEQ ID NO 264 | SEQ ID NO 263<br>SEQ ID NO 265 | SEQ ID NO 161 |
| Lh633.2 | SEQ ID NO 266<br>SEQ ID NO 268 | SEQ ID NO 267<br>SEQ ID NO 269 | SEQ ID NO 164 |
| Lh634.1 | SEQ ID NO 270<br>SEQ ID NO 272 | SEQ ID NO 271<br>SEQ ID NO 273 | SEQ ID NO 166 |
| Lh595 | SEQ ID NO 274<br>SEQ ID NO 276 | SEQ ID NO 275<br>SEQ ID NO 277 | SEQ ID NO 169 |
| Lh596 | SEQ ID NO 278<br>SEQ ID NO 280 | SEQ ID NO 279<br>SEQ ID NO 281 | SEQ ID NO 173 |

TABLE 7

| Target ID | cDNA sequence (sense strand) 5' → 3' |
|---|---|
| Ld594 | SEQ ID NO 174 |
| Ld594(b) | SEQ ID NO 404 |
| Ld619 | SEQ ID NO 176 |
| Ld620 | SEQ ID NO 178 |
| Ld583 | SEQ ID NO 386 |
| Ld584 | SEQ ID NO 387 |
| Ld586 | SEQ ID NO 388 |
| Ld588 | SEQ ID NO 389 |
| Ld513 | SEQ ID NO 394 |

TABLE 8

| Target ID | Corresponding amino acid sequence of cDNA clone as represented in Table 9 |
|---|---|
| Ld594 | SEQ ID NO 349 |
| Ld594(b) | SEQ ID NO 405 |
| Ld619 | SEQ ID NO 350 |
| Ld620 | SEQ ID NO 351 |
| Ld583 | SEQ ID NO 390 |
| Ld584 | SEQ ID NO 391 |
| Ld586 | SEQ ID NO 392 |
| Ld588 | SEQ ID NO 393 |
| Ld513 | SEQ ID NO 395 |

TABLE 9

| Target ID | Primers Forward 5' → 3' | Primers Reverse 5' → 3' | dsRNA: sense strand represented by equivalent DNA Sequence 5' → 3' |
|---|---|---|---|
| Ld594 | SEQ ID NO 282 | SEQ ID NO 283 | SEQ ID NO 175 |
|  | SEQ ID NO 284 | SEQ ID NO 285 |  |
| Ld619 | SEQ ID NO 286 | SEQ ID NO 287 | SEQ ID NO 177 |
|  | SEQ ID NO 288 | SEQ ID NO 289 |  |
| Ld620 | SEQ ID NO 290 | SEQ ID NO 291 | SEQ ID NO 179 |
|  | SEQ ID NO 292 | SEQ ID NO 293 |  |
| Ld513 | SEQ ID NO 396 | SEQ ID NO 397 | SEQ ID NO 400 |
|  | SEQ ID NO 398 | SEQ ID NO 399 |  |

TABLE 10

| Target ID | cDNA Sequence (sense strand) 5' → 3' |
|---|---|
| NI594 | SEQ ID NO 180 |
| NI619 | SEQ ID NO 182 |
| NI626 | SEQ ID NO 184 |
| NI537 | SEQ ID NO 186 |

TABLE 11

| Target ID | Corresponding amino acid sequence of cDNA clone as represented in Table 12 |
|---|---|
| NI594 | SEQ ID NO 352 |
| NI619 | SEQ ID NO 353 |
| NI626 | SEQ ID NO 354 |
| NI537 | SEQ ID NO 355 |

TABLE 12

| Target ID | Primers Forward 5' → 3' | Primers Reverse 5' → 3' | dsRNA: sense strand represented by equivalent DNA Sequence 5' → 3' |
|---|---|---|---|
| NI594 | SEQ ID NO 294 | SEQ ID NO 295 | SEQ ID NO 181 |
|  | SEQ ID NO 296 | SEQ ID NO 297 |  |
| NI619 | SEQ ID NO 298 | SEQ ID NO 299 | SEQ ID NO 183 |
|  | SEQ ID NO 300 | SEQ ID NO 301 |  |
| NI626 | SEQ ID NO 302 | SEQ ID NO 303 | SEQ ID NO 185 |
|  | SEQ ID NO 304 | SEQ ID NO 305 |  |
| NI537 | SEQ ID NO 306 | SEQ ID NO 307 | SEQ ID NO 187 |
|  | SEQ ID NO 308 | SEQ ID NO 309 |  |

TABLE 13

| Target | Fw primer sequence | Reverse primer sequence |
|---|---|---|
| Ap594 | SEQ ID NO 369 | SEQ ID NO 370 |
| Ap423 | SEQ ID NO 371 | SEQ ID NO 372 |
| Ap537 | SEQ ID NO 373 | SEQ ID NO 374 |
| Ap560 | SEQ ID NO 375 | SEQ ID NO 376 |

TABLE 14

| Target ID | cDNA Sequence (sense strand) 5' → 3' |
|---|---|
| Ap594 | SEQ ID NO 188 |
| Ap423 | SEQ ID NO 200 |
| Ap537 | SEQ ID NO 202 |
| Ap560 | SEQ ID NO 204 |

TABLE 15

| Target ID | Corresponding amino acid sequence of cDNA clone as represented in Table 16 |
|---|---|
| Ap594 | SEQ ID NO 356 |
| Ap423 | SEQ ID NO 357 |
| Ap537 | SEQ ID NO 358 |
| Ap560 | SEQ ID NO 359 |

TABLE 16

| Target ID | Primers Forward 5' → 3' | Primers Reverse 5' → 3' | dsRNA: sense strand represented by equivalent DNA sequence 5' → 3' |
|---|---|---|---|
| Ap594 | SEQ ID NO 310 | SEQ ID NO 311 | SEQ ID NO 189 |
|  | SEQ ID NO 312 | SEQ ID NO 313 |  |
| Ap423 | SEQ ID NO 314 | SEQ ID NO 315 | SEQ ID NO 201 |
|  | SEQ ID NO 316 | SEQ ID NO 317 |  |
| Ap537 | SEQ ID NO 318 | SEQ ID NO 319 | SEQ ID NO 203 |
|  | SEQ ID NO 320 | SEQ ID NO 321 |  |
| Ap560 | SEQ ID NO 322 | SEQ ID NO 323 | SEQ ID NO 205 |
|  | SEQ ID NO 324 | SEQ ID NO 325 |  |

TABLE 17

| Target | Forward primer | Reverse primer |
|---|---|---|
| Ld594 | SEQ ID NO 377 | SEQ ID NO 378 |

TABLE 18

| Target | Forward primer | Reverse primer |
|---|---|---|
| NI594 | seq id no 379 | seq id no 380 |
| NI619 | seq id no 381 | seq id no 382 |
| NI626 | seq id no 383 | seq id no 384 |

TABLE 19

| Target ID | Best *Drosophila* hit | NAME | SYMBOL |
|---|---|---|---|
| Ld583 | CG4759 | Ribosomal protein L27 | RpL27 |
| Ld584 | CG 17331 | Proteasome, beta-type subunit |  |
| Ld586 | CG13704 | unknown |  |
| Ld588 | CG4157 | Rpn12 |  |

TABLE 20

| Target ID | Best *Drosophila* hit | NAME | SYMBOL |
|---|---|---|---|
| NI594 | CG7178 | wings up A (troponin I) | wupA |
| NI619 | CG7107 | troponin T (upheld) | up |

TABLE 20-continued

| Target ID | Best *Drosophila* hit | NAME | SYMBOL |
|---|---|---|---|
| N1626 | *CG9073, CG7930, CG2981, CG12408, CG6514, CG2981, CG7930, CG9073, CG6514, CG12408 | troponin C | |
| N1537 | CG32744 | Ubiquitin-5E; protein modification process | |

*unclear: multiple hits in family

TABLE 21

| Target ID | Best *Drosophila* hit | NAME | SYMBOL |
|---|---|---|---|
| Ap594 | CG7178 | wings up A (troponin I) | wupA |
| Ap423 | CG2746 | ribosomal protein L19 | RpL19 |

TABLE 21-continued

| Target ID | Best *Drosophila* hit | NAME | SYMBOL |
|---|---|---|---|
| Ap537 | CG32744 | Ubiquitin-5E; protein modification process | |
| Ap560 | CG10423 | ribosomal protein S27 | RpS27 |

It will be appreciated by persons skilled in the art that numerous variations and/or modifications may be made to the above mentioned assays without departing from the spirit or scope of this assay as generically described. Those skilled in the art will recognize, or be able to ascertain using no more than routine experimentation, many equivalents to the specific examples, and such equivalents are intended to be encompassed by the present invention. The present example, therefore, is to be considered in all respects as illustrative and not restrictive.

What is claimed:

1. An interfering ribonucleic acid (RNA) that functions upon uptake by an insect pest species to down-regulate expression of a ribosomal protein S18 target gene in said insect pest, wherein the RNA comprises at least one silencing element, wherein the silencing element is a region of double-stranded RNA comprising annealed complementary strands, one strand of which comprises or consists of a sequence of nucleotides which is at least partially complementary to a target nucleotide sequence within the ribosomal protein S18 target gene, and wherein the interfering RNA is encoded by:
   (i) a nucleotide sequence comprising any of SEQ ID NOs 13, 14, or the complement thereof, or a nucleotide sequence that is at least 85% identical to any of SEQ ID NOs 13, 14, or the complement thereof,
   (ii) a nucleotide sequence comprising a fragment of at least 21 contiguous nucleotides of any of SEQ ID NOs 13, 14, or the complement thereof,
   (iii) a nucleotide sequence comprising a fragment of at least 21 contiguous nucleotides of any of SEQ ID NOs 13, 14, or the complement thereof, and wherein said nucleotide sequence of said fragment is at least 85% identical to said corresponding fragment of any of SEQ ID NOs 13, 14, or the complement thereof, or
   (iv) a nucleotide sequence comprising a fragment of at least 21 contiguous nucleotides of a nucleotide sequence encoding an amino acid sequence encoded by SEQ ID NO: 13, 14, or the complement thereof.

2. The interfering RNA of claim 1 wherein the silencing element comprises or consists of a sequence of at least 21 contiguous nucleotides which is complementary or at least partially complementary to a target nucleotide sequence within the ribosomal protein S18 target gene.

3. The interfering RNA of claim 1 wherein the RNA comprises at least two silencing elements, wherein each silencing element comprises or consists of a sequence of nucleotides which is at least partially complementary to a target nucleotide sequence within the ribosomal protein S18 target gene.

4. The interfering RNA of claim 3 wherein each of the silencing elements comprises or consists of a different sequence of nucleotides which is complementary to a different target nucleotide sequence within the ribosomal protein S18 target gene.

5. The interfering RNA of claim 4 wherein the different ribosomal protein S18 target nucleotide sequences originate from a single ribosomal protein S18 target gene or from different ribosomal protein S18 target genes.

6. The interfering RNA of claim 5 wherein the different target genes originate from the same insect pest species or different insect pest species.

7. The interfering RNA of claim 1 wherein the insect pest species is a plant pest.

8. The interfering RNA of claim 7 wherein the plant pest is an insect pest species selected from the insect species belonging to the orders Coleoptera, Hemiptera, Lepidoptera, Diptera, Dichyoptera, Orthoptera, and Siphonaptera.

9. The interfering RNA of claim 8 wherein the insect pest species is selected from the group consisting of *Leptinotarsa* spp., *Nilaparvata* spp., *Lygus* spp., *Myzus* spp., and *Diabrotica* spp.

10. The interfering RNA of claim 1 wherein down-regulating expression of the ribosomal protein S18 target gene causes decreased growth, development, reproduction, or survival of the insect pest as compared with the insect pest exposed to an interfering ribonucleic acid targeting a non-essential gene or an interfering ribonucleic acid that does not down-regulate any genes within the insect pest.

11. A polynucleotide comprising a sequence of nucleotides encoding the interfering RNA of claim 1.

12. The polynucleotide of claim 11 which is comprised in a DNA construct.

13. The DNA construct of claim 12 which is an expression construct, wherein the polynucleotide sequence encoding the interfering RNA is operably linked to at least one regulatory sequence capable of driving expression of the polynucleotide sequence.

14. A host cell comprising the interfering RNA of claim 1.

15. The host cell of claim 14 wherein the host cell is a prokaryotic or a eukaryotic cell.

16. The host cell of claim 15 wherein the host cell is a bacterial cell.

17. A composition for preventing and/or controlling insect pest infestation comprising the interfering ribonucleic acid (RNA) of claim 1 and at least one suitable carrier, excipient or diluent.

18. The composition of claim 17 wherein the interfering RNA is encoded by a polynucleotide comprising a sequence of nucleotides encoding the interfering RNA which is comprised in a DNA construct, which optionally is an expression construct, wherein the polynucleotide sequence encoding the interfering RNA is operably linked to at least one regulatory sequence capable of driving expression of the polynucleotide sequence.

19. The composition of claim 18, wherein the interfering RNA is produced by a host cell capable of expressing the interfering RNA.

20. The composition of claim 19 wherein the host cell is a bacterial cell.

21. The composition of claim 17 wherein the composition is in a form suitable for ingestion by an insect.

22. The composition of claim 17 wherein the composition is in solid, liquid or gel form.

23. The composition of claim 17 wherein the composition is formulated as an insecticidal spray.

24. The composition of claim 23 wherein the spray is a pressurized/aerosolized spray or a pump spray.

25. The composition of claim 17 wherein the composition further comprises at least one pesticidal agent selected from the group consisting of a chemical insecticide, a patatin, a *Bacillus thuringiensis* insecticidal protein, a Xenorhabdus insecticidal protein, a Photorhabdus insecticidal protein, a *Bacillus laterosporus* insecticidal protein, and a *Bacillus sphaericus* insecticidal protein.

26. The composition of claim 25 wherein said *Bacillus thuringiensis* insecticidal protein is selected from the group consisting of a Cry1, a Cry3, a TIC851, a CryET170, a Cry22, a TIC901, a TIC201, a TIC407, a TIC417, a binary insecticidal protein CryET80and CryET76, a binary insecticidal protein TIC100and TIC101, a combination of an insecticidal protein ET29or ET37with an insecticidal protein TIC810or TIC812, and a binary insecticidal protein PS149B1.

27. A housing or trap for an insect pest which contains the composition as defined in claim 17.

28. A combination for preventing and/or controlling pest infestation comprising the composition of claim 17 and at least one other active agent.

29. The combination of claim 28 wherein the combination is for preventing and/or controlling pest infestation of a plant and the other active agent is an agronomical agent.

30. The combination of claim 29 wherein the agronomical agent comprises a herbicide.

31. The combination of claim 29 wherein the agronomical agent comprises a pesticide.

32. The combination of claim 31 further comprising a second pesticide, wherein the second pesticide is selected from the group consisting of a chemical insecticide, a patatin, a *Bacillus thuringiensis Bacillus thuringiensis* insecticidal protein, a Xenorhabdus insecticidal protein, a Photorhabdus insecticidal protein, a *Bacillus laterosporus* insecticidal protein, and a *Bacillus sphaericus* insecticidal protein.

33. The combination of claim 32 wherein said *Bacillus thuringiensis* insecticidal protein is selected from the group consisting of a Cry1, a Cry3, a TIC851, a CryET170, a Cry22, a TIC901, a TIC201, a TIC407, a TIC417, a binary insecticidal protein CryET80and CryET76, a binary insecticidal protein TIC100 and TIC101, a combination of an insecticidal protein ET29 or ET37 with an insecticidal protein TIC810 or TIC812, and a binary insecticidal protein PS149B1.

34. A method for down-regulating expression of a target gene in an insect pest species in order to prevent and/or control pest infestation, comprising contacting said insect pest species with at least one interfering ribonucleic acid (RNA), wherein the interfering RNA functions upon uptake by the insect pest to down-regulate the expression of the ribosomal protein S18 target gene within said insect pest, wherein the interfering RNA is the interfering RNA of claim 1.

35. The method of claim 34 wherein down-regulation of expression of the ribosomal protein S18 target gene in an insect pest species is used to obtain at least 20% pest control or at least 20% pest mortality as compared to control insect pests contacted with an interfering ribonucleic acid (RNA) targeting a non-essential pest gene or a target gene not expressed in said insect pest.

36. The method of claim 34 wherein the method is used to prevent and/or control pest infestation of a plant.

37. The method of claim 36 wherein the plant is selected from the group consisting of cotton, potato, rice, canola, sunflower, sorghum, pearl millet, corn, strawberries, soy, alfalfa, tomato, eggplant, pepper and tobacco.

38. A kit comprising the interfering ribonucleic acid (RNA) of claim 1, the DNA construct of claim 13, or the composition of claim 17 for preventing and/or controlling insect pest infestation.

* * * * *

UNITED STATES PATENT AND TRADEMARK OFFICE
CERTIFICATE OF CORRECTION

PATENT NO. : 10,329,565 B2
APPLICATION NO. : 15/838522
DATED : June 25, 2019
INVENTOR(S) : Beghyn et al.

Page 1 of 1

It is certified that error appears in the above-identified patent and that said Letters Patent is hereby corrected as shown below:

On the Title Page

The correct name of the Assignee should read "DEVGEN NV, Zwijnaarde (BE)" instead of "Syngenta Participations AG, Basel (CH)".

In the Claims

At Column 346, Line 22, "CryET80and" should read "CryEt80 and"

At Column 346, Line 23, "TIC100and" should read "TIC100 and"

At Column 346, Line 24, "ET29or ET37with" should read "ET29 or ET37 with"

At Column 346, Line 25, "TIC810or" should read "TIC810 or"

At Column 346, Line 51, "CryET80and" should read "CryET80 and"

Signed and Sealed this
Twenty-ninth Day of October, 2019

Andrei Iancu
*Director of the United States Patent and Trademark Office*